(12) United States Patent
Kobayashi et al.

(10) Patent No.: US 7,972,809 B2
(45) Date of Patent: Jul. 5, 2011

(54) METHYLOTROPHIC YEAST PRODUCING MAMMALIAN TYPE SUGAR CHAIN

(75) Inventors: Kazuo Kobayashi, Takasaki (JP);
Yoshinori Kitagawa, Takasaki (JP);
Toshihiro Komeda, Kanagawa (JP);
Nagako Kawashima, Takasaki (JP);
Yoshifumi Jigami, Tsukuba (JP);
Yasunori Chiba, Tsukuba (JP)

(73) Assignees: National Institute of Advanced Industrial Science & Technology, Tokyo (JP); Kirin Beer Kabushiki Kaisha, Tokyo (JP)

( * ) Notice: Subject to any disclaimer, the term of this patent is extended or adjusted under 35 U.S.C. 154(b) by 1488 days.

(21) Appl. No.: 10/511,436

(22) PCT Filed: Apr. 28, 2003

(86) PCT No.: PCT/JP03/05464
§ 371 (c)(1),
(2), (4) Date: Aug. 16, 2005

(87) PCT Pub. No.: WO03/091431
PCT Pub. Date: Nov. 6, 2003

(65) Prior Publication Data
US 2006/0148039 A1    Jul. 6, 2006

(30) Foreign Application Priority Data

Apr. 26, 2002  (JP) ................................. 2002-127677

(51) Int. Cl.
*C12P 21/00* (2006.01)
*C12N 15/01* (2006.01)

(52) U.S. Cl. ...................................... 435/69.1; 435/471

(58) Field of Classification Search .................... None
See application file for complete search history.

(56) References Cited

U.S. PATENT DOCUMENTS

2007/0077642 A1*  4/2007  Strauss et al. .............. 435/254.2

FOREIGN PATENT DOCUMENTS

| EP | 0 173 378 | 3/1989 |
|---|---|---|
| EP | 0 314 096 | 5/1989 |
| JP | 61-92569 | 5/1986 |
| JP | 2-419 | 1/1990 |
| JP | 6-506117 | 7/1994 |
| JP | 09-003097 | 1/1997 |
| JP | 2000-78978 | 3/2000 |
| JP | 2001-501475 | 2/2001 |
| JP | 2003-503030 | 1/2003 |
| WO | WO-92/17595 | 10/1992 |
| WO | WO 95/23857 | 9/1995 |
| WO | WO-98/14600 | 4/1998 |
| WO | WO-00/14259 | 3/2000 |
| WO | WO-00/78978 | 12/2000 |
| WO | WO-02/00856 | 1/2002 |
| WO | WO-02/00879 | 1/2002 |

OTHER PUBLICATIONS

Wim Martinet et al., "Modification of the protein glycosylation pathway in the methylotrophic yeast *Pichia patoris*", Biotechnology Letters, vol. 20, No. 12, 1998, pp. 1171-1177.
Yasunori Chiba et al., "Production of Human Compatible High Mannose-type (Man$_5$GlcNAc$_2$) Sugar Chains in *Saccharomyces cerevisiae*\*", The Journal of Biological Chemsitry, vol. 273, No. 41, Issue of Oct. 9, 1998, pp. 26298-26304.
P. Lu et al., "Cloning and disruption of the β-isopropylmalate dehydrogenase gene (LEU2) of *Pichia stipitis* with *URA3* and recovery of the double auxotroph", Appl. Microbiol. Biotechnol. (1998) 49: 141-146.
International Search Report of PCT/JP03/05464.
Azaryan et al., "Purification and Characterization of a Paired Basic Residue-Specific Yeast Aspartic Protease Encoded by the YAP3 Gene," The Journal of Biological Chemistry, 1993, vol. 268, No. 16, pp. 11968-11975.
Buurman et al., "Molecular Analysis of CaMnt1p, a Mannosyl Transferase Important for Adhesion and Virulence of *Candida albicans*," Proc. Natl. Sci. USA, Jun. 1998, vol. 95, pp. 7670-7675.
Casano et al., "Cloning and Sequence Analysis of the *Pichia pastoris* TRP1, IPP1 and HIS 3 Genes," Yeast, 1998, vol. 14, pp. 861-867.
Komon0 et al., "Shared Functions in vivo of a Glycosyl-Phosphatidylinositol-Linked Aspartyl Protease, Mkc7, and the Proprotein Processing Protease Kex2 in Yeast," Proc. Natl. Acad. Sci. USA, 1995, vol. 92, pp. 10752-10756.
Ledeboer et al., "Molecular Cloning and Characterization of a Gene Coding for Methanol Oxidase in *Hansenula polymorpha*," Nucleic Acids Research, 1985, vol. 13, No. 9, pp. 3063-3082.
Nishiya et al., "Primary Structure of ADE1 Gene from *Candida utilis*," Bioscience Biotechnology and Biochemistry, 1994, vol. 58, No. 1, pp. 208-210.
Sakai et al., "Directed Mutagenesis in an Asporogenous Methylotrophic Yeast: Cloning, Sequencing and One-Stop Gene Disruption of the 3-Isopropylmalate Dehydrogenase Gene (LEU2) of *Canadida boidinii* to Device Doubly Auxotrophic Marker Strains," Journal of Bacteriology, 1992, vol. 174, No. 18, pp. 5988-5993.

(Continued)

*Primary Examiner* — Nancy Vogel
(74) *Attorney, Agent, or Firm* — Stephen A. Bent; Foley & Lardner LLP

(57) ABSTRACT

This invention is to provide a process for producing a glycoprotein comprising a mammalian type sugar chain, characterized in that the process comprises introducing an α-1,2-mannosidase gene into a methylotrophic yeast having a mutation of a sugar chain biosynthesizing enzyme gene, so that the α-1,2-mannosidase gene is expressed under the control of a potent promoter in the yeast; culturing in a medium the methylotrophic yeast cells with a heterologous gene transferred thereinto; and obtaining the glycoprotein comprising a mammalian type sugar chain from the culture. Using the newly created methylotrophic yeast having a sugar chain mutation, a neutral sugar chain identical with a high mannose type sugar chain produced by mammalian cells such as human cells, or a glycoprotein comprising such a neutral sugar chain, can be produced in a large amount at a high purity. By introducing a mammalian type sugar chain biosynthesizing gene into the above-described mutant, a mammalian type sugar chain, such as a hybrid or complex, or a protein comprising a mammalian type sugar chain can be efficiently produced.

52 Claims, 35 Drawing Sheets

OTHER PUBLICATIONS

Sakai et al., "The Orotidine-5'-Phosphate Decarboxylase Gene (URA3) of a Methylotrophic Yeast, *Candida boidinii*: Nucleotide Sequence and Its Expression in *Escherichia coli*", Journal of Fermentation and Bioengineering, 1992, vol. 73, No. 4, pp. 255-260.

Yamada et al., "The Phylogenetic Relationships of Methanol-Assimilating Yeasts Based on the Partial Sequences of 18S and 25S Ribosomal RNAs: The Proposal of Komagataella Gen. Nov. (Saccharomycetaceae)," vol. 59, No. 3, pp. 439-444.

Yang et al., "High-Efficiency Transformation of *Pichia stipitis* Based on Its URA3 Gene and a Homologous Autonomous Replication Sequence, ARS2," Applied and Environmental Microbiology, 1994, vol. 60, No. 12, pp. 4245-4254.

Zhang et al., "LEU2 Gene Homolog in *Kluyveromyces lactis*," Yeast 1992, vol. 8, pp. 801-804.

Japanese Office Action JP2004-501993 dated May 12, 2009.

* cited by examiner

\* : Possible phosphorylation site
n : 50-100
m : 10-25

1: Control antibody

2: Antibody produced by *Ogataea minuta* TK9-IgB-aM strain

← Full length heavy chain
← Decomposed heavy chain
← Full length light chain

1. Culture supernatant
2. Column non-adsorbed fraction
3. Wash fraction
4. Elution fraction
5. Control antibody 1. Control antibody 2. Antibody produced by *Ogataea minuta* TK9-IgB-aM strain A. *Ogataea minuta* TK9-IgB strain B. *Ogataea minuta* TK9-IgB-aM strain Reduced   Unreduced 1 Molecular weight marker
2 Yeast culture supernatant
3 Protein A Elution fraction
4 Control antibody Lanes 1, 3, 5 ;
    Control strain (<u>Ogataea minuta</u> YK3-IgB1-aM strain)
Lanes 2, 4, 6 ;
PDI-transferred strain (<u>Ogataea minuta</u> YK3-IgB1-aM-P strain)
    Lanes 1, 2:  Reduced (Culture supernatant)
    Lanes 3, 4:  Unreduced (Culture supernatant)
    Lanes 5, 6:  Unreduced (Cell extract)

SEQUENCE LISTING

```
<160> NUMBER OF SEQ ID NOS: 121

<210> SEQ ID NO 1
<211> LENGTH: 11
<212> TYPE: PRT
<213> ORGANISM: Saccharomyces cerevisiae

<400> SEQUENCE: 1

Ala Tyr Met Phe Lys Tyr Asp Ser Thr His Gly
 1               5                  10

<210> SEQ ID NO 2
<211> LENGTH: 11
<212> TYPE: PRT
<213> ORGANISM: Saccharomyces cerevisiae

<400> SEQUENCE: 2

Asp Gly Pro Ser His Lys Asp Trp Arg Gly Gly
 1               5                  10

<210> SEQ ID NO 3
<211> LENGTH: 32
<212> TYPE: DNA
<213> ORGANISM: Artificial Sequence
<220> FEATURE:
<223> OTHER INFORMATION: Description of Artificial Sequence: Synthetic
      primer PGP5 for amplification of 5'-region of
      Ogataea minuta GAP gene
<220> FEATURE:
<221> NAME/KEY: modified_base
<222> LOCATION: (3)
<223> OTHER INFORMATION: a, c, g or t
<220> FEATURE:
<221> NAME/KEY: modified_base
<222> LOCATION: (24)
<223> OTHER INFORMATION: a, c, g or t
<220> FEATURE:
<221> NAME/KEY: modified_base
<222> LOCATION: (27)
<223> OTHER INFORMATION: a, c, g or t

<400> SEQUENCE: 3
gcntayatgt tyaartayga ywsnacncay gg                                   32

<210> SEQ ID NO 4
<211> LENGTH: 32
<212> TYPE: DNA
<213> ORGANISM: Artificial Sequence
<220> FEATURE:
<223> OTHER INFORMATION: Description of Artificial Sequence: Synthetic
      primer PGP3 for amplification of 3'-region of
      Ogataea minuta GAP gene
<220> FEATURE:
<221> NAME/KEY: modified_base
<222> LOCATION: (3)
<223> OTHER INFORMATION: a, c, g or t
<220> FEATURE:
<221> NAME/KEY: modified_base
<222> LOCATION: (6)
<223> OTHER INFORMATION: a, c, g or t
<220> FEATURE:
<221> NAME/KEY: modified_base
<222> LOCATION: (21)
<223> OTHER INFORMATION: a, c, g or t
```

```
<220> FEATURE:
<221> NAME/KEY: modified_base
<222> LOCATION: (24)
<223> OTHER INFORMATION: a, c, g or t
<220> FEATURE:
<221> NAME/KEY: modified_base
<222> LOCATION: (27)
<223> OTHER INFORMATION: a, c, g or t

<400> SEQUENCE: 4
ccnccnckcc artcyttrtg nswnggnccr tc                                      32

<210> SEQ ID NO 5
<211> LENGTH: 3186
<212> TYPE: DNA
<213> ORGANISM: Ogataea minuta

<400> SEQUENCE: 5
aagctttact ggttcaaggg gttaagtagg ggcgcggtct ggtctttgtg gttgtttcta        60
cacggaccac agttgacagc atcgactgct catcgaaaac ggtcgcagtg cggcaatctg       120
ctctatctaa tcccaggcta ctcgatccct gcacaaccta cagagtgatc cgaccgcact       180
gcccgagatt cagcagactc tcgcagcgca gcgtgcgttt taatccctca aatcaaggct       240
gtgcagaccc ggaggatgtg aagctgggac ggcgggaggg aagtctggag tggtgagaga       300
atgtgggagc tgtgcaaagg ggcaatggtc actcagcgca gagcgatggt ggcgcggggg       360
ccaatatctc ggcaacaaga acgcccgagg acgacgggac tctgaatgcg agcacgttgt       420
ctttcagaca gtccacccgg attccaatat tcgcaggact cgcgctcaga aacgcaaccc       480
cggcagattc gcgtccagtc aggccatctg cggcgagctg ctgcgctcgc gggctgcgcc       540
acaacgcatc gccacatata cgtcaccgcc cgcccgctgg caacctgagg tttttccgca       600
acgggtgcac tgattgctgc gttaacgagg caactggaga tgtcagaggc caagtggagc       660
catatcacag cggactgcgc atctctggcc tgccggacgc ggtagcgtcc cgtctttttg       720
cggacagctt cttaaaacct ggctgaaact aagcgagacc tgcgacctgg aacgcccgca       780
cacccgtaca cctccggagt tgtatcctca gaagcggagt aacctgcagg cctacgcaag       840
aaaagagccc gggacccatc gaccggaaaa gaggggtgga gctagtgggg tagccttgga       900
gcagacctgg ggcagacctg ggttagtacc agggccgaaa agggtcagag gaatcagggt       960
ggcacggcag tctataccgt agaagctctt ctcgacagca gcgagcagaa actgcacaga      1020
ggtccgttcg ccagtctcgt accaccaccg catgacccaa tcagcattga tgctcccaca      1080
tgggtagtgc gcgcgaacgc ctggcaccca aacacaccac ttacgcttcc cgcaccgcgg      1140
tggttaacac tggcccggag tagtcatata cggagatttt ggcatgattc taattccggg      1200
tcgggacacg acctaagtgg cgtgcaaagc tcggggggcta aatgtttccc ggcgctcgcg      1260
gcgactcttg tgcgcgcccg cggcggttcg cgggagacgg gggaaagaga ggggtgaccg      1320
cagcgagcga tggtgtgcca gatctcaggc cgagtcaaga caatatataa agagaggatt      1380
gtccactttt ctccaatagt atttgacccg ggttgctctc tgttgatttt ttctagatca      1440
tacaattatt gtttgaattc actcaattaa catcacaaa tacaatacaa aatggcttac       1500
aacgtcggta tcaacggatt cggaagaatt ggtagactcg ttcttagaat tgctttgtcc      1560
agaaaggaca tcaacgtggt tgccgtgaat gatccattca tcgctgccga gtacgctgct      1620
tacatgttca gtacgactc cactcacgga agataccaag gtgaagtcac cttcgaggga      1680
aagtaccttg tgatcgacgg tcagaagatt gaggtgttcc aagagagaga ccctgctgac      1740
atcccatggg gtaaggaggg cgttgacttt gtcattgact ccaccggtgt gttcaccacc      1800
```

```
accgccggcg ctcaaaagca cattgatgct ggtgccaaga aggttatcat cactgctcca    1860
tccgctgacg ctccaatgtt cgttatgggt gtcaaccaca aggagtacac caaggacttg    1920
tccattgtct ccaacgcttc ctgtaccacc aactgtctgg ctccattggc caaggttgtt    1980
aacgacgttt tcggtattga gtctggtttg atgaccaccg tccactctat cactgccacc    2040
caaaagaccg ttgacggtcc atcccacaag gactggagag gaggaagaac cgcttccggt    2100
aacatcattc catcctccac cggtgccgct aaggctgtcg gtaaggtctt gccagctctt    2160
gctggtaagt tgactggtat gtctctgaga gttcctacca ccgatgtttc cgttgttgac    2220
ttgactgtca acttgaagac cccaaccacc tacgcagaga tctccgccgc catcaagaag    2280
gcctctgagg gtgaacttgc cggtatcttg ggttacactg aggacgccgt tgtctccact    2340
gacttcttga ccgacaacag atcttcgatc tttgacgcct ctgccggtat cttgttgacc    2400
ccaactttcg tcaagttgat ctcctggtac gataacgagt acggttactc caccagagtt    2460
gtcgacttgc ttgagcacgt tgccaaggtc tcttccgctt aagtggatag atgaccaatg    2520
gcctctttaa gtaaacattt cgttttgaat atatttcaag ttgaataatg aaagccttgt    2580
tgtagactta ctccgaagct ccggggcttc ggctccctga atttattttt tacatctctg    2640
caccggaaaa ctggctattt gaaaaatttc gacgttttgc ttgaaactcg agttgaggag    2700
cattgccaaa ttcgatcgtt ttctaacgga cgccagtcga gttattgtta tgtcacgtga    2760
catcaattgt cctctattcc ttttggccg atctcgtttg tgctgacggc ctccgaacag    2820
ttacttctac cggcagggat tggggatgat cgggatcgat gtcctcaact ccagaggctg    2880
atccgatgcg gtgggacttc atgcgtccaa atctgttgga tgatgtgctc ttctgctttt    2940
ttggtgacca aacgagatga caattgactg cattgaaaag gttattagct tttttggtct    3000
tctcctgtgt cgattcgagc ggtaccgtag gtaggtctgc tatggaggca tgcgtcataa    3060
gtcagccttg attaactttc ggagctgcgc gatccacatc tctgcaccgc gcggaggcct    3120
ttgactgcag cattttaatt aatctcgtaa aataagctct taaacgagat tagcttacgg    3180
ggatcc                                                              3186
```

<210> SEQ ID NO 6
<211> LENGTH: 336
<212> TYPE: PRT
<213> ORGANISM: Ogataea minuta

<400> SEQUENCE: 6

Met Ala Tyr Asn Val Gly Ile Asn Gly Phe Gly Arg Ile Gly Arg Leu
1               5                   10                  15

Val Leu Arg Ile Ala Leu Ser Arg Lys Asp Ile Asn Val Ala Val
            20                  25                  30

Asn Asp Pro Phe Ile Ala Ala Glu Tyr Ala Ala Tyr Met Phe Lys Tyr
        35                  40                  45

Asp Ser Thr His Gly Arg Tyr Gln Gly Glu Val Thr Phe Glu Gly Lys
    50                  55                  60

Tyr Leu Val Ile Asp Gly Gln Lys Ile Glu Val Phe Gln Glu Arg Asp
65                  70                  75                  80

Pro Ala Asp Ile Pro Trp Gly Lys Glu Gly Val Asp Phe Val Ile Asp
                85                  90                  95

Ser Thr Gly Val Phe Thr Thr Ala Gly Ala Gln Lys His Ile Asp
            100                 105                 110

Ala Gly Ala Lys Lys Val Ile Ile Thr Ala Pro Ser Ala Asp Ala Pro
        115                 120                 125

| Met | Phe | Val | Met | Gly | Val | Asn | His | Lys | Glu | Tyr | Thr | Lys | Asp | Leu | Ser |
| | | 130 | | | | | 135 | | | | | 140 | | | |

| Ile | Val | Ser | Asn | Ala | Ser | Cys | Thr | Thr | Asn | Cys | Leu | Ala | Pro | Leu | Ala |
| 145 | | | | | 150 | | | | | 155 | | | | | 160 |

| Lys | Val | Val | Asn | Asp | Val | Phe | Gly | Ile | Glu | Ser | Gly | Leu | Met | Thr | Thr |
| | | | | 165 | | | | | 170 | | | | | 175 | |

| Val | His | Ser | Ile | Thr | Ala | Thr | Gln | Lys | Thr | Val | Asp | Gly | Pro | Ser | His |
| | | | 180 | | | | | 185 | | | | | 190 | | |

| Lys | Asp | Trp | Arg | Gly | Gly | Arg | Thr | Ala | Ser | Gly | Asn | Ile | Ile | Pro | Ser |
| | | | 195 | | | | | 200 | | | | | 205 | | |

| Ser | Thr | Gly | Ala | Ala | Lys | Ala | Val | Gly | Lys | Val | Leu | Pro | Ala | Leu | Ala |
| | 210 | | | | | 215 | | | | | 220 | | | | |

| Gly | Lys | Leu | Thr | Gly | Met | Ser | Leu | Arg | Val | Pro | Thr | Thr | Asp | Val | Ser |
| 225 | | | | | 230 | | | | | 235 | | | | | 240 |

| Val | Val | Asp | Leu | Thr | Val | Asn | Leu | Lys | Thr | Pro | Thr | Thr | Tyr | Ala | Glu |
| | | | | 245 | | | | | 250 | | | | | 255 | |

| Ile | Ser | Ala | Ala | Ile | Lys | Lys | Ala | Ser | Glu | Gly | Glu | Leu | Ala | Gly | Ile |
| | | | 260 | | | | | 265 | | | | | 270 | | |

| Leu | Gly | Tyr | Thr | Glu | Asp | Ala | Val | Val | Ser | Thr | Asp | Phe | Leu | Thr | Asp |
| | | | 275 | | | | | 280 | | | | | 285 | | |

| Asn | Arg | Ser | Ser | Ile | Phe | Asp | Ala | Ser | Ala | Gly | Ile | Leu | Leu | Thr | Pro |
| | 290 | | | | | 295 | | | | | 300 | | | | |

| Thr | Phe | Val | Lys | Leu | Ile | Ser | Trp | Tyr | Asp | Asn | Glu | Tyr | Gly | Tyr | Ser |
| 305 | | | | | 310 | | | | | 315 | | | | | 320 |

| Thr | Arg | Val | Val | Asp | Leu | Leu | Glu | His | Val | Ala | Lys | Val | Ser | Ser | Ala |
| | | | | 325 | | | | | 330 | | | | | 335 | |

<210> SEQ ID NO 7
<211> LENGTH: 1491
<212> TYPE: DNA
<213> ORGANISM: Ogataea minuta

<400> SEQUENCE: 7

```
aagctttact ggttcaaggg gttaagtagg ggcgcggtct ggtctttgtg gttgtttcta    60
cacggaccac agttgacagc atcgactgct catcgaaaac ggtcgcagtg cggcaatctg   120
ctctatctaa tcccaggcta ctcgatccct gcacaaccta cagagtgatc cgaccgcact   180
gcccgagatt cagcagactc tcgcagcgca gcgtgcgttt taatccctca aatcaaggct   240
gtgcagaccc ggaggatgtg aagctgggac ggcgggaggg aagtctggag tggtgagaga   300
atgtgggagc tgtgcaaagg ggcaatggtc actcagcgca gagcgatggt ggcgcggggg   360
ccaatatctc ggcaacaaga acgcccgagg acgacgggac tctgaatgcg agcacgttgt   420
ctttcagaca gtccacccgg attccaatat tcgcaggact cgcgctcaga acgcaaccc    480
cggcagattc gcgtccagtc aggccatctg cggcgagctg ctgcgctcgc gggctgcgcc   540
acaacgcatc gccacatata cgtcaccgcc cgcccgctgg caacctgagg ttttccgca    600
acgggtgcac tgattgctgc gttaacgagg caactggaga tgtcagaggc caagtggagc   660
catatcacag cggactgcgc atctctggcc tgccggacgc ggtagcgtcc cgtcttttg    720
cggacagctt cttaaaacct ggctgaaact aagcgagacc tgcgacctgg aacgcccgca   780
caccctgtaca cctccggagt tgtatcctca gaagcggagt aacctgcagg cctacgcaag   840
aaaagagccc ggaccccatc gaccggaaaa gaggggtgga gctagtgggg tagccttgga   900
gcagacctgg ggcagacctg ggttagtacc agggccgaaa agggtcagag gaatcaggt    960
```

```
ggcacggcag tctataccgt agaagctctt ctcgacagca gcgagcagaa actgcacaga    1020
ggtccgttcg ccagtctcgt accaccaccg catgacccaa tcagcattga tgctcccaca    1080
tgggtagtgc gcgcgaacgc ctggcaccca aacacaccac ttacgcttcc cgcaccgcgg    1140
tggttaacac tggcccggag tagtcatata cggagatttt ggcatgattc taattccggg    1200
tcgggacacg acctaagtgg cgtgcaaagc tcggggcta aatgtttccc ggcgctcgcg     1260
gcgactcttg tgcgcgcccg cggcggttcg cgggagacgg gggaaagaga ggggtgaccg    1320
cagcgagcga tggtgtgcca gatctcaggc cgagtcaaga caatatataa agagaggatt    1380
gtccactttt ctccaatagt atttgacccg ggttgctctc tgttgatttt ttctagatca    1440
tacaattatt gtttgaattc actcaattaa catacacaaa tacaatacaa a             1491

<210> SEQ ID NO 8
<211> LENGTH: 524
<212> TYPE: DNA
<213> ORGANISM: Ogataea minuta

<400> SEQUENCE: 8
gtggatagat gaccaatggc ctctttaagt aaacatttcg ttttgaatat atttcaagtt    60
gaataatgaa agccttgttg tagacttact ccgaagctcc ggggcttcgg ctccctgaat    120 ttattttta catctctgca ccggaaaact ggctatttga aaatttcga cgttttgctt      180 gaaactcgag ttgaggagca ttgccaaatt cgatcgtttt ctaacggacg ccagtcgagt    240
tattgttatg tcacgtgaca tcaattgtcc tctattcctt tttggccgat ctcgtttgtg    300
ctgacggcct ccgaacagtt acttctaccg gcagggattg gggatgatcg ggatcgatgt    360
cctcaactcc agaggctgat ccgatgcggt gggacttcat gcgtccaaat ctgttggatg    420
atgtgctctt ctgcttttt ggtgaccaaa cgagatgaca attgactgca ttgaaaaggt     480
tattagcttt tttggtcttc tcctgtgtcg attcgagcgg tacc                     524

<210> SEQ ID NO 9
<211> LENGTH: 113
<212> TYPE: DNA
<213> ORGANISM: Artificial Sequence
<220> FEATURE:
<223> OTHER INFORMATION: Description of Artificial Sequence: Synthetic
      primer for production of an expression cassette
      with GAP gene promoter and terminator from
      Ogataea minuta

<400> SEQUENCE: 9
gtttgaattc actcaattaa catacacaaa tacaatacaa agtcgacaaa aaatgcatgt    60
ggatagatga ccaatggcct ctttaagtaa acatttcgtt ttgaatatat ttc           113

<210> SEQ ID NO 10
<211> LENGTH: 38
<212> TYPE: DNA
<213> ORGANISM: Artificial Sequence
<220> FEATURE:
<223> OTHER INFORMATION: Description of Artificial Sequence: Synthetic
      primer for production of an expression cassette
      with GAP gene promoter and  terminator from
      Ogataea minuta

<400> SEQUENCE: 10
tttttactag tacggtaccg ctcgaatcga cacaggag                            38

<210> SEQ ID NO 11
<211> LENGTH: 12
<212> TYPE: PRT
```

```
<213> ORGANISM: Saccharomyces cerevisiae

<400> SEQUENCE: 11

Gly Pro Tyr Ile Cys Leu Val Lys Thr His Ile Asp
 1               5                  10

<210> SEQ ID NO 12
<211> LENGTH: 11
<212> TYPE: PRT
<213> ORGANISM: Saccharomyces cerevisiae

<400> SEQUENCE: 12

Gly Arg Gly Leu Phe Gly Lys Gly Arg Asp Pro
 1               5                  10

<210> SEQ ID NO 13
<211> LENGTH: 35
<212> TYPE: DNA
<213> ORGANISM: Artificial Sequence
<220> FEATURE:
<223> OTHER INFORMATION: Description of Artificial Sequence: Synthetic
      primer PUR5 for amplification of 5'-region of
      Ogataea Minuta URA3 gene
<220> FEATURE:
<221> NAME/KEY: modified_base
<222> LOCATION: (3)
<223> OTHER INFORMATION: a, c, g or t
<220> FEATURE:
<221> NAME/KEY: modified_base
<222> LOCATION: (6)
<223> OTHER INFORMATION: a, c, g or t
<220> FEATURE:
<221> NAME/KEY: modified_base
<222> LOCATION: (18)
<223> OTHER INFORMATION: a, c, g or t
<220> FEATURE:
<221> NAME/KEY: modified_base
<222> LOCATION: (21)
<223> OTHER INFORMATION: a, c, g or t
<220> FEATURE:
<221> NAME/KEY: modified_base
<222> LOCATION: (27)
<223> OTHER INFORMATION: a, c, g or t

<400> SEQUENCE: 13
ggnccntaya thtgyytngt naaracncay athga                              35

<210> SEQ ID NO 14
<211> LENGTH: 32
<212> TYPE: DNA
<213> ORGANISM: Artificial Sequence
<220> FEATURE:
<223> OTHER INFORMATION: Description of Artificial Sequence: Synthetic
      primer PUR3 for amplification of 3'-region of
      Ogataea Minuta URA3 gene
<220> FEATURE:
<221> NAME/KEY: modified_base
<222> LOCATION: (6)
<223> OTHER INFORMATION: a, c, g or t
<220> FEATURE:
<221> NAME/KEY: modified_base
<222> LOCATION: (9)
<223> OTHER INFORMATION: a, c, g or t
<220> FEATURE:
<221> NAME/KEY: modified_base
<222> LOCATION: (15)
<223> OTHER INFORMATION: a, c, g or t
<220> FEATURE:
<221> NAME/KEY: modified_base
<222> LOCATION: (21)
<223> OTHER INFORMATION: a, c, g or t
<220> FEATURE:
<221> NAME/KEY: modified_base
<222> LOCATION: (24)
```

```
<223> OTHER INFORMATION: a, c, g or t
<220> FEATURE:
<221> NAME/KEY: modified_base
<222> LOCATION: (27)
<223> OTHER INFORMATION: a, c, g or t
<220> FEATURE:
<221> NAME/KEY: modified_base
<222> LOCATION: (30)
<223> OTHER INFORMATION: a, c, g or t

<400> SEQUENCE: 14
ggrtcncknc cyttnccraa narnccnckn cc                                32

<210> SEQ ID NO 15
<211> LENGTH: 3113
<212> TYPE: DNA
<213> ORGANISM: Ogataea minuta

<400> SEQUENCE: 15
gccgcggccg ctgctgctgc ttccactaaa acagcaacga gcaacgcgtc tgccgaaaac        60
tccttgaatc aagacctgga caatcatttg acgttgggca gagagcattt cgacaccact       120
gaggttccta ccgcggacgg gtccaaagtg gaggttctcc gaaacatgtc tgtcgagacg       180
ggtcctgccg acgatcttaa caaaaacccc tccaccagcg agctggtgca tctggaggaa       240
aaatcacagg aaagcgcatc cgaggaagag gtcaggacct cgaaccatgc cgacacagcc       300
ggaacagaac caggtccaga acacgtccat ggcaacgata aagcggaggg cgagggcgag       360
tcctcagaag atgaccagga aatggtggac gctccactgc ctccttcgga cgataaggag       420
actgagaacg cgctgccgac ggagactaaa gtggagtcga ccaaagacga tgtagaccag       480
gaagaagagg aagaagagga ggaagaggaa gaaacagtac cttccaagt ctctaaaaag        540 gtatccaagg aggaagaaat ttcagctccg acgccggagc ccactacgcc tacgtcggcg       600
aacgagagcg aggaggaagg cgataccagg ccccggaaaa ggcggcggtc ggagtcgatt       660
tcggccgcct ccagcaagag atttttggct cttggtactc aactgttgag ccaagtttcg       720
tcgaatcggt ttgcgtcgat gtttttgcag ccagtgaaca aaaacgagga gcctgagtat       780
tacaagctca tccaccagcc gatcgatctc aagacgctgt cgaagtcggt ccgaaccggc       840
gagattcagt cgttcgatga ccttgagttc cagctgcaac tcatgttcag caatgcaatc       900
atgtacaacg acacctacca gacgaaaacg tacaaatgga cgatcgagat gatggaggaa       960
gcccagaatc tgattgaaat gttcagggaa acttccaaca actgagatca actgcgacta      1020
cttctgttgg ctggctggac gggttgtatt actatcttgg acaacgctat gtaaccttat      1080
ctaaatacaa gaattcatgt acaaaatcat tgtgcgggc gcagagacga gcgacgagtt       1140
gccgaaatca cccggctgct cagttaccac ctctcatttg gttcatgagc atttgattct      1200
gctcctggaa tctagatccg actctctcac tgtgcttgag gaacttctca gcacacttgt      1260
tcaaacaggt ctcctctctg gagctgagct tgttggaggt gaagtcattg acacagtcgt      1320
tgaaacatct gtcgacaaga ttggtgtaca actggggcaa ataatgtta gtcgtggttc       1380 atcaaaggct cgacgtcatt tgctgtctc tagtaactta ccctcatgaa gtcgttcatc       1440
tgcttctgct cgacgatttt ctggaattcc tgttgttctt tgtagttgag ttgatccatt      1500
ttgctgtttt tctagttctg ctttgctaga ctgttggcca atatctggtt atccctctag      1560
cttatcgtgg agaagggtgt tttttgcta ccaaaagctg aaaattctga aaatttcg         1620 gatttgaatt ttttttacc cggcacttt tgaccccata ctagttgtac caaactgaaa        1680
gagactgcag ttggtctttg cggggagatt ttggcagata aacaggcgac tatgtcctcg      1740
```

```
actaagacat acgcgcaaag ggcggcggct catccgtcgc ctgtggccag aagactgctg      1800
aacttgatgg aatccaagaa gacgaacttg tgtgcctcgg tcgatctcac ctctacaaag      1860
gaccttttgg agctgttgga caagctggga ccgttcattt gtctggtcaa gacacacatc      1920
gacattgtgg aagactttc gtacgaaaac accgtggtgc cgctgctgaa actggccaag      1980
aaacacaact tcatgatctt cgaggaccga aaatttgccg atataggcaa caccgtcaaa      2040
ctccagtaca agggaggagt ttaccaaatc gcaaagtggg ccgatatcac caacgcccac      2100
ggagtgaccg gctcgcgaat tgtctcgggt ctcagacagg ctgcccagga gaccaccgac      2160
gagccaagag gtctgctcat gctggctgag ctgtcgtctg aaggctcgct cgcgtacgga      2220
gagtacacca aaaagacggt tgaaatcgca aagtccgaca gagattttgt gatcggtttc      2280
attgcgcaaa acgacatggg tggccgcgat gagggcttcg actggctcat catgaccca       2340
ggtgtcggac tcgacgacac cggtgacgct ctgggccagc agtaccgcac ggtcagcgcc      2400
gttatgaaga cggaactga catcataatc gtgggcaggg gactgttcgg caagggaaga      2460
gaccctgtcg tggaaggcga agatacaga aaggctggat gggacgctta tttgagtcgt       2520
gtcgcatgat ttcgggtcac gtgactatat agctattggt atgtacaaga attaattagc      2580
ggagtttgtc gccaaactct tcggccaact cgatgctcag tttctggcgt gaaatttcga      2640
acaccagcag cccgatggag gtagccggta gacttgttgt tgcagttctc gcgaatcccc      2700
tgtagaagaa gcccagtagg gagagatggg acttgcggta tctggtcatc atgatttcga      2760
aagtttcgag gtatgaattg tagtagagct taaagaaacg gcttctctct agatggtggg      2820
cctcgttgta cagatcaagc gactccagtc tggacagatg gaccttctgg attttgttga      2880
acggaaattg gattgccagc agggttgtgg cggcactggc tccagccaaa gaatgaagg       2940
tcagccggag agctttgatc gatttcgagt gtttgtccag gtccgggttc ttctctccgt      3000
ataacagacg ggctttccag tactggtacc agtttatcat gctctgagtt ctgtggaagc      3060
cctggttttt cacaaactca acacggaga agtagaacgc aaacccaaag ctt             3113
```

<210> SEQ ID NO 16  
<211> LENGTH: 265  
<212> TYPE: PRT  
<213> ORGANISM: Ogataea minuta

<400> SEQUENCE: 16

```
Met Ser Ser Thr Lys Thr Tyr Ala Gln Arg Ala Ala His Pro Ser
 1               5                  10                  15

Pro Val Ala Arg Arg Leu Leu Asn Leu Met Glu Ser Lys Lys Thr Asn
            20                  25                  30

Leu Cys Ala Ser Val Asp Leu Thr Ser Thr Lys Asp Leu Leu Glu Leu
        35                  40                  45

Leu Asp Lys Leu Gly Pro Phe Ile Cys Leu Val Lys Thr His Ile Asp
    50                  55                  60

Ile Val Glu Asp Phe Ser Tyr Glu Asn Thr Val Val Pro Leu Leu Lys
65                  70                  75                  80

Leu Ala Lys Lys His Asn Phe Met Ile Phe Glu Asp Arg Lys Phe Ala
                85                  90                  95

Asp Ile Gly Asn Thr Val Lys Leu Gln Tyr Lys Gly Val Tyr Gln
            100                 105                 110

Ile Ala Lys Trp Ala Asp Ile Thr Asn Ala His Gly Val Thr Gly Ser
        115                 120                 125

Arg Ile Val Ser Gly Leu Arg Gln Ala Ala Gln Glu Thr Thr Asp Glu
    130                 135                 140
```

```
Pro Arg Gly Leu Leu Met Leu Ala Glu Leu Ser Ser Glu Gly Ser Leu
145                 150                 155                 160

Ala Tyr Gly Glu Tyr Thr Lys Lys Thr Val Glu Ile Ala Lys Ser Asp
                165                 170                 175

Arg Asp Phe Val Ile Gly Phe Ile Ala Gln Asn Asp Met Gly Gly Arg
            180                 185                 190

Asp Glu Gly Phe Asp Trp Leu Ile Met Thr Pro Gly Val Gly Leu Asp
        195                 200                 205

Asp Thr Gly Asp Ala Leu Gly Gln Gln Tyr Arg Thr Val Ser Ala Val
    210                 215                 220

Met Lys Thr Gly Thr Asp Ile Ile Ile Val Gly Arg Gly Leu Phe Gly
225                 230                 235                 240

Lys Gly Arg Asp Pro Val Val Glu Gly Glu Arg Tyr Arg Lys Ala Gly
                245                 250                 255

Trp Asp Ala Tyr Leu Ser Arg Val Ala
                260                 265

<210> SEQ ID NO 17
<211> LENGTH: 30
<212> TYPE: DNA
<213> ORGANISM: Artificial Sequence
<220> FEATURE:
<223> OTHER INFORMATION: Description of Artificial Sequence: Synthetic
      primer for amplification of a gene fragment
      conferring resistance against chloramphenicol

<400> SEQUENCE: 17
atggagaaaa aaactagtgg atataccacc                                     30

<210> SEQ ID NO 18
<211> LENGTH: 30
<212> TYPE: DNA
<213> ORGANISM: Artificial Sequence
<220> FEATURE:
<223> OTHER INFORMATION: Description of Artificial Sequence: Synthetic
      primer for amplification of a gene fragment
      conferring resistance against chloramphenicol

<400> SEQUENCE: 18
ctgagacgaa aaagatatct caataaaccc                                     30

<210> SEQ ID NO 19
<211> LENGTH: 28
<212> TYPE: DNA
<213> ORGANISM: Artificial Sequence
<220> FEATURE:
<223> OTHER INFORMATION: Description of Artificial Sequence: Synthetic
      primer DU5 used for confirmation of destruction
      of Ogataea minuta URA3 gene

<400> SEQUENCE: 19
aggaagaaga ggaggaagag gaagaaac                                       28

<210> SEQ ID NO 20
<211> LENGTH: 28
<212> TYPE: DNA
<213> ORGANISM: Artificial Sequence
<220> FEATURE:
<223> OTHER INFORMATION: Description of Artificial Sequence: Synthetic
      primer DUC5 used for confirmation of destruction
      of Ogataea minuta URA3 gene

<400> SEQUENCE: 20
cgatgccatt gggatatatc aacggtgg                                       28
```

<210> SEQ ID NO 21
<211> LENGTH: 29
<212> TYPE: DNA
<213> ORGANISM: Artificial Sequence
<220> FEATURE:
<223> OTHER INFORMATION: Description of Artificial Sequence: Synthetic
      primer DU3 used for confirmation of destruction
      of Ogataea minuta URA3 gene

<400> SEQUENCE: 21
ccgtgtttga gtttgtgaaa aaccagggc                                    29

<210> SEQ ID NO 22
<211> LENGTH: 28
<212> TYPE: DNA
<213> ORGANISM: Artificial Sequence
<220> FEATURE:
<223> OTHER INFORMATION: Description of Artificial Sequence: Synthetic
      primer DUC3 used for confirmation of destruction
      of Ogataea minuta URA3 gene

<400> SEQUENCE: 22
tgtggcgtgt tacggtgaaa acctggcc                                     28

<210> SEQ ID NO 23
<211> LENGTH: 14
<212> TYPE: PRT
<213> ORGANISM: Saccharomyces cerevisiae

<400> SEQUENCE: 23

Phe Val Ala Thr Asp Arg Ile Ser Ala Tyr Asp Val Ile Met
 1               5                  10

<210> SEQ ID NO 24
<211> LENGTH: 14
<212> TYPE: PRT
<213> ORGANISM: Saccharomyces cerevisiae

<400> SEQUENCE: 24

Gln Asp Ser Tyr Asp Lys Gln Phe Leu Arg Asp Trp Leu Thr
 1               5                  10

<210> SEQ ID NO 25
<211> LENGTH: 42
<212> TYPE: DNA
<213> ORGANISM: Artificial Sequence
<220> FEATURE:
<223> OTHER INFORMATION: Description of Artificial Sequence: Synthetic
      primer PAD5 for amplification of 5'-region of
      Ogataea minuta ADE1 gene
<220> FEATURE:
<221> NAME/KEY: modified_base
<222> LOCATION: (6)
<223> OTHER INFORMATION: a, c, g or t
<220> FEATURE:
<221> NAME/KEY: modified_base
<222> LOCATION: (9)
<223> OTHER INFORMATION: a, c, g or t
<220> FEATURE:
<221> NAME/KEY: modified_base
<222> LOCATION: (12)
<223> OTHER INFORMATION: a, c, g or t
<220> FEATURE:
<221> NAME/KEY: modified_base
<222> LOCATION: (18)
<223> OTHER INFORMATION: a, c, g or t
<220> FEATURE:
<221> NAME/KEY: modified_base
<222> LOCATION: (24)
<223> OTHER INFORMATION: a, c, g or t

```
<220> FEATURE:
<221> NAME/KEY: modified_base
<222> LOCATION: (27)
<223> OTHER INFORMATION: a, c, g or t
<220> FEATURE:
<221> NAME/KEY: modified_base
<222> LOCATION: (36)
<223> OTHER INFORMATION: a, c, g or t

<400> SEQUENCE: 25
ttygtngcna cngaymgnat hwsngcntay gaygtnatha tg                   42

<210> SEQ ID NO 26
<211> LENGTH: 41
<212> TYPE: DNA
<213> ORGANISM: Artificial Sequence
<220> FEATURE:
<223> OTHER INFORMATION: Description of Artificial Sequence: Synthetic
      primer PAD3 for amplification of 3'-region of
      Ogataea minuta ADE1 gene
<220> FEATURE:
<221> NAME/KEY: modified_base
<222> LOCATION: (3)
<223> OTHER INFORMATION: a, c, g or t
<220> FEATURE:
<221> NAME/KEY: modified_base
<222> LOCATION: (12)
<223> OTHER INFORMATION: a, c, g or t
<220> FEATURE:
<221> NAME/KEY: modified_base
<222> LOCATION: (15)
<223> OTHER INFORMATION: a, c, g or t
<220> FEATURE:
<221> NAME/KEY: modified_base
<222> LOCATION: (33)
<223> OTHER INFORMATION: a, c, g or t

<400> SEQUENCE: 26
gtnarccart cncknarraa ytgyttrtcr tanswrtcyt g                    41

<210> SEQ ID NO 27
<211> LENGTH: 2560
<212> TYPE: DNA
<213> ORGANISM: Ogataea minuta

<400> SEQUENCE: 27
gatatcccaa gaacctatgc cgagggttca gctcacggcc gataaaccaa tcaaagacaa    60
cgtttcctga gtttcctcca acggccagga ttatctcgtg agttcccaga ccgttcggct   120
tgcgtgtggg cacgaacgag cccacgtaga caaacaggct caaagccaac gaaaactcgt   180
acgcagtcac catcaattcc agaaagttct cgtggatgaa cgacagctca ggaaggttga   240
actttgtgag ataagctctg ctggcaagaa ttcccacgag aagagtgctc aattcttttcc  300 cgttgacgag atagttgagc tttgttccgt ctcgtaacag gactccctct ttatggtagc   360
caggcatcac aagatccacc aacgtcagag tgaagaacca caccaggtaa accttccagc   420
acgtgacatt taacacaaga tcccgccagt tgccgactat cttggactcg aaaagcgttt   480
tcagcgtggc aaaatcgatg cttgcgcctt caaccacata ctcctcatta cagcaaaagt   540
agaggaaaag gaccactgaa gggagaaata ctgacaaaac gaccgctccc ggtgtcccgc   600
agaaatcttt atgcgtagtc ttggggttca attcagacat ggtagattgg tgagggtaat   660
tgtgaagagg attcgataaa gagagggaa cagcaccgga gatagttctt agatcaaaat    720 gttttttctga cctttttttgc tctttctcgt ttagctcgcg tacagtcgac gcgtcggttt   780
gcgtcgaaaa gagtcaagcc gcgatcgcga ttaaaaatga atccggagaa gtcaaaaata   840
tgtaatttaa accatcacag tatataagta ggcgggaagc gcacaatttc taggcattcc   900
```

```
acagatcagc taaccaggac attccactgg agccaacaat gtcactcaca acaaccaacc    960
tcgacggcat cttgccgcta attgccaagg gcaaagtcag agacatctat caagttgacg   1020
aggaaagcct gctgttcgtg gcaacagacc ggatttccgc ctacgatgtg atcatggaga   1080
atggaatcaa agacaagggt aaaatactga ctcagctgtc agtattctgg tttgatttgc   1140
tgaaagacac tatcaagaac caccttatcg catccactga cgacgaagtg tttgccagac   1200
ttccacagga gctgtctcag ccaaagtaca agtcgcagct gagtggaaga gcactggtgg   1260
tgagaaagca caaattgatc cccctggagg tgattgtcag aggctacatc accggaagtg   1320
catggaagga gtacaacaag agcaagaccg tgcacggtct cgaggttggc gcagagctga   1380
aggagagtca agagttcccc gttccgattt tcaccccgtc aacgaaagct gaacaaggcg   1440
aacacgacga aaacatttcc cccgagaaag ctgcagagat tgtcgggaa caactgtgtg   1500
cgcggctcgc agaaaaggct gtgcagctgt actccaaggc cagaacttac gccaaaagca   1560
agggtatcat tctcgccgac acaaagtttg agtttggaat tgacgagaac gacgaattgg   1620
ttcttgtgga cgaggttttg accctgatt cctcgagatt ttgggacgca aagacttaca   1680
agatcggaca gtcgcaggac tcttacgaca acagtttct gagagactgg ctcacgtcca   1740
acggtctgaa cgggaaagac ggtgtctcta tgaccgcgga gatcgctgaa cgcacgggtg   1800
cgaagtacgt cgaggcattt gagtctctga cgggaagaaa gtggacgtag ttttgataa    1860
tagtaaccct ggaaatttga tatgtggcgg tgtagtctgt ggcggtggaa taaaatctaa   1920
attgaattta gtcgcttccc aaaacagcaa tttgtcaaca cttagtctgt gcacagcctt   1980
gacggcattt gagccatccc agggtctggc agttacaggg ctttgatcaa agaaaactg    2040
gtgaagtttg acaacaggct acagctgcca agtcgcaact gggtagtag ctcattcgtc    2100
gaacaccagt gcgccatgtc catcgccaac gagttccagc ccttggagct tattggtagg   2160
ggttcctttg gatgtgttcg gaaagtgcgc cgcaagtcgg acggcaagat atttgtgaga   2220
aaggagatct cctacatcgc catgaacacc aaagagaagc agcagctcac agcagagttt   2280
cgtattctca gagaactaaa gcatcccaac attgtccatt atgtccacca cgaccacgtc   2340
caggaggaac agaccgtcca tctgtacatg gaatactgcg atggggcga cttgtcggtg    2400
ttgatcagga agtacaaagg aaagaacgag tttatcccgg agaacttgat ctggcaaatc   2460
ttcacccagg ttctcaacgc tctctatcaa tgccactatg gggtcaatat tgaggctgtg   2520
caagaacttt tccagtccac tccagagatt gcaccccggg                          2560

<210> SEQ ID NO 28
<211> LENGTH: 303
<212> TYPE: PRT
<213> ORGANISM: Ogataea minuta

<400> SEQUENCE: 28

Met Ser Leu Thr Thr Thr Asn Leu Asp Gly Ile Leu Pro Leu Ile Ala
  1               5                  10                  15

Lys Gly Lys Val Arg Asp Ile Tyr Gln Val Asp Glu Glu Ser Leu Leu
             20                  25                  30

Phe Val Ala Thr Asp Arg Ile Ser Ala Tyr Asp Val Ile Met Glu Asn
         35                  40                  45

Gly Ile Lys Asp Lys Gly Lys Ile Leu Thr Gln Leu Ser Val Phe Trp
     50                  55                  60

Phe Asp Leu Leu Lys Asp Thr Ile Lys Asn His Leu Ile Ala Ser Thr
 65                  70                  75                  80
```

```
Asp Asp Glu Val Phe Ala Arg Leu Pro Gln Glu Leu Ser Gln Pro Lys
            85                  90                  95
Tyr Lys Ser Gln Leu Ser Gly Arg Ala Leu Val Val Arg Lys His Lys
            100                 105                 110
Leu Ile Pro Leu Glu Val Ile Val Arg Gly Tyr Ile Thr Gly Ser Ala
            115                 120                 125
Trp Lys Glu Tyr Asn Lys Ser Lys Thr Val His Gly Leu Glu Val Gly
            130                 135                 140
Ala Glu Leu Lys Glu Ser Gln Glu Phe Pro Val Pro Ile Phe Thr Pro
145                 150                 155                 160
Ser Thr Lys Ala Glu Gln Gly Glu His Asp Glu Asn Ile Ser Pro Glu
            165                 170                 175
Lys Ala Ala Glu Ile Val Gly Glu Gln Leu Cys Ala Arg Leu Ala Glu
            180                 185                 190
Lys Ala Val Gln Leu Tyr Ser Lys Ala Arg Thr Tyr Ala Lys Ser Lys
            195                 200                 205
Gly Ile Ile Leu Ala Asp Thr Lys Phe Glu Phe Gly Ile Asp Glu Asn
            210                 215                 220
Asp Glu Leu Val Leu Val Asp Glu Val Leu Thr Pro Asp Ser Ser Arg
225                 230                 235                 240
Phe Trp Asp Ala Lys Thr Tyr Lys Ile Gly Gln Ser Gln Asp Ser Tyr
            245                 250                 255
Asp Lys Gln Phe Leu Arg Asp Trp Leu Thr Ser Asn Gly Leu Asn Gly
            260                 265                 270
Lys Asp Gly Val Ser Met Thr Ala Glu Ile Ala Glu Arg Thr Gly Ala
            275                 280                 285
Lys Tyr Val Glu Ala Phe Glu Ser Leu Thr Gly Arg Lys Trp Thr
            290                 295                 300
```

<210> SEQ ID NO 29
<211> LENGTH: 60
<212> TYPE: DNA
<213> ORGANISM: Artificial Sequence
<220> FEATURE:
<223> OTHER INFORMATION: Description of Artificial Sequence: Synthetic
      5'-primer for amplification of upstream region
      of URA3 structural gene

<400> SEQUENCE: 29
ccccgagctc aaaaaaaagg taccaatttc agctccgacg ccggagccca ctacgcctac     60

<210> SEQ ID NO 30
<211> LENGTH: 38
<212> TYPE: DNA
<213> ORGANISM: Artificial Sequence
<220> FEATURE:
<223> OTHER INFORMATION: Description of Artificial Sequence: Synthetic
      3'-primer for amplification of upstream region
      of URA3 structural gene

<400> SEQUENCE: 30
gggaagcttc cccagttgta caccaatctt gtcgacag                             38

<210> SEQ ID NO 31
<211> LENGTH: 50
<212> TYPE: DNA
<213> ORGANISM: Artificial Sequence
<220> FEATURE:
<223> OTHER INFORMATION: Description of Artificial Sequence: Synthetic
      primer Dad1-5 used for destruction of Ogataea
      minuta ADE1 gene

<400> SEQUENCE: 31
aaaaagcggc cgctcccggt gtcccgcaga aatctttatg cgtagtcttg        50

<210> SEQ ID NO 32
<211> LENGTH: 56
<212> TYPE: DNA
<213> ORGANISM: Artificial Sequence
<220> FEATURE:
<223> OTHER INFORMATION: Description of Artificial Sequence: Synthetic
      primer Dad1-3 used for destruction of Ogataea
      minuta ADE1 gene

<400> SEQUENCE: 32
cccccggatc ctttttttta agcttgttgt actccttcca tgcacttccg gtgatg    56

<210> SEQ ID NO 33
<211> LENGTH: 59
<212> TYPE: DNA
<213> ORGANISM: Artificial Sequence
<220> FEATURE:
<223> OTHER INFORMATION: Description of Artificial Sequence: Synthetic
      primer Dad2-5 used for destruction of Ogataea
      minuta ADE1 gene

<400> SEQUENCE: 33
ttttcacccc gtcaaggatc cctgaacaag gcgaacacga cgaaaacatt tcccccgag    59

<210> SEQ ID NO 34
<211> LENGTH: 44
<212> TYPE: DNA
<213> ORGANISM: Artificial Sequence
<220> FEATURE:
<223> OTHER INFORMATION: Description of Artificial Sequence: Synthetic
      primer Dad2-3 used for destruction of Ogataea
      minuta ADE1 gene

<400> SEQUENCE: 34
tttttgggcc cacctgggtg aagatttgcc agatcaagtt ctcc    44

<210> SEQ ID NO 35
<211> LENGTH: 30
<212> TYPE: DNA
<213> ORGANISM: Artificial Sequence
<220> FEATURE:
<223> OTHER INFORMATION: Description of Artificial Sequence: Synthetic
      primer DA5 used for confirmation of destruction
      of Ogataea minuta ADE1 gene

<400> SEQUENCE: 35
gatgcttgcg ccttcaacca catactcctc    30

<210> SEQ ID NO 36
<211> LENGTH: 30
<212> TYPE: DNA
<213> ORGANISM: Artificial Sequence
<220> FEATURE:
<223> OTHER INFORMATION: Description of Artificial Sequence: Synthetic
      primer DA3 used for confirmation of destruction
      of Ogataea minuta ADE1 gene

<400> SEQUENCE: 36
aaaagttctt gcacagcctc aatattgacc    30

<210> SEQ ID NO 37
<211> LENGTH: 30
<212> TYPE: DNA
<213> ORGANISM: Artificial Sequence
<220> FEATURE:

```
<223> OTHER INFORMATION: Description of Artificial Sequence: Synthetic
      primer DOU5 used for confirmation of destruction
      of Ogataea minuta ADE1 gene

<400> SEQUENCE: 37
atcgatttcg agtgtttgtc caggtccggg                                        30

<210> SEQ ID NO 38
<211> LENGTH: 10
<212> TYPE: PRT
<213> ORGANISM: Saccharomyces cerevisiae
<220> FEATURE:
<221> NAME/KEY: MOD_RES
<222> LOCATION: (3)
<223> OTHER INFORMATION: His or Arg
<220> FEATURE:
<221> NAME/KEY: MOD_RES
<222> LOCATION: (4)
<223> OTHER INFORMATION: Ile or Val

<400> SEQUENCE: 38

Pro Gln Xaa Xaa Trp Gln Thr Trp Lys Val
  1               5                  10

<210> SEQ ID NO 39
<211> LENGTH: 11
<212> TYPE: PRT
<213> ORGANISM: Saccharomyces cerevisiae

<400> SEQUENCE: 39

Trp Tyr Ala Arg Arg Ile Gln Phe Cys Gln Trp
  1               5                  10

<210> SEQ ID NO 40
<211> LENGTH: 29
<212> TYPE: DNA
<213> ORGANISM: Artificial Sequence
<220> FEATURE:
<223> OTHER INFORMATION: Description of Artificial Sequence: Synthetic
      primer POH5 for amplification of 5'-region of
      Ogataea minuta OCH1 gene
<220> FEATURE:
<221> NAME/KEY: modified_base
<222> LOCATION: (3)
<223> OTHER INFORMATION: a, c, g or t
<220> FEATURE:
<221> NAME/KEY: modified_base
<222> LOCATION: (21)
<223> OTHER INFORMATION: a, c, g or t

<400> SEQUENCE: 40
ccncarcryr thtggcarac ntggaargt                                         29

<210> SEQ ID NO 41
<211> LENGTH: 33
<212> TYPE: DNA
<213> ORGANISM: Artificial Sequence
<220> FEATURE:
<223> OTHER INFORMATION: Description of Artificial Sequence: Synthetic
      primer POH3 for amplification of 3'-region of
      Ogataea minuta OCH1 gene
<220> FEATURE:
<221> NAME/KEY: modified_base
<222> LOCATION: (19)
<223> OTHER INFORMATION: a, c, g or t
<220> FEATURE:
<221> NAME/KEY: modified_base
<222> LOCATION: (22)
<223> OTHER INFORMATION: a, c, g or t
<220> FEATURE:
<221> NAME/KEY: modified_base
<222> LOCATION: (25)
```

<223> OTHER INFORMATION: a, c, g or t

<400> SEQUENCE: 41
ccaytgrcar aaytgdatnc knckngcrta cca    33

<210> SEQ ID NO 42
<211> LENGTH: 2527
<212> TYPE: DNA
<213> ORGANISM: Ogataea minuta

<400> SEQUENCE: 42

| | | | | | |
|---|---|---|---|---|---|
| agatctgttg | acactggtca | agcgtgtagc | caagagaata | ggaaacggaa | tttcatactg | 60 |
| ccggcacaca | aggacaataa | gggcgtccgg | ggctgtcgaa | attgtcgaga | ccgtagagct | 120 |
| attgttacct | caataagttg | ctctacgatt | gtttccgtct | ttgacaaagc | agtaggcctt | 180 |
| tctcaaggtg | gtgtacgggt | gtttcatttt | taatttgcat | cgagaacgcg | tagtgcgcca | 240 |
| atggatctgc | aggggggctcg | gctgattgca | ctgaaatttc | agcaataaat | agctgaggat | 300 |
| attcaggcac | aacggtacca | acggggcagg | cttgatcgcg | aagcagcagg | agaaggcagc | 360 |
| gaagtgactg | aagagacgag | aaggagacga | atcagcctac | ccctggaacc | ataaacaaag | 420 |
| tcgagccgtt | ttttttaggga | cagaaaccgt | tctggatatt | tattcgacgc | agagactcgg | 480 |
| tagtcatctc | tacgttcagc | acacaccatg | aactatcacg | acttgtacga | tgatagcaaa | 540 |
| cggcagtcgt | tgatgcgaaa | ggcgcgaaag | ttcgctgaga | tgaacaagaa | gttggtggtg | 600 |
| gtggtcattt | taacgatgta | cgttgtgtcg | cgtctggcgt | cggttggaag | cacgaaacag | 660 |
| gagtcgattc | caggactcac | catgaaagag | tcagagttag | aggtgaattt | taaaacattt | 720 |
| ggaatggatc | tgcagaagcg | gaacgagcta | ccggccgcaa | gtgcaacgct | gagagaaaaa | 780 |
| ctatcgtttt | acttccccta | tgaccctgaa | aaaccagtgc | ccaaccaaat | atggcagacg | 840 |
| tggaaagtgg | acatcaacga | caaatcattc | ccgagacact | tccgtaagtt | ccaagagaca | 900 |
| tggccacaac | taaacagcgg | gtacacgtac | catctcattc | cagacagtat | tgtggacgag | 960 |
| ttcatgagga | gtcttttttgc | caatgtccct | gaggttattg | cagcctacaa | catgttaccg | 1020 |
| aaaaatatcc | tcaaggcgga | ttttttccgg | tatttggtga | ttttttgcgcg | cggtggaact | 1080 |
| tattcggata | tcgacacgat | ctgcctcaaa | ccagtgaacg | aatgggccac | gtttaacgaa | 1140 |
| caaactgtca | tttcgcacta | tctcaagacc | aacggtaaaa | cctcgcagtt | gccagaagtg | 1200 |
| gaccccctcca | cgcgcaaaac | accgatcgga | ctcaccattg | gaatagaggc | cgacccagac | 1260 |
| agacccgact | ggcacgaatg | gtacgctaga | cgtattcagt | tctgtcaatg | gacgatccag | 1320 |
| ggcaagcaag | gccatcccat | gctgcgcgag | ttgatcatcc | gtatagtgga | gcaaactttc | 1380 |
| cgcaaagagg | ccatgggcaa | tttgaaaaaa | gtagagggga | aggatatggg | tggtgacatc | 1440 |
| atgcagtgga | caggacccgg | ggttttcaca | gataccctgt | ttgattatct | caataacgtg | 1500 |
| gtgagtgacg | gaaagctggg | agacggttac | ggagtcgggt | ccaagtactg | gaacagtcac | 1560 |
| gccaagtaca | agctgtctca | cattgaggtg | gatgccaaca | acgagccgat | gcactctgac | 1620 |
| aagcaaacta | tcagctggaa | gtccatgagt | aagctatcgg | agcccctgat | tatagatgac | 1680 |
| gtgatgatcc | tgccaatcac | tagcttcagc | cccggcgtgg | gccagatggg | ctcgcattcg | 1740 |
| cccgaccacc | cgctcgcatt | tgtccggcac | atgttccagg | gcagctggaa | accagatgca | 1800 |
| gagaagatgt | gactgcatat | aggaacgcat | tttatacagt | agatcaagtt | aaaagtttga | 1860 |
| acttttgcgg | ggaagtggtg | taagggtgtt | tgacgagggc | ctgaacccgt | gagtcaacgc | 1920 |
| gcttggacgg | aagaacgggt | gcacgccgca | tggggctgtt | cgttcagttt | tgacgctgct | 1980 |

```
aacgagagag tagcttgcag attgcaatcc cgactgagtc cacccggttg agctagtcac    2040
acgactgcgt cttttctttc tggtgtacgg gtgtcaatac attttcggtt taaaaacgat    2100
aagatgcaac aaggtatctt ctgtagctaa accccacttc tccagacacc ttccaccagc    2160
cgatgactat gacagacagg ttttggagg attacaagaa gtttctcccc aaagcgcacg     2220
atttgagggg cacgcactca cggctttca cgacggcggg cggggccgat gcggggagtt     2280
tggctgattg gagagagtgg acagatgatt tgggtcattc gcaggagtat tacgagctga    2340
aacaggagat caattgtctt gttcttaact accttatcta cgaaggatat gttggtgctg    2400
ttcgagagtt ttcgaaagag ctgggattcg attttatcgt ggaggagttg gaaggaattg    2460
aagaggagaa gggaggccac caagaggacg gagagtacac gaccatgtca gacactgacg    2520
tactagt                                                             2527
```

<210> SEQ ID NO 43
<211> LENGTH: 434
<212> TYPE: PRT
<213> ORGANISM: Ogataea minuta

<400> SEQUENCE: 43

```
Met Asn Tyr His Asp Leu Tyr Asp Asp Ser Lys Arg Gln Ser Leu Met
 1               5                  10                  15

Arg Lys Ala Arg Lys Phe Ala Glu Met Asn Lys Lys Leu Val Val Val
             20                  25                  30

Val Ile Leu Thr Met Tyr Val Val Ser Arg Leu Ala Ser Val Gly Ser
         35                  40                  45

Thr Lys Gln Glu Ser Ile Pro Gly Leu Thr Met Lys Glu Ser Glu Leu
     50                  55                  60

Glu Val Asn Phe Lys Thr Phe Gly Met Asp Leu Gln Lys Arg Asn Glu
 65                  70                  75                  80

Leu Pro Ala Ala Ser Ala Thr Leu Arg Glu Lys Leu Ser Phe Tyr Phe
                 85                  90                  95

Pro Tyr Asp Pro Glu Lys Pro Val Pro Asn Gln Ile Trp Gln Thr Trp
            100                 105                 110

Lys Val Asp Ile Asn Asp Lys Ser Phe Pro Arg His Phe Arg Lys Phe
        115                 120                 125

Gln Glu Thr Trp Pro Gln Leu Asn Ser Gly Tyr Thr Tyr His Leu Ile
    130                 135                 140

Pro Asp Ser Ile Val Asp Glu Phe Met Arg Ser Leu Phe Ala Asn Val
145                 150                 155                 160

Pro Glu Val Ile Ala Ala Tyr Asn Met Leu Pro Lys Asn Ile Leu Lys
                165                 170                 175

Ala Asp Phe Phe Arg Tyr Leu Val Ile Phe Ala Arg Gly Gly Thr Tyr
            180                 185                 190

Ser Asp Ile Asp Thr Ile Cys Leu Lys Pro Val Asn Glu Trp Ala Thr
        195                 200                 205

Phe Asn Glu Gln Thr Val Ile Ser His Tyr Leu Lys Thr Asn Gly Lys
    210                 215                 220

Thr Ser Gln Leu Pro Glu Val Asp Pro Ser Thr Arg Lys Thr Pro Ile
225                 230                 235                 240

Gly Leu Thr Ile Gly Ile Glu Ala Asp Pro Asp Arg Pro Asp Trp His
                245                 250                 255

Glu Trp Tyr Ala Arg Arg Ile Gln Phe Cys Gln Trp Thr Ile Gln Gly
            260                 265                 270

Lys Gln Gly His Pro Met Leu Arg Glu Leu Ile Ile Arg Ile Val Glu
```

-continued

```
                275                 280                 285
Gln Thr Phe Arg Lys Glu Ala Met Gly Asn Leu Lys Lys Val Glu Gly
        290                 295                 300

Lys Asp Met Gly Gly Asp Ile Met Gln Trp Thr Gly Pro Gly Val Phe
305                 310                 315                 320

Thr Asp Thr Leu Phe Asp Tyr Leu Asn Asn Val Val Ser Asp Gly Lys
                325                 330                 335

Leu Gly Asp Gly Tyr Gly Val Gly Ser Lys Tyr Trp Asn Ser His Ala
        340                 345                 350

Lys Tyr Lys Leu Ser His Ile Glu Val Asp Ala Asn Asn Glu Pro Met
                355                 360                 365

His Ser Asp Lys Gln Thr Ile Ser Trp Lys Ser Met Ser Lys Leu Ser
370                 375                 380

Glu Pro Leu Ile Ile Asp Asp Val Met Ile Leu Pro Ile Thr Ser Phe
385                 390                 395                 400

Ser Pro Gly Val Gly Gln Met Gly Ser His Ser Pro Asp His Pro Leu
                405                 410                 415

Ala Phe Val Arg His Met Phe Gln Gly Ser Trp Lys Pro Asp Ala Glu
                420                 425                 430

Lys Met
```

<210> SEQ ID NO 44
<211> LENGTH: 30
<212> TYPE: DNA
<213> ORGANISM: Artificial Sequence
<220> FEATURE:
<223> OTHER INFORMATION: Description of Artificial Sequence: Synthetic
      primer DO3 used for confirmation of destruction
      of Ogataea minuta OCH1 gene

<400> SEQUENCE: 44
ccattgtcag ctccaattct ttgataaacg                                    30

<210> SEQ ID NO 45
<211> LENGTH: 30
<212> TYPE: DNA
<213> ORGANISM: Artificial Sequence
<220> FEATURE:
<223> OTHER INFORMATION: Description of Artificial Sequence: Synthetic
      primer DO5 used for confirmation of destruction
      of Ogataea minuta OCH1 gene

<400> SEQUENCE: 45
acacttccgt aagttccaag agacatggcc                                    30

<210> SEQ ID NO 46
<211> LENGTH: 30
<212> TYPE: DNA
<213> ORGANISM: Artificial Sequence
<220> FEATURE:
<223> OTHER INFORMATION: Description of Artificial Sequence: Synthetic
      primer DO3-2 used for confirmation of destruction
      of Ogataea minuta OCH1 gene

<400> SEQUENCE: 46
tcaccacgtt attgagataa tcaaacaggg                                    30

<210> SEQ ID NO 47
<211> LENGTH: 8
<212> TYPE: PRT
<213> ORGANISM: Saccharomyces cerevisiae

<400> SEQUENCE: 47

-continued

Thr Asn Tyr Leu Asn Ala Gln Tyr
 1               5

<210> SEQ ID NO 48
<211> LENGTH: 8
<212> TYPE: PRT
<213> ORGANISM: Saccharomyces cerevisiae

<400> SEQUENCE: 48

Lys Ala Tyr Trp Glu Val Lys Phe
 1               5

<210> SEQ ID NO 49
<211> LENGTH: 23
<212> TYPE: DNA
<213> ORGANISM: Artificial Sequence
<220> FEATURE:
<223> OTHER INFORMATION: Description of Artificial Sequence: Synthetic
      primer PPA5 for amplification of 5'-region of
      Ogataea minuta PEP4 gene
<220> FEATURE:
<221> NAME/KEY: modified_base
<222> LOCATION: (3)
<223> OTHER INFORMATION: a, c, g or t
<220> FEATURE:
<221> NAME/KEY: modified_base
<222> LOCATION: (12)
<223> OTHER INFORMATION: a, c, g or t
<220> FEATURE:
<221> NAME/KEY: modified_base
<222> LOCATION: (18)
<223> OTHER INFORMATION: a, c, g or t

<400> SEQUENCE: 49
acnaaytayy tnaaygcnca rta                                           23

<210> SEQ ID NO 50
<211> LENGTH: 23
<212> TYPE: DNA
<213> ORGANISM: Artificial Sequence
<220> FEATURE:
<223> OTHER INFORMATION: Description of Artificial Sequence: Synthetic
      primer PPA3 for amplification of 3'-region of
      Ogataea minuta PEP4 gene
<220> FEATURE:
<221> NAME/KEY: modified_base
<222> LOCATION: (6)
<223> OTHER INFORMATION: a, c, g or t
<220> FEATURE:
<221> NAME/KEY: modified_base
<222> LOCATION: (18)
<223> OTHER INFORMATION: a, c, g or t

<400> SEQUENCE: 50
aayttnacyt cccartangc ytt                                           23

<210> SEQ ID NO 51
<211> LENGTH: 1951
<212> TYPE: DNA
<213> ORGANISM: Ogataea minuta
<220> FEATURE:
<221> NAME/KEY: modified_base
<222> LOCATION: (35)
<223> OTHER INFORMATION: a, c, g or t

<400> SEQUENCE: 51
catatgtatt catcaatcta cagcttttct aatcngtgtg acttcagtca catgatcctc      60
tgacccgcca cgaccttgct ggcttccagc gcgcgaaact cactcccaat tttcggatta    120
gctaatcacg aagatttttg gatttcctga tctgtagtgt atccatcctg ccttaatcgt    180

```
tttcgataca tttgttatcc gaattgggaa tggcattagt cgtgcgccac ccgactcgcc    240
accccccattc tagtggcaaa caggattgaa agagggctaa aaggtaactt agtgttttat    300
ctctgaatct tccttctgat atcaatcaac aattgttaaa cgattgaaag ttttgaaaca    360
ttcattgaac ttgcgaagcg ctcacacagc atcgttcggt tagcagttac aacagtttag    420
gttttttttcc ccacaaaaag gctcacgctg cctcctcact cttgcctctt ttcttgatga    480
aactctcgct tgcattgctc gcccttggtg gtttccaaga ggcccacgcc aaggttcatc    540
atgcgccaat caagaagact cctgccgcgg aaacttacaa ggacgtgagt ttcggcgact    600
acgtggattc tctgaagggc aagtatgtct ctatgtttgc taagcatgct gcggagtcct    660
cccaaaacgc ctttgtccct tttgttcagg aagtgcaaga cccagagttt actgttcagg    720
agggacacaa ctcccctctc acgaactacg tgaacgctca gtacttcact gagattcaaa    780
ttggtacccc gggccaaccg ttcaaggtca tcctcgacac tggttcgtcc aatttgtggg    840
ttccaggctc ggattgttct tctcttgctt gctacctgca tcagaagtac gaccacgact    900
cttcgtcaac ctacaaggcc aacggctctg aatttgctat cagatacggc tctggttcgc    960
tggagggttt tgtctcccag gacaccctga ctcttggtga cctcatcatt ccaaagcaag   1020
actttgccga ggccaccagt gagccaggtc tcgcatttgc ctttggtaag tttgacggta   1080
ttctcggact tgcgtacgac accatctcgg tggacaagat tgttcctcct atctacaacg   1140
ctttgaacct ggggcttttg acgagcctc agttcgcctt ctacctcgga gacactgcca   1200
agtctgaggc agacggtgga gtggctactt tcggaggtgt tgacgaaact aagtacgacg   1260
gaaagatcac ttggttgcca gtgagaagaa aggcttactg ggaggtgaag tttgacggta   1320
tcgctcttgg tgacgagtac gcgactttag acggatatgg cgctgccatc gacacaggta   1380
cctctcttaat tgctttgcct tcccaattgg ctgagatttt gaactctcaa atcggtgccg   1440
agaagtcctg gtccggccag tacaccattg actgtgaaaa gagagcatct ttgccagacc   1500
tcactttcaa ctttgacggt tacaatttct ctatctccgc gtacgactac actcttgagg   1560
tttcaggctc gtgcatttcc gccttcactc gatggactt ccctgccccca attggccctc   1620
tcgccatcat tggtgatgct ttcctgagaa agtattactc cgtgtacgac ttgggcaagg   1680
acgctgttgg attggctaag gccgtttaat ctctagcctt ctagttattg attgctattg   1740
ttaattctgc catcctggat tggcatgaat ggttggttgg tacgcatata cggttggcgg   1800
tggtatgttt attgctttta ttacgtgacc aaatgttggt ttttctttca ccttttactc   1860
tgcactactt cactctttca ttggctttgg aagtacgtta ttttttttcac cctatgtaac   1920
tgaattgcac aaatttaaag attgctctag a                                    1951
```

<210> SEQ ID NO 52
<211> LENGTH: 410
<212> TYPE: PRT
<213> ORGANISM: Ogataea minuta

<400> SEQUENCE: 52

```
Met Lys Leu Ser Leu Ala Leu Leu Ala Leu Gly Gly Phe Gln Glu Ala
 1               5                  10                  15

His Ala Lys Val His His Ala Pro Ile Lys Lys Thr Pro Ala Ala Glu
            20                  25                  30

Thr Tyr Lys Asp Val Ser Phe Gly Asp Tyr Val Asp Ser Leu Lys Gly
        35                  40                  45

Lys Tyr Val Ser Met Phe Ala Lys His Ala Ala Glu Ser Ser Gln Asn
    50                  55                  60
```

Ala Phe Val Pro Phe Val Gln Glu Val Gln Asp Pro Glu Phe Thr Val
 65                  70                  75                  80

Gln Glu Gly His Asn Ser Pro Leu Thr Asn Tyr Val Asn Ala Gln Tyr
             85                  90                  95

Phe Thr Glu Ile Gln Ile Gly Thr Pro Gly Gln Pro Phe Lys Val Ile
            100                 105                 110

Leu Asp Thr Gly Ser Ser Asn Leu Trp Val Pro Gly Ser Asp Cys Ser
            115                 120                 125

Ser Leu Ala Cys Tyr Leu His Gln Lys Tyr Asp His Asp Ser Ser Ser
        130                 135                 140

Thr Tyr Lys Ala Asn Gly Ser Glu Phe Ala Ile Arg Tyr Gly Ser Gly
145                 150                 155                 160

Ser Leu Glu Gly Phe Val Ser Gln Asp Thr Leu Thr Leu Gly Asp Leu
                165                 170                 175

Ile Ile Pro Lys Gln Asp Phe Ala Glu Ala Thr Ser Glu Pro Gly Leu
            180                 185                 190

Ala Phe Ala Phe Gly Lys Phe Asp Gly Ile Leu Gly Leu Ala Tyr Asp
        195                 200                 205

Thr Ile Ser Val Asp Lys Ile Val Pro Pro Ile Tyr Asn Ala Leu Asn
210                 215                 220

Leu Gly Leu Leu Asp Glu Pro Gln Phe Ala Phe Tyr Leu Gly Asp Thr
225                 230                 235                 240

Ala Lys Ser Glu Ala Asp Gly Gly Val Ala Thr Phe Gly Gly Val Asp
                245                 250                 255

Glu Thr Lys Tyr Asp Gly Lys Ile Thr Trp Leu Pro Val Arg Arg Lys
            260                 265                 270

Ala Tyr Trp Glu Val Lys Phe Asp Gly Ile Ala Leu Gly Asp Glu Tyr
        275                 280                 285

Ala Thr Leu Asp Gly Tyr Gly Ala Ala Ile Asp Thr Gly Thr Ser Leu
    290                 295                 300

Ile Ala Leu Pro Ser Gln Leu Ala Glu Ile Leu Asn Ser Gln Ile Gly
305                 310                 315                 320

Ala Glu Lys Ser Trp Ser Gly Gln Tyr Thr Ile Asp Cys Glu Lys Arg
                325                 330                 335

Ala Ser Leu Pro Asp Leu Thr Phe Asn Phe Asp Gly Tyr Asn Phe Ser
            340                 345                 350

Ile Ser Ala Tyr Asp Tyr Thr Leu Glu Val Ser Gly Ser Cys Ile Ser
        355                 360                 365

Ala Phe Thr Pro Met Asp Phe Pro Ala Pro Ile Gly Pro Leu Ala Ile
    370                 375                 380

Ile Gly Asp Ala Phe Leu Arg Lys Tyr Tyr Ser Val Tyr Asp Leu Gly
385                 390                 395                 400

Lys Asp Ala Val Gly Leu Ala Lys Ala Val
                405                 410

<210> SEQ ID NO 53
<211> LENGTH: 11
<212> TYPE: PRT
<213> ORGANISM: Saccharomyces cerevisiae
<220> FEATURE:
<221> NAME/KEY: MOD_RES
<222> LOCATION: (2)
<223> OTHER INFORMATION: Gly or Leu

<400> SEQUENCE: 53

Asp Xaa Asn Gly His Gly Thr His Cys Ala Gly

<210> SEQ ID NO 54
<211> LENGTH: 11
<212> TYPE: PRT
<213> ORGANISM: Saccharomyces cerevisiae
<220> FEATURE:
<221> NAME/KEY: MOD_RES
<222> LOCATION: (6)
<223> OTHER INFORMATION: Ser or Thr
<220> FEATURE:
<221> NAME/KEY: MOD_RES
<222> LOCATION: (9)
<223> OTHER INFORMATION: Val or Ile
<220> FEATURE:
<221> NAME/KEY: MOD_RES
<222> LOCATION: (10)
<223> OTHER INFORMATION: Ala or Val

<400> SEQUENCE: 54

Gly Thr Ser Met Ala Xaa Pro His Xaa Xaa Gly
 1               5                  10

<210> SEQ ID NO 55
<211> LENGTH: 32
<212> TYPE: DNA
<213> ORGANISM: Artificial Sequence
<220> FEATURE:
<223> OTHER INFORMATION: Description of Artificial Sequence: Synthetic
      primer PPB5 for amplification of 5'-region of
      Ogataea minuta PRB1 gene
<220> FEATURE:
<221> NAME/KEY: modified_base
<222> LOCATION: (6)
<223> OTHER INFORMATION: a, c, g or t
<220> FEATURE:
<221> NAME/KEY: modified_base
<222> LOCATION: (12)
<223> OTHER INFORMATION: a, c, g or t
<220> FEATURE:
<221> NAME/KEY: modified_base
<222> LOCATION: (18)
<223> OTHER INFORMATION: a, c, g or t
<220> FEATURE:
<221> NAME/KEY: modified_base
<222> LOCATION: (21)
<223> OTHER INFORMATION: a, c, g or t
<220> FEATURE:
<221> NAME/KEY: modified_base
<222> LOCATION: (30)
<223> OTHER INFORMATION: a, c, g or t

<400> SEQUENCE: 55
gaybknaayg gncayggnac ncaytgykcn gg                                   32

<210> SEQ ID NO 56
<211> LENGTH: 32
<212> TYPE: DNA
<213> ORGANISM: Artificial Sequence
<220> FEATURE:
<223> OTHER INFORMATION: Description of Artificial Sequence: Synthetic
      primer PPB3 for amplification of 3'-region of
      Ogataea minuta PRB1 gene
<220> FEATURE:
<221> NAME/KEY: modified_base
<222> LOCATION: (3)
<223> OTHER INFORMATION: a, c, g or t
<220> FEATURE:
<221> NAME/KEY: modified_base
<222> LOCATION: (6)
<223> OTHER INFORMATION: a, c, g or t
<220> FEATURE:
<221> NAME/KEY: modified_base
<222> LOCATION: (12)
<223> OTHER INFORMATION: a, c, g or t

```
<220> FEATURE:
<221> NAME/KEY: modified_base
<222> LOCATION: (15)
<223> OTHER INFORMATION: a, c, g or t
<220> FEATURE:
<221> NAME/KEY: modified_base
<222> LOCATION: (18)
<223> OTHER INFORMATION: a, c, g or t
<220> FEATURE:
<221> NAME/KEY: modified_base
<222> LOCATION: (24)
<223> OTHER INFORMATION: a, c, g or t
<220> FEATURE:
<221> NAME/KEY: modified_base
<222> LOCATION: (27)
<223> OTHER INFORMATION: a, c, g or t
<220> FEATURE:
<221> NAME/KEY: modified_base
<222> LOCATION: (30)
<223> OTHER INFORMATION: a, c, g or t

<400> SEQUENCE: 56
ccnrcnayrt gnggnwsngc catnwsngtn cc                                  32

<210> SEQ ID NO 57
<211> LENGTH: 2214
<212> TYPE: DNA
<213> ORGANISM: Ogataea minuta

<400> SEQUENCE: 57
ggatcccctc tctcgctagc gagtttcgcc tgctctgcga taagagaaaa ccggctgtgc     60
agctttcacc ccaacacgtc actttctgca gtcgtgcgcc ggcttgcatt aggtcgtgcg    120
cagatcccaa atttgccacc agactaaatt ggggcattct ggtgagggaa tagggggaaat   180 aagagggtgt tttgacgttt catatacatt gctctttctt ttcttggacg gttagcggta    240
ttgccataga ttatcttgcg cagttcagca tccttaggag ttattctttc ttgtaggtct    300
tttttcagaa cagaaaaatc gccaatcaca gaaagattca gtcctaattg aagccttatc    360
ttatcttatc tcacctcaac cacttgaacc aaaatgaagt tatcccagtc tgctgcggtg    420
gctattctgt cttcgttggc agcagtggag gccttggtca tcccgttatt tgacgacttg    480
ccagcagagt ttgcccttgt tccaatggat gcgaaagcgg aagtcatttc tgacgttcct    540
gtcgactcgg ccattagtga tgctcctatc gcggcactaa atgatgctcc aagccctctc    600
gtcacatcgc tgatcgcatc tcaaaatttg attccaaact cttatattgt cgttttcaag    660
aatggcctag cttccggggc agttgacttc cacatggagt ggctcaagga aacgcactcc    720
caaaccctgg ctgctttgtc taaggacatg ccagcagaag aattggccgc cgaaggtttc    780
gtttccgaaa gcattgatct tactgaggtg tttagcatct ccgatttgtt cagtggatat    840
accggatact tcccggagaa ggtggttgac ctcatcagaa gacaccctga cgtggcgttc    900
gttgagcagg actcgagagt tttcgccgat aagtcgtcta ctcaaaacgg tgctccttgg    960
ggtttgtcta gaatctctca cagagagcct ctcagtctcg gcaatttcaa cgagtacgtt   1020
tacgacgatc ttgctggaga tggcgtcacg gcttatgtca ttgataccgg tatcaatgtg   1080
aagcacgagc agttcggtgg cagagcagag tggggtaaga ccatcccaac cggtgatgat   1140
gatattgacg gaaacggtca cggtactcac tgcgctggta caattggctc ggaagattat   1200
ggagtttcta gaactccaa aattgtcgca gtgaaggttt tgagatctaa cggttctggt   1260
tccatgtctg acgtgatcaa gggtgttgaa ttcgctgcaa atgatcacgt tgccaagtct   1320
aaagccaaga aggacggttt caagggatcg actgccaaca tgtctttggg aggtggcaag   1380
tctcctgctc ttgacttggc tgtcaatgcc gctgtcaaag ctggtttaca ctttgctgtt   1440
```

```
gccgctggta acgacaatgc tgacgcatgc aactattctc ctgctgctgc agagaacgca    1500
gtcactgttg gtgcgtccac tttgtctgac tctagagctt acttttccaa ctatggtaaa    1560
tgtgttgaca ttttgctcc gggcttgaac atcctttcca cctacatagg ttctgacact     1620
gccaccgcca ctctttctgg tacatcgatg gcctcccctc acgtttgtgg tctgttgacc    1680 tacttttga gcttgcaacc agaatcgtcg tcgttgtttt cttcggcagc tatctcccct     1740
gctcagctga agaagaacct gatcaagttt ggtacgaaga acgttttgtc tgagattcca    1800
tcggacggaa ccccaaatat tctcatttac aacggtgctg gcaagaacat cagtgacttc    1860
tgggcgtttg aagacgaggc ctcggccaag tccgacttga agaaggctgt cgatattgcc    1920
acaagtgttg acttagacct gcaagatatc aaggagaagt tcaaccatat tttggaggag    1980
gtcgccgaag aggttgctga tttgttcgat taggtttcta acaattcagt gatcttgtct    2040
ttactgtggt ttcggaaact gggtttagac agcggtcctg ttactcatat tgcgcttgat    2100
cgcttttcct tttttttctg ttgtttggag tgtttgtttt tctggataat gtggttagtt    2160
tttcaagttg cttccaatat tgtttgtcca gattagagtc attgcttgaa gctt          2214
```

<210> SEQ ID NO 58
<211> LENGTH: 539
<212> TYPE: PRT
<213> ORGANISM: Ogataea minuta

<400> SEQUENCE: 58

```
Met Lys Leu Ser Gln Ser Ala Ala Val Ala Ile Leu Ser Ser Leu Ala
 1               5                  10                  15

Ala Val Glu Ala Leu Val Ile Pro Leu Phe Asp Asp Leu Pro Ala Glu
                20                  25                  30

Phe Ala Leu Val Pro Met Asp Ala Lys Ala Glu Val Ile Ser Asp Val
            35                  40                  45

Pro Val Asp Ser Ala Ile Ser Asp Ala Pro Ile Ala Ala Leu Asn Asp
        50                  55                  60

Ala Pro Ser Pro Leu Val Thr Ser Leu Ile Ala Ser Gln Asn Leu Ile
    65                  70                  75                  80

Pro Asn Ser Tyr Ile Val Val Phe Lys Asn Gly Leu Ala Ser Gly Ala
                85                  90                  95

Val Asp Phe His Met Glu Trp Leu Lys Glu Thr His Ser Gln Thr Leu
            100                 105                 110

Ala Ala Leu Ser Lys Asp Met Pro Ala Glu Glu Leu Ala Ala Glu Gly
        115                 120                 125

Phe Val Ser Glu Ser Ile Asp Leu Thr Glu Val Phe Ser Ile Ser Asp
    130                 135                 140

Leu Phe Ser Gly Tyr Thr Gly Tyr Phe Pro Glu Lys Val Val Asp Leu
145                 150                 155                 160

Ile Arg Arg His Pro Asp Val Ala Phe Val Glu Gln Asp Ser Arg Val
                165                 170                 175

Phe Ala Asp Lys Ser Ser Thr Gln Asn Gly Ala Pro Trp Gly Leu Ser
            180                 185                 190

Arg Ile Ser His Arg Glu Pro Leu Ser Leu Gly Asn Phe Asn Glu Tyr
        195                 200                 205

Val Tyr Asp Asp Leu Ala Gly Asp Gly Val Thr Ala Tyr Val Ile Asp
    210                 215                 220

Thr Gly Ile Asn Val Lys His Glu Gln Phe Gly Gly Arg Ala Glu Trp
225                 230                 235                 240
```

-continued

Gly Lys Thr Ile Pro Thr Gly Asp Asp Ile Asp Gly Asn Gly His
            245                 250                 255

Gly Thr His Cys Ala Gly Thr Ile Gly Ser Glu Asp Tyr Gly Val Ser
        260                 265                 270

Lys Asn Ser Lys Ile Val Ala Val Lys Val Leu Arg Ser Asn Gly Ser
    275                 280                 285

Gly Ser Met Ser Asp Val Ile Lys Gly Val Glu Phe Ala Ala Asn Asp
290                 295                 300

His Val Ala Lys Ser Lys Ala Lys Asp Gly Phe Lys Gly Ser Thr
305                 310                 315                 320

Ala Asn Met Ser Leu Gly Gly Gly Lys Ser Pro Ala Leu Asp Leu Ala
                325                 330                 335

Val Asn Ala Ala Val Lys Ala Gly Leu His Phe Ala Val Ala Ala Gly
            340                 345                 350

Asn Asp Asn Ala Asp Ala Cys Asn Tyr Ser Pro Ala Ala Glu Asn
        355                 360                 365

Ala Val Thr Val Gly Ala Ser Thr Leu Ser Asp Ser Arg Ala Tyr Phe
    370                 375                 380

Ser Asn Tyr Gly Lys Cys Val Asp Ile Phe Ala Pro Gly Leu Asn Ile
385                 390                 395                 400

Leu Ser Thr Tyr Ile Gly Ser Asp Thr Ala Thr Ala Thr Leu Ser Gly
                405                 410                 415

Thr Ser Met Ala Ser Pro His Val Cys Gly Leu Leu Thr Tyr Phe Leu
            420                 425                 430

Ser Leu Gln Pro Glu Ser Ser Ser Leu Phe Ser Ser Ala Ala Ile Ser
        435                 440                 445

Pro Ala Gln Leu Lys Lys Asn Leu Ile Lys Phe Gly Thr Lys Asn Val
    450                 455                 460

Leu Ser Glu Ile Pro Ser Asp Gly Thr Pro Asn Ile Leu Ile Tyr Asn
465                 470                 475                 480

Gly Ala Gly Lys Asn Ile Ser Asp Phe Trp Ala Phe Glu Asp Glu Ala
                485                 490                 495

Ser Ala Lys Ser Asp Leu Lys Lys Ala Val Asp Ile Ala Thr Ser Val
            500                 505                 510

Asp Leu Asp Leu Gln Asp Ile Lys Glu Lys Phe Asn His Ile Leu Glu
        515                 520                 525

Glu Val Ala Glu Glu Val Ala Asp Leu Phe Asp
    530                 535

<210> SEQ ID NO 59
<211> LENGTH: 9
<212> TYPE: PRT
<213> ORGANISM: Saccharomyces cerevisiae
<220> FEATURE:
<221> NAME/KEY: MOD_RES
<222> LOCATION: (1)
<223> OTHER INFORMATION: His or Asn
<220> FEATURE:
<221> NAME/KEY: MOD_RES
<222> LOCATION: (5)
<223> OTHER INFORMATION: Val or Thr

<400> SEQUENCE: 59

Xaa Tyr Asp Trp Xaa Phe Leu Asn Asp
 1               5

<210> SEQ ID NO 60
<211> LENGTH: 12
<212> TYPE: PRT

<213> ORGANISM: Saccharomyces cerevisiae

<400> SEQUENCE: 60

Tyr Asn Leu Cys His Phe Trp Ser Asn Phe Glu Ile
 1               5                  10

<210> SEQ ID NO 61
<211> LENGTH: 26
<212> TYPE: DNA
<213> ORGANISM: Artificial Sequence
<220> FEATURE:
<223> OTHER INFORMATION: Description of Artificial Sequence: Synthetic
      primer PKR5 for amplification of 5'-region of
      Ogataea minuta KTR1 gene
<220> FEATURE:
<221> NAME/KEY: modified_base
<222> LOCATION: (15)
<223> OTHER INFORMATION: a, c, g or t
<220> FEATURE:
<221> NAME/KEY: modified_base
<222> LOCATION: (21)
<223> OTHER INFORMATION: a, c, g or t

<400> SEQUENCE: 61
maytaygayt ggrynttyyt naayga                                          26

<210> SEQ ID NO 62
<211> LENGTH: 35
<212> TYPE: DNA
<213> ORGANISM: Artificial Sequence
<220> FEATURE:
<223> OTHER INFORMATION: Description of Artificial Sequence: Synthetic
      primer PKR3 for amplification of 3'-region of
      Ogataea minuta KTR1 gene
<220> FEATURE:
<221> NAME/KEY: modified_base
<222> LOCATION: (12)
<223> OTHER INFORMATION: a, c, g or t
<220> FEATURE:
<221> NAME/KEY: modified_base
<222> LOCATION: (27)
<223> OTHER INFORMATION: a, c, g or t

<400> SEQUENCE: 62
atytcraart tnswccaraa rtgrcanarr ttrta                                35

<210> SEQ ID NO 63
<211> LENGTH: 1930
<212> TYPE: DNA
<213> ORGANISM: Ogataea minuta

<400> SEQUENCE: 63
gagctctata tttagctttg gacattggta ctagttggac tgttgatcgg ttgacttgac      60
agtgagttct atagaaagac aggctacaaa gaccaccaag gctggcaaat tgcgagatt     120 acaatggcta gagcgaatgc gaggctgatc cggtttgcaa tctttgctac cgtgttggtt    180
ttatgtggat acatttttatc caagggctcg tctacttcgt atacgatttc gacgccagag   240
tccggctcga gttccagtgg cactgttgct aatactgaga atctgccct cgcagtgggt     300 gagaaaagcg ttgcaggcgc agccgagaaa agcgttcctg cagctgacgt cccagatgga    360
aaggtgaagg ccacttttgt ctctttggcc agaaaccagg atctgtggga gctggtgaac    420
tcgatcagac aggtcgaaga ccgtttcaac aacaagtatc attacgattg ggtgttcttg    480
aacgacgcgg aattcaacga cgagttcaag aaggtgacct ctcaggtctg ttcgggtaag    540
accaagtatg tgtcattcc aaaggaacag tggagcttcc cttcgtggat cgacactgat    600
aaggctgctg ccaccagaga gcaaatgaga aaggacaaga tcatctacgg agactccatc    660

```
tcgtacagac acatgtgcag atacgagtcg ggattcttct tcaaacaccc agaactcgca      720
gagtacgagt actactggag agtggagcca agcatcaaga tctactgtga cattgactac      780
gacatcttca agttcatgaa ggacaacaag aagtcgtacg gatggaccat ttctcttcct      840
gagtacaagg agaccatccc aactctgtgg aagaccacta gagacttcat gaaggaaaac      900
ccacagtacg ttgcccagga caacctgatc aactttattt cggacgacgg aggaagcagc      960
tacaatggat gtcacttctg gtctaacttc gaggtcggct cgctcgagtt ctggagaggc     1020
gaagcctaca ccaagtactt tgaggcgttg gaccaggctg gtgggttctt ctacgaaaga     1080
tggggagatg cccctatcca ctcgattgcc gttgctctgt tcatgcctaa ggacgaggtt     1140
catttcttcg acgacgtcgg atacttccac aatccgttcc acaactgccc gatcgacaac     1200
gctgtcagag aggccaagaa ctgtgtctgc aaccaagccg acgacttcac cttccagcac     1260
tactcctgta cccctaagtt ttaccaggag atgggttttga aaaagcctgc taactgggag     1320
cagtacatcc attagttgac ccaggccacg ggttgatttc gcctggttgt tttttgtttt     1380
tacaagtctt tcaatactaa attagctgga ttcaagtgat acgagatgat tttcatctcc     1440
ggggtttctg taattttttgt ttcgagaaaa ataaatctac aaaaaaacgt gccagatact     1500
tgtctcccgg gggcaaacaa cgtgctctct ctgctactaa gtgttttgtt tctgtccaca     1560
acgcccgcag gtaaacgcaa tgtccgatac agattctgag tcagtctcga cgatcacaca     1620
gatgagcttc gagaacgttc tcgaggttct agaagactct gcgtctgagt gctccaagaa     1680
caaggacttc ctctccttct cgacgatcat cgacgtccat ctgggtgatc tttccattta     1740
cactgagtcc gagcgacttg agctgttgtc gaaactgaca tctattctga gcaatgacca     1800
ccaattggtt tacgaggtag gatgggactt accaccgatc atattcagct tcctggactc     1860
tgaatcttcg cccagtgagg ggctgatgaa cagcaaggtc acggttcttt tcttgaagct     1920
gtttgagctc                                                             1930

<210> SEQ ID NO 64
<211> LENGTH: 403
<212> TYPE: PRT
<213> ORGANISM: Ogataea minuta

<400> SEQUENCE: 64

Met Ala Arg Ala Asn Ala Arg Leu Ile Arg Phe Ala Ile Phe Ala Thr
 1               5                  10                  15

Val Leu Val Leu Cys Gly Tyr Ile Leu Ser Lys Gly Ser Ser Thr Ser
             20                  25                  30

Tyr Thr Ile Ser Thr Pro Glu Ser Gly Ser Ser Ser Gly Thr Val
         35                  40                  45

Ala Asn Thr Glu Lys Ser Ala Leu Ala Val Gly Glu Lys Ser Val Ala
     50                  55                  60

Gly Ala Ala Glu Lys Ser Val Pro Ala Ala Asp Val Pro Asp Gly Lys
 65                  70                  75                  80

Val Lys Ala Thr Phe Val Ser Leu Ala Arg Asn Gln Asp Leu Trp Glu
                 85                  90                  95

Leu Val Asn Ser Ile Arg Gln Val Glu Asp Arg Phe Asn Asn Lys Tyr
            100                 105                 110

His Tyr Asp Trp Val Phe Leu Asn Asp Ala Glu Phe Asn Asp Glu Phe
        115                 120                 125

Lys Lys Val Thr Ser Gln Val Cys Ser Gly Lys Thr Leu Tyr Gly Val
    130                 135                 140
```

```
Ile Pro Lys Glu Gln Trp Ser Phe Pro Ser Trp Ile Asp Thr Asp Lys
145                 150                 155                 160

Ala Ala Ala Thr Arg Glu Gln Met Arg Lys Asp Lys Ile Ile Tyr Gly
            165                 170                 175

Asp Ser Ile Ser Tyr Arg His Met Cys Arg Tyr Glu Ser Gly Phe Phe
        180                 185                 190

Phe Lys His Pro Glu Leu Ala Glu Tyr Glu Tyr Tyr Trp Arg Val Glu
    195                 200                 205

Pro Ser Ile Lys Ile Tyr Cys Asp Ile Asp Tyr Asp Ile Phe Lys Phe
210                 215                 220

Met Lys Asp Asn Lys Lys Ser Tyr Gly Trp Thr Ile Ser Leu Pro Glu
225                 230                 235                 240

Tyr Lys Glu Thr Ile Pro Thr Leu Trp Lys Thr Thr Arg Asp Phe Met
                245                 250                 255

Lys Glu Asn Pro Gln Tyr Val Ala Gln Asp Asn Leu Ile Asn Phe Ile
                260                 265                 270

Ser Asp Asp Gly Gly Ser Ser Tyr Asn Gly Cys His Phe Trp Ser Asn
            275                 280                 285

Phe Glu Val Gly Ser Leu Glu Phe Trp Arg Gly Glu Ala Tyr Thr Lys
290                 295                 300

Tyr Phe Glu Ala Leu Asp Gln Ala Gly Gly Phe Phe Tyr Glu Arg Trp
305                 310                 315                 320

Gly Asp Ala Pro Ile His Ser Ile Ala Val Ala Leu Phe Met Pro Lys
                325                 330                 335

Asp Glu Val His Phe Phe Asp Asp Val Gly Tyr Phe His Asn Pro Phe
            340                 345                 350

His Asn Cys Pro Ile Asp Asn Ala Val Arg Glu Ala Lys Asn Cys Val
            355                 360                 365

Cys Asn Gln Ala Asp Asp Phe Thr Phe Gln His Tyr Ser Cys Thr Pro
370                 375                 380

Lys Phe Tyr Gln Glu Met Gly Leu Lys Lys Pro Ala Asn Trp Glu Gln
385                 390                 395                 400

Tyr Ile His

<210> SEQ ID NO 65
<211> LENGTH: 10
<212> TYPE: PRT
<213> ORGANISM: Saccharomyces cerevisiae

<400> SEQUENCE: 65

Thr Ser Trp Val Leu Trp Leu Asp Ala Asp
1               5                   10

<210> SEQ ID NO 66
<211> LENGTH: 10
<212> TYPE: PRT
<213> ORGANISM: Saccharomyces cerevisiae

<400> SEQUENCE: 66

Glu Thr Glu Gly Phe Ala Lys Met Ala Lys
1               5                   10

<210> SEQ ID NO 67
<211> LENGTH: 29
<212> TYPE: DNA
<213> ORGANISM: Artificial Sequence
<220> FEATURE:
<223> OTHER INFORMATION: Description of Artificial Sequence: Synthetic
      primer PMN5 for amplification of 5'-region of
```

```
            Ogataea minuta MNN9 gene
<220> FEATURE:
<221> NAME/KEY: modified_base
<222> LOCATION: (3)
<223> OTHER INFORMATION: a, c, g or t
<220> FEATURE:
<221> NAME/KEY: modified_base
<222> LOCATION: (6)
<223> OTHER INFORMATION: a, c, g or t
<220> FEATURE:
<221> NAME/KEY: modified_base
<222> LOCATION: (12)
<223> OTHER INFORMATION: a, c, g or t
<220> FEATURE:
<221> NAME/KEY: modified_base
<222> LOCATION: (15)
<223> OTHER INFORMATION: a, c, g or t
<220> FEATURE:
<221> NAME/KEY: modified_base
<222> LOCATION: (21)
<223> OTHER INFORMATION: a, c, g or t
<220> FEATURE:
<221> NAME/KEY: modified_base
<222> LOCATION: (27)
<223> OTHER INFORMATION: a, c, g or t

<400> SEQUENCE: 67
acnwsntggg tnytntggyt ngaygcnga                                    29

<210> SEQ ID NO 68
<211> LENGTH: 29
<212> TYPE: DNA
<213> ORGANISM: Artificial Sequence
<220> FEATURE:
<223> OTHER INFORMATION: Description of Artificial Sequence: Synthetic
      primer PMN3 for amplification of 3'-region of
      Ogataea minuta MNN9 gene
<220> FEATURE:
<221> NAME/KEY: modified_base
<222> LOCATION: (3)
<223> OTHER INFORMATION: a, c, g or t
<220> FEATURE:
<221> NAME/KEY: modified_base
<222> LOCATION: (12)
<223> OTHER INFORMATION: a, c, g or t
<220> FEATURE:
<221> NAME/KEY: modified_base
<222> LOCATION: (18)
<223> OTHER INFORMATION: a, c, g or t
<220> FEATURE:
<221> NAME/KEY: modified_base
<222> LOCATION: (24)
<223> OTHER INFORMATION: a, c, g or t

<400> SEQUENCE: 68
ttngccatyt tngcraancc ytcngtytc                                    29

<210> SEQ ID NO 69
<211> LENGTH: 2221
<212> TYPE: DNA
<213> ORGANISM: Ogataea minuta

<400> SEQUENCE: 69
gggcccagag gaggaggtag gagtgggggg atcgccaatt ttctggcgcg ctactccgcg    60
ctgccccgca cttcggccgc accgccaacc ttttctttgc gcaccccctc tccaacgttt   120
ccggcctttc cattgaagcg agctaagcag tcagagagca ccaccgggag acgtgatcgc   180
agcccctgtt tgccccgaaa ccgggttaga caaaacgcgg ttcggcttca acggactctc   240
atctttcaga tggccgcagg ttgctggcag cttcgggctg acaacatcat ggctgacgta   300
ggctagtcag tagggcaccc tgcgggttag taagtctccc tgcaggtcac cgttgcttga   360
```

```
gcatcgcagg agtgttaagc ggcagaaaag aggaggtgga gtggggacga gagatccggg    420
taaccgtagt cggcgcgcga gtccgagaag ttaatcgacg cgtcgaaact gggtcttttg    480
ttacccaaaa gaagcaggac tggaaggaaa cagaccggga ttggtgtgta tttctgtcag    540
ggcacactgg acggtcatcc tagtgtggtt ccgctcaccg cttacctggc tggtgttcct    600
ggtccatccc ctagcaaact cgagccggat caccctattc tggccggttt tgctatttcc    660
cgcctcgaaa tccccttgaa gtacacagcc tgaaatttgg cttttcttc actgtcgtgc    720
aagacgcaaa acgccttact ttgaacaaca tcaacatcta gcaaatgctg acgaaatttg    780
agaaacacaa gagctttacc aacctctaaa aataaccta ggctcccgtt tgcagctccg    840
catctctttc agcaccatta tagaactccg gaaagcatat tcacagcacg tgagacgcgg    900
attggctaaa taatcagtgc tgatttggac atgttgaaag gcgttttgaa acaccctctg    960
gtacaccaga tacgaaggaa acccgtgaag gtgttggttc ccgtcttcgg attggctgtt   1020
ttgttgtttc tggtgtttgg aggctcgtct ccaacagaa agaccaacag tccctactcg   1080
tacaagcgca acaacagaga tgaggtgatt ccacgtaatt tgccagcgga tcacatctcc   1140
cactatgacc tgaacaacct tgcgtcgacg ccgatggctg cttacaacaa ggagagagtg   1200
ttgattttga cgccaatggc gaagtttctg gacggatact gggacaactt gctgaaattg   1260
acatatccac gtgacctgat cgagctcgga ttcattgtgc cgcgcacagc agagggagac   1320
caagcattga gaagctgga gcacgcggtg aagattatcc agaacccaaa gaacaccaag   1380
gaacctaagt tcgccaaagt cacgatcctc agacaggaca cgagtccct ttcgtcacag   1440
tcggaaaagg acagacacgc gttcaaggtg cagaaagaac ggcgcgcaca aatggccaca   1500
gccagaaact cgctgctgtt caccaccatt ggcccgtaca cctcatgggt tctgtggctt   1560
gactcagata tcgtggagtc gcctcacacg ttgatccagg atcttgtttc gcacgacaag   1620
ccagtcattg ctgccaattg ctaccagaga tactacgacg aggacaagaa ggaggactcc   1680
atccgtcctt acgacttcaa caactggatc gagtctgaag agggactacg gatcgcatcc   1740
acgatgtcgg acgacgagat catcgtggaa gcgtacgcag aaattgccac ctatcgtcca   1800
ctgatgggcc atttctatga tcctaacggc gacctgggaa ccgagatgca actggatggt   1860
gtcggaggaa cctgtctgat ggtgaaggcc gacgtccatc gcgacggggc catgttcccg   1920
aacttcccct ctaccatct catcgaaacc gaagggttcg ccaaaatggc caaacggctt   1980
ggctaccagg tgtttggtct tccaaactat cttgttttcc actacaacga gtgactcttg   2040
gtcttttata tagttgagca aaaatgaaaa aacatgtcaa aaatagcaag acaacgtgaa   2100
atgtgtcgcg acgcgacgcc gtagttgttg caccgcaacg cgaacttctg tcgcgcctgt   2160
caactagaat aggttcgcac acgaccccac cgttccgatt tccttatcag caaagagatc   2220
t                                                                    2221

<210> SEQ ID NO 70
<211> LENGTH: 367
<212> TYPE: PRT
<213> ORGANISM: Ogataea minuta

<400> SEQUENCE: 70

Met Leu Lys Gly Val Leu Lys His Pro Leu Val His Gln Ile Arg Arg
  1               5                  10                  15

Lys Pro Val Lys Val Leu Val Pro Val Phe Gly Leu Ala Val Leu Leu
             20                  25                  30

Phe Leu Val Phe Gly Gly Ser Ser Ser Asn Arg Lys Thr Asn Ser Pro
         35                  40                  45
```

Tyr Ser Tyr Lys Arg Asn Asn Arg Asp Glu Val Ile Pro Arg Asn Leu
            50                   55                   60

Pro Ala Asp His Ile Ser His Tyr Asp Leu Asn Asn Leu Ala Ser Thr
 65                   70                   75                   80

Pro Met Ala Ala Tyr Asn Lys Glu Arg Val Leu Ile Leu Thr Pro Met
                 85                   90                   95

Ala Lys Phe Leu Asp Gly Tyr Trp Asp Asn Leu Leu Lys Leu Thr Tyr
            100                  105                  110

Pro Arg Asp Leu Ile Glu Leu Gly Phe Ile Val Pro Arg Thr Ala Glu
            115                  120                  125

Gly Asp Gln Ala Leu Lys Lys Leu Glu His Ala Val Lys Ile Ile Gln
            130                  135                  140

Asn Pro Lys Asn Thr Lys Glu Pro Lys Phe Ala Lys Val Thr Ile Leu
145                  150                  155                  160

Arg Gln Asp Asn Glu Ser Leu Ser Ser Gln Ser Glu Lys Asp Arg His
                 165                  170                  175

Ala Phe Lys Val Gln Lys Glu Arg Arg Ala Gln Met Ala Thr Ala Arg
            180                  185                  190

Asn Ser Leu Leu Phe Thr Thr Ile Gly Pro Tyr Thr Ser Trp Val Leu
            195                  200                  205

Trp Leu Asp Ser Asp Ile Val Glu Ser Pro His Thr Leu Ile Gln Asp
210                  215                  220

Leu Val Ser His Asp Lys Pro Val Ile Ala Ala Asn Cys Tyr Gln Arg
225                  230                  235                  240

Tyr Tyr Asp Glu Asp Lys Lys Glu Asp Ser Ile Arg Pro Tyr Asp Phe
                 245                  250                  255

Asn Asn Trp Ile Glu Ser Glu Gly Leu Arg Ile Ala Ser Thr Met
            260                  265                  270

Ser Asp Asp Glu Ile Ile Val Glu Ala Tyr Ala Glu Ile Ala Thr Tyr
            275                  280                  285

Arg Pro Leu Met Gly His Phe Tyr Asp Pro Asn Gly Asp Leu Gly Thr
            290                  295                  300

Glu Met Gln Leu Asp Gly Val Gly Gly Thr Cys Leu Met Val Lys Ala
305                  310                  315                  320

Asp Val His Arg Asp Gly Ala Met Phe Pro Asn Phe Pro Phe Tyr His
                 325                  330                  335

Leu Ile Glu Thr Glu Gly Phe Ala Lys Met Ala Lys Arg Leu Gly Tyr
            340                  345                  350

Gln Val Phe Gly Leu Pro Asn Tyr Leu Val Phe His Tyr Asn Glu
            355                  360                  365

<210> SEQ ID NO 71
<211> LENGTH: 30
<212> TYPE: DNA
<213> ORGANISM: Artificial Sequence
<220> FEATURE:
<223> OTHER INFORMATION: Description of Artificial Sequence: Synthetic
      primer DMN5

<400> SEQUENCE: 71
agatgaggtg attccacgta atttgccagc                                    30

<210> SEQ ID NO 72
<211> LENGTH: 30
<212> TYPE: DNA
<213> ORGANISM: Artificial Sequence
<220> FEATURE:

<223> OTHER INFORMATION: Description of Artificial Sequence: Synthetic
primer DMN3

<400> SEQUENCE: 72
ttttgattgt catctatttc gcacaccctg                                    30

<210> SEQ ID NO 73
<211> LENGTH: 12
<212> TYPE: PRT
<213> ORGANISM: Pichia pastoris

<400> SEQUENCE: 73

Gly Gly Gly Ser Ser Ile Asn Phe Met Met Tyr Thr
 1               5                  10

<210> SEQ ID NO 74
<211> LENGTH: 10
<212> TYPE: PRT
<213> ORGANISM: Pichia pastoris

<400> SEQUENCE: 74

Asp Met Trp Pro Met Val Trp Ala Tyr Lys
 1               5                  10

<210> SEQ ID NO 75
<211> LENGTH: 35
<212> TYPE: DNA
<213> ORGANISM: Artificial Sequence
<220> FEATURE:
<223> OTHER INFORMATION: Description of Artificial Sequence: Synthetic
primer PAX5 for amplification of 5'-region of
Ogataea minuta AOX1 gene
<220> FEATURE:
<221> NAME/KEY: modified_base
<222> LOCATION: (3)
<223> OTHER INFORMATION: a, c, g or t
<220> FEATURE:
<221> NAME/KEY: modified_base
<222> LOCATION: (6)
<223> OTHER INFORMATION: a, c, g or t
<220> FEATURE:
<221> NAME/KEY: modified_base
<222> LOCATION: (9)
<223> OTHER INFORMATION: a, c, g or t
<220> FEATURE:
<221> NAME/KEY: modified_base
<222> LOCATION: (12)
<223> OTHER INFORMATION: a, c, g or t
<220> FEATURE:
<221> NAME/KEY: modified_base
<222> LOCATION: (15)
<223> OTHER INFORMATION: a, c, g or t

<400> SEQUENCE: 75
ggnggnggnw snwsnathaa yttyatgatg tayac                              35

<210> SEQ ID NO 76
<211> LENGTH: 29
<212> TYPE: DNA
<213> ORGANISM: Artificial Sequence
<220> FEATURE:
<223> OTHER INFORMATION: Description of Artificial Sequence: Synthetic
primer PAX3 for amplification of 3'-region of
Ogataea minuta AOX1 gene
<220> FEATURE:
<221> NAME/KEY: modified_base
<222> LOCATION: (6)
<223> OTHER INFORMATION: a, c, g or t
<220> FEATURE:
<221> NAME/KEY: modified_base
<222> LOCATION: (12)
<223> OTHER INFORMATION: a, c, g or t

```
<220> FEATURE:
<221> NAME/KEY: modified_base
<222> LOCATION: (18)
<223> OTHER INFORMATION: a, c, g or t

<400> SEQUENCE: 76
ttrtangccc anaccatngg ccacatrtc                                        29

<210> SEQ ID NO 77
<211> LENGTH: 5817
<212> TYPE: DNA
<213> ORGANISM: Ogataea minuta

<400> SEQUENCE: 77
aagctttctt tcgcaaacag ctctttggta gaggagaata gagtgcccag ctgataaaga      60
aggcgcactt taaaagataa tctacatcca gaaaaataaa aaaataaaac tgaaccggca     120
tttgcgatta cgtaagccac aaaatttcag gaaactcgta caagatcagg ttggcgaggg     180
ggctagcgat agaatgtatc agtgttatta gtggctctag gagtagaaaa caatagaata     240
aagatccgaa gaaagggagc aagaaggcca cgccagacgt tctagtaggt agcccaatcg     300
tcaatgtagc tgttcaggtc tttcaacagg ttccttggtct cgtctggact ggagatccaa    360
caagtcgttg ctgcggttcg actggcatag tcgttggcgc cgagggagct gaactggtcg     420
ccgacgtgca gggtgttttc gggcttgatg gttcggttgt cgttgcagct gaggaactct     480
tggaggattt tcaccccgta ggacttgtcg ccaatatcga cccagatgtc cgagcctccg     540
ttgaaagcgc accatctgat tttcttagag aagggaagt ggcggagacg tttgtctacg      600
cgcagaacca cctcttccag ctgctcgcga acgagtttgt agccttcttt ggggaccagt     660
ccaacggcac gctcctttct gatgatgatg gcatgcaatg aaagtttctt gatcaggtcc     720
gagaagatct cctgcgcaaa gtccagggtc cggatgatgt cttcctcgga ccagtcgagc     780
atgttttcaa gcagccattt gtctttggag aagaactcga gtccgccaag ctcgttggag    840
tagcggaata ggtagtttgc ttcgcctccc atcaccagaa cgttctggcg ctgtctgtcg     900
gtgagctttg gggtggtctt cacctcgtct atgagcccct tgagtcgggc gtagtacttg     960
gagccgtcgg agtagcccgc ggcagtgacg atgccgacat agaggtcttt ggcgagcagc    1020
ttgatgagat ggggcaagat cggcgacgag gcgtcgaagt tggagccgtc atcgtagaga    1080
gtgatgtctc cgtcaaaagt cacgagctgg agtctgcggt gtacggatgt tttgttgtgg    1140
aaagtgttgg agagctcgag aagttgcgcc gtgttcagaa tgagccgaat gtcgttgaac    1200
gagggcgcta caagtctcct tttgctgatt gtgcggcgtc cgtcctcgat gtagaacgcc    1260
ttctccaggg gcaatcgggt gaagaaacag ccaacggaag gcaccaattg gaccaatctg    1320
gacatttcag gcattcccgc ctgggtcatc tcgatgttgt cgttgatcag cagctcgagg    1380
tcatggaaga tttccgcgta gcgtcgcttc gcttccgaat tcaccatgag gtcgtccact    1440
gcggagatcc cattggactt gactgcatag agaacaaacg gggtggccag caagcccttg    1500
atccactcaa tcagtccgtc tcggcggtgc tccttgagcg cgtactcgac tctgtatctg    1560
gttgtcattt gcgggagggg tgtaaagcag ctcagccggt gactgtgcaa ggacgaacgg    1620
ttcctacttg aatgctaggc tggctaattg ggtatggcac aaacggcaca acggcagat     1680
gactgcaaat gacgacggta aacagaatcc actcagctgg cactaactgg gtgtagacta    1740
agagttcgag ccgggagggg agtgacgatg cagccagaaa aagagccggt acgcaatcag    1800
ggaaatagcc gtcaaaagaa aaacagaagg ggctgcagtt ttgctgccgc cgccgcgcg     1860
cccgcgctgg ctttccccgg ccggggaggc agccggctaa agaaaatagc ctatttcgat    1920
```

| | |
|---|---|
| ttcgcgtagc ccctcggttg cctattgagg gttacttttc gctccctctt ttgggccaac | 1980 |
| tgacagtttg tggggtaaca acggtgtccg aggccagcta ttcggcaaac aatagacaga | 2040 |
| ttagagacct actacggagt ttcagtgtct tcggaagctg cacagcccga atgtcggagc | 2100 |
| ccgtgtgacg acaccccgc atggcttttg gcaatctcac atcgccctc cctgcgtctc | 2160 |
| cactctgggc atgagcagtg gtgtgcctgg tgtatctctg gccccgcgg ggcagacagc | 2220 |
| aaactgcgta taaatagcta cttccatctc ctacttgttg caccattgcc atagtaagaa | 2280 |
| aagaagcaga tcactcaact tgttcaaaga ctcttgtgtt ctgttacgac ttacgactta | 2340 |
| cgaaaaaat ggctattcct gacgaattcg atatcatcgt tgtgggtgga ggctcatgcg | 2400 |
| gctgcgccat cgccggtaga ctcggtaacc tcgacccgga cgttactgtg gctctcatcg | 2460 |
| agggtggtga gaacaacatc aataacccat gggtctacct tcctggtgtc tatccaagaa | 2520 |
| acatgagact cgactccaag acggctacct tctacaactc gagaccatcc aagcacctga | 2580 |
| acggcagaag ggccattgtc ccctgcgcta acattcttgg tggaggttcc tccatcaact | 2640 |
| tcctcatgta caccagagcc tcggcctccg actacgacga ctgggagcaa gagggatgga | 2700 |
| ccaccgacga gctgcttccg ctcatgaaga agctcgagac gtatcaacgt ccttgcaaca | 2760 |
| acagggaggt gcacggtttc gacggtccga tcaaggtctc cttcggtaac tacacctacc | 2820 |
| caactgccca agacttcctg agagcctgcg agtcgcaggg tattccttc aacgacgatc | 2880 |
| ttgaagacct caaggcctcg cacggagctg agtactggct caagtggatc aacagggatc | 2940 |
| tcggtagaag atcggactcg gcacacgcct acatccaccc taccatgaga aacaagagca | 3000 |
| atctgttcct cattacgtcc accaaggctg acaaggtgat cattgagaac ggcgttgctg | 3060 |
| tcggtgtcag gaccgttcca atgaagccgg tcgagaccaa aaaccctcca agcaggatct | 3120 |
| tcaaggccag aaagcaaatt gtggtttcgt gcggtacgat ctcctctcca ttggtgctgc | 3180 |
| aaagatctgg tatcggtgcg gcccacaagc tgagacaagc gggcatcaag ccgatcgtcg | 3240 |
| acttgcctgg tgtcggtgag aacttccagg accactactg cttcttcacc ccatactatt | 3300 |
| ccaagccaga ggttccaacc tttgacgact tgtcagagg tgacccagtc gctcaaaagt | 3360 |
| ccgcctttga ccagtggtac tccaacaagg acggtcctct taccaccaac ggtatcgagg | 3420 |
| ctggtgtcaa gatcagacca accgacgagg agttggccac ggctgacgat gacttcatcc | 3480 |
| aagggtacca cgagtacttt gacaacaagc cagacaagcc actgatgcat tactctgtca | 3540 |
| tttccggttt cttcggtgac cacaccaaga ttccaaacgg caagttcttc accatgttcc | 3600 |
| actttttgga gtacccattt tcgagaggtt tcgtttatgc tgtttcccca gacccatacg | 3660 |
| aagctccaga ctttgatcca ggtttcctga acgattccag agacatgtgg cctatggttt | 3720 |
| ggtcttacaa gaagtcgaga cagacagcca gaagaatgga gtcgtttgct ggtgaagtca | 3780 |
| cctcgcacca cccactctac ccggttgact ctccagcccg tgccaaggac ttggatctcg | 3840 |
| agacatgcaa ggcatttgct ggaccaaacc acttcaccgc caacttgtac cacggttcct | 3900 |
| ggactgttcc aattgagaag ccaacgccaa agaacgactc gcacgtgacc tgcaaccagg | 3960 |
| tcgagatctt ctccgacatt gactactctg ccgaggacga tgaggctatt gtcaagtaca | 4020 |
| tcaaggagca cactgagacc acctggcact gtttgggaac ctgttcgatg gctccacaag | 4080 |
| aaggtagcaa gatcgctcca aagggtggtg ttgtcgatgc cagattgaac gtgtacgaag | 4140 |
| tgaagaacct caaggttgcc gacctgtcga tctgcccaga taacgttgga tgtaatactt | 4200 |
| actccactgc tcttctgatt ggtgagaagg ctgccacttt ggtcgccgag gacctgggat | 4260 |
| actcaggatc tgatctcgcc atgaccattc caaacttcaa gctaggtact tacgaggaga | 4320 |

-continued

```
agggtctggc tagattctaa gagacggtgc ccgactcttg ttcaattctt ttggttcttt    4380
ttctgttttt ctctacgatt ctacttgatg atgtatgacg agtgaagatt gtgtttttt    4440 ctctctatag ttttgactgt aatgaaaata gtctacatga atgaaagaga tagctgacca    4500
atacggggcg tctggtcacg tgatgtatca cgtgatcttt aagttttcga aatgactaaa    4560
tttataacga aaaaagagt ctaaatgaaa aaaaatcgat ctctgccaaa gactcatcga    4620
taggctaact caggaagcat tccgagcaac gcataatgcc ctcaaccaca gtctcagaga    4680
tgcgcaaaaa ggtgctgatg atcgacaatt acgactcgtt cacatggaac ttgtacgagt    4740
atctttgtca agagggagcc gatgtcgagg tctatcgtaa cgacaagatc acaattgaag    4800
aaatcgagga aatgaagcct gacattatag tgatttcgcc aggccccgga catccgagat    4860
cggactctgg tatctctcga aagactattg agattttcaa gggccggatt cctgtttttg    4920
gagtgtgcat gggccaacag tgcatttacg aggttttcgg gggagacgtt gagtacgctg    4980
gtgaaattgt tcacggaaaa acctcttctg tgacccacga caatcgtgga gtcttcaaga    5040
acgttccgca gggagttgct gtgacgagat accattcgtt ggctggaacg ctaaaaactt    5100
tgcccagcga gttggaggtg actgcccgta ccactaacgg tatcattatg ggtgtcaggc    5160
ataaaagata cactattgaa ggcgttcagt ttcacccgga gtccatttg acagaagagg    5220 ggcacttaat gatcaagaac attttgaaga gtagcggtgg ttactggaac gaggaggagg    5280
aggaggtaaa acaaggcggt gccaagaagg agtcgatttt agacaagatt tacggcgaga    5340 gaaaaaggc gtacgaagag attgaaaaac agccaggtcg ctcgtttgcc gatttggagg    5400
cctatttgga gctatgtggt gccccagacg ttttgaactt ctacgaccgg ttaaatgaga    5460
acgtcaagca aggaaagcct gccatttga gtgaaatcaa gagagcctcg ccttcgaaag    5520
gggctattca gatgggtgcc aatgctgcaa acaggcgta cacctatgcc acggcggggg    5580
tttcggctat atccgttttg acagagccaa actggttcaa aggaacgatt gaggatttac    5640
gagttgcgcg tcagacggtt ggaaaactcc aacaccgtcc gtgcattttg cgcaaggagt    5700 tgtctttg caagtaccag attctggagg ccagactggc gggcgcagac actgttttgc    5760
tgattgtcaa gatgctttca ggagctgagt tgcgcgaact ggttggctat tcccggg    5817
```

<210> SEQ ID NO 78
<211> LENGTH: 663
<212> TYPE: PRT
<213> ORGANISM: Ogataea minuta

<400> SEQUENCE: 78

```
Met Ala Ile Pro Asp Glu Phe Asp Ile Ile Val Val Gly Gly Gly Ser
 1               5                  10                  15

Cys Gly Cys Ala Ile Ala Gly Arg Leu Gly Asn Leu Asp Pro Asp Val
                20                  25                  30

Thr Val Ala Leu Ile Glu Gly Gly Glu Asn Asn Ile Asn Asn Pro Trp
            35                  40                  45

Val Tyr Leu Pro Gly Val Tyr Pro Arg Asn Met Arg Leu Asp Ser Lys
        50                  55                  60

Thr Ala Thr Phe Tyr Asn Ser Arg Pro Ser Lys His Leu Asn Gly Arg
    65                  70                  75                  80

Arg Ala Ile Val Pro Cys Ala Asn Ile Leu Gly Gly Ser Ser Ile
                85                  90                  95

Asn Phe Leu Met Tyr Thr Arg Ala Ser Ala Ser Asp Tyr Asp Asp Trp
            100                 105                 110
```

-continued

| | | | | | | | | | | | | | |
|---|---|---|---|---|---|---|---|---|---|---|---|---|---|
|Glu|Gln|Glu|Gly|Trp|Thr|Thr|Asp|Glu|Leu|Leu|Pro|Leu|Met|Lys|Lys|
| |115| | | | |120| | | |125| | | |

Leu Glu Thr Tyr Gln Arg Pro Cys Asn Asn Arg Glu Val His Gly Phe
          130                 135                 140

Asp Gly Pro Ile Lys Val Ser Phe Gly Asn Tyr Thr Tyr Pro Thr Ala
145                 150                 155                 160

Gln Asp Phe Leu Arg Ala Cys Glu Ser Gln Gly Ile Pro Phe Asn Asp
              165                 170                 175

Asp Leu Glu Asp Leu Lys Ala Ser His Gly Ala Glu Tyr Trp Leu Lys
          180                 185                 190

Trp Ile Asn Arg Asp Leu Gly Arg Arg Ser Asp Ser Ala His Ala Tyr
          195                 200                 205

Ile His Pro Thr Met Arg Asn Lys Ser Asn Leu Phe Leu Ile Thr Ser
      210                 215                 220

Thr Lys Ala Asp Lys Val Ile Ile Glu Asn Gly Val Ala Val Gly Val
225                 230                 235                 240

Arg Thr Val Pro Met Lys Pro Val Glu Thr Lys Asn Pro Pro Ser Arg
                  245                 250                 255

Ile Phe Lys Ala Arg Lys Gln Ile Val Val Ser Cys Gly Thr Ile Ser
              260                 265                 270

Ser Pro Leu Val Leu Gln Arg Ser Gly Ile Gly Ala Ala His Lys Leu
          275                 280                 285

Arg Gln Ala Gly Ile Lys Pro Ile Val Asp Leu Pro Gly Val Gly Glu
          290                 295                 300

Asn Phe Gln Asp His Tyr Cys Phe Phe Thr Pro Tyr Tyr Ser Lys Pro
305                 310                 315                 320

Glu Val Pro Thr Phe Asp Asp Phe Val Arg Gly Asp Pro Val Ala Gln
                  325                 330                 335

Lys Ser Ala Phe Asp Gln Trp Tyr Ser Asn Lys Asp Gly Pro Leu Thr
              340                 345                 350

Thr Asn Gly Ile Glu Ala Gly Val Lys Ile Arg Pro Thr Asp Glu Glu
          355                 360                 365

Leu Ala Thr Ala Asp Asp Phe Ile Gln Gly Tyr His Glu Tyr Phe
          370                 375                 380

Asp Asn Lys Pro Asp Lys Pro Leu Met His Tyr Ser Val Ile Ser Gly
385                 390                 395                 400

Phe Phe Gly Asp His Thr Lys Ile Pro Asn Gly Lys Phe Phe Thr Met
              405                 410                 415

Phe His Phe Leu Glu Tyr Pro Phe Ser Arg Gly Phe Val Tyr Ala Val
              420                 425                 430

Ser Pro Asp Pro Tyr Glu Ala Pro Asp Phe Asp Pro Gly Phe Leu Asn
              435                 440                 445

Asp Ser Arg Asp Met Trp Pro Met Val Trp Ser Tyr Lys Lys Ser Arg
450                 455                 460

Gln Thr Ala Arg Arg Met Glu Ser Phe Ala Gly Glu Val Thr Ser His
465                 470                 475                 480

His Pro Leu Tyr Pro Val Asp Ser Pro Ala Arg Ala Lys Asp Leu Asp
              485                 490                 495

Leu Glu Thr Cys Lys Ala Phe Ala Gly Pro Asn His Phe Thr Ala Asn
          500                 505                 510

Leu Tyr His Gly Ser Trp Thr Val Pro Ile Glu Lys Pro Thr Pro Lys
          515                 520                 525

Asn Asp Ser His Val Thr Cys Asn Gln Val Glu Ile Phe Ser Asp Ile
530                 535                 540

```
Asp Tyr Ser Ala Glu Asp Glu Ala Ile Val Lys Tyr Ile Lys Glu
545                 550                 555                 560

His Thr Glu Thr Thr Trp His Cys Leu Gly Thr Cys Ser Met Ala Pro
                565                 570                 575

Gln Glu Gly Ser Lys Ile Ala Pro Lys Gly Gly Val Val Asp Ala Arg
            580                 585                 590

Leu Asn Val Tyr Glu Val Lys Asn Leu Lys Val Ala Asp Leu Ser Ile
        595                 600                 605

Cys Pro Asp Asn Val Gly Cys Asn Thr Tyr Thr Ala Leu Leu Ile
    610                 615                 620

Gly Glu Lys Ala Ala Thr Leu Val Ala Glu Asp Leu Gly Tyr Ser Gly
625                 630                 635                 640

Ser Asp Leu Ala Met Thr Ile Pro Asn Phe Lys Leu Gly Thr Tyr Glu
                645                 650                 655

Glu Lys Gly Leu Ala Arg Phe
            660
```

<210> SEQ ID NO 79
<211> LENGTH: 2348
<212> TYPE: DNA
<213> ORGANISM: Ogataea minuta

<400> SEQUENCE: 79

```
aagcttttctt tcgcaaacag ctctttggta gaggagaata gagtgcccag ctgataaaga      60
aggcgcactt taaagataa tctacatcca gaaaataaa aaaataaaac tgaaccggca        120
tttgcgatta cgtaagccac aaaatttcag gaaactcgta caagatcagg ttggcgaggg     180
ggctagcgat agaatgtatc agtgttatta gtggctctag gagtagaaaa caatagaata     240
aagatccgaa gaaagggagc aagaaggcca cgccagacgt tctagtaggt agcccaatcg     300
tcaatgtagc tgttcaggtc tttcaacagg ttcttggtct cgtctggact ggagatccaa     360
caagtcgttg ctgcggttcg actggcatag tcgttggcgc cgagggagct gaactggtcg     420
ccgacgtgca gggtgttttc gggcttgatg gttcggttgt cgttgcagct gaggaactct     480
tggaggattt tcaccccgta ggacttgtcg ccaatatcga cccagatgtc cgagcctccg     540
ttgaaagcgc accatctgat tttcttagag aagggaagt ggcggagacg tttgtctacg     600
cgcagaacca cctcttccag ctgctcgcga acgagtttgt agccttcttt ggggaccagt     660
ccaacggcac gctcctttct gatgatgatg gcatgcaatg aaagtttctt gatcaggtcc     720
gagaagatct cctgcgcaaa gtccagggtc cggatgatgt cttcctcgga ccagtcgagc     780
atgttttcaa gcagccattt gtcttttggag aagaactcga gtccgccaag ctcgttggag     840
tagcggaata ggtagtttgc ttcgcctccc atcaccagaa cgttctggcg ctgtctgtcg     900
gtgagctttg gggtggtctt cacctcgtct atgagcccct tgagtcgggc gtagtacttg     960
gagccgtcgg agtagcccgc ggcagtgacg atgccgacat agaggtcttt ggcgagcagc    1020
ttgatgagat ggggcaagat cggcgacgag gcgtcgaagt tggagccgtc atcgtagaga    1080
gtgatgtctc cgtcaaaagt cacgagctgg agtctgcggt gtacggatgt tttgttgtgg    1140
aaagtgttgg agagctcgag aagttgcgcc gtgttcagaa tgagccgaat gtcgttgaac    1200
gagggcgcta caagtctcct tttgctgatt gtgcggcgtc cgtcctcgat gtagaacgcc    1260
ttctccaggg gcaatcgggt gaagaaacag ccaacggaag gcaccaattg gaccaatctg    1320
gacatttcag gcattcccgc ctgggtcatc tcgatgttgt cgttgatcag cagctcgagg    1380
tcatggaaga tttccgcgta gcgtcgcttc gcttccgaat tcaccatgag gtcgtccact    1440
```

```
gcggagatcc cattggactt gactgcatag agaacaaacg gggtggccag caagcccttg    1500
atccactcaa tcagtccgtc tcggcggtgc tccttgagcg cgtactcgac tctgtatctg    1560
gttgtcattt gcgggagggg tgtaaagcag ctcagccggt gactgtgcaa ggacgaacgg    1620
ttcctacttg aatgctaggc tggctaattg ggtatggcac aaacggcaca aacggcagat    1680
gactgcaaat gacgacggta aacagaatcc actcagctgg cactaactgg gtgtagacta    1740
agagttcgag ccggggaggg agtgacgatg cagccagaaa aagagccggt acgcaatcag    1800
ggaaatagcc gtcaaaagaa aaacagaagg ggctgcagtt ttgctgccgc ccgccgcgcg    1860
cccgcgctgg cttccccgg ccggggaggc agccggctaa agaaaatagc ctatttcgat    1920
ttcgcgtagc ccctcggttg cctattgagg gttactttc gctccctctt ttgggccaac    1980
tgacagtttg tggggtaaca acggtgtccg aggccagcta ttcggcaaac aatagacaga    2040
ttagagacct actacggagt ttcagtgtct tcggaagctg cacagcccga atgtcggagc    2100
ccgtgtgacg acaccccgc atggcttttg gcaatctcac atcgccctc cctgcgtctc    2160 cactctgggc atgagcagtg gtgtgcctgg tgtatctctg gccccgcgg ggcagacagc    2220 aaactgcgta taaatagcta cttccatctc ctacttgttg caccattgcc atagtaagaa    2280
aagaagcaga tcactcaact tgttcaaaga ctcttgtgtt ctgttacgac ttacgactta    2340
cgaaaaaa                                                             2348

<210> SEQ ID NO 80
<211> LENGTH: 802
<212> TYPE: DNA
<213> ORGANISM: Ogataea minuta

<400> SEQUENCE: 80
gagacggtgc ccgactcttg ttcaattctt ttggttcttt ttctgttttt ctctacgatt      60
ctacttgatg atgtatgacg agtgaagatt gtgttttttt ctctctatag ttttgactgt     120
aatgaaaata gtctacatga atgaaagaga tagctgacca atacggggcg tctggtcacg     180
tgatgtatca cgtgatcttt aagttttcga aatgactaaa tttataacga aaaaagagt      240 ctaaatgaaa aaaaatcgat ctctgccaaa gactcatcga taggctaact caggaagcat     300
tccgagcaac gcataatgcc ctcaaccaca gtctcagaga tgcgcaaaaa ggtgctgatg     360
atcgacaatt acgactcgtt cacatggaac ttgtacgagt atctttgtca agagggagcc     420
gatgtcgagg tctatcgtaa cgacaagatc acaattgaag aaatcgagga atgaagcct      480 gacattatag tgatttcgcc aggccccgga catccgagat cggactctgg tatctctcga     540
aagactattg agattttcaa gggccggatt cctgttttg gagtgtgcat gggccaacag     600
tgcatttacg aggttttcgg gggagacgtt gagtacgctg gtgaaattgt tcacggaaaa     660
acctcttctg tgacccacga caatcgtgga gtcttcaaga acgttccgca gggagttgct     720
gtgacgagat accattcgtt ggctggaacg ctaaaaactt tgcccagcga gttggaggtg     780
actgcccgta ccactaacgg ta                                              802

<210> SEQ ID NO 81
<211> LENGTH: 30
<212> TYPE: DNA
<213> ORGANISM: Artificial Sequence
<220> FEATURE:
<223> OTHER INFORMATION: Description of Artificial Sequence: Synthetic
      primer OAP5 for production of an expression
      cassette with AOX1 gene promoter and terminator

<400> SEQUENCE: 81
```

```
ctgcagcccc ttctgttttt cttttgacgg                                    30

<210> SEQ ID NO 82
<211> LENGTH: 90
<212> TYPE: DNA
<213> ORGANISM: Artificial Sequence
<220> FEATURE:
<223> OTHER INFORMATION: Description of Artificial Sequence: Synthetic
      primer OAP3 for production of an expression
      cassette with AOX1 gene promoter and terminator

<400> SEQUENCE: 82
cccccggatc caggaacccg ggaacagaat ctagattttt tcgtaagtcg taagtcgtaa   60
cagaacacaa gagtctttga acaagttgag                                    90

<210> SEQ ID NO 83
<211> LENGTH: 47
<212> TYPE: DNA
<213> ORGANISM: Artificial Sequence
<220> FEATURE:
<223> OTHER INFORMATION: Description of Artificial Sequence: Synthetic
      primer OAT5 for production of an expression
      cassette with AOX1 gene promoter and terminator

<400> SEQUENCE: 83
ccccccggga tccgagacgg tgcccgactc ttgttcaatt cttttgg                 47

<210> SEQ ID NO 84
<211> LENGTH: 33
<212> TYPE: DNA
<213> ORGANISM: Artificial Sequence
<220> FEATURE:
<223> OTHER INFORMATION: Description of Artificial Sequence: Synthetic
      primer OAT3 for production of an expression
      cassette with AOX1 gene promoter and terminator

<400> SEQUENCE: 84
cccataatgg taccgttagt ggtacgggca gtc                                33

<210> SEQ ID NO 85
<211> LENGTH: 29
<212> TYPE: DNA
<213> ORGANISM: Artificial Sequence
<220> FEATURE:
<223> OTHER INFORMATION: Description of Artificial Sequence: Synthetic
      primer HGP5 for amplification of a gene conferring
      resistance against hygromycin B

<400> SEQUENCE: 85
gtcgacatga aaaagcctga actcaccgc                                     29

<210> SEQ ID NO 86
<211> LENGTH: 27
<212> TYPE: DNA
<213> ORGANISM: Artificial Sequence
<220> FEATURE:
<223> OTHER INFORMATION: Description of Artificial Sequence: Synthetic
      primer HGP3 for amplification of a gene conferring
      resistance against hygromycin B

<400> SEQUENCE: 86
actagtctat tcctttgccc tcggacg                                       27

<210> SEQ ID NO 87
<211> LENGTH: 39
<212> TYPE: DNA
<213> ORGANISM: Artificial Sequence
```

-continued

```
<220> FEATURE:
<223> OTHER INFORMATION: Description of Artificial Sequence: Synthetic
      primer for amplification of 5'-region of
      fi-mannosidase gene

<400> SEQUENCE: 87 gggggtcga catggtggtc ttcagcaaaa ccgctgccc                          39

<210> SEQ ID NO 88
<211> LENGTH: 43
<212> TYPE: DNA
<213> ORGANISM: Artificial Sequence
<220> FEATURE:
<223> OTHER INFORMATION: Description of Artificial Sequence: Synthetic
      primer for amplification of 5'-region of
      fi-mannosidase gene

<400> SEQUENCE: 88 gggggcggc cgcgtgatgt tgaggttgtt gtacggaacc ccc                     43

<210> SEQ ID NO 89
<211> LENGTH: 40
<212> TYPE: DNA
<213> ORGANISM: Artificial Sequence
<220> FEATURE:
<223> OTHER INFORMATION: Description of Artificial Sequence: Synthetic
      primer for amplification of Saccharomyces
      cerevisiae SUC2 gene

<400> SEQUENCE: 89
ggggactagt atgcttttgc aagctttcct tttccttttg                        40

<210> SEQ ID NO 90
<211> LENGTH: 39
<212> TYPE: DNA
<213> ORGANISM: Artificial Sequence
<220> FEATURE:
<223> OTHER INFORMATION: Description of Artificial Sequence: Synthetic
      primer for amplification of Saccharomyces
      cerevisiae SUC2 gene

<400> SEQUENCE: 90
ccccagatct tattttactt cccttacttg gaacttgtc                         39

<210> SEQ ID NO 91
<211> LENGTH: 711
<212> TYPE: DNA
<213> ORGANISM: Homo sapiens

<400> SEQUENCE: 91
ctcaccatga gggtccccgc tcagctcctg gggctcctgc tgctctggct cccaggtgca   60
cgatgtgaca tccagatgac ccagtctcca tcttccgtgt ctgcatctgt aggagacaga  120
gtcaccatca cttgtcgggc gagtcaggtt attagcagct ggttagcctg gtatcagcag  180
aaaccaggga agcccctaa gctcctgatc tatgctgcat ccagtttgca aagtggggtc   240
ccatcaaggt tcagcggcag tggatctggg acagatttca ctctcaccat cagcagcctg  300
cagcctgaag attttgcaac ttactattgt caacaggcta acagtttccc tccgacgttc  360
ggccaaggga ccaaggtgga aatcaaacgt acggtggctg caccatctgt cttcatcttc  420
ccgccatctg atgagcagtt gaaatctgga actgcctctg ttgtgtgcct gctgaataac  480
ttctatccca gagaggccaa agtacagtgg aaggtggata acgccctcca atcgggtaac  540
tcccaggaga gtgtcacaga gcaggacagc aaggacagca cctacagcct cagcagcacc  600
ctgacgctga gcaaagcaga ctacgagaaa cacaaagtct acgcctgcga agtcacccat  660
```
cagggcctga gctcgcccgt cacaaagagc ttcaacaggg gagagtgttg a        711

<210> SEQ ID NO 92
<211> LENGTH: 234
<212> TYPE: PRT
<213> ORGANISM: Homo sapiens

<400> SEQUENCE: 92

Met Arg Val Pro Ala Gln Leu Leu Gly Leu Leu Leu Trp Leu Pro
 1               5                  10                  15

Gly Ala Arg Cys Asp Ile Gln Met Thr Gln Ser Pro Ser Ser Val Ser
                20                  25                  30

Ala Ser Val Gly Asp Arg Val Thr Ile Thr Cys Arg Ala Ser Gln Val
            35                  40                  45

Ile Ser Ser Trp Leu Ala Trp Tyr Gln Gln Lys Pro Gly Lys Ala Pro
        50                  55                  60

Lys Leu Leu Ile Tyr Ala Ala Ser Ser Leu Gln Ser Gly Val Pro Ser
 65                 70                  75                  80

Arg Phe Ser Gly Ser Gly Ser Gly Thr Asp Phe Thr Leu Thr Ile Ser
                85                  90                  95

Ser Leu Gln Pro Glu Asp Phe Ala Thr Tyr Tyr Cys Gln Gln Ala Asn
            100                 105                 110

Ser Phe Pro Pro Thr Phe Gly Gln Gly Thr Lys Val Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230

<210> SEQ ID NO 93
<211> LENGTH: 1428
<212> TYPE: DNA
<213> ORGANISM: Homo sapiens

<400> SEQUENCE: 93
atgggttgga gcctcatctt gctcttcctt gtcgctgttg ctacgcgtgt ccagtctgag     60
gtgcagctgg tggagtctgg gggaggcctg gtcaagcctg ggggtccct gagactctcc    120 tgtgcagcct ctggattcac cttcagtagc tatagcatga actgggtccg ccaggctcca    180 gggaagggc tggagtgggt ctcatccatt agtagtagta gtagttacat atactacgca    240
gactcagtga aggccgatt caccatctcc agagacaacg ccaagaactc actgtatctg    300
caaatgaaca gcctgagagc cgaggacacg gctgtgtatt actgtgcgag agatcggatt    360
attatggttc ggggagtcta ctactactac ggtatggacg tctggggcca agggaccacg    420
gtcaccgtct cctcagctag caccaagggc ccatcggtct tccccctggc accctcctcc    480

```
aagagcacct ctgggggcac agcggccctg ggctgcctgg tcaaggacta cttccccgaa    540
ccggtgacgg tgtcgtggaa ctcaggcgcc ctgaccagcg gcgtgcacac cttcccggct    600
gtcctacagt cctcaggact ctactccctc agcagcgtgg tgaccgtgcc ctccagcagc    660
ttgggcaccc agacctacat ctgcaacgtg aatcacaagc ccagcaacac caaggtggac    720
aagaaagttg agcccaaatc ttgtgacaaa actcacacat gcccaccgtg cccagcacct    780
gaactcctgg ggggaccgtc agtcttcctc ttccccccaa aacccaagga caccctcatg    840
atctcccgga cccctgaggt cacatgcgtg gtggtggacg tgagccacga agaccctgag    900
gtcaagttca actggtacgt ggacggcgtg gaggtgcata atgccaagac aaagccgcgg    960
gaggagcagt acaacagcac gtaccgtgtg gtcagcgtcc tcaccgtcct gcaccaggac   1020
tggctgaatg gcaaggagta caagtgcaag gtctccaaca aagccctccc agcccccatc   1080
gagaaaacca tctccaaagc caagggcag ccccgagaac acaggtgta caccctgccc   1140 ccatcccggg atgagctgac caagaaccag gtcagcctga cctgcctggt caaaggcttc   1200
tatcccagcg acatcgccgt ggagtgggag agcaatgggc agccggagaa caactacaag   1260
accacgcctc ccgtgctgga ctccgacggc tccttcttcc tctacagcaa gctcaccgtg   1320
gacaagagca ggtggcagca ggggaacgtc ttctcatgct ccgtgatgca tgaggctctg   1380
cacaaccact acacgcagaa gagcctctcc ctgtctccgg gtaaatga                1428
```

<210> SEQ ID NO 94
<211> LENGTH: 475
<212> TYPE: PRT
<213> ORGANISM: Homo sapiens
<400> SEQUENCE: 94

```
Met Gly Trp Ser Leu Ile Leu Leu Phe Leu Val Ala Val Ala Thr Arg
  1               5                  10                  15

Val Gln Ser Glu Val Gln Leu Val Glu Ser Gly Gly Gly Leu Val Lys
             20                  25                  30

Pro Gly Gly Ser Leu Arg Leu Ser Cys Ala Ala Ser Gly Phe Thr Phe
         35                  40                  45

Ser Ser Tyr Ser Met Asn Trp Val Arg Gln Ala Pro Gly Lys Gly Leu
     50                  55                  60

Glu Trp Val Ser Ile Ser Ser Ser Ser Tyr Ile Tyr Tyr Ala
 65                  70                  75                  80

Asp Ser Val Lys Gly Arg Phe Thr Ile Ser Arg Asp Asn Ala Lys Asn
                 85                  90                  95

Ser Leu Tyr Leu Gln Met Asn Ser Leu Arg Ala Glu Asp Thr Ala Val
            100                 105                 110

Tyr Tyr Cys Ala Arg Asp Arg Ile Ile Met Val Arg Gly Val Tyr Tyr
        115                 120                 125

Tyr Tyr Gly Met Asp Val Trp Gly Gln Gly Thr Thr Val Thr Val Ser
    130                 135                 140

Ser Ala Ser Thr Lys Gly Pro Ser Val Phe Pro Leu Ala Pro Ser Ser
145                 150                 155                 160

Lys Ser Thr Ser Gly Gly Thr Ala Ala Leu Gly Cys Leu Val Lys Asp
                165                 170                 175

Tyr Phe Pro Glu Pro Val Thr Val Ser Trp Asn Ser Gly Ala Leu Thr
            180                 185                 190

Ser Gly Val His Thr Phe Pro Ala Val Leu Gln Ser Ser Gly Leu Tyr
        195                 200                 205

Ser Leu Ser Ser Val Val Thr Val Pro Ser Ser Ser Leu Gly Thr Gln
```

```
                210                 215                 220
Thr Tyr Ile Cys Asn Val Asn His Lys Pro Ser Asn Thr Lys Val Asp
225                 230                 235                 240

Lys Lys Val Glu Pro Lys Ser Cys Asp Lys Thr His Thr Cys Pro Pro
                245                 250                 255

Cys Pro Ala Pro Glu Leu Leu Gly Gly Pro Ser Val Phe Leu Phe Pro
                260                 265                 270

Pro Lys Pro Lys Asp Thr Leu Met Ile Ser Arg Thr Pro Glu Val Thr
                275                 280                 285

Cys Val Val Val Asp Val Ser His Glu Asp Pro Glu Val Lys Phe Asn
290                 295                 300

Trp Tyr Val Asp Gly Val Glu Val His Asn Ala Lys Thr Lys Pro Arg
305                 310                 315                 320

Glu Glu Gln Tyr Asn Ser Thr Tyr Arg Val Val Ser Val Leu Thr Val
                325                 330                 335

Leu His Gln Asp Trp Leu Asn Gly Lys Glu Tyr Lys Cys Lys Val Ser
                340                 345                 350

Asn Lys Ala Leu Pro Ala Pro Ile Glu Lys Thr Ile Ser Lys Ala Lys
                355                 360                 365

Gly Gln Pro Arg Glu Pro Gln Val Tyr Thr Leu Pro Pro Ser Arg Asp
                370                 375                 380

Glu Leu Thr Lys Asn Gln Val Ser Leu Thr Cys Leu Val Lys Gly Phe
385                 390                 395                 400

Tyr Pro Ser Asp Ile Ala Val Glu Trp Glu Ser Asn Gly Gln Pro Glu
                405                 410                 415

Asn Asn Tyr Lys Thr Thr Pro Pro Val Leu Asp Ser Asp Gly Ser Phe
                420                 425                 430

Phe Leu Tyr Ser Lys Leu Thr Val Asp Lys Ser Arg Trp Gln Gln Gly
                435                 440                 445

Asn Val Phe Ser Cys Ser Val Met His Glu Ala Leu His Asn His Tyr
                450                 455                 460

Thr Gln Lys Ser Leu Ser Leu Ser Pro Gly Lys
465                 470                 475

<210> SEQ ID NO 95
<211> LENGTH: 7
<212> TYPE: PRT
<213> ORGANISM: Saccharomyces cerevisiae

<400> SEQUENCE: 95

Val Gly Phe Leu Asp His Met
 1               5

<210> SEQ ID NO 96
<211> LENGTH: 7
<212> TYPE: PRT
<213> ORGANISM: Saccharomyces cerevisiae

<400> SEQUENCE: 96

Pro Ser Thr Lys Gly Val Leu
 1               5

<210> SEQ ID NO 97
<211> LENGTH: 20
<212> TYPE: DNA
<213> ORGANISM: Artificial Sequence
<220> FEATURE:
<223> OTHER INFORMATION: Description of Artificial Sequence: Synthetic
      primer PHI5 for amplification of Ogataea minuta
```

-continued

```
      HIS3 gene
<220> FEATURE:
<221> NAME/KEY: modified_base
<222> LOCATION: (2)
<223> OTHER INFORMATION: a, c, g or t
<220> FEATURE:
<221> NAME/KEY: modified_base
<222> LOCATION: (5)
<223> OTHER INFORMATION: a, c, g or t
<220> FEATURE:
<221> NAME/KEY: modified_base
<222> LOCATION: (11)
<223> OTHER INFORMATION: a, c, g or t

<400> SEQUENCE: 97
tnggnttyyt ngaycayatg                                           20

<210> SEQ ID NO 98
<211> LENGTH: 20
<212> TYPE: DNA
<213> ORGANISM: Artificial Sequence
<220> FEATURE:
<223> OTHER INFORMATION: Description of Artificial Sequence: Synthetic
      primer PHI3 for amplification of Ogataea minuta
      HIS3 gene
<220> FEATURE:
<221> NAME/KEY: modified_base
<222> LOCATION: (3)
<223> OTHER INFORMATION: a, c, g or t
<220> FEATURE:
<221> NAME/KEY: modified_base
<222> LOCATION: (6)
<223> OTHER INFORMATION: a, c, g or t
<220> FEATURE:
<221> NAME/KEY: modified_base
<222> LOCATION: (12)
<223> OTHER INFORMATION: a, c, g or t
<220> FEATURE:
<221> NAME/KEY: modified_base
<222> LOCATION: (15)
<223> OTHER INFORMATION: a, c, g or t
<220> FEATURE:
<221> NAME/KEY: modified_base
<222> LOCATION: (18)
<223> OTHER INFORMATION: a, c, g or t

<400> SEQUENCE: 98
arnacnccyt tngtnswngg                                           20

<210> SEQ ID NO 99
<211> LENGTH: 3831
<212> TYPE: DNA
<213> ORGANISM: Ogataea minuta

<400> SEQUENCE: 99
ctgcagatgc gccgttgctg ctgagcaaag tgaaagagca cagagccaaa attgcctctg    60
ttttggaaca gattgacccg aagttggagg aactgaacaa agaaaaagaa gctcacattt   120
ccagtgaaga tatccgggac ggttggaaca gctctttat caacaagaaa tctgagattg    180
aggaaccagc gtccaacaca aaaagcgact ctgcttcgtc tgtcaagaag accaaggcga   240
tagagaccat taacagtcca aaattgtcga agaaccgac cccgtccaaa ccgttagacc     300
aattgggcga gctggaactg ttggaagaga ccgaacgatt cgcccagatc tcgtctcaag   360
acctgcttaa atcgatcaag tttcttgaga gacatctata catagtgagc gagcagcaga   420
aggacgcgtt gatgatgaag tgttttgact acgagctgga cggtgactcc cagcgtgcca   480
aacagagcgt tcaccaggcg ctgattctgc aatatttgga tgatcgttc aaagccgctg     540 gcggcccgcg cgccagtcca caccagaagg agcaggctat tggtctgttc attgggaaac   600
```

```
tgcttgacaa aacgacgcct gcctcgcggg cttttgaggc cgattggaag aagacttatc    660
atcacattgt ttccagatgc gagattatca agcaagaaca cgaacaagag ggccaagaag    720
agcccgaggg ggttgaacag atacagctga gatccatgga ccccaactcg gagctggtga    780
tcaacctgcc ttcccagaaa accccggagt acgaggcttt caagcaacta ccggagccaa    840
tgcagaaggc gattgaaacc gaaaaattgg acgaaatcaa ccgtgttttt gcctccatgt    900
cggtggaaga cgccgagggt gttttggaac tgtttgaccg ctgcggggtg attcagatac    960
aggcattgct ggagaacgag gaggagttca accagttgaa acatgagtac gagggagaac   1020
ctcttgagca aatcgaagaa gagcgaccac aaaccgcaaa ggaagagaac gcttttatac   1080
aaacagctga ccttgttgat tgaagctcaa attacgctaa acgatatata catgtcaatt   1140
gcacttaatc catattttttg agaggaggca ttcaagaat ctctctagtt ttgttctcgc    1200
```

```
gcaggcgctc tgggagttta ttcctactac tacgagaacc agcgtgagtc cttcaacaga    3060
gcccgtctga cctcccctat acgatccggt tctcctcaaa ctaagctcac tgccagaccg    3120
tccaaggtgt ccgaggtttc cggcccaatc aacttaatca actcaatgtc gtctcctata    3180
ccccatttgc cctcttctcc gacgcctcgc atgtcccgtt ctaacggcca cgccaatgga    3240
caatctccca caactccgtt caagacagca gatatgccgt cacgagtcag cacgccgtcg    3300
tcgtactcgc gacagctggg ctcgccgccc aaactcgacc tggtgaaccc tgccccggtg    3360
acggacgagg aactcatggt gacgagccgc gagctcattc aggacgcaat gcgctcaaga    3420
agcgtacaca gagagcct tc gcagctggaa ctgtggatca agtgatgtc gttgctcacg    3480 ggaaaagata aggtagggaa gtgtcttcaa tacggaatac ggattctgat cgcatactcg    3540
gtccgggcca ggaagacgcc cttcctgtcc gacttcaagc tcacgggcgt tgacttcacg    3600
gggtccaaag agaacgttct gttgcagctg gtgcggaaac agaactgct ggtgattctg    3660 tttctaggcc agtttgagtc caaactcgtc gggcttacca aaatcctctc catctacaga    3720
cagatgctgc gagccggtac tgttccgttc aaggtaatca aactgttcgg cagactgaca    3780
gactcagttc agatactcag cacaaacgat aaggcgtctt tgaagctgca g              3831
```

<210> SEQ ID NO 100
<211> LENGTH: 238
<212> TYPE: PRT
<213> ORGANISM: Ogataea minuta

<400> SEQUENCE: 100

```
Met Ser Glu Glu Asn Lys Lys Arg Lys Leu Glu Asn Gly Thr Asn Asp
 1               5                   10                  15

Ala Lys Ala Ala Arg Phe Ala Glu Val Arg Arg Val Thr Asn Glu Thr
             20                  25                  30

Ser Ile Gln Ile Ile Leu Asn Leu Asp Gly Gly Leu Ile Glu Cys Lys
         35                  40                  45

Glu Ser Ile Leu Gly Ala Thr Tyr Glu Lys Glu Ser His Ala Ala Gln
     50                  55                  60

Asn Thr Ser Ala Gln Val Ile Ser Ile Lys Thr Gly Leu Gly Phe Leu
 65                  70                  75                  80

Asp His Met Leu His Ala Leu Ala Lys His Ser Gly Trp Ser Leu Ile
                 85                  90                  95

Val Glu Cys Ile Gly Asp Leu His Ile Asp Asp His His Thr Ala Glu
            100                 105                 110

Asp Val Gly Ile Ala Leu Gly Glu Thr Phe Lys Arg Ala Leu Gly Pro
        115                 120                 125

Val Lys Gly Leu Lys Arg Phe Gly His Ala Tyr Ala Pro Leu Asp Glu
    130                 135                 140

Ala Leu Ser Arg Ala Val Val Asp Leu Ser Asn Arg Pro Phe Ala Val
145                 150                 155                 160

Val Glu Leu Gly Leu Arg Arg Glu Lys Ile Gly Asp Leu Ser Cys Glu
                165                 170                 175

Met Ile Pro His Val Leu Glu Ser Phe Ala Thr Ser Ala His Ile Thr
            180                 185                 190

Met His Val Asp Cys Leu Arg Gly Phe Asn Asp His His Arg Ser Glu
        195                 200                 205

Ser Ala Phe Lys Ala Leu Ala Val Ala Ile Arg Asp Ala Thr Ser Tyr
    210                 215                 220

Thr Gly Arg Asp Asp Val Pro Ser Thr Lys Gly Val Leu Met
225                 230                 235
```

<210> SEQ ID NO 101
<211> LENGTH: 20
<212> TYPE: DNA
<213> ORGANISM: Artificial Sequence
<220> FEATURE:
<223> OTHER INFORMATION: Description of Artificial Sequence: Synthetic
      primer DHI5

<400> SEQUENCE: 101
ggcccaatag tagatatccc                                              20

<210> SEQ ID NO 102
<211> LENGTH: 21
<212> TYPE: DNA
<213> ORGANISM: Artificial Sequence
<220> FEATURE:
<223> OTHER INFORMATION: Description of Artificial Sequence: Synthetic
      primer DHI3

<400> SEQUENCE: 102
cacggcccgt gtagctcgtg g                                            21

<210> SEQ ID NO 103
<211> LENGTH: 8
<212> TYPE: PRT
<213> ORGANISM: Saccharomyces cerevisiae

<400> SEQUENCE: 103

Ala Val Gly Gly Pro Lys Trp Gly
 1               5

<210> SEQ ID NO 104
<211> LENGTH: 7
<212> TYPE: PRT
<213> ORGANISM: Saccharomyces cerevisiae

<400> SEQUENCE: 104

Ala Ala Met Met Leu Lys Leu
 1               5

<210> SEQ ID NO 105
<211> LENGTH: 23
<212> TYPE: DNA
<213> ORGANISM: Artificial Sequence
<220> FEATURE:
<223> OTHER INFORMATION: Description of Artificial Sequence: Synthetic
      primer PLE5 for amplification of Ogataea minuta
      LEU2 gene
<220> FEATURE:
<221> NAME/KEY: modified_base
<222> LOCATION: (3)
<223> OTHER INFORMATION: a, c, g or t
<220> FEATURE:
<221> NAME/KEY: modified_base
<222> LOCATION: (6)
<223> OTHER INFORMATION: a, c, g or t
<220> FEATURE:
<221> NAME/KEY: modified_base
<222> LOCATION: (9)
<223> OTHER INFORMATION: a, c, g or t
<220> FEATURE:
<221> NAME/KEY: modified_base
<222> LOCATION: (12)
<223> OTHER INFORMATION: a, c, g or t
<220> FEATURE:
<221> NAME/KEY: modified_base
<222> LOCATION: (15)
<223> OTHER INFORMATION: a, c, g or t

<400> SEQUENCE: 105

```
<210> SEQ ID NO 106
<211> LENGTH: 21
<212> TYPE: DNA
<213> ORGANISM: Artificial Sequence
<220> FEATURE:
<223> OTHER INFORMATION: Description of Artificial Sequence: Synthetic
      primer PLE3 for amplification of Ogataea minuta
      LEU2 gene
<220> FEATURE:
<221> NAME/KEY: modified_base
<222> LOCATION: (1)
<223> OTHER INFORMATION: a, c, g or t
<220> FEATURE:
<221> NAME/KEY: modified_base
<222> LOCATION: (7)
<223> OTHER INFORMATION: a, c, g or t
<220> FEATURE:
<221> NAME/KEY: modified_base
<222> LOCATION: (16)
<223> OTHER INFORMATION: a, c, g or t
<220> FEATURE:
<221> NAME/KEY: modified_base
<222> LOCATION: (19)
<223> OTHER INFORMATION: a, c, g or t

<400> SEQUENCE: 106
naryttnarc atcatngcng c                                               21

<210> SEQ ID NO 107
<211> LENGTH: 5615
<212> TYPE: DNA
<213> ORGANISM: Ogataea minuta

<400> SEQUENCE: 107
```

| | | | | |
|---|---|---|---|---|
| ggatccttcc | tcgagatccg | ggctgttttt | caccgaccca | tccgatcctg | acttcaaccc     60 |
| cgacttctcc | tacgacagac | tgtgggagtg | tctcgtcagg | gcagaacaga | tgaccggtga    120 |
| cgagaaagag | ctgctcaggt | cgaacgccaa | ttacgttgcg | aaaaccaagt | tggaaagaa     180 |
| ggttttcggc | gaacaatgga | ccaagctgct | cgcctttgtt | gtcagcttgg | agctgtacaa    240 |
| aagacgccag | cgggggaagg | tggaggagct | gtattgaata | aggaatgagg | agaatggttt    300 |
| tggaaagagc | cagtttatac | atccgtacac | cggatctaac | aactgttttc | acgaaatgca    360 |
| cgacttttca | atttttttt  | ttacttctaa | aattttttat | ctctaaaaag | ctgtagatct    420 |
| aagggtatgt | gtgttgtatt | tgcagcagtc | cacttagcaa | gaacacacac | acacgaatga    480 |
| ctgaagttgg | ccagaaactg | aacagcaacc | ctgaggttct | tctcaagaag | agaaagcaag    540 |
| ccgacagact | ccgtctggag | aaacaggaac | aggctagaaa | gagaatcgaa | gacaaaaaga    600 |
| gaaagaagca | ggaaagaaga | aaggccaagt | tcatcagagc | agagacacta | gttgccaagc    660 |
| acagaaccac | tgaaagagag | cagtacagag | tgaaaagagt | gacgcagaac | gagaaaatca    720 |
| agaccgaaac | cgagtccgcc | aagcaagaag | cagctgggga | ggatgaatcc | aagcttcttt    780 |
| tcgttgtgag | agtgccaggc | ccgcacggtg | ccaaggttcc | aggaaaagcc | agaaaggttc    840 |
| tgtcgttgct | gcgtcttgaa | cacacctaca | cgggaacttt | cataaagtcc | aatgccacca    900 |
| taagacctct | tttgagactg | atcaacccgt | atgtggtgat | tggaactcct | tcgctggcca    960 |
| ctgtgagaaa | cctgatacaa | aagagagcta | cagtgaccgt | gacaagcgaa | gacggttctg   1020 |
| ctagagaggt | taacttggat | gacaacaatc | tcatcgaaga | gaaattggga | gagtgtggta   1080 |
| tcatttgcgc | agaagatctt | attcacgaga | tcgtctcttt | gggagactac | ttcaagccct   1140 |
| ccgtcaagtt | cctgaatcct | ttccaactga | acgctcctgt | ccacggctgg | ggtccgctca   1200 |

```
gtaagttaaa gagactcgag ctgagagaag agagcaagaa ccacaaggtg aacaacgctg    1260
gaaacgctcc tttgaacgag gttgacattg accagttcat cgctgagcag atctgagggt    1320
atttaagtaa gcatgttcga gtaatgacaa gatctgtcca cagtaagatt tgaaataatg    1380
gtctatcaat ctcgcgtcga tcgacgcgcg acgcctggcc gcttccctcc ggtttccggc    1440
gccgccagct cctgcgaccg gagaatattg ttttttatct tgattttccg aggggattga    1500
gcattaattt ttcacccaca aaatagctag atttcggttt tcaggagcta cagagtcatc    1560
gtgaacagaa ttgtgacctt ttatcgcagc ttttttacat tcagaatgac cacaaagaac    1620
atagttttgc tgcctggtga ccacgttggc ccggaggttg ttgacgaggc cgtcaaagtt    1680
ctcaacgcca tttcggccgc caagccggaa atcaagttca acttcgaaca ccacttgatc    1740
gggggtgctg ctatcgacgc cactggccag ccaatcacag acgcggctct cgaggcttcc    1800
aagaaagcag atgctgtcct gctaggatct gtcggaggtc ctaaatgggg tactggtcaa    1860
gttcgtcctg agcaagggtt gctgaagatc agaaaagagc tcaacttgta cgccaacctg    1920
agaccgtgca gctttgcatc ggacgccttg ttggacctgt cgcctctgaa gccggaaatt    1980
gtcagaggta ccgacttcgt tgttgtcaga gagcttgttg gaggaatcta cttcggtgag    2040
agaaaggagg acgacggatc aggattcgct tccgacactg aggcctactc cgtgcccgaa    2100
gttcaaagaa tcaccagaat ggctgctttc atggccctgc aaagtgaccc ccctctccca    2160
gtgtattcgc tggacaaggc caacgttctg gcttcgtccc gtctgtggag aaagaccgtt    2220
gaagagacta tcaagaacga gtttcctcag ctgaagctgc aacaccatct gatcgactca    2280
gccgctatga ttttggtgaa gtccccaacc aaactgaacg tgttgttct cacatccaac     2340 atgtttggag acatcatctc tgacgaagct tcggtgattc ccggttcgct gggcctgctg    2400
ccgtccgcat ctctggcttc tcttccagac tccaacgagg cgttcggtct gtacgagcct    2460
tgccacggtt ccgctcccga tctcgccaaa ggactggtga accgctggc taccattctc     2520 tcggccgcca tgatgctcaa gttgtcgctc aaccttgttg aggagggccg tgccgtcgaa    2580
aaggctgtca gagccgttct ggaccaaggc atcatgactg cagacttggg cggatcgtcg    2640
tcgaccactg aggttggaga cgctgttgcc aaggaagtga ccaaattgct gggctaaagg    2700
ggtcaatttt gtcctgatcc ggcagagatt gttccatgca ctcgtcgagc ttccatgcag    2760
cgagcaacct gtccctcgtg tagcagctgt tcccctcaat atactggtgg ctcgccctat    2820
agtgagccag ctaccttctt ctataaatag cctaggcata cccgaatttc ttttgctccc    2880
cgagaacgta gcccgacgcg cgcctgaaca atagaaaaaa ttacaaacaa tagcggctcc    2940
aaaaatctat tgtcggagcg ttttttcaca gacttctatt cgaggtttgg tgatcctgtt    3000 tgttttttgtt ttgttgttat atgtcaccaa tcgtgaaatt ttcagacccg tagttcaacc    3060
ttgtcaggaa ctcaatcact ggttcaagtc tctgccaatc gcctcggcac aaactactcc    3120
cgtcctgcat ttcatcctct tctgaacggt tgcaagcact ctaggtgttt cagaattggc    3180
tgtacgacaa gcaacacaag gcaacaccag gcagcaaaac aagcaaaaca agcaaaaaaa    3240
ggcaccgtca attggaacaa cctgttgaac ggtgatagca tcacgtgtct ttgaaataac    3300
gaaacagcat cctcattcaa caccctgac ctgtatttct ctggctccat cctgttccac     3360
gatgacagcc tcctgcggtc cgttcaagct cgcactcagt ctgctgttga tctcgccatc    3420
gacgctcgca tccttctcgt acttgggatg ctactcctcg tcttccgtcg actcccttc     3480 gctgtcggac tcatacatct accagtcctc gttgcattgc aagtcgcaat gctccggtag    3540
cgcggtggcc gctctgaccg gcggaaataa gtgctattgc ggcgactcag taccttctgg    3600
```

```
cgacgccagc agcgactcca aatgctcgac cgcctgtgac gggtacggct cggaaaactg    3660
cggtggcagc gggtactatt cggtgtatgt tgactccgac caagaaaacg actcgagctc    3720
gggatcgtcc agttcggaaa ccaccagctc acaagctcc acaagctcca ccagctccag    3780
ctccacctcg agttctacct cgacaagttc aagctcaaca agctcaacga gctcgtccac    3840
tttgacgagc tcctcctctt cgtcatcatc aacttcgacg tcgagctcct ccgcttcgtc    3900
ggtctctgaa ataatcacca gttcggcttc ggaaacctcc tccgagacaa ccagcacccc    3960
atcaacctca tcatcgtcct cgtcgtcatc gtcatcgtca tccgcatcgt cctcttcgtc    4020
gtcctctacg acgtcgacca cgtcttcatc ctcgtcctcg atctcctcta catcagccac    4080
aacctcagcc acaacatcag ccacaccaac aacaacctct ccggctgtgc tcgtttccac    4140
ctctgtttcc cccggagcaa ccatgacgtc tctgatctac atcacccagt cgatctccgc    4200
ttccagcggg ctgccatcgc cctcttcatc ggcaagcacg ggcaacagct cggcccacga    4260
ctcaaaaaaa tcctcctcgg gctccaagct tagcggagga gctatagccg gaatagtcat    4320
cggagtcatt gtgggggtgg cagcgctcat cgcagccgtc ctcttttttc tgtggtacaa    4380
gaaaagatcc gacgaagacg aagagtccat caacgaaaaa gacgttccgg agatgctcaa    4440
ttcgccgaga aacaccgttt ctggcctcac ggccgccgca atcggagtca ataagttcgg    4500
cttcctcagc gaagacgacc gactggacca cccgggagca aaccgaagat tcagcgacgg    4560
ttcgctgcca aacgcagcgg ccggagcccc cggtgaccaa tcgcgcaagt ccaaagccgg    4620
aggtcttagg gttatcaatc cagacctcag tgacgaagaa tgaaaaattg tttcttgtct    4680
tttacggtcg agttcgtccc gttaattagc atatccctcc ttttgtatgg ttattcccca    4740
acatccttcc gaacactgtg tattttaaac cggcctgtct gcttgttagc gtctaggcta    4800
cttggtggcg ttctggagtg cttcttctta cgtctttcaa tataatcttg actacttatt    4860
caagcctcga atagtataat ttggggagat ccagtcacaa gagtacaata tacacaaaaa    4920
cgctcaaaaa caggtccaat ctccgtactt tgggggtgtc cttaacctta atgaccagcc    4980
cactcgatcg agttcaaatc aatacccctcg ttcaccatct cccacagcgg actcaattct    5040
ctcaaaaact tgacccgctc ggtcagcgct ttcacaacgt aatcaacctc ctcctcggtg    5100
gtaaatcttc caacaccgaa tctgatcgaa gagtgggcca aagcgtcgtc cgcacccaac    5160
gcgtgcaaaa catatgatgg ctccaacgag gcggaagtac atgccgaccc cgaggaaaga    5220
gcaatgtcct tcaacgccat caacagcgac tcaccctcca cgtacgcgaa cgaaacgttc    5280
acacagccgg ggtaccggcg tgttttggaa ccgttcagtt gcgtgtgttc catggccaga    5340
agattgttca tcaatttgtt cgacaaccgg gtgatatgct cgtggtcggc gtcgtactcg    5400
gattgcatca atctggcagc ctctccaaat ccacaaacaa gcggaggagc cagagttccc    5460
gacctcagtc ctcttttcctg tcctcctccg ttgatcaatg ggtccagccg gacacggggt    5520
cttcttctca cgtaacaagc acccactccc atcggcccgt aaatcttgtg cgacgaaatg    5580
gacatcaggt caatgttgca cttgttcaca tcgat                              5615
```

<210> SEQ ID NO 108
<211> LENGTH: 363
<212> TYPE: PRT
<213> ORGANISM: Ogataea minuta

<400> SEQUENCE: 108

Met Thr Thr Lys Asn Ile Val Leu Leu Pro Gly Asp His Val Gly Pro
 1               5                  10                  15

-continued

```
Glu Val Val Asp Glu Ala Val Lys Val Leu Asn Ala Ile Ser Ala Ala
            20                  25                  30
Lys Pro Glu Ile Lys Phe Asn Phe Glu His His Leu Ile Gly Gly Ala
            35                  40                  45
Ala Ile Asp Ala Thr Gly Gln Pro Ile Thr Asp Ala Ala Leu Glu Ala
        50                  55                  60
Ser Lys Lys Ala Asp Ala Val Leu Leu Gly Ser Val Gly Gly Pro Lys
65                  70                  75                  80
Trp Gly Thr Gly Gln Val Arg Pro Glu Gln Gly Leu Leu Lys Ile Arg
                85                  90                  95
Lys Glu Leu Asn Leu Tyr Ala Asn Leu Arg Pro Cys Ser Phe Ala Ser
            100                 105                 110
Asp Ala Leu Leu Asp Leu Ser Pro Leu Lys Pro Glu Ile Val Arg Gly
            115                 120                 125
Thr Asp Phe Val Val Arg Glu Leu Val Gly Gly Ile Tyr Phe Gly
            130                 135                 140
Glu Arg Lys Glu Asp Asp Gly Ser Gly Phe Ala Ser Asp Thr Glu Ala
145                 150                 155                 160
Tyr Ser Val Pro Glu Val Gln Arg Ile Thr Arg Met Ala Ala Phe Met
                165                 170                 175
Ala Leu Gln Ser Asp Pro Pro Leu Pro Val Tyr Ser Leu Asp Lys Ala
            180                 185                 190
Asn Val Leu Ala Ser Ser Arg Leu Trp Arg Lys Thr Val Glu Glu Thr
            195                 200                 205
Ile Lys Asn Glu Phe Pro Gln Leu Lys Leu Gln His His Leu Ile Asp
        210                 215                 220
Ser Ala Ala Met Ile Leu Val Lys Ser Pro Thr Lys Leu Asn Gly Val
225                 230                 235                 240
Val Leu Thr Ser Asn Met Phe Gly Asp Ile Ile Ser Asp Glu Ala Ser
                245                 250                 255
Val Ile Pro Gly Ser Leu Gly Leu Leu Pro Ser Ala Ser Leu Ala Ser
            260                 265                 270
Leu Pro Asp Ser Asn Glu Ala Phe Gly Leu Tyr Glu Pro Cys His Gly
            275                 280                 285
Ser Ala Pro Asp Leu Ala Lys Gly Leu Val Asn Pro Leu Ala Thr Ile
        290                 295                 300
Leu Ser Ala Ala Met Met Leu Lys Leu Ser Leu Asn Leu Val Glu Glu
305                 310                 315                 320
Gly Arg Ala Val Glu Lys Ala Val Arg Ala Val Leu Asp Gln Gly Ile
                325                 330                 335
Met Thr Ala Asp Leu Gly Gly Ser Ser Ser Thr Thr Glu Val Gly Asp
            340                 345                 350
Ala Val Ala Lys Glu Val Thr Lys Leu Leu Gly
        355                 360

<210> SEQ ID NO 109
<211> LENGTH: 20
<212> TYPE: DNA
<213> ORGANISM: Artificial Sequence
<220> FEATURE:
<223> OTHER INFORMATION: Description of Artificial Sequence: Synthetic
      primer DL5

<400> SEQUENCE: 109
caggagctac agagtcatcg                                              20
```

```
<210> SEQ ID NO 110
<211> LENGTH: 20
<212> TYPE: DNA
<213> ORGANISM: Artificial Sequence
<220> FEATURE:
<223> OTHER INFORMATION: Description of Artificial Sequence: Synthetic
      primer DL3

<400> SEQUENCE: 110
acgagggaca ggttgctcgc                                                 20

<210> SEQ ID NO 111
<211> LENGTH: 8
<212> TYPE: PRT
<213> ORGANISM: Saccharomyces cerevisiae

<400> SEQUENCE: 111

Asp Thr Gly Ser Ser Asp Leu Trp
 1               5

<210> SEQ ID NO 112
<211> LENGTH: 8
<212> TYPE: PRT
<213> ORGANISM: Saccharomyces cerevisiae

<400> SEQUENCE: 112

Phe Gly Ala Ile Asp His Ala Lys
 1               5

<210> SEQ ID NO 113
<211> LENGTH: 24
<212> TYPE: DNA
<213> ORGANISM: Artificial Sequence
<220> FEATURE:
<223> OTHER INFORMATION: Description of Artificial Sequence: Synthetic
      primer PLE5 for amplification of Ogataea minuta YPS1 gene
<220> FEATURE:
<221> NAME/KEY: modified_base
<222> LOCATION: (6)
<223> OTHER INFORMATION: a, c, g or t
<220> FEATURE:
<221> NAME/KEY: modified_base
<222> LOCATION: (12)
<223> OTHER INFORMATION: a, c, g or t
<220> FEATURE:
<221> NAME/KEY: modified_base
<222> LOCATION: (15)
<223> OTHER INFORMATION: a, c, g or t
<220> FEATURE:
<221> NAME/KEY: modified_base
<222> LOCATION: (21)
<223> OTHER INFORMATION: a, c, g or t

<400> SEQUENCE: 113
gayacngght cntcngayyt ntgg                                            24

<210> SEQ ID NO 114
<211> LENGTH: 23
<212> TYPE: DNA
<213> ORGANISM: Artificial Sequence
<220> FEATURE:
<223> OTHER INFORMATION: Description of Artificial Sequence: Synthetic
      primer PLE3 for amplification of Ogataea minuta YPS1 gene
<220> FEATURE:
<221> NAME/KEY: modified_base
<222> LOCATION: (9)
<223> OTHER INFORMATION: a, c, g or t
<220> FEATURE:
<221> NAME/KEY: modified_base
<222> LOCATION: (21)
<223> OTHER INFORMATION: a, c, g or t
```

<400> SEQUENCE: 114
ttygghgcna tygaycaygc naa                                        23

<210> SEQ ID NO 115
<211> LENGTH: 3661
<212> TYPE: DNA
<213> ORGANISM: Ogataea minuta

<400> SEQUENCE: 115

| | | | | | |
|---|---|---|---|---|---|
| gaattcacca | gttatctgga | cgaggcttgt | gtttcagacg | agttgctgta | cagtcaaatt | 60 |
| tgccaggatt | attgctcatt | gattgggctt | tcttccaact | ctcccctgta | caacacccct | 120 |
| ctctctagtt | tcattgcact | gcccagtttt | atcaaatacc | acaggatatc | caagctttct | 180 |
| ggtaagctca | actggacaac | ggaaaacgag | ctgccgtttg | aaatcaatct | gccactgttt | 240 |
| ctgcaatttc | attctgtgtt | tatctgcccc | atctccaaag | aggagactac | tcctacgaat | 300 |
| ccgcctatag | ttctgggttg | ccatcacatc | atatcgaagg | agagcgctga | caagctattg | 360 |
| aaacagattt | tccgggtgaa | gtgtccatac | tgtccaatga | cttggtatga | agatcgtctc | 420 |
| aaagaggctc | gctttgtgga | tatatgattt | gaaagattac | agcgattgta | agacggttat | 480 |
| ttgatacaag | ttggttgatt | tttcaaggct | gtgtaggaaa | atttggagta | aaaaaaattt | 540 |
| tggatctcaa | attaagttat | caaaagctac | gtaggggctg | ccgagacga | cagcactgaa | 600 |
| tcaataaacc | atcagtgatg | agcgacgcac | agataagaaa | cggagcgcag | aagagcaaga | 660 |
| aggcgaaccg | gaggtcgagg | aagaagcgga | gaaccgagga | tttctcgtcg | tcttctgaga | 720 |
| gctcagattc | agacagagag | gaggaagtga | aggagagcgt | tgaagctacc | gaggaggttg | 780 |
| aaacattaga | gccagaggcc | atggatctgg | ctatcgatca | gctgaatgtt | acaggtgccg | 840 |
| acgcggcaat | gacgcaggat | ttggacaaga | ccagactgaa | cttacgccgt | cttgatgccc | 900 |
| cgttggaggt | gacgaggctt | gggcagaccg | ttgactccgg | acgcgctgca | agttgggcg | 960 |
| ggaacgaact | gcagggcgcg | cagtccaagg | ttgagggggc | ccgtaatgag | ctgagaaatg | 1020 |
| cttacttggg | caagatgttg | gggctctaca | gtgacgactt | ggatgctctc | aggcagcaga | 1080 |
| gcgatttcac | cgagaactcg | ctgtccatgt | tggcgcagct | actgaaaaac | agcggtaatg | 1140 |
| tgtttgatga | cgaggcgctg | aagtcattag | ttgaatagaa | aacaggcaaa | taattttggc | 1200 |
| agggccgttt | tgccgatgcg | atataggctc | tgttgccgat | acgttcccgg | ggagcttccc | 1260 |
| tacggttgct | gttctgtcgg | tcttggcgag | ttttccactt | tgcggccgc | acgaagccca | 1320 |
| gactagccag | tcataccagc | cgtggactcc | gcctacttga | cggggaaatt | tttcccgtgc | 1380 |
| cacttttccc | ggggcaaaat | aagtggctaa | gcagcagaca | agaaaaaaag | gctcgaaaaa | 1440 |
| gttaaaagaa | gtaacagcag | aatatatata | gccaagtgtg | gtttgtcaga | agcaaagcac | 1500 |
| gctaatttga | agcattttca | cgggtgaaca | gcacacaaag | atctccaggg | gggcgttctg | 1560 |
| gttgtgaatt | ttatatagag | agcaaaaagg | atttagaaat | cgccgaaatt | tgtttggttt | 1620 |
| agaagtgctt | ttattgtgag | acgttttcgt | gtatcagaag | ggcatcttga | cactcggtta | 1680 |
| gaatatgagg | tgcaaaaaca | ttttggaagc | aatgttgttg | gtggccgggg | gcacagtccc | 1740 |
| cgtggcgggg | ttgcctgctg | gcgagtcgaa | ggcaaactcg | agtccggggt | atctgcgaat | 1800 |
| ggaggccgag | atctacagag | ggcattcgtt | tgagacgtcc | caacgcggag | gacggccgta | 1860 |
| tatgctggag | aagcgagccg | aggacggatc | ggtgctaatg | gagctgcaga | acaaccaatc | 1920 |
| atttttacaaa | gtggagcttg | aagtgggttc | agacaagcaa | aagattggtg | tcttagtgga | 1980 |
| tacgggttcg | tcagatctgt | ggatcatgaa | ccaaaacaac | tcgtactgtg | agtcctcgtc | 2040 |

```
ctcgtcctcc aagatgcggg aacgcaaggg cagaaagctg agtgatctca gaaacctgaa      2100
cttagacgtg agcgaaaaaa acgtgaaggc tgtcggggct gcagagactg aaacgatgac      2160
cttatcggtg ggagaaggtc tgttttcctg gttcgaaact cagacggacg gcagcggggg      2220
agaaacagaa acggcttccg gagacagctc cgaggccacc attgattgct ctgtttacgg      2280
gacattcgac ccgtcctcct ccgatacgtt caaatcgaac ggaacggagt tttcgatttc      2340
atacgccgat gacagtttcg ccaagggaac atggggcacc gacgatgtga ccttcaacgg      2400
tgtcacggtg gatcaattgt ctatggcaat gctgatgag  accaactcgt cgatgggagt      2460
tcttggaatt ggactcaagg gcctggagac tacgtactcc ggagacgtga cgaatgcgta      2520
cacgtacgaa aacttgccgt acaagatgca gtcccaggga ctgatcagca gccggtcta     2580
ctcggtttat ttgaacgaca gcgagtccag cgctgcgtcg attttgtttg gagccgttga      2640
ccacgacaag tacactggaa cgttgacgtt gctcccgatc atcaacacgg ccgaaagcct      2700
gggctactcg accccgtca  gactcgaggt gacactgtca aagctttaca cgggctcgtc      2760
ctcgaataaa acggccgtga gcatcgcgtc tggggctgcg gcagctctgt ggacacggg      2820
aaccacgttg acgtacgttc cttcggacat catctctaca atcgtggacc agtacggctt      2880
tcaatacagc agttcggttg aacgtatgt ggccaagtgc gactcgctcg acgatgctga      2940
gattgtcttt gacttccagg gaaccaagat atgggttccg ttctcgtcgt ttgcggtctc      3000
actcaccacc aacggaggct cgcagtcgtc gtactgtgcg cttggcttga tggacagcgg      3060
agacgacacc ttcactctgg gagactcgtt cctcaacaac gtctacttcg ttgccgatct      3120
agagaacctg cagattgcca ttgctccggc taacctggac tccacgtcgg aggacattga      3180
agtggtgagc gactcgggaa tcccgtctgc aaagtccgct tctgcctact cttccagttg      3240
gggtgcgtct ggctccgcgg tggcctcgtc gttgtctgtt caaaccggcg cagaaaccgt      3300
cacctccacc gatgctggct ccgactccac gggatctgcg tctgggtcgt ccggttcggc      3360
ctcgtcctcc tcgtccaagt cttctgcgtc ctcctcgtct ggttcgtccg gctcgtcgtc      3420
caagtcgggc tcgagctcgt ccaagtacgc tgccggaaac gcctggggaa tgagcgtctg      3480
cagcctggct ttcaccatcg cggtctcggt gttggtgatt ggctaacctg ccgcagccg      3540
ctttgcttcc atcctgctga ccccgccggt aactctggtc ggattgtatt acatacatac      3600
atacctccca cgcgtttgat atcacgatgt gacttatttt tctgtgcaca gcccggaatt      3660
c                                                                    3661
```

<210> SEQ ID NO 116
<211> LENGTH: 604
<212> TYPE: PRT
<213> ORGANISM: Ogataea minuta

<400> SEQUENCE: 116

Met Leu Leu Val Ala Gly Gly Thr Val Pro Val Ala Gly Leu Pro Ala
1               5                   10                  15

Gly Glu Ser Lys Ala Asn Ser Ser Pro Gly Tyr Leu Arg Met Glu Ala
            20                  25                  30

Glu Ile Tyr Arg Gly His Ser Phe Glu Thr Ser Gln Arg Gly Gly Arg
        35                  40                  45

Pro Tyr Met Leu Glu Lys Arg Ala Glu Asp Gly Ser Val Leu Met Glu
    50                  55                  60

Leu Gln Asn Asn Gln Ser Phe Tyr Lys Val Glu Leu Glu Val Gly Ser
65                  70                  75                  80

Asp Lys Gln Lys Ile Gly Val Leu Val Asp Thr Gly Ser Ser Asp Leu

```
                     85                   90                      95
Trp Ile Met Asn Gln Asn Asn Ser Tyr Cys Glu Ser Ser Ser Ser Ser
                100                 105                 110

Ser Lys Met Arg Glu Arg Lys Gly Arg Lys Leu Ser Asp Leu Arg Asn
        115                 120                 125

Leu Asn Leu Asp Val Ser Glu Lys Asn Val Lys Ala Val Gly Ala Ala
        130                 135                 140

Glu Thr Glu Thr Met Thr Leu Ser Val Gly Glu Gly Leu Phe Ser Trp
145                 150                 155                 160

Phe Glu Thr Gln Thr Asp Gly Ser Gly Gly Glu Thr Glu Thr Ala Ser
                    165                 170                 175

Gly Asp Ser Ser Glu Ala Thr Ile Asp Cys Ser Val Tyr Gly Thr Phe
                180                 185                 190

Asp Pro Ser Ser Asp Thr Phe Lys Ser Asn Gly Thr Glu Phe Ser
                195                 200                 205

Ile Ser Tyr Ala Asp Asp Ser Phe Ala Lys Gly Thr Trp Gly Thr Asp
            210                 215                 220

Asp Val Thr Phe Asn Gly Val Thr Val Asp Gln Leu Ser Met Ala Ile
225                 230                 235                 240

Ala Asp Glu Thr Asn Ser Ser Met Gly Val Leu Gly Ile Gly Leu Lys
                245                 250                 255

Gly Leu Glu Thr Thr Tyr Ser Gly Asp Val Thr Asn Ala Tyr Thr Tyr
                260                 265                 270

Glu Asn Leu Pro Tyr Lys Met Gln Ser Gln Gly Leu Ile Ser Lys Pro
            275                 280                 285

Val Tyr Ser Val Tyr Leu Asn Asp Ser Glu Ser Ser Ala Ala Ser Ile
    290                 295                 300

Leu Phe Gly Ala Val Asp His Asp Lys Tyr Thr Gly Thr Leu Thr Leu
305                 310                 315                 320

Leu Pro Ile Ile Asn Thr Ala Glu Ser Leu Gly Tyr Ser Thr Pro Val
                325                 330                 335

Arg Leu Glu Val Thr Leu Ser Lys Leu Tyr Thr Gly Ser Ser Ser Asn
                340                 345                 350

Lys Thr Ala Val Ser Ile Ala Ser Gly Ala Ala Ala Leu Leu Asp
        355                 360                 365

Thr Gly Thr Thr Leu Thr Tyr Val Pro Ser Asp Ile Ile Ser Thr Ile
    370                 375                 380

Val Asp Gln Tyr Gly Phe Gln Tyr Ser Ser Val Gly Thr Tyr Val
385                 390                 395                 400

Ala Lys Cys Asp Ser Leu Asp Asp Ala Glu Ile Val Phe Asp Phe Gln
                405                 410                 415

Gly Thr Lys Ile Trp Val Pro Phe Ser Ser Phe Ala Val Ser Leu Thr
                420                 425                 430

Thr Asn Gly Gly Ser Gln Ser Ser Tyr Cys Ala Leu Gly Leu Met Asp
            435                 440                 445

Ser Gly Asp Asp Thr Phe Thr Leu Gly Asp Ser Phe Leu Asn Asn Val
    450                 455                 460

Tyr Phe Val Ala Asp Leu Glu Asn Leu Gln Ile Ala Ile Ala Pro Ala
465                 470                 475                 480

Asn Leu Asp Ser Thr Ser Glu Asp Ile Glu Val Val Ser Asp Ser Gly
                485                 490                 495

Ile Pro Ser Ala Lys Ser Ala Ser Ala Tyr Ser Ser Trp Gly Ala
            500                 505                 510
```

```
Ser Gly Ser Ala Val Ala Ser Ser Leu Ser Val Gln Thr Gly Ala Glu
        515                 520                 525

Thr Val Thr Ser Thr Asp Ala Gly Ser Asp Ser Thr Gly Ser Ala Ser
    530                 535                 540

Gly Ser Ser Gly Ser Ala Ser Ser Ser Ser Lys Ser Ser Ala Ser
545                 550                 555                 560

Ser Ser Ser Gly Ser Ser Gly Ser Ser Ser Lys Ser Gly Ser Ser
                565                 570                 575

Ser Lys Tyr Ala Ala Gly Asn Ala Trp Gly Met Ser Val Cys Ser Leu
            580                 585                 590

Ala Phe Thr Ile Ala Val Ser Val Leu Val Ile Gly
        595                 600

<210> SEQ ID NO 117
<211> LENGTH: 21
<212> TYPE: DNA
<213> ORGANISM: Artificial Sequence
<220> FEATURE:
<223> OTHER INFORMATION: Description of Artificial Sequence: Synthetic
      primer DY5

<400> SEQUENCE: 117
ctcaagggcc tggagactac g                                           21

<210> SEQ ID NO 118
<211> LENGTH: 22
<212> TYPE: DNA
<213> ORGANISM: Artificial Sequence
<220> FEATURE:
<223> OTHER INFORMATION: Description of Artificial Sequence: Synthetic
      primer DY3

<400> SEQUENCE: 118
cgggattccc gagtcgctca cc                                          22

<210> SEQ ID NO 119
<211> LENGTH: 33
<212> TYPE: DNA
<213> ORGANISM: Artificial Sequence
<220> FEATURE:
<223> OTHER INFORMATION: Description of Artificial Sequence: Synthetic
      primer PDI5 for amplification of 5'-region of
      Saccharomyces cerevisiae PDI gene

<400> SEQUENCE: 119
tctagaatga agttttctgc tggtgccgtc ctg                              33

<210> SEQ ID NO 120
<211> LENGTH: 33
<212> TYPE: DNA
<213> ORGANISM: Artificial Sequence
<220> FEATURE:
<223> OTHER INFORMATION: Description of Artificial Sequence: Synthetic
      primer PDI3 for amplification of 3'-region of
      Saccharomyces cerevisiae PDI gene

<400> SEQUENCE: 120
ggatccttac aattcatcgt gaatggcatc ttc                              33

<210> SEQ ID NO 121
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 121

His Asp Glu Leu
1

METHYLOTROPHIC YEAST PRODUCING MAMMALIAN TYPE SUGAR CHAIN

TECHNICAL FIELD

The present invention provides a process for mass production of non-antigenic mammalian type glycoproteins comprising a sugar chain structure at their asparagine residues using a methylotrophic yeast wherein the sugar chain structure is identical to that produced by mammalian cells. More specifically, the present invention relates to a novel mutant yeast capable of producing a glycoprotein comprising a mammalian type sugar chain, which is created by introducing an α-1,2-mannosidase gene into a methylotrophic yeast having a mutation of sugar chain biosynthesizing enzyme genes, so that the α-1,2-mannosidase gene is highly expressed under the control of a potent promoter in the yeast, and the α-1,2-mannosidase exists in the endoplasmic reticulum (ER); and to a process for producing a glycoprotein comprising a mammalian type sugar chain wherein the process comprises culturing the methylotrophic yeast cells with a heterologous gene transferred thereinto in a medium and obtaining the glycoprotein comprising mammalian type sugar chains from the culture.

BACKGROUND OF THE INVENTION

Yeast has been intensively studied as a host for production of foreign genes since establishment of yeast transformation systems. The use of a yeast for production of foreign proteins involves advantages in that molecular-genetic manipulation and culture of yeasts are as easy as those of prokaryotic organisms, and that yeasts bear eukaryotic type functions to allow post-translational modifications of proteins such as glycosylation. However, since production of proteins using *Saccharomyces cerevisiae* is low with exception of some successes, protein production systems using yeasts other than *Saccharomyces cerevisiae* have been developed, including systems using, for example, *Shizosaccharomyces pombe*, *Kluyveromyces lactis*, methylotrophic yeasts, or the like.

A methylotrophic yeast (or methanol-utilizing yeast), which can grow on methanol as a single carbon source, has been developed as a host for production of foreign proteins (K. Wolf (ed.) "Non Conventional Yeasts in Biotechnology" (1996)). This is because methods of culturing yeasts have been established in industrial scale and because the yeast has a potent promoter controlled by methanol. At that time when a methylotrophic yeast was discovered, the use thereof as SCP (Single Cell Protein) was studied and, as a result, a high-density culture technique at a dry cell weight of 100 g/L or more was established in an inexpensive culture medium, which contains minerals, trace elements, biotin, and carbon sources.

Researches on elucidation of a C1 compound-metabolic pathway, as well as on application of C1 compounds, revealed that a group of enzymes required for the methanol metabolism was strictly regulated by carbon sources. The methanol metabolism in a methanol-utilizing yeast generates formaldehyde and hydrogen peroxide from methanol and oxygen by alcohol oxidase in the first reaction. The generated hydrogen peroxide is decomposed into water and oxygen by catalase, while formaldehyde is oxidized to carbon dioxide by actions of formaldehyde dehydrogenase, S-formylglutathione hydrolase, and alcohol oxidase, and NADH generated during the oxidation is utilized as an energy source of the cell. At the same time, formaldehyde is condensed with xylulose-5-phosphate by dihydroxyacetone synthase, then converted into glyceraldehyde-3-phosphate and dihydroxyacetone, which subsequently enter the pentose phosphate pathway and serve as cell components.

Alcohol oxidase, dihydroxyacetone synthase, and formate dehydrogenase are not detected in the cell when it is cultured in the presence of glucose, but they are induced in the cell cultured in methanol, so that the amount of them is dozens of percentage of the total inner cell protein. Since the production of these enzymes is controlled at a transcription level, inducible expression of a foreign gene of interest is enabled under the regulation of promoters of the genes which encode the enzymes. The foreign gene expression system using a promoter for a methanol metabolizing enzyme gene has been estimated so highly among yeast expression systems due to its efficient production, with an example in which the expression amount of a foreign gene was dozens of percentage of the total protein in cell or several g/L culture medium in secretion.

To date, four types of the transformation and foreign gene expression systems have been established in the methylotrophic yeasts: *Candida boidinii*, *Hansenula polymorpha*, *Pichia pastoris* and *Pichia methanolica*. Differences are recognized among the expression systems in terms of codon usage, expression regulation, and integration of expression plasmid, which provide characteristics of each expression system.

In the meantime, it is known that naturally occurring proteins are classified into two types, i.e., the one being a simple protein comprising amino acids alone, the other being a complex protein comprising sugar chains, lipids, phosphates or the like attached thereto, and that most of cytokines are glycoproteins. Recently, besides conventional analyses with lectin, new analyses using HPLC, NMR or FAB-MAS have been developed in analyzing sugar chain structures, by which new sugar chain structures of a glycoprotein have been found successively. On the other hand, studies on functional analysis of sugar chains lead to elucidation of the fact that the sugar chain plays an important role in lots of bio-mechanisms, such as intercellular recognition, molecular recognition, keeping of protein structures, contribution to protein activity, in vivo clearance, secretion, localization, etc.

For example, it has been revealed that erythropoietin (EPO), tissue plasminogen activator (TPA) or the like did not exhibit its inherent bioactivity when the sugar chains are removed (Akira Kobata, Tanpakushitsu-Kakusan-Koso, 36, 775-788 (1991)). Importance of sugar chains has been pointed out in erythropoietin, which was the first glycoprotein medicament in history produced by transgenic animal cells as the host. Specifically, the sugar chains of erythropoietin act in inhibitory manner against binding to receptor, whereas they have a decisive contribution to keeping of active structures and to improvement in in vivo pharmacokinetics, and are totally essential for expression of the pharmacological activity (Takeuchi and Kobata, Glycobiology, 1, 337-346 (1991)). Furthermore, high correlation between the structure, type and number of branches (i.e., the number of branches formed by GlcNAc attached to Man3GlcNAc2) of sugar chains and the pharmacological effect of erthropoietin has been found (Takeuchi et al., Proc. Natl. Acad. Sci. USA, 86, 7819-7822 (1989)). It was reported that a main cause of this phenomenon was that erythropoietin with immature branch structure is prone to occur its rapid clearance from the kidney, resulting in a shorter retention time in the body (Misaizu et al., Blood, 86, 4097-4104 (1995)). Another similar example is observed in serum glycoproteins including fetuin. That is, it was found that when removal of sialic acid at the end of a sugar chain leads to exposure of galactose, the galactose is recognized by lectin on the surface of liver cells, whereby the serum glycoprotein disappears promptly from the blood (Ashwell and Harford, Annu. Rev. Biochem., 51, 531-554 (1982); Morell et al., J. Biol. Chem., 243, 155-159 (1968)).

Glycoprotein sugar chains are largely classified into Asn-linked (N-linked), mucin type, O-GlcNAc type, GPI-anchored type, and proteoglycan type (Makoto Takeuchi, Glycobiology Series 5, Glycotechnology; edited by Akira Kibata and Senichiro Hakomori, Katsutaka Nagai, Kodansha Scientific, 191-208 (1994)), each of which has an intrinsic biosynthesis pathway and serves for individual physiological functions. Of them, for the biosynthesis pathway of Asn-linked sugar chains, there are many findings and detailed analyses.

Biosynthesis of Asn-linked sugar chains starts with synthesis of a precursor comprising N-acetylglucosamine, mannose and glucose on a lipid carrier intermediate, which precursor is converted to a specific sequence (Asn-X-Ser or -Thr) of a glycoprotein in the endoplasmic reticulum (ER). It is then subjected to processing (i.e., cleavage of glucose and specific mannose residues) to synthesize an M8 high-mannose type sugar chain comprising eight mannose residues and two N-acetylglucosamine residues (Man8GlcNAc2). The protein including high mannose type sugar chains is transported to the Golgi apparatus which undergoes a variety of modifications significantly different between yeast and mammal (Gemmill, T. R., Trimble, R. B., Biochim. Biophys. Acta., 1426, 227 (1999)).

In mammalian cells, in many cases, α-mannosidase I (α-1,2-mannosidase), an exomannosidase which cleaves an α-1,2-mannoside linkage, acts on high mannose type sugar chains to cut off several mannose residues. The sugar chain (Man5-8GlcNAc2) generated in this process is a sugar chain referred to as a high mannose type. N-acetylglucosaminyl transferase (GnT) I acts on an M5 high mannose type sugar chain (Man5GlcNAc2) from which three mannose residues have been cut off, to transfer one N-acetylglucosamine residue to the sugar chain, resulting in formation of a sugar chain comprising GlcNAcMan5GlcNAc2. The thus formed sugar chain is referred to as a hybrid type. Further, when α-mannosidase II and GnT II act, the sugar chain structure GlcNAc2Man3GlcNAc2, referred to as a complex type, is formed. Thereafter, a variety of mammalian type sugar chains are formed through the action of a group of ten-odd glycosyltransferase enzymes, by which addition of N-acetylglucosamine, galactose, sialic acid, etc. occurs (FIG. 1).

Accordingly, the mammalian type sugar chain as defined in this application means an N-linked (or Asn-linked) sugar chain present in mammals, which is generated in the sugar chain biosynthesis process of mammals. Specifically, they include an M8 high mannose type sugar chain represented by Man8GlcNAc2; an M5, M6 or M7 high mannose type sugar chain represented by Man5GlcNAc2, Man6GlcNAc2 or Man7GlcNAc2, respectively, generated from Man8GlcNAc by action of α-mannosidase I; a hybrid type sugar chain represented by GlcNAcMan5GlcNAc2 generated from Man5GlcNAc2 by action of GlcNAc transferase-I (GnT-I); a double-stranded complex type sugar chain represented by GlcNAc2Man3GlcNAc2 generated from GlcNAcMan5GlcNAc2 by action of α-mannosidase-I and GlcNAc transferase-II (GnT-II); and a double-stranded complex type sugar chain represented by Gal2GlcNAc2Man3GlcNAc2 generated from GlcNAc2Man3GlcNAc2 by action of galactosyl transferase (GalT).

In mammals, any of high mannose type, hybrid type and complex type sugar chains can be found. In one case, sugar chains to be attached are different depending on a protein, or in another, different types of sugar chains are attached within a protein. These sugar chains exhibit important functions, such as biosynthesis of glycoproteins, sorting within a cell, concealment of antigenicity, in vivo stability, organ-targeting properties, and the like, depending on the type or class of sugar chains attached to a glycoprotein (Tamao Endo, Tosa Kogaku (Sugar chain engineering), Sangyo Chosakai, 64-72 (1992)).

On the other hand, in yeast a mannan-type sugar chain (outer sugar chain) is produced, in which several to 100 or more mannose residues are attached to M8 high mannose type sugar chain. For example, the biosynthesis of outer sugar chains in *Saccharomyces cerevisiae* known as baker's yeast or laboratory yeast is considered to proceed along a pathway as shown in FIG. 2 (Ballou et al., Proc. Natl. Acad. Sci. USA, 87, 3368-3372 (1990)). That is, a reaction for initiating elongation begins in which a mannose is first attached to M8 high mannose type sugar chain through α-1,6 linkage (FIG. 2, Reaction I, B). The enzyme performing this reaction is clarified as a protein encoded by OCH1 gene (Nakayama et al., EMBO J., 11, 2511-2519 (1992)). Further, sequential elongation of mannose by α-1,6-linkage reaction (FIG. 2, II), forms a poly α-1,6-mannose linkage being the backbone of an outer sugar chain (FIG. 2, E). The α-1,6-mannose linkage sometimes contains a branch of α-1,2-linked mannose (FIG. 2: C, F, H), and additionally, α-1,3-linked mannose is attached to the end of the branched α-1,2-linked mannose chain (FIG. 2: D, G, H, I). The addition of the α-1,3-linked mannose is caused by a MNN1 gene product (Nakanishi-Shindo et al., J. Biol. Chem., 268, 26338-26345 (1993)). Formation of an acidic sugar chain, in which mannose-1-phosphate has been attached to high mannose type sugar chain moieties and outer chain moieties, is known as well (FIG. 2, *; a possible phosphorylation site corresponding to * in the above formula (I)). This reaction was found to be caused by a protein encoded by MNN6 gene (Wang et al., J. Biol. Chem., 272, 18117-18124 (1997)). Further, a gene (MNN4) coding for a protein positively regulating the transfer reaction was clarified (Odani et al., Glycobiology, 6, 805-810 (1996); Odani et al., FEBS Letters, 420, 186-190 (1997)).

Production of substances using microorganisms including yeast has some advantages as mentioned above, such as low production costs and utilizing culture technology developed as fermentation engineering, as compared with the production of substances using animal cells. There is a problem, however, that microorganisms cannot attach sugar chains with the same structure as human glycoprotein. Specifically, glycoproteins from cells of an animal including human have a variety of mucin type sugar chains in addition to three kinds of Asn-linked sugar chains, i.e., complex type, hybrid type and high mannose type as shown in FIG. 1, while the Asn-linked sugar chain whose attachment is observed even in baker's yeast (*Saccharomyces cerevisiae*), is only a high mannose type, and a mucin type is attached only to a sugar chain mainly composed of mannose.

Such sugar chains of yeast may produce a heterogeneous protein product resulting in difficulties in purification of the protein or in reduction of specific activity (Bekkers et al., Biochim. Biophys. Acta, 1089, 345-351 (1991)). Furthermore, since the structure of the sugar chains significantly differ, glycoproteins produced by yeast may not have the same detectable biological activity as those of the mammalian origin, or have strong immunogenicity to a mammal, etc. Thus, yeast is unsuitable as a host for producing useful glycoproteins from mammalian origin, and in general microorganisms are not suitable for DNA recombinant production of a glycoprotein, such as erythropoietin as described above, in which sugar chain has an important function. Indeed, for production of erythropoietin, Chinese hamster ovary (CHO) cells are used.

Thus, it is expected that the sugar chain of a glycoprotein not only has a complicated structure but also plays an important role in expression of biological activity. However, since the correlation of the structure of sugar chain with biological activity is not necessarily clear, development of the technology, which enables to freely modify or control the structure (the type of sugar, a linking position, chain length, etc.) of a sugar chain attached to a protein moiety, is needed. When developing a glycoprotein especially as medicament, the structure and function analyses of the glycoprotein become important. Under these circumstances, the development of yeast, which can produce a glycoprotein with biological activity equivalent to that of the mammalian origin, i.e., a glycoprotein comprising a mammalian type sugar chain, is desired by the academic society and the industrial world.

In order to produce a mammalian type sugar chain using yeast, it is important to prepare a mutant having the sugar chain biosynthesis system, which does not comprise a reaction as mentioned above of attaching a lot of mannose residues to modify the glycoprotein sugar chain as seen particularly in yeast; in which no outer sugar chains are attached; and the synthesis of sugar chains generates M5 high mannose type sugar chain. Subsequently, M8 high mannose type sugar chain, a precursor for this mammalian type sugar chain, might be produced by introducing biosynthetic genes for the mammalian type sugar chain into the mutant yeast.

To obtain a glycoprotein lacking outer sugar chains, use of a mutant strain deficient in enzymes for producing outer sugar chains in yeast, particularly a mutant of *Saccharomyces cerevisiae*, has been studied so far. Methods to obtain such a deficient mutant strain include obtaining a gene mutant by chemicals, ultraviolet irradiation or natural mutation, or obtaining it by artificial disruption of a target gene.

As to the former methods, there are many reports thereon. For example, mnn2 mutant is defective in the step of branching which causes α-1,2 linkage from the α-1,6 backbone of an outer sugar chain, and mnn1 mutant is defective in the step of producing α-1,3-linked mannose at the end of the branch. However, these mutants do not have defects in α-1,6 mannose linkage as the backbone of outer sugar chains and so they produce a long outer sugar chain in length. Mutants like mnn7, 8, 9, 10 mutants have been isolated as mutants having only about 4 to 15 molecules of the α-1,6 mannose linkage. In these mutants, the outer sugar chains are merely shortened, but the elongation of high mannose type sugar chains does not stop (Ballou et al., J. Biol. Chem., 255, 5986-5991 (1980); Ballou et al., J. Biol. Chem., 264, 11857-11864 (1989)). Defects in the addition of outer sugar chains are also observed in, for example, secretion mutants such as sec18 in which the transportation of a protein from endoplasmic reticulum to Golgi apparatus is temperature-sensitive. However, in a sec mutant, since the secretion of a protein itself is inhibited at a high temperature, the sec mutant is not suitable for secretion and production of glycoproteins.

Accordingly, since these mutants cannot completely biosynthesize the high mannose type sugar chain of interest, they are considered unsuitable as host yeast for producing a mammalian type sugar chain.

On the other hand, as to the latter, the deficient mutant strain in which a plurality of target genes have been disrupted can be established by development of genetic engineering techniques in recent years. Specifically, through in vitro operation, a target gene DNA on plasmid is first fragmented or partially deleted, and an adequate selectable marker DNA is inserted at the fragmented or deleted site to prepare a construct in which the selectable marker is sandwiched between upstream and downstream regions of the target gene. Subsequently, the linear DNA having this structure is transferred into a yeast cell to cause two homologous recombinations at portions homologous between both ends of the introduced fragment and the target gene on chromosome, thereby substituting the target gene with a DNA construct in which the selectable marker has been sandwiched (Rothstein, Methods Enzymol., 101, 202-211 (1983)).

Molecular cloning of a yeast strain deficient in outer sugar chain has already been described by Jigami et al. in Japanese Patent Publication (Kokai) No. 6-277086A (1994) and No. 9-266792A (1997). Jigami et al. succeeded in cloning of the *S. cerevisiae* OCH1 gene (which expresses α-1,6-mannosyl transferase), the OCH1 enzyme being assumed to be a key enzyme for elongation of the α-1,6 linked mannose. The glycoprotein of the OCH1 gene knockout mutant (Δoch1) had three types of attached sugar chains, i.e., Man8GlcNAc2, Man9GlcNAc2 and Man10GlcNAc2. Of them, the Man8GlcNAc2 chain had the same structure (i.e., the structure shown in FIG. 2A) as the ER core sugar chain which was common between *S. cerevisiae* and mammalian cell, while the Man9GlcNAc2 and Man10GlcNAc2 chains had a structure where α-1,3-linked mannose was attached to this ER core sugar chain [Nakanish-Shindo, Y., Nakayama, K., Tanaka, A., Toda, Y. and Jigami, Y., (1994), J. Biol. Chem.]. Furthermore, a *S. cerevisiae* host which can attach only the Man8GlcNAc2 chain having the same structure as the ER core sugar chain, which structure is common between *S. cerevisiae* and mammalian cell, was successfully produced by preparing a Δoch1mnn1 dual mutant and inhibiting the α-1,3-linked mannose transfer at the end. It is supposed that this Δoch1mnn1 double mutant serves as a host useful in case where the mammalian glycoprotein, which has a high mannose type sugar chain, is produced by DNA recombinant technology [Yoshifumi Jigami (1994) Tanpakushitsu-Kakusan-Koso, 39, 657].

It was found, however, that sugar chains of the glycoprotein produced by the double mutant (Δoch1mnn1) described in Japanese Patent Publication (Kokai) No. 6-277086 (1994) comprised acidic sugar chains containing a phosphate residue. This acidic sugar chain has a structure which is not present in sugar chains of mammals including human, and it is likely to be recognized as a foreign substance in mammal, thereby exhibiting antigenicity (Ballou, Methods Enzymol., 185, 440-470 (1990)). Hence, a quadruple mutant (as described in Japanese Patent Publication (Kokai) No. 9-266792A (1997)) was constructed in which the functions of a gene for positively regulating the transfer of mannose-1-phosphate (MNN4) and of a mannose transferase gene for performing the elongation reaction for an O-linked sugar chain (KRE2) have been disrupted. It was revealed that the sugar chain of a glycoprotein produced by the yeast strain described therein had the M8 high mannose type sugar chain of interest. It was further found that a strain in which *Aspergillus saitoi*-derived α-1,2-mannosidase gene is transferred to a yeast cell where a gene involved in the particular sugar chain biosynthesis system of yeast has been disrupted, had a high mannose type sugar chain (Man5-8GlcNAc2) in which one to several mannose residues were cleaved (Chiba et al., J. Biol. Chem., 273, 26298-26304 (1998)). Furthermore, they attempted production of a mammalian type glycoprotein in yeast by transfer of a gene involved in the mammalian sugar chain biosynthesis system into this prepared strain (PCT/JP 00/05474). However, despite that an α-1,2-mannosidase gene was expressed using a promoter for glyceraldehyde-3-phosphate dehydrogenase gene which is considered to be the highest in the expression amount as a constitutive expression promoter according to the disclosure, the conversion efficiency to Man5GlcNAc2 by carboxypeptidaseY (CPY) in the cell wall-derived mannoprotein is as low as 10-30% and so it is hard to say that its application to various glycoproteins is sufficiently prospective, although the rate of conversion to a high mannose type sugar chain (Man5GlcNAc2) was almost 100% in FGF as a foreign protein.

Separately, Schwientek et al. reported on the expression of the activity of human β-1,4-galactosyl transferase gene in *S. cerevisiae* in 1994 [Schwientek, T. and Ernst, J. F., Gene, 145, 299 (1994)]. Similarly, Krezdrn et al. achieved the expression of the activity of human β-1,4-galactosyl transferase gene and α-2,6-sialyl transferase in *S. cerevisiae* [Krezdrn, C. H. et al., Eur.J.Biochem.220, 809 (1994)].

However, when these findings are tried to be applied to other yeast, various problems arise. First of all, it is known that yeasts themselves have various sugar chain structures (K. Wolf et al., Nonconventional Yeasts in Biotechnology (1995)).

For example, a divided yeast *Schizosaccharomyces pombe* contains galactose. *Kluyveromyces lactis* has GlcNAc. Both the methylotrophic yeast *Pichia pastoris* and the pathogenic yeast *Candida albicans* have been confirmed to contain β-mannoside linkage. Even yeasts having xylose and rhamnose as sugar chain components exist (Biochim. et Biophy. Acta, 1426, 1999, 227-237).

In fact, no yeasts capable of producing mammalian type sugar chains have been obtained except *Saccharomyces cerevisiae* as reported by Jigami et al. Also, although use of a methylotrophic yeast as the host for producing a foreign protein was exemplified in Japanese Patent Publication (Kokai) No. 9-3097A (1997), substantially no other example has been given.

In Japanese Patent Publication (Kokai) No. 9-3097A (1997), a homologue of *Pichia pastoris* OCH1 gene and a *Pichia pastoris* mutant strain in which the OCH1 gene was knockout were prepared, to obtain from them a modified methylotrophic yeast strain whose ability to extend a sugar chain was inhibited as compared with natural methylotrophic yeast strain. This publication, however, provides only information on SDS-PAGE of the produced glycoprotein, and no such support as structural analysis data. That is, it did not actually identify the activity but only pointed out about possibility of being α-1,6-mannosyl transferase. In fact, although HOC1 gene (GenBank accession number; U62942), which is an OCH1 gene homologue, exists also in *Saccharomyces cerevisiae*, the activity and function thereof are unknown at present.

Moreover, in the same publication a sugar chain having β-mannoside linkage in *P. pastoris* was identified, but it did not describe about the structure of the chain in any way. Indeed, structural analysis of the sugar chain was neither performed nor identified the produced sugar chain. So, it was not demonstrated whether or not the obtained gene is actually the OCH1 gene, and whether or not the sugar chain of the knockout strain was a mammalian type. Accordingly, one cannot safely say that the technique disclosed in Japanese Patent Publication (Kokai) No. 9-3097A (1997) produces a mammalian type sugar chain bearing glycoprotein and is sufficient as the production system that can be adapted for production of medicaments.

There is also a study using a filamentous fungus *Trichoderma reesei* by Maras et al. as an attempt to produce a mammalian type sugar chain using a microorganism other than yeast (U.S. Pat. No. 5,834,251). The disclosed method comprises making α-1,2-mannosidase and GnT-I to act on filamentous fungus and yeast to synthesize a hybrid type sugar chain (i.e., GN1Man5 sugar chain).

Filamentous fungi inherently express α-1,2-mannosidase, and consequently it is believed that little sugar chain modification occurs as compared with the case of yeast. On the other hand, since yeast attaches a particular outer sugar chain, all sugar chains are not obtained as Man5 by the procedure in which only α-1,2-mannosidase is introduced. In fact, produced in *Saccharomyces cerevisiae* as disclosed in this patent publication was a mixture of Man5 as the final product with sugar chains of Man6 or more as partial decomposition products, which mixture is produce by action of the outer sugar chain synthesizing gene OCH1, as described by Jigami or Chiba et al. (supra). It would accordingly be hard to say that the mammalian type sugar chain was produced in *S. cerevisiae*, and so this purpose cannot be attained without disrupting a sugar chain biosynthesizing gene of yeast. Maras et al. did not mention the gene disruption in the sugar chain biosynthesis system inherent to yeast at all, so obviously this technique could not be applied to yeasts (*Pichia pastoris, Hansenula polymorpha, Kluyveromyces lactis, Saccharomyces cerevisiae, Yarrowia lipolytica*). Moreover, Maras et al. refers to RNaseB as a heterologous expression protein in the Examples, but RNaseB has originally a high mannose type sugar chain of Man5 or Man6. Many of the sugar chains of the animal cell origin are complex type sugar chains having complicated structures, and many of glycoproteins such as cytokines expected to be applied to medicaments etc. have complex type sugar chains. In fact, it is known that the sugar chain structure changes greatly depending on kinds of foreign glycoproteins expressed (Method in Molecular Biologylogy, 103, 95-105 (1998)). Therefore, it is considered inappropriate to use as an example RNaseB which is a glycoprotein originally having a high mannose type sugar chain, in the application to glycoproteins having complex type sugar chains.

Furthermore, filamentous fungi are commonly used for the production of industrial enzymes, food enzymes, etc., and the transformation system is established, and production of enzymes by DNA recombinant technology has also been conducted. Nevertheless, there are the following disadvantages:

1) Since the protease activity is very strong, proteins produced are prone to receive limited proteolysis.
2) Since the fungi produce many proteins secreted outside the cell, they are unsuitable for the production of proteinous medicaments where homogeneity would be required.

*Ogataea minuta* as defined in the present invention is a strain once referred to as *Pichia minuta* or *Hansenulla minuta*, and was named *Ogataea minuta* by Ogata et al. (Biosci. Biotecnol. Biochem., 58, 1245-1257 (1994)). *Ogataea minuta* produces significant amounts of alcohol oxidase, dihydroxyacetone synthase and the formate dehydrogenase within the cell as in other methylotrophic yeasts, but nothing was known about the genes relating to these methanol utilization enzyme nor about sugar chain structures of this yeast.

Under the above-mentioned circumstances, the object of the present invention is to solve the above-described problems in production of glycoproteins in yeast, and to provide a process for mass production of non-antigenic mammalian type sugar chains and glycoproteins containing the sugar chains using a methylotrophic yeast wherein the sugar chain structures are identical to those of sugar chains as produced in human and other mammalian cells.

DISCLOSURE OF THE INVENTION

For the purpose of constructing a production technique of glycoproteins having mammalian cell compatible sugar chain structures using a methylotrophic yeast, we conducted intensive researches to achieve the above-mentioned object. Consequently, we have found that sugar chains in *Ogataea minuta*, which is a kind of methylotrophic yeast, comprises mainly α-1,2-mannoside linkage, by NMR analysis of the cell wall sugar chain and by α-1,2-mannosidase digestion test, and further that glycoproteins having mammalian type sugar chains can be obtained by introducing an α-1,2-mannosidase gene into a mutant strain comprising mutated sugar chain biosynthesizing enzyme genes (for example, an OCH1 gene (α-1,6-mannosyl transferase) knockout mutant, which is considered to be a key enzyme for the elongation reaction where mannose residues attach to an M8 high mannose type sugar chain one by one via α-1,6 linkage), and expressing it under the control of a potent promoter such as methanol-inducible promoter, followed by culturing the *Ogataea minuta* transformed with a heterologous gene in a culture medium, thereby to obtain a glycoprotein from the culture. By this finding was completed the present invention. Thus, it was found that a mammalian type sugar chain could be produced without disrupting MNN1 and MNN4 genes in *Saccharomyces cerevisiae*.

In summary, the invention comprises:

1) A methylotrophic yeast strain producing a mammalian type sugar chain, obtained by introducing an α-1,2-mannosidase gene into a mutant strain comprising a mutated sugar chain biosynthesizing enzyme gene (for example, an OCH1 gene (α-1,6-mannosyl transferase) knockout mutant, which is considered to be a key enzyme for the elongation reaction where mannose residues attach to an M8 high mannose type sugar chain one by one via α-1,6 linkage), and expressing it under the control of a potent promoter such as methanol-inducible promoter;

2) A process of producing a glycoprotein comprising a mammalian type sugar chain, comprising culturing in a culture medium the yeast strain bred by introducing heterologous genes into a mutant yeast which comprises mutated sugar chain biosynthesizing enzyme genes and expressing these genes, and obtaining the glycoprotein comprising a mammalian sugar chain from the culture; and 3) A glycoprotein comprising a mammalian type sugar chain, produced by this production process.

More specifically, the invention provides the following 1 to 122.

1. A process for producing a methylotrophic yeast capable of producing a mammalian type sugar chain, which comprises the steps of
1) disrupting an OCH1 gene which encodes α-1,6-mannosyl transferase, in a methylotrophic yeast; and
2) introducing an α-1,2-mannosidase gene into the yeast and expressing it therein.

2. A process according to (1), wherein the mammalian type sugar chain is represented by the following structural formula (Man$_5$GlcNAc$_2$):

Structural Formula 2

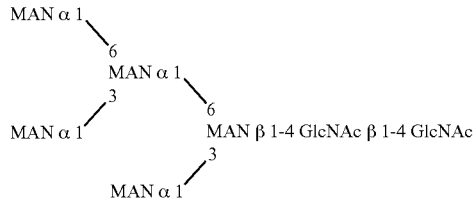

3. A process according to (1) or (2), wherein the methylotrophic yeast belongs to the genus *Pichia, Hansenula, Candida*, or *Ogataea*.
4. A process according to (1) or (2), wherein the methylotrophic yeast is *Ogataea minuta*.
5. A process according to any one of (1) to (4), wherein the methylotrophic yeast is a strain from *Ogataea minuta* strain IFO 10746.
6. A process according to any one of (1) to (5), wherein the α-1,2-mannosidase gene is expressed under the control of a methanol-inducible promoter.
7. A process according to (6), wherein the methanol-inducible promoter is a promoter of an alcohol oxidase (AOX) gene.
8. A process according to (7), wherein the alcohol oxidase (AOA) gene is from *Ogataea minuta*.
9. A process according to any one of (1) to (8), characterized in that the α-1,2-mannosidase gene to be introduced is attached to a yeast endoplasmic reticulum (ER) retention signal (HDEL) (SEQ ID NO: 121).
10. A process according to any one of (1) to (9), wherein the α-1,2-mannosidase gene is from *Aspergillus saitoi*.
11. A process according to any one of (1) to (10), which further comprises a step of transforming a heterologous gene into the yeast.
12. A process according to (11), wherein the heterologous gene is transferred using an expression vector and is expressed in the yeast.
13. A process according to (12), wherein the expression vector comprises a methanol-inducible promoter.
14. A process according to (13), wherein the methanol-inducible promoter is a promoter of an alcohol oxidase (AOX) gene.
15. A process according to (14), wherein the alcohol oxidase (AOX) gene is from *Ogataea minuta*.
16. A process according to (12), wherein the expression vector comprises a promoter of a glyceraldehyde-3-phosphate dehydrogenase (GAPDH) gene.
17. A process according to any one of (11) to (16), wherein 20% or more of N-linked sugar chains produced of the protein encoded by a heterologous gene is the mammalian type sugar chain represented by Structural Formula 2.
18. A process according to any one of (11) to (16), wherein 40% or more of N-linked sugar chains produced of the protein encoded by a heterologous gene is the mammalian type sugar chain represented by Structural Formula 2.
19. A process according to any one of (11) to (16), wherein 60% or more of N-linked sugar chains produced of the protein encoded by a heterologous gene is the mammalian type sugar chain represented by Structural Formula 2.
20. A process according to any one of (11) to (16), wherein 80% or more of N-linked sugar chains produced of the protein encoded by a heterologous gene is the mammalian type sugar chain represented by Structural Formula 2.
21. A process according to any one of (11) to (20), wherein the protein encoded by a heterologous gene is from humans.
22. A process according to any one of (11) to (21), wherein the protein encoded by a heterologous gene is an antibody or a fragment thereof.
23. A methylotrophic yeast produced by a process according to any one of (1) to (22).
24. A process for producing a protein encoded by a heterologous gene, wherein the process comprises culturing the methylotrophic yeast of (23) in a medium to obtain the protein encoded by a heterologous gene comprising a mammalian type sugar chain from the culture.

25. A protein comprising a mammalian type sugar chain encoded by a heterologous gene, wherein the protein is produced by the process of (24).
26. An orotidine-5'-phosphate decarboxylase (URA3) gene DNA encoding an amino acid sequence substantially represented by SEQ ID NO: 16.
27. A URA3 gene DNA comprising a nucleotide sequence substantially represented by SEQ ID NO: 15.
28. A recombinant expression vector substantially comprising the gene DNA of (26) or (27) or a fragment thereof as a selectable marker.
29. An *Ogataea minuta* strain transformed with a recombinant expression vector of (28).
30. An *Ogataea minuta* strain according to (29), the strain being from the strain IFO 10746.
31. A phosphoribosyl-amino-imidazole succinocarboxamide synthase (ADE1) gene DNA encoding an amino acid sequence substantially represented by SEQ ID NO:28.
32. An ADE1 gene DNA comprising a nucleotide sequence substantially represented by SEQ ID NO:27.
33. A recombinant expression vector substantially comprising the gene DNA of (31) or (32) or a fragment thereof as a selectable marker.
34. An *Ogataea minuta* strain transformed with the recombinant expression vector of (33).
35. An *Ogataea minuta* strain according to (34), the strain being from the strain IFO 10746.
36. An imidazole-glycerol-phosphate dehydratase (HIS3) gene DNA encoding an amino acid sequence substantially represented by SEQ ID NO:100.
37. An HIS3 gene DNA comprising a nucleotide sequence substantially represented by SEQ ID NO:99.
38. A recombinant expression vector substantially comprising the gene DNA of (36) or (37) or a fragment thereof as a selectable marker.
39. A *Ogataea minuta* strain transformed with a recombinant expression vector of (38).
40. An *Ogataea minuta* train according to (39), the strain being from the strain IFO 10746.
41. A 3-isopropylmalate dehydrogenase (LEU2) gene DNA encoding an amino acid sequence substantially represented by SEQ ID NO:108.
42. A LEU2 gene DNA comprising a nucleotide sequence substantially represented by SEQ ID NO:107.
43. A recombinant expression vector substantially comprising the gene DNA of (41) or (42) or a fragment thereof as a selectable marker.
44. An *Ogataea minuta* strain transformed with the recombinant expression vector of (43).
45. An *Ogataea minuta* stain according to claim 44, the strain being from the IFO 10746.
46. An α-1,6-mannosyl transferase (OCH1) gene DNA encoding an amino acid sequence substantially represented by SEQ ID NO:43.
47. An OCH1 gene DNA comprising a nucleotide sequence substantially represented by SEQ ID NO:42.
48. An *Ogataea minuta* strain wherein the gene of (46) or (47) has been disrupted.
49. An *Ogataea minuta* strain according to (48), the strain being from the strain IFO 10746 strain.
50. A proteinase A (PEP4) gene DNA encoding an amino acid sequence substantially represented by SEQ ID NO:52.
51. A PEP4 gene DNA comprising a nucleotide sequence substantially represented by SEQ ID NO:51.
52. An *Ogataea minuta* strain wherein the gene of (50) or (51) has been disrupted.
53. An *Ogataea minuta* strain according to (52), the strain being from the strain IFO 10746.
54. A proteinase B (PRB1) gene DNA encoding an amino acid sequence substantially represented by SEQ ID NO:58.
55. A PRB1 gene DNA comprising a nucleotide sequence substantially represented by SEQ ID NO:57.
56. An *Ogataea minuta* strain wherein the gene of (54) or (55) has been disrupted.
57. An *Ogataea minuta* strain according to (56), the strain being from the strain IFO 10746.
58. A YPS1 gene DNA encoding an amino acid sequence substantially represented by SEQ ID NO:116.
59. A YPS1 gene DNA comprising a nucleotide sequence substantially represented by SEQ ID NO:115.
60. An *Ogataea minuta* strain wherein the gene of (58) or (59) has been disrupted.
61. An *Ogataea minuta* strain according to (60), the strain being from the strain IFO 10746.
62. A process for producing a protein encoded by a heterologous gene, wherein the heterologous gene is transferred into the *Ogataea minuta* strain of (60) or (61).
63. A process according to (62), wherein the heterologous gene encodes an antibody or a fragment thereof.
64. A process for preventing from decomposition of an antibody or a fragment thereof, comprising disrupting a YPS1 gene in a methylotrophic yeast.
65. A process according to (64), wherein the methylotrophic yeast is an *Ogataea minuta* strain.
66. A process according to (65), wherein the *Ogataea minuta* strain is from the strain IFO 10746.
67. A process according to any one of (64) to (66), wherein the class of the antibody is IgG.
68. A process according to (67), wherein the subclass of the antibody is IgG1.
69. A process according to any one of (64) to (68), wherein the antibody is a human antibody.
70. A KTR1 gene DNA encoding an amino acid sequence substantially represented by SEQ ID NO:64.
71. A KTR1 gene DNA comprising a nucleotide sequence substantially represented by SEQ ID NO:63.
72. An *Ogataea minuta* strain wherein the gene of (70) or (71) has been disrupted.
73. An *Ogataea minuta* strain according to (72), the strain being from the strain IFO 10746.
74. An MNN9 gene DNA encoding an amino acid sequence substantially represented by SEQ ID NO:70.
75. An MNN9 gene DNA comprising a nucleotide sequence substantially represented by SEQ ID NO:69.
76. An *Ogataea minuta* strain wherein the gene of (74) or (75) has been disrupted.
77. An *Ogataea minuta* strain according to claim 76, the strain being from the strain IFO 10746.
78. An alcohol oxidase (AOX) gene DNA encoding an amino acid sequence substantially represented by SEQ ID NO:78.
79. An AOX gene DNA comprising a nucleotide sequence substantially represented by SEQ ID NO:77.
80. A DNA comprising a promoter of alcohol oxidase (AOX), wherein the DNA comprises a nucleotide sequence substantially represented by SEQ ID NO:79.
81. A DNA comprising a terminator of alcohol oxidase (AOX), wherein the DNA comprises a nucleotide sequence substantially represented by SEQ ID NO:80.
82. A gene expression cassette comprising a DNA comprising a promoter as defined in (80), a heterologous gene, and a DNA comprising a terminator as defined in (81).
83. A recombinant expression vector comprising a gene expression cassette of (82).

84. An *Ogataea minuta* strain transformed with the recombinant expression vector of (83).
85. An *Ogataea minuta* strain according to (84), the strain being from the strain IFO 10746.
86. A glyceraldehyde-3-phosphate dehydrogenase (GAPDH) gene DNA encoding an amino acid sequence substantially represented by SEQ ID NO:6.
87. A glyceraldehyde-3-phosphate dehydrogenase (GAPDH) gene DNA comprising a nucleotide sequence substantially represented by SEQ ID NO:5.
88. A DNA comprising a promoter of glyceraldehyde-3-phosphate dehydrogenase (GAPDH), wherein the DNA comprises an amino acid sequence substantially represented by SEQ ID NO:7.
89. A DNA comprising a terminator of glyceraldehyde-3-phosphate dehydrogenase (GAPDH), wherein the DNA comprises an amino acid sequence substantially represented by SEQ ID NO:8.
90. A gene expression cassette comprising a DNA comprising a promoter as defined in (88), a heterologous gene, and a DNA comprising a terminator as defined in (89).
91. A recombinant expression vector comprising the gene expression cassette of (90).
92. An *Ogataea minuta* strain transformed with a recombinant expression vector of (91).
93. An *Ogataea minuta* strain according to claim 92, the strain being from the strain IFO 10746.
94. A process for producing an *Ogataea minuta* strain, which is capable of producing a mammalian type sugar chain represented by the following structural formula (Man$_5$GlcNAc$_2$):

Structural Formula 2

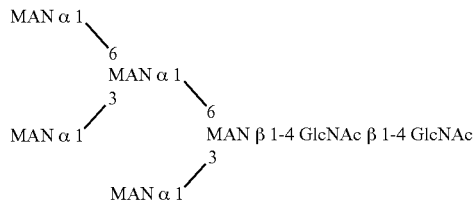

comprising a step of disrupting OCH1 gene (SEQ ID NO:42) in the *Ogataea minuta* strain.
95. A process of (94), wherein the *Ogataea minuta* strain is from the strain IFO 10746.
96. A process according to (94) or (95), which further comprises a step of disrupting at least one gene selected from the group consisting of a URA3 gene comprising the nucleotide sequence represented by SEQ ID NO:15, an ADE1 gene comprising the nucleotide sequence represented by SEQ ID NO:27, an HIS3 gene comprising the nucleotide sequence represented by SEQ ID NO:99, and a LEU2 gene comprising the nucleotide sequence represented by SEQ ID NO:107.
97. A process according to any one of (94) to (96), which further comprises a step of disrupting at least one gene selected from the group consisting of a PEP4 gene comprising the nucleotide sequence represented by SEQ ID NO:51, a PRB1 gene comprising the nucleotide sequence represented by SEQ ID NO:57, and a YPS1 gene comprising the nucleotide sequence represented by SEQ ID NO:115.
98. A process according to any one of (94) to (97), which further comprises a step of disrupting a KTR1 gene comprising the nucleotide sequence represented by SEQ ID NO:63 and/or an MNN9 gene comprising the sequence represented by SEQ ID NO:69.
99. A process according to any one of (94) to (98), which further comprises a step of introducing and expressing an α-1,2-mannosidase gene from *Aspergillus saitoi*.
100. A process according to (99), wherein the α-1,2-mannosidase gene is transferred into the vector of (83) and expressed.
101. A process according to any one of (94) to (100), which further comprises a step of introducing and expressing a PDI gene.
102. A process according to (101), wherein the PDI gene is a gene (M62815) from *Saccharomyces cerevisiae*.
103. A process according to (101) or (102), wherein the PDI gene is transferred into the vector of claim 83 and expressed.
104. A process according to any one of (94) to (103), which further comprises a step of introducing and expressing a heterologous gene.
105. A process according to (104), wherein the heterologous gene is transferred into the vector of claim 83 and expressed.
106. A process for producing a protein encoded by a heterologous gene, which comprises culturing *Ogataea minuta* produced by the process of (104) or (105) in a medium, to obtain the protein comprising a mammalian type sugar chain encoded by the heterologous gene from the culture.
107. A protein comprising a mammalian type sugar chain encoded by a heterologous gene, wherein the protein has been produced by the process of (106).
108. A process for producing an *Ogataea minuta* strain, which is capable of producing a mammalian type sugar chain represented by the following structural formula (Man$_5$GlcNAc$_2$):

Structural Formula 2

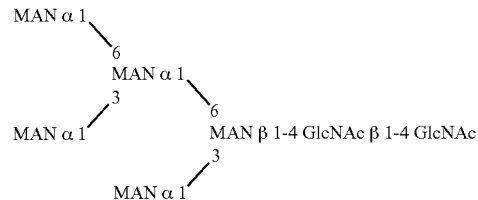

wherein the process comprises the steps of:
  disrupting an OCH1 gene represented by SEQ ID NO:42 in an Ogataea minuta strain; and
  disrupting a URA3 gene represented by SEQ ID NO:15 in the same strain; and
  disrupting a PEP4 gene represented by SEQ ID NO:51 in the same strain; and
  disrupting a PRB1 gene represented by SEQ ID NO:57 in the same strain.
109. A process according to (108), wherein the *Ogataea minuta* strain is from the strain IFO 10746.
110. A process according to (108) or (109), which further comprises a step of disrupting an ADE1 gene comprising the nucleotide sequence represented by SEQ ID NO:27.
111. A process according to (110), which further comprises a step of disrupting a KTR1 gene comprising the nucleotide sequence represented by SEQ ID NO:63.
112. A process according to (111), which further comprises a step of disrupting an HIS3 gene comprising the nucleotide sequence represented by SEQ ID NO:99.

113. A process according to (111), which further comprises a step of disrupting a LEU2 gene comprising the nucleotide sequence represented by SEQ ID NO:107.
114. A process according to (111), which further comprises the step of:
1) disrupting a YPS1 gene comprising the nucleotide sequence represented by SEQ ID NO:115.
115. A process according to any one of (108) to (114), which further comprises a step of introducing and expressing an α-1,2-mannosidase gene.
116. A process according to (115), wherein the α-1,2-mannosidase gene is transferred into the vector of (83) and expressed.
117. A process according to any one of claims 108 to 116, which further comprises a step of introducing and expressing a PDI gene (M62815).
118. A process according to (117), wherein the PDI gene (M62815) is transferred into the vector of (83) and expressed.
119. A process according to any one of (108) to (118), which further comprises a step of introducing and expressing a heterologous gene.
120. A process according to claim 119, wherein the heterologous gene is transferred into the vector of (83) and expressed.
121. A process for producing a protein encoded by a heterologous gene comprising a mammalian type sugar chain, wherein the process comprises culturing *Ogataea minuta* produced by the process of (119) or (120) in a medium to obtain the protein from the culture.
122. A protein encoded by a heterologous gene comprising a mammalian type sugar chain, wherein the protein has been produced by the process of(121).

This specification includes the contents disclosed by the specification and/or drawings of the Japanese Patent Application No. 2002- 127677, which is the basis of the priority claim of this application.

ABBREVIATION

Figure 1:
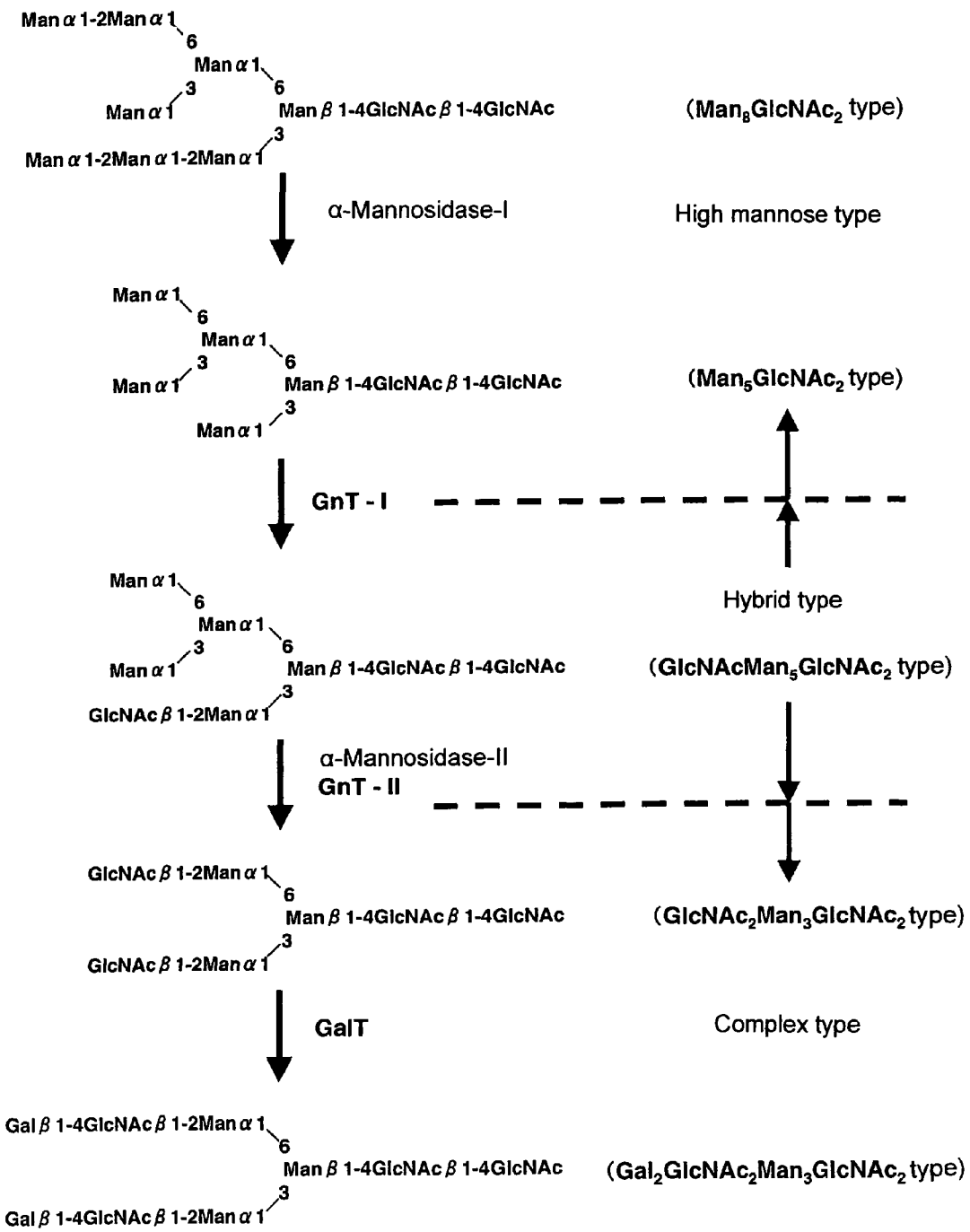
FIG. 1 shows the biosynthesis pathway of N-linked sugar chains, which is general in mammals.
Figure 2:
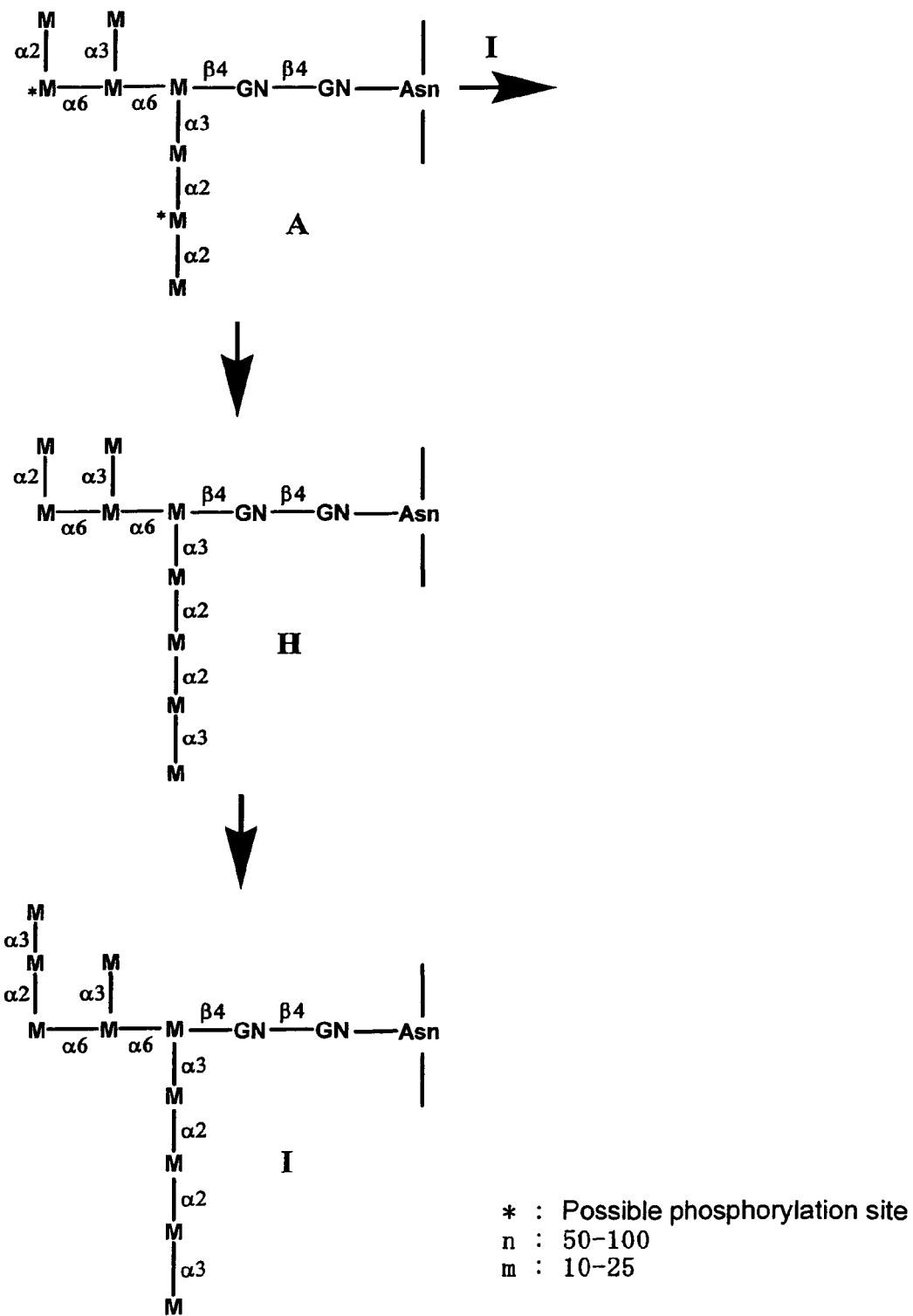
FIG. 2 shows the biosynthesis pathway of N-linked sugar chains in yeast (*S. cerevisiae*), wherein M is mannose, and α2, α3, α6 and β4 mean α-1,2 linkage, α-1,3 linkage, α-1,6 linkage and β-1,4 linkage, respectively.
Figure 2:
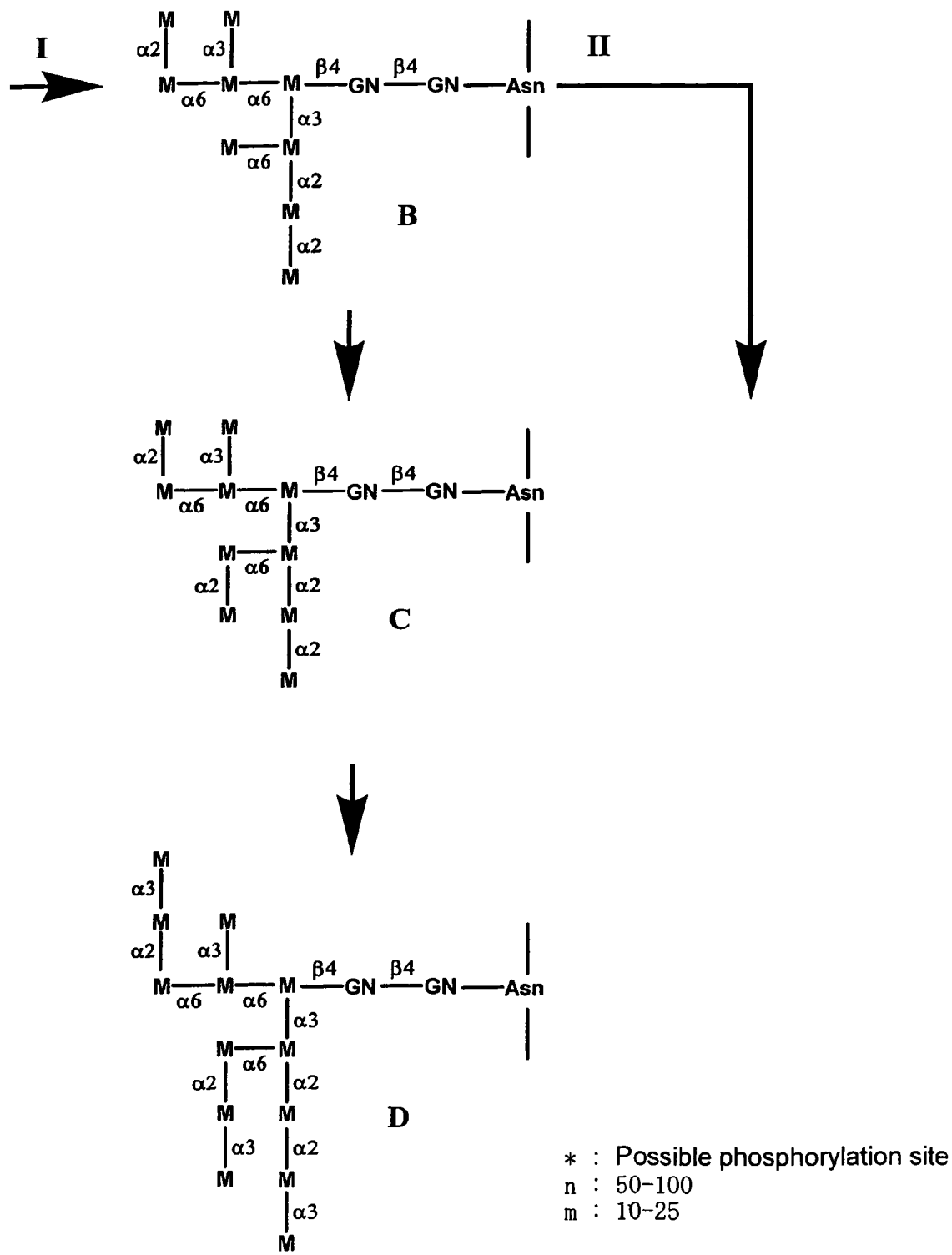
Figure 2:
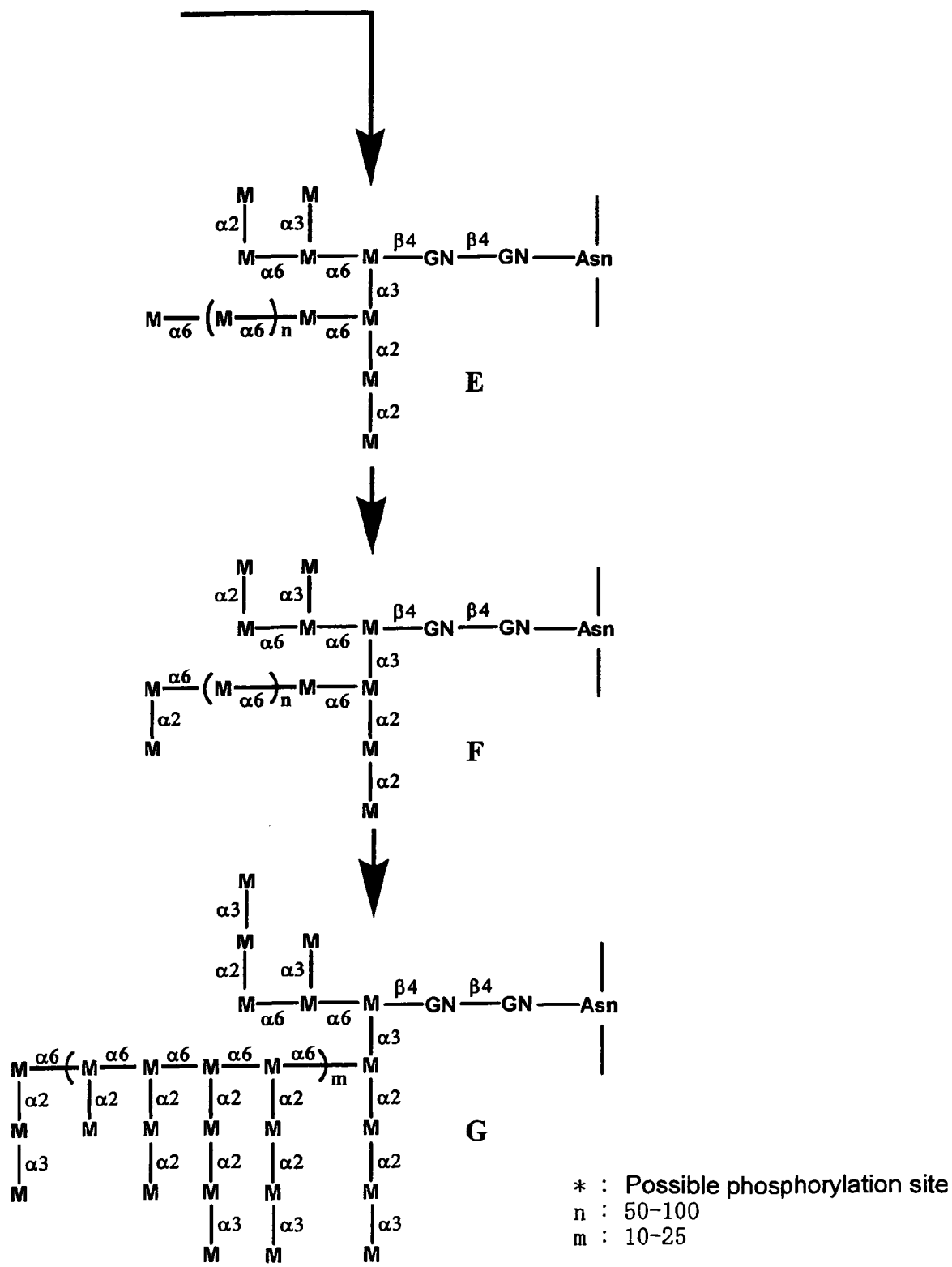

GlcNAc, GN: N-acetylglucosamine
Man, M: mannose
PA: 2-amino pyridylation

MODES FOR CARRYING OUT THE INVENTION

Hereinafter, the invention will be described in detail.

According to the invention, the process for producing a glycoprotein comprising a mammalian type sugar chain(s) comprises the following steps of:

1) breeding a methylotrophic yeast strain producing a mammalian type sugar chain, by introducing an α-1,2-mannosidase gene into a mutant strain comprising mutated sugar chain biosynthesizing enzyme genes (for example, an OCH1 gene α-1,6-mannosyl transferase) knockout mutant, which is considered to be a key enzyme for the elongation reaction where mannose residues attach to an M8 high mannose type sugar chain one by one via α-1,6 linkage), and expressing it under the control of a potent promoter such as methanol-inducible promoter; and 2) culturing in a medium the yeast strain bred by introducing heterologous genes into a mutant yeast which comprises mutated sugar chain biosynthesizing enzyme genes and expressing these genes, and obtaining the glycoproteins comprising a mammalian sugar chain from the culture.

1. Preparation of Mammalian Type Sugar Chain Producing Strains

According to the present invention, mutant strains of yeast capable of producing mammalian type sugar chains, wherein the mutant strain has a disruption in its outer chain biosynthesis gene specific to yeast and has been deprived of sugar chains specific to yeast, can be prepared in the following manner.

1-1 Preparation of Man5 Type Sugar Chain ("High Mannose Type Sugar Chain") Producing Yeasts Mutation trait necessary for the mutant yeast of the invention is a mutation of a gene(s) peculiar to yeast associated with the outer sugar chain biosynthesis system, and specifically at least a mutation of OCH1 gene. That is, as long as the mutant yeast has the above-mentioned mutation, it may be either a natural mutant strain or an artificial mutant strain.

The OCH1 gene means a gene encoding α-1,6 mannosyl transferase, which catalyses the initial reaction of the outer sugar chain formation in yeast, and works to further transfer a mannose residue to the core sugar chain of N-linked sugar chain of a glycoprotein of yeast via α-1,6-linkage. This reaction functions as a trigger for attaching mannose excessively compared with the glycoproteins of animal cells ("hypermannosylation"), thereby forming a mannan-type sugar chain peculiar to yeast. Therefore, OCH1 gene encodes a protein having the above-mentioned activity and function strictly, and it does not refer to a gene which simply has a homology to the gene sequence or the amino acid sequence deduced from the gene sequence.

However, in order to change the sugar chain of yeast into a mammalian type sugar chain, just the manipulation that disrupts this OCH1 gene is not enough.

As mentioned above, in a mammalian cell, α-mannosidase I acts on a high mannose type sugar chain to cut off several mannose residues, and finally generates a Man5 high mannose type sugar chain ("Man5GlcNAc2"). This Man5 type sugar chain serves as a prototype of mammalian type sugar chain. N-acetylglucosaminyl transferase (GnT) I acts on this sugar chain, and causes the transfer of one N-acetylglucosamine residue to generate a hybrid type sugar chain which comprises GlcNAcMan5GlcNAc2, followed by successive formation of complex type sugar chains. Therefore, to make a yeast cell to produce a mammalian type sugar chain(s), it would be necessary to create a yeast which produces a Man5 high mannose type sugar chain (i.e., Man5GlcNAc2) first.

α-1,2-mannosidase (also referred to as α-mannosidase-I) as used in the invention is not limited as long as it has the above-mentioned enzyme activity. For example, α-mannosidase-I involved in the above-mentioned sugar chain biosynthesis system in mammalian cells, α-mannosidase enzymes from other animals such as nematode, and α-1,2-mannosidase enzymes from fungi such as *Aspergillus saitoi* can be used.

In order to effect the invention efficiently, the expression site of α-1,2-mannosidase is important. It is said that α-1,2-mannosidase functions in the cis Golgi in mammalian cells. On the other hand, addition of a sugar chain peculiar to yeast in the yeast cell is performed in the cis, medial or trans Golgi. Therefore, it is necessary to make α-1,2-mannosidase act prior to the modification in which a sugar chain peculiar to yeast is attached, i.e., modification in Golgi apparatus. If the expression site is in the Golgi apparatus which exists downstream in the transportation pathway of glycoprotein, then Man5 type sugar chains cannot be generated efficiently.

Therefore, to attain this purpose, endoplasmic reticulum (ER) retention signal (for example, amino acid sequence shown by His-Asp-Glu-Leu) in yeast may be attached to the C terminus of the protein of α-1,2-mannosidase thereby localizing the enzyme within ER to cause expression of the activity so that the attachment of sugar chain peculiar to yeast can be inhibited. This method was already reported by inventors (Chiba et al., J. Biol. Chem., 273, 26298-26304 (1998)).

However, when the sugar chain of a certain protein is changed into a mammalian type sugar chain in order to use this protein as a drug, it is required to remove sugar chains peculiar to yeast almost completely, and use of only the above-mentioned technique is supposed to be insufficient. In fact, although in the above-mentioned report Chiba et al. use the promoter of glyceraldehyde-3-phosphate dehydrogenase, which is known to be the strongest promoter functioning in *Saccharomyces cerevisiae*, in the expression of the glyceraldehyde-3-phosphate dehydrogenase, the results of analyzing the sugar chains of cell wall glycoproteins reveal that Man5 type sugar chains were generated in the level of only about 10%.

The system using the sugar chain mutant of *Ogataea minuta* in the invention enables formation of a Man5 type sugar chain in the amount of 20% or more, preferably 40% or more, more preferably 60% or more, most preferably 80% or more of the sugar chains of the cell wall glycoproteins which the yeast produces as in the Examples below. Also, Man5 type sugar chains are formed in the amount of 20% or more, preferably 40% or more, more preferably 60% or more, most preferably 80% or more in the example of the secretion and expression of a heterologous gene. Thus the problems in *Saccharomyces cerevisiae* have been solved. The application of *Ogataea minuta* in the invention to various glycoproteins will be expected from these results.

On the other hand, Chiba et al. uses the Δoch1Δmnn1Δmnn4 strain which generates only the Man8 type sugar chain, a core sugar chain. MNN1 gene is presumed to be a gene peculiar to *Saccharomyces cerevisiae*, and the sugar chain synthesis pathway and sugar chain synthesizing genes was isolated and analyzed, but sugar chain structure was not fully analyzed for other yeasts. For example, the existence of a sugar chain which has β-mannoside linkage is known for *Pichia pastoris* as mentioned above (Higgins (ed.), *Pichia* Protocols, 1998, pp. 95-105, Humana Press and Biochim.et Biophy. Acta, 1426, 227-237 (1999)). Moreover, the results of SDS-PAGE of the glycoproteins produced by the OCH1 gene homologue knockout mutant disclosed in Japanese Patent Publication (Kokai) No. 9-3097A (1997) surely presented the data indicating that the sugar chains have been shortened into lower molecules; namely, it is presumed that they are not glycoproteins having a single sugar chain like Man8 type sugar chain. No gene involved in the synthesis of these sugar chains has been isolated, and great labors are needed for isolating and disrupting the gene.

Thus, to allow a yeast strain to produce Man5 type sugar chains, it is necessary to cause α-1,2-mannosidase to highly express, and for this purpose, a potent promoter is needed. In these circumstances, the invention was completed by using an alcohol oxidase (AOX) gene promoter (inducible by methanol) from methylotrophic yeast known as the strongest inducible expression promoter. Other inducible expression promoters usable in the invention include, but not limited to, promoters for dihydroxyacetone synthetase (DAS) gene and formate dehydrogenase (FDH) gene, and any promoter can used as long as it has an ability to express the enzyme gene in the methylotrophic yeast of the invention.

Thus, mammalian type sugar chains can be produced without disrupting an outer sugar chain synthesis gene peculiar to yeast, by preliminarily trimming (removing) the sites on the sugar chain to which sugar chains peculiar to yeast is attached in the ER and Golgi apparatus. Accordingly, the acquisition of a gene for forming β-mannoside linkage and of an MNN4 gene, which is for addition of mannose phosphate, becomes unnecessary.

However, OCH1 exists quite ubiquitously in yeast, and the location thereof is relatively near the reducing terminal side of the core sugar chain and so it is believed that the gene should be destroyed in order to remove its activity.

Yeast strains applicable to the invention include any strain in which the sugar chain of glycoprotein mainly comprises α-1,2-mannoside linkage, and methylotrophic yeasts are not limited as long as they produce N-linked sugar chains which mainly comprise α-1,2-mannoside linkage, including as specific examples *Ogataea minuta*, *Candida succiphila*, *Pichia pastoris*, *Pichia trehalophila*, *Pichia methanolica*, *Pichia angusta*, *Hansenulla polymorpha*, etc. Preferred is *Ogataea minuta*.

Therefore, the procedures disclosed by the invention are inapplicable to yeast strains having the structure where sugar chains other than α-1,6 mannose have been attached directly to the core sugar chain by the OCH1 gene. That is, any yeast strain which generates glycoproteins with sugar chains peculiar to yeast attached to moieties of the core sugar chain, strictly to moieties of the Man5 type sugar chain, cannot utilize in the procedures of the invention.

Furthermore, mammalization can be more efficiently attained by auxiliary disruption of a KTR gene homologue belonging to (α-mannosyl transferase gene family (for example, KTR1 gene of *Ogataea minuta* as found in the invention), or of an MNN9 gene homologue (for example, MNN9 gene of *Ogataea minuta* as found by the invention) which is believed to be involved in the attachment of sugar chains in the Golgi apparatus.

Furthermore, since sugar chain mutants have generally shorter sugar chains in glycoproteins, and as a result, the cell wall becomes weaker, so the drug susceptibility increases or the resistance to osmotic pressure decreases in the mutants. In such a case problems may occur in cell culture. On the contrary, in the procedure of the invention, which utilizes a methanol-inducible promoter and expresses α-1,2-mannosidase, mammalian type sugar chains can be produced as a by-product along with a glycoprotein encoded by a heterologous gene. Hence, the culture and production can be performed without applying a burden at the time of multiplication of the yeast cell.

The term "a gene(s) associated with the mammalian type sugar chain biosynthesis" as described above means an appropriate number of transgenes, which belong to a group of one or more of the above-mentioned genes, required to produce a sugar chain of interest. When the transgenes are plural, they may belong to a group of homo-type genes or to a group of hetero-type genes.

In order to obtain the produced sugar chains and glycoproteins in high yield, it is desirable to make the above-mentioned enzymes to express highly in a suitable organ (for example, Golgi apparatus). Therefore, it is effective to use genes compatible to the codon usage of yeast. Also, to localize the enzymes in a suitable organ, the addition of a signal sequence or the like of yeast will become effective. For the transfer of a gene, use of vectors such as chromosome integration type (YIp type) vector may be considered. Promoters required to express the gene include, but are not limited to, constitutive expression promoters such as GAPDH and PGK, inducible expression promoters such as AOX1, etc. However, since multiplication of yeast may be affected when one or more glycosidase, glycosyltransferases, or sugar nucleotide transporter genes are expressed, it is necessary to take into consideration the use of an inducible promoter or the appropriate order of introducing genes.

The mutant yeast which produces the above-mentioned mammalian type sugar chain, or the mutant to which the above-mentioned foreign gene has been transferred, is cultured in a culture medium, thereby to produce glycoproteins comprising the same Asn-linked sugar chain as the high-mannose type sugar chain ($Man_5GlcNAc_2$), the hybrid type sugar chain (GlcNAcMan$_5$GlcNAc$_2$) or the complex type sugar chain (for example, Gal$_2$GlcNAc$_2$Man$_3$GlcNAc$_2$), which the mammalian cell produces, either intracellularly or extracellularly. In this case, the content of an outer sugar chain peculiar to yeast is significantly reduced.

Specifically, the transfer of a GnT-I gene into the above-mentioned mutant enables production of a hybrid type sugar chain, and the transfer of a gene(s) associated with the mammalian type sugar chain biosynthesis system (α-mannosidase II, GnT-II, GalT, UDP-GlcNAc Transporter, and/or UDP-Gal Transporter genes) enables production of a double-stranded complex type sugar chain (Gal$_2$GlcNAc$_2$Man$_2$GlcNAc$_2$).

2. Different Genes from *Ogataea minuta* Usable in the Invention

The proteins usable in the invention are not particularly limited as long as they have respective activities, and specifically they are proteins comprising an amino acid sequence substantially represented by the SEQ ID NO described in the Examples below. As used herein, the term "an amino acid sequence substantially represented by SEQ ID NO:X" means that the amino acid sequence includes:
 (a) the amino acid sequence represented by SEQ ID NO:X; or
 (b) an amino acid sequence which comprises a deletion(s), a substitution(s) or an addition(s) of one or several amino acids in the amino acid sequence represented by SEQ ID NO:X.

That is, the above amino acid sequence may be partially modified (for example, substitution, deletion, insertion or addition of an amino acid residue(s) or a peptide chain(s), etc.). Herein, the term "several" in relation to the number of deleted, substituted or added amino acids means any number in the range capable of being introduced by the methods usually used in art, preferably 2 to 10, more preferably 2 to 5, and most preferably 2 to 3.

DNAs comprising a nucleotide sequence, which encodes the protein usable in the invention, are characterized by comprising the nucleotide sequences encoding the above-mentioned proteins from Ogataea minuta as defined in the invention. Such nucleotide sequences are not particularly limited as long as they are the nucleotide sequences encoding the proteins of the invention, and their examples are the nucleotide sequences which encode amino acid sequences substantially represented by the SEQ ID NOs described in the Examples below. As used herein, the term "a nucleotide sequence substantially represented by SEQ ID NO:X" means that the nucleotide sequence includes:
 (a) the nucleotide sequence represented by SEQ ID NO:X; or
 (b) a nucleotide sequence comprising a deletion, a substitution or an addition of one or several nucleotides in the nucleotide sequence represented by SEQ ID NO:X.

This DNA may be conventionally produced by the known procedures. For example, all or part of the DNA may be synthesized by using a DNA synthesizer based on the nucleotide sequence illustrated in the invention, or may be prepared by PCR amplification using chromosome DNA. Here, the term "several" in relation to the number of deleted, substituted or added nucleotides means any number in the range capable of being introduced by the methods usually used in art, for example, site-directed mutagenesis (e.g., Molecular Cloning, A Laboratory Manual, second edition, ed. by Sambrook et al., Cold Spring Harbor Laboratory Press, 1989; Current Protocols in Molecular Biology, John Wiley & Sons (1987-1997)), for example, 2 to 10, preferably 2 to 5, and more preferably 2 to 3.

3. Obtaining Genes

Isolation of a target gene fragment can be performed by extracting genomic DNA from a yeast strain, and selecting the target gene, by using general procedures (Molecular Cloning (1989), Methods in Enzymology 194 (1991)). In the above, the genomic DNA from *Ogataea minuta* can be extracted, for example, by the methods of Cryer et al. (Methods in Cell Biology, 12, 39-44 (1975)) and of P. Philippsen et al. (Methods Enzymol., 194, 169-182 (1991)).

For example, the protoplast prepared from yeast can be subjected to a conventional DNA extraction method, an alcohol precipitation method after removing cell debris under high salt concentration, an alcohol precipitation method after extracting with phenol and/or chloroform, etc. Besides the above method utilizing the preparation of protoplast, DNA may be extracted by break of cells with glass beads. The protoplast method is preferable because preparation of high molecular weight DNA is easy.

A target gene can be obtained, for example, by the PCR method (PCR Technology, Henry A. Erlich, Atockton press (1989)). The PCR is a technique which enables in vitro amplification of a specific DNA fragment to hundreds of thousands fold or more in about 2 to 3 hours, using a combination of sense/antisense primers annealed at each end of the target region, a heat-resistant DNA polymerase, and a DNA amplification system. In the amplification of a target gene, 25-30mer synthetic single-stranded DNAs and genomic DNA can be used as primers and as a template, respectively. The amplified gene may be identified in terms of its nucleotide sequence before use.

The DNA sequence of a gene can be determined by usual methods such as, for example, dideoxy method (Sanger et al., Proc. Natl. Acad. Sci., USA, 74, 5463-5467 (1977)). Alternatively, the nucleotide sequence of DNA can easily be determined by use of commercially available sequencing kits or the like.

The isolation, purification, etc. of the DNA can also be carried out by ordinary methods, and in the case of *E. coli* for example, the DNA may be extracted by the alkali/SDS method and ethanol precipitation, and the DNA subsequently purified by RNase treatment, PEG precipitation or the like.

A target gene can also be obtained by: (a) extracting the total DNA of the above-mentioned yeast, transferring a gene transfer vector, which comprises a DNA fragment derived from said DNA, into a host, thereby to prepare a gene library of the yeast, and (b) subsequently selecting the desired clone from the gene library, followed by amplifying the clone.

The gene library can be prepared as a genomic library by partially digesting the chromosomal DNA obtained by the above-mentioned method with appropriate restriction enzymes (such as Sau3AI) to obtain fragments thereof, ligating the fragments with an appropriate vector, and transforming an appropriate host with the vector. Alternatively, it is also possible by amplifying a fragment of the target gene by PCR first, screening for restriction sites by the genomic Southern analysis so that the target gene can be obtained efficiently, and digesting the chromosomal DNA by this restriction enzyme to obtain the desired fragment. Vectors usable for this purpose include commercially available plasmids such as pBR system, pUC system, Bluescript system, etc., usually known as the known vectors for preparing a gene library. Phage vectors of Charon system or EMBL system etc. or cosmids can be also used widely. The host to be transformed or transduced with the prepared vector for preparation of gene library can be selected depending on the type of the above-mentioned vectors.

Clones can be selected and obtained from the above-mentioned gene library using a labeled probe which comprises a sequence peculiar to a target gene, by means of colony hybridization, plaque hybridization or the like. A sequence peculiar to target gene used as a probe can be obtained by synthesizing a corresponding oligonucleotide of the gene which encodes the amino acid sequence of a target protein purified from *Ogataea minuta*, specifically amplifying the desired DNA fragment by PCR using the chromosomal DNA of *Ogataea minuta* as a template, to obtain it. The peculiar sequence may also be obtained by searching for a gene which encodes a protein homolog from different species in DNA databases such as GenBank or protein databases such as SWISS-PROT, to obtain the sequence information, synthesizing an oligonucleotide corresponding to the conserved amino acid sequence analyzed with an analyzing software such as homology search programs such as BLAST, GENETYX (Software Development), and DNAsis (Hitachi Software), and specifically amplifying the desired DNA fragment by PCR using the chromosomal DNA of *Ogataea minuta* as a template. The synthesized oligonucleotide may be used as a probe. Once the nucleotide sequence is determined, the desired gene can be obtained by chemical synthesis or PCR using primers synthesized based on the determined nucleotide sequence, or by hybridization using as a probe the DNA fragment comprising the above-mentioned nucleotide sequence.

4. Gene Disruption

In the invention, a target gene is basically disrupted in accordance with the method disclosed by Rothstein, in Methods Enzymol., 101, 202-211 (1983). Specifically, a target gene DNA obtained by the above-described method is first cut or partially deleted, an appropriate selectable marker gene DNA is inserted at the cut or deleted site, thereby to prepare a DNA structure in which the selectable marker has been sandwiched between upstream and downstream regions of the target gene. Subsequently, this structure is transferred to a yeast cell. The above manipulation results in two recombinations at homologous moieties between each end of the transferred fragment (i.e., the DNA structure with a selectable marker sandwiched) and a target gene on chromosome, thereby substituting the target gene on chromosome with the transferred fragment. Auxotrophic markers and drug resistant markers, as shown below, may be used as the selectable marker for gene disruption. In this case, one selectable marker will generally be required for disrupting one gene. When URA43 gene is used, ura3 trait can be efficiently reproduced and so it is often used for this purpose.

Specific explanation is provided using an example of the preparation of an OCH1 gene knockout strain. A plasmid carrying URA3 gene, which comprises a repeated structure before and after structural gene, is constructed, and the gene cassette cleaved out with a restriction enzyme is inserted at a target gene on the plasmid, thereby to construct a disrupted allele. Gene-knockout strain can be obtained by substituting with a target gene on the chromosome using this plasmid. As the URA3 gene inserted into the chromosome is sandwiched by the repeated structures, it is dropped out of the chromosome due to homologous recombination between the repeated structures. The selection of this URA3 deficient strain can be carried out by use of 5-fluoroorotic acid (5-FOA). A ura3 mutant is resistant to 5-FOA (Boeke et al., Mol. Gen. Genet., 197, 345-346 (1984); Boeke et al., Methods Enzymol., 154, 165-174 (1987)), and a cell strain having URA3+ phenotype can no longer grow in the 5-FOA medium. Thus, separating a strain with resistant trait in a medium to which 5-FOA is supplemented, enables manipulations using a URA3 gene marker again. Therefore, the mutated auxotrophic trait of the original yeast strain is not damaged by gene destruction in the "artificial knockout mutant" which has undergone the gene disruption artificially by this technique.

In addition, in the "natural mutant" where the gene disruption occurs naturally without using the above-mentioned procedures but spontaneously, the number of the mutated auxotrophic traits is not decreased nor increased.

5. Marker for Gene Transfer

The auxotrophic marker for transfer of a heterologous gene into the mutant yeast of the invention is defined by yeast strains to be used, and is specifically selected from ura3, his3, leu2, ade1 and trp1 mutations. Although the number of auxotrophic markers depends on the number of transfer genes, generally one auxotrophic marker is required for transfer of one gene. When plural of genes are transferred, a larger number of auxotrophic markers become necessary as the number of transfer genes increases more and more, since the transfer gene fragment is longer, and transfer efficiency decreases, and as a result, expression efficiency also decreases.

In the invention, the gene which complements the auxotrophy is a gene associated with the in vivo synthetic system of biological components such as amino acids and nucleic acids. The complementing gene is an original functional gene itself, since the mutated traits include such a mutation that the gene fails to function. Therefore, the gene from the original yeast strain is desirable.

Usable selectable markers other than the above-mentioned auxotrophic markers include drug resistance markers, which impart resistance to drugs such as G418, cerulenin, aureobasidin, zeocin, canavanine, cycloheximide, hygromycin and blastcidin, and may be used to transfer and disrupt a gene. Also, it is possible to perform the transfer and disruption of a gene by using, as a marker, the gene which imparts a solvent resistance like ethanol resistance, an osmotic pressure resistance like resistance to salt or glycerol, and a metal ion resistance like resistance to copper, etc.

6. Method for Transfer of DNA into Cell and Transformation with Same

Methods for transferring a DNA into a cell for its transformation with the DNA in the above procedures include general methods, for example, a method of incorporating a plasmid into a cell after the cell is treated with lithium salt so that the DNA is prone to be naturally transferred into the cell (Ito et al., Agric. Biol. Chem., 48, 341 (1984)), or a method of electrically transferring a DNA into a cell, a protoplast method (Creggh et al., Mol. Cell. Biol., 5, 3376 (1985)), and the like (Becker and Guarente, Methods Enzymol., 194, 182-187 (1991)). The expression vector of the invention can be incorporated into the host chromosome DNA, and can exist stably.

7. Expression of Heterologous Gene

The term "heterologous gene" as used herein is a gene of interest to be expressed, and means any gene different from the gene for *Ogataea minuta*-derived alcohol oxidase or glyceraldehyde-3-phosphate dehydrogenase. Examples of heterologous genes include: enzyme genes such as acidic phosphatase gene, α-amylase gene and α-galactosidase gene; interferon genes such as interferon α gene and interferon γ gene; interleukin (IL) genes such as IL1 and IL2; cytokine genes such as erythropoietin (EPO) gene and granulocyte colony stimulating factor (G-CSF) gene; growth factor genes; and antibody genes. These genes may be obtained by any procedures.

To utilize the invention efficiently, a gene encoding a glycoprotein produced by a mammal cell, particularly human cell, can be used. That is, since the object of the invention is to produce a glycoprotein which has the same or similar sugar chain structure as that of mammals particularly human, the invention is effectively applied to the glycoprotein which has a sugar chain structure on the protein molecule, and additionally to useful physiologically active proteins including antibodies. An antibody has been used as a medicament for many years. The antibody, however, was from an origin other than a human and so it causes the production of an antibody against the administered antibody itself. Accordingly, multiple administrations cannot be conducted, so its use is limited. In recent years, humanized antibody in which the amino acid sequence except the antigen-binding site is replaced by a sequence of human antibody, has been prepared. Furthermore, a mouse producing human antibody into which human antibody gene has been transferred has been created. Complete human antibody is now available and the use of an antibody as drug has prevailed quickly. These antibodies can be produced by hybridomas or by cultured cells such as CHO cell, which comprise a transfer gene encoding an antibody, however there are many problems in respect of productivity, safety, etc. Under such a circumstance, production of antibodies using yeast is expected, because the above problems may be overcome by the use of yeast. In this case, as the antibody molecule is a glycoprotein to which N-type sugar chains are attached at two or more sites in each heavy chain, and when the antibody is produced with yeast, sugar chains peculiar to yeast are attached thereto. These sugar chains have antigenicity by themselves as mentioned above, and/or an action to decrease physiological activity. Hence, when the antibody produced with yeast is used as a medicament, the conversion of the sugar chain to a mammalian type is unavoidable.

In the meantime, the method for preparing antibodies with high ADCC activity has been reported, which method comprises removal of α-1,6-fucose attached to GlcNAc on the side of the reduced terminus of a sugar chain (PCT/JP00/02260). Although α-1,6-fucosyl transferase gene (FUT8) is known as a gene involved in addition of α-1,6-fucose, this gene is present ubiquitously in animal cells, and unless the cells deficient in this enzyme activity or the cells in which this gene is artificially disrupted are used, part of the prepared antibody is inevitably attached with α-1,6-fucose.

On the contrary, since the yeast generally has no synthetic systems of fucose and α-1,6-fucosyl transferase gene (FUT8), glycoproteins free from α-1,6-fucose can be produced without artificial gene disruption. So, highly active antibodies could be naturally produced.

While there is a report on high production of antibody fragments such as Fab and ScFv in yeast, there is almost no report on high production of a full-length antibody. Since antibody fragments such as Fab and ScFv do not comprise the Fc domain which exists in the heavy chain of an antibody, they have neither antibody-dependent cellular cytotoxicity (ADCC) nor complement-dependent cytotoxicity (CDC), which is a physiological activity peculiar to an antibody, and their use as drug is restricted. The antibody has 14 disulfide (S—S) linkages in total, and it is presumed that the reason why full-length antibody cannot be highly produce within a yeast cell is due to that the antibody molecule cannot appropriately fold. Although this cause is not clear, it cannot be denied that the phenomenon may possibly be caused by difference in the structure of N-type sugar chain attached to the antibody heavy chain. So, use of the yeast of the invention producing mammalian sugar chains may enable the efficient production of an antibody molecule having suitable conformation. Probably, functional antibody may also be highly produced by introducing Protein Disulfide Isomerase (PDI), a molecule chaperon. In addition, according to the invention, it is possible to produce either an intact antibody molecule or other antibody fragments as mentioned above, or other antibody fragments as long as it has a desired function. The antibody is not particularly limited, but preferred antibody includes a humanized antibody in which an antibody-binding site of another mammalian antibody is introduced into a mammalian, particularly preferably human type framework, or a human antibody. Although not limited particularly, the antibody to be expressed is preferably in the class of IgG and more preferably in the subclass of IgG1.

When a heterologous protein is produced by the gene recombinant technology, it is sometimes degraded by a protease in the host. In such a case, the production of the protein of interest decreases, heterogeneous proteins generate, and the purification of the protein becomes difficult due to the contamination of proteolysis products.

In order to circumvent these problems, such a culture method that the activity of a protease degrading the desired protein is inhibited has been studied, for example, a method of adjusting the pH of a medium for culturing a recombinant cell to inhibit a protease activity. However, this method will affect the growth of host yeast which expresses a certain type of heterologous protein, and is effective only for the degradation of the protein outside the cell.

There is an example which increased the production of cell proteins present inside and outside the cell by using a protease deficient strain in which proteinase A and proteinase B have been inactivated in *Saccharomyces cerevisiae*, *Pichia pastoris*, or *Candida boidinii* (Japanese Patent Publication (Kohyo) No. 6-506117A (1994), Weis, H. M. et al., FEBS Lett., 377, 451 (1995), Inoue, K. et al., Plant Cell Physiol., 38 (3), 366 (1997), and Japanese Patent Publication (Kokai) No. 2000-78978).

Proteinase A and proteinase B are proteases located in the vacuole and are encoded by PEP4 gene and PRB1 gene, respectively. According to researches on yeast *Saccharomyces cerevisiae*, proteinase A and proteinase B activate themselves and other proteases such as carboxypeptidase Y (vandenHazel, H. B. et al., YEAST, 12, 1 (1996)).

In the meantime, Yapsin is a protease which exists widely in the Golgi apparatus and cell membrane, and according to researches on *Saccharomyces cerevisiae*, it was isolated as a homologue of the protein encoded by KEX2 gene known as a processing enzyme of α-factor. To date, genes of Yapsin1 (Aspartic proteinase 3, YAP3), Yapsin2 (Aspartic proteinase MKC7), Yapsin3, Yapsin6, Yapsin7, etc. are known (Egel-Mitani, M. et al., Yeast 6 (2), 127-137 (1990); Komano, H. et al., Proc. Natl. Acad. Sci. U.S.A. 92(23), 10752-10756 (1995); and *Saccharomyces* Genome Database (SGD)). Of them, Yapsin1 is encoded by YPS1 gene.

An example in which the production of cell proteins present inside and outside the cell was increased by using a protease deficient *Saccharomyces cerevisiae* strain in which Yapsin1 has been inactivated is known (M. Egel-Mitani et al., Enzyme and Microbial Technology, 26, 671 (2000); Bourbonniais, Y. et al., Protein Expr. Purif, 20, 485 (2000)).

*Ogataea minuta* strains of the invention deficient in PEP4 gene, PEP4PRB1 gene or PEP4PRB1YPS1 gene, whose protease activities have been reduced, maintain an ability to grow themselves equivalent to the wild strain under culture conditions of using a nutrition medium, and are thus very good hosts for the production of heterologous proteins. Therefore, the above-mentioned yeasts can efficiently produce heterologous proteins, such as an antibody highly susceptible to protease, due to suppressing the degradation of the yeasts.

8. Construction of Expression Cassette for Heterologous Gene

The expression system useful for production of proteins can be prepared by various methods. A protein expression vector comprises at least a promoter area, a DNA encoding the protein, and the transcription terminator area in the direction of the reading frame of transcription. These DNAs are arranged as related operably to each other so that the DNA encoding the desired glycoprotein may be transcribed to RNA.

The high expression promoter which can be used in the invention is preferably a methanol-inducible expression promoter, and includes, for example, alcohol oxidase (AOX) gene promoter of *Ogataea minuta*, dihydroxyacetone synthase (DAS) gene promoter of *Ogataea minuta*, formate dehydrogenase (FDH) gene promoter of *Ogataea minuta*, etc.

The constitutive expression promoter includes glyceraldehyde-3-phosphate dehydrogenase (GAPDH) gene promoter of *Ogataea minuta*, phosphoglycerokinase (PGK) gene promoter of *Ogataea minuta*, etc.

The transcription terminator may be the sequence that has an activity to cause the termination of the transcription directed by the promoter, and may be identical to or different from the promoter gene.

According to one aspect of the invention, we (1) obtained the nucleotide sequences of an *Ogataea minuta* alcohol oxidase(AOX) gene as a methanol-inducible expression cassette and a glyceraldehyde-3-phosphate dehydrogenase (GAPDH) gene as a constitutive expression cassette, along with their promoters and terminators, (2) isolated the promoters and terminators, (3) constructed expression vectors, and (4) used the expression vectors of the invention to prepare transformed cells, and confirmed that when expressed in the transformed cells, heterologous genes are expressed in the same manner as the genes from *Ogataea minuta*. The expression cassette of a heterologous gene using the promoter and terminator for the alcohol oxidase (AOX) gene will be described below as an example.

8-1 Cloning of Alcohol Oxidase (AOX) Gene

In order to obtain the expression cassette of the invention, alcohol oxidase (AOX) gene was cloned at first. As the starting material, yeast such as *Ogataea minuta* strain IFO 10746 is exemplified. Cloning of the gene can be performed by a method as mentioned above.

8-2 Isolation of Promoter and Terminator Areas

Promoter and terminator areas can be cut out with a restriction enzyme(s) but generally a convenient restriction site does not necessarily exist at a suitable position. Accordingly, the nucleotide sequence may be cleaved in order from restriction sites in the coding area toward the promoter area by an endonuclease, thereby to find a clone deleted until the suitable position. Recently, a primer with a restriction enzyme recognition site at the end has been used to be easily able to amplify and obtain desired promoter and terminator areas by PCR.

It is also possible to chemically synthesize those areas, or alternatively, to make semi-synthesized promoter and terminator by use of both a DNA whose partial area is chemically synthesized and which is then cloned using the partial DNA, and a restriction enzyme site(s).

The sequence comprising a promoter area or a terminator area is illustrated in SEQ ID NO:79 or in SEQ ID NO:80, respectively. They are, however, not to be limited to the specific sequences, and the nucleotide sequences thereof may be modified by deletion, insertion, substitution, addition, or the like, as long as they essentially hold transcription activity.

Modification of the nucleotide sequences can be performed by any known mutagenesis method (e.g., by the method using TAKARALA LA PCR in vitro Mutagenesis kit, TAKARA SHUZO CO., LTD., Japan), or the like. When the promoter area is deleted widely, this deletion may appropriately be conducted by PCR using a commercially available kit for deletion (e.g., Deletion kit for kilo sequences of TAKARA SHUZO CO., LTD.).

8-3 Construction of Expression Vector

The expression vector of the invention can be obtained by inserting AOX promoter, a heterologous structural gene, an AOX terminator, a marker gene and a homologous area into an appropriate vector. Examples of the vector used for this purpose include, but are not limited to, *E. coli* plasmid vectors such as the above-mentioned pBR system, pUC system and Bluescript system. Inserting the components of the expression vector into a vector can easily be carried out by those skilled in the art with reference to the description of Examples as described below or by conventional techniques. Those skilled in the art can determine the selectable marker gene and the homologous area easily. Examples of the marker gene include antibiotic resistance genes such as the above-mentioned G-418 and hygromycin resistant genes, and auxotrophy complementing genes such as URA3, ADE1 (phosphoribosyl-amino-imidazole succinocarboxamide synthase), HIS3 (imidazole-glycerol-phosphate dehydratase), LEU2 (3-isopropylmalate dehydrogenase) genes.

DNA encoding a secretion signal sequence which functions in a yeast cell may be added to a heterologous structural gene. Since this expression system allows production and secretion of a glycoprotein out of the host cell, the desired glycoprotein can easily be isolated and purified. The secretion signal sequence includes secretion signal sequences of *Saccharomyces cerevisiae* α-mating factor (α-MF), *Saccharomyces cerevisiae* invertase (SUC2), human α-galactosidase, human antibody light chains, etc.

The constructed expression vector is a chromosome integration type vector, and the desired gene is incorporated by being integrated onto the chromosome. In the case of an auxotrophic marker type vector, a part of the marker gene is cleaved by a restriction enzyme(s) to form a single stranded marker gene. Then the transformation is performed and the vector is generally integrated into a part of the allele on the chromosome. In the case of a drug resistance marker, no allele exists, and so the expression promoter or terminator area is cleaved by a restriction enzyme(s) to form a single stranded promoter or terminator. Then the transformation is performed and the vector is generally integrated onto the above-mentioned part on the chromosome. Once the gene is integrated, it exists on a chromosome, and maintained stably.

8-4 Use of Expression Vector

The expression vector using the AOX promoter of the invention is effective not only for expression of α-1,2-mannosidase gene and heterologous genes of interest but also for expression of other genes. By using expression vectors to which different types of selectable markers have been attached, the vectors can be transferred sequentially into a yeast cell, and high expression of plural genes can be achieved.

For example, the yeast is not a host which originally generates a significant amount of secreted proteins, when compared with mold or the like. Thus, it is expected that the yeast bears no complete secretion mechanism. In fact, as mentioned above, the productivity of an antibody in yeast is originally low.

Therefore, in order to enhance secretion efficiency, it is effective that a molecule chaperon or the like is introduced to attain high expression.

9. Production of Glycoprotein Having Mammalian Type Sugar Chain

To produce glycoproteins having the above-mentioned sugar chains from a heterogeneous organism, the above-mentioned yeast mutant strain is used as a host, and a gene in which a heterologous gene (e.g., cDNA) is ligated downstream of a promoter and can be expressed in the above-mentioned yeast, is prepared. The gene is integrated into the above-mentioned yeast host by homologous recombination or inserted into a plasmid to carry out transformation of the above-mentioned host. The thus prepared transformant of the above-mentioned host is cultured by known methods. The glycoprotein, which is encoded by the heterologous gene, produced intracellularly or extracelluraly is collected and purified, thereby obtaining the glycoprotein.

The above-mentioned mammalian type sugar chain producing yeast mutant strain maintains an ability to grow itself almost equivalent to the wild yeast strain, and this yeast mutant can be cultured by conventional methods as commonly used for culture of yeast. For example, the synthesized medium (containing carbon source, nitrogen source, mineral salts, amino acids, vitamins, etc.) supplemented with various culture-medium ingredients as supplied from Difco and free from amino acids as supplied by a marker required for duplication and maintenance of the plasmid can be used (Scherman, Methods Enzymol., 194, 3-57 (1991)).

The culture medium for expression of a heterologous gene by an expression vector which is controlled by a methanol-inducible promoter to produce the desired gene expression product may contain a compound which has an oxygen atom(s) or a nitrogen atom(s) and at least one C1 substituent which binds to the atom. For example, methanol can be added as the compound which has an oxygen atom, and at least one compound selected from the group consisting of methylamine, dimethylamine, trimethylamine, and an ammonium compound with N-substituted methyl (e.g., choline) can be added as the compound having a nitrogen atom(s).

The medium may contain, in addition to methanol as the carbon source, one or more nitrogen sources such as yeast extract, tryptone, meat extract, casamino acid and ammonium salt, and mineral salts such as phosphate, sodium, potassium, magnesium, calcium, iron, copper, manganese and cobalt, and if necessary, trace nutrients such as various types of vitamins and nucleotide, and appropriately carbohydrate materials for growth of yeast cells before the methanol induction. Specifically, the medium includes YPM medium (0.67% yeast nitrogen base, 1% yeast extract, 2% peptone, 0.5% methanol), BYPM medium (0.67% yeast nitrogen base, 1% yeast extract, 2% peptone, 0.5% methanol, 0.1M phosphate buffer pH 6.0), BM medium (0.67% yeast nitrogen base, 0.5% methanol, 0.1M phosphate buffer pH 6.0), etc.

The culture medium for expressing heterologous genes by an expression vector, which is controlled by a constitutive expression promoter, to produce a desired gene expression product includes culture mediums suitable for cell growth. For example, synthesized media such as natural culture media such as YPD medium (1% yeast extract, 2% peptone, 2% glucose) and SD medium (0.67% yeast nitrogen base, 2% glucose) can be used. Complementary nutrients may be supplemented in the above-mentioned media for yeast strains having an auxotrophic marker.

pH of the culture medium is suitably adjusted to 5.5 to 6.5. Culture temperature is 15-30° C., preferably around 28° C. When the protein has a complex conformation like an antibody, culturing at low temperature is desirable in order to perform folding more efficiently within the cell. Culture time is about 24-1,000 hours, and culture can be conducted by means of standing culture, shaking culture, stirring culture, batch culture or continuous culture under aeration, or the like.

Conventional methods for isolation and purification of proteins can be used for isolating and purifying the expression product of a heterologous gene from the above-mentioned culture (i.e., culture broth or cultured cells).

For example, the cells may be collected by centrifugation after the culture, suspended in an aqueous buffer, and disrupted by ultrasonicator, French press, Manton-Gaulin homogenizer, Dynomill or the like, to obtain a cell-free extract. When the desired protein is produced in the culture supernatant, the culture broth itself can be used. If necessary, a protease inhibitor may be added to the medium. It is effective to use a protease deficient strain in order to suppress degradation of the expression product of a heterologous gene. Purified preparation or standard can be obtained by a conventional method for isolating and purifying proteins, from the supernatant obtained by centrifugation of the cell-free extract or supernatant. Specifically, the purification can be conducted by using: for example, removal of nucleic acids by protamine treatment; precipitation by fractionating with ammonium sulfate, alcohol, acetone added; anion exchange chromatography using resins such as DEAE Sepharose and Q Sepharose; cation exchange chromatography using resins such as S-Sepharose FF (Pharmacia); hydrophobic chromatography using resins such as butylsepharose and phenylsepharose; gel filtration using molecular sieves; chelate columns such as His Bind resin (Novagen); affinity chromatography using resins such as Protein A Sepharose, specific dye-adsorbed resins such as Blue Sepharose; or lectin columns such as a ConA Sepharose; reverse phase chromatography; chromatofocusing; and electrofocusing; electrophoresis using polyacrylamide gel, singly or in combination, thereby to obtain the purified preparation or standard. However, the above-mentioned culture and purification methods are specific examples and are not limited thereto.

The amino acid sequence of the purified gene product can be identified by the known amino acid analyses, such as the automated amino acid sequencing using the Edman degradation method.

EXAMPLES

The invention will now be described in detail with reference to specific examples. These are for illustrative purposes only, and are not intended to be limiting in any way the scope of the invention. The plasmids, enzymes such as restriction enzymes, T4 DNA ligase, and other substances are all commercially available and can be used by conventional methods. Manipulations used in DNA cloning, sequencing, transformation of host cells, culture of transformed cells, harvest of enzymes from resultant cultures, purification, etc. are also well known to those skilled in the art or can be known from the literature.

The restriction sites in restriction maps of various types of genes are shown by the following abbreviation. Ac; AccI, Ap; ApaI, Bl; BalI, Bm; BamHI, Bg; BglII, Bt; BtgI, Bw; BsiWI, Cl; ClaI, RI; EcoRI, RV; EcoRV, TI; EcoT22I, Hc; HincII, Hd; HindIII, Kp; KpnI, Nd; NdeI, Nh; NheI, Nt; NotI, Pf; PflMI, Pm; PmaCI, Ps; PstI, Sc; SacI, SI; SalI, Sm; SmaI, Sp; SpeI, Sh; SphI, Su; StuI, St; StyI, Xb; XbaI, and Xh; XhoI.

Example 1

Selection of Methylotrophic Yeast Suitable for Production of Mammalian Type Sugar Chain

Figure 3:
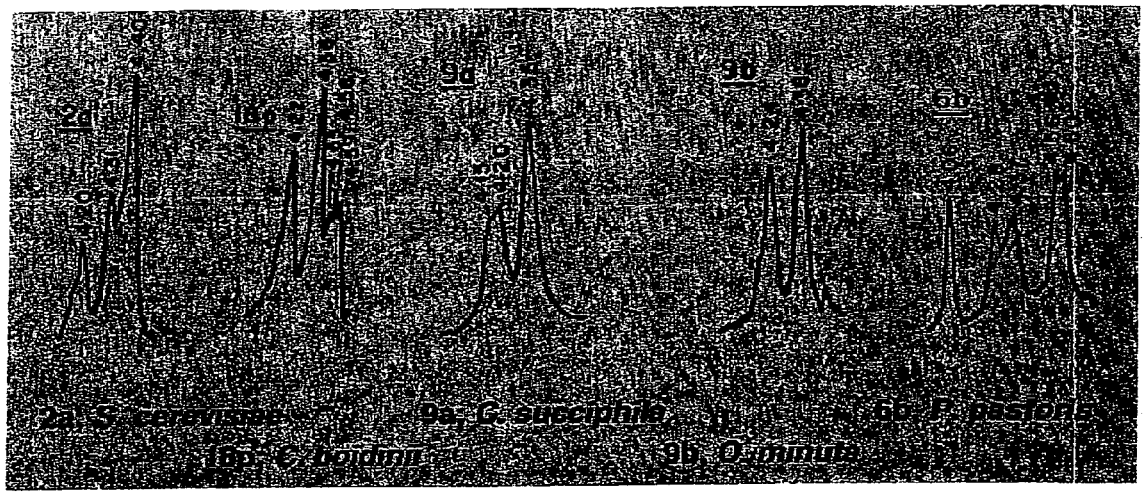
FIG. 3 shows the $^1$H-NMR analysis of cell wall sugar chains of various yeasts.

To obtain a mammalian type sugar chain producing yeast using methylotrophic yeast, it is necessary to clone and inactivate a sugar chain synthesizing gene peculiar to the methylotrophic yeast. The sugar chain structure differs largely with the type of the yeast, as described above. In other words, the enzyme and gene involved in the biosynthesis of sugar chain also differ depending on the type of the yeast. Accordingly, when intending to disrupt the gene involved in the biosynthesis of sugar chain to remove the sugar chain peculiar to the yeast, the first thing to do is to isolate the gene. As such isolation, however, requires a large number of steps, we decided to select a methylotrophic yeast, which requires the smallest possible number of isolation steps. The selection of strains suitable for the isolation was made using NMR data on the cell wall of yeast as an indication of selection (FIG. 3) (P. A. J. Gorin et al. (eds), Advanced in Carbohydrate Chemistry and Biochemistry, Vol. 23, 367-417 (1968)). Specifically, in a primary selection, strains suitable for isolation were selected, which had an α-1,2-mannoside linkage-related signal at around 4.3 ppm as a main peak but neither a α-1,3-mannoside linkage-related signal at around 4.4 ppm nor any signals at 4.5 ppm or larger. Then a secondary selection was made by extracting N-linked sugar chains from mannoprotein on the surface of the cells from the yeast strains and analyzing the extracted sugar chains by α-1,2-mannosidase digestion and HPLC. The methylotrophic yeast for the secondary selection were *Candida succiphila* IFO 1911 and *Ogataea minuta* IFO 10746. At the same time, both of *Saccharomyces cerevisiae* having α-1,3-mannoside linkage at unreduced termini of sugar chains, and *Candida boidinii* ATCC 48180 which is a methylotrophic yeast having a peak at 4.5 ppm or larger on the above NMR data, were also analyzed as controls.

Fifty ml of YPD medium containing the above strains was put into a 500 ml Sakaguchi flask, and cultured at 30° C. for 24-48 hours, and cells were harvested from the culture by centrifugation, suspended in 10 ml of 100 mM sodium citrate buffer (pH 7.0) and heated in autoclave at 121° C. for 1 hour. After cooling, the suspension was centrifuged to collect the supernatant, 10 ml of water was added to the solid matter, and a mixture was heated in the same manner as above and centrifuged to collect the supernatant. The combined cell extracts were poured into 3 volumes of ethanol. The resultant white precipitate was dried, which was then dissolved in concanavalin A (ConA) column buffer (0.1 M sodium phosphate buffer containing 0.15 M sodium chloride, 0.5 mM calcium chloride (pH 7.2)), applied to a ConA-agarose column (0.6×2 cm, Honen Corporation), washed with ConA column buffer, and eluted with ConA column buffer containing 0.2 M α-methylmannoside. Concanavalin A is a lectin that has an affinity for sugar chains containing two or more α-D-mannose residues whose C-3, C-4 and C-6 hydroxyl groups remain unsubstituted, and the column with immobilized lectin enables the separation of mannan protein from glucan, chitin and the like, which are yeast cell wall polysaccharides (Peat et al. J. Chem. Soc., 29 (1961)). The resultant fraction was dialyzed and freeze-dried to yield mannan protein.

Then, the obtained mannan protein was treated with enzyme to cut out Asn-linked sugar chains. Specifically, the freeze-dried standard was dissolved in 100 µl of N-glycosidase F buffer (0.1 M Tris-HCl buffer containing 0.5% SDS, 0.35% 2-mercaptoethanol (pH 8.0)) and boiled for 5 minutes. After cooling the boiled solution to room temperature, 50 µl of 7.5% Nonidet P-40, 138 µl of $H_2O$ and 12 µl of N-glycosidase F (Boehringer Ingelheim) were added and treated at 37° C. for 16 hours. After desalting with a BioRad AG501-X8 column, the equal amount of phenol:chloroform (1:1) was added and vigorously shaken to remove the detergent and proteins, to yield a sugar chain preparation.

To fluorescence-label (pyridylamination; referred to as PA) the obtained sugar chains, the following were carried out. After concentrating the sugar chain preparation to dryness, 40 µl of a coupling agent (552 mg of 2-aminopyridine dissolved in 200 µl of acetic acid) was added, sealed, and treated at 90° C. for 60 minutes. After cooling to room temperature, 140 µl of a reducing agent (200 mg of borane-dimethylamine complex dissolved in 50 µl of $H_2O$ and 80 µl of acetic acid) was added, sealed, followed by treating at 80° C. for 80 minutes. After reaction, 200 µl of aqueous ammonia was added, the equal amount of phenol:chloroform (1:1) was added and vigorously shaken to recover the water layer that contained PA-oligosaccharides. A series of the steps was repeated 7 times to remove unreacted 2-aminopyridine. The supernatant was filtered through a 0.22 µm filter to yield a PA-oligosaccharide preparation.

The obtained sugar chains were cleaved with *Aspergillus saitoi* α-1,2-mannosidase (SEIKAGAKU CORPORATION, Japan) and then analyzed by HPLC. HPLC using an amide column enables PA-oligosaccharides to be separated depending on the chain length. The HPLC conditions were as follows.

Figure 4:
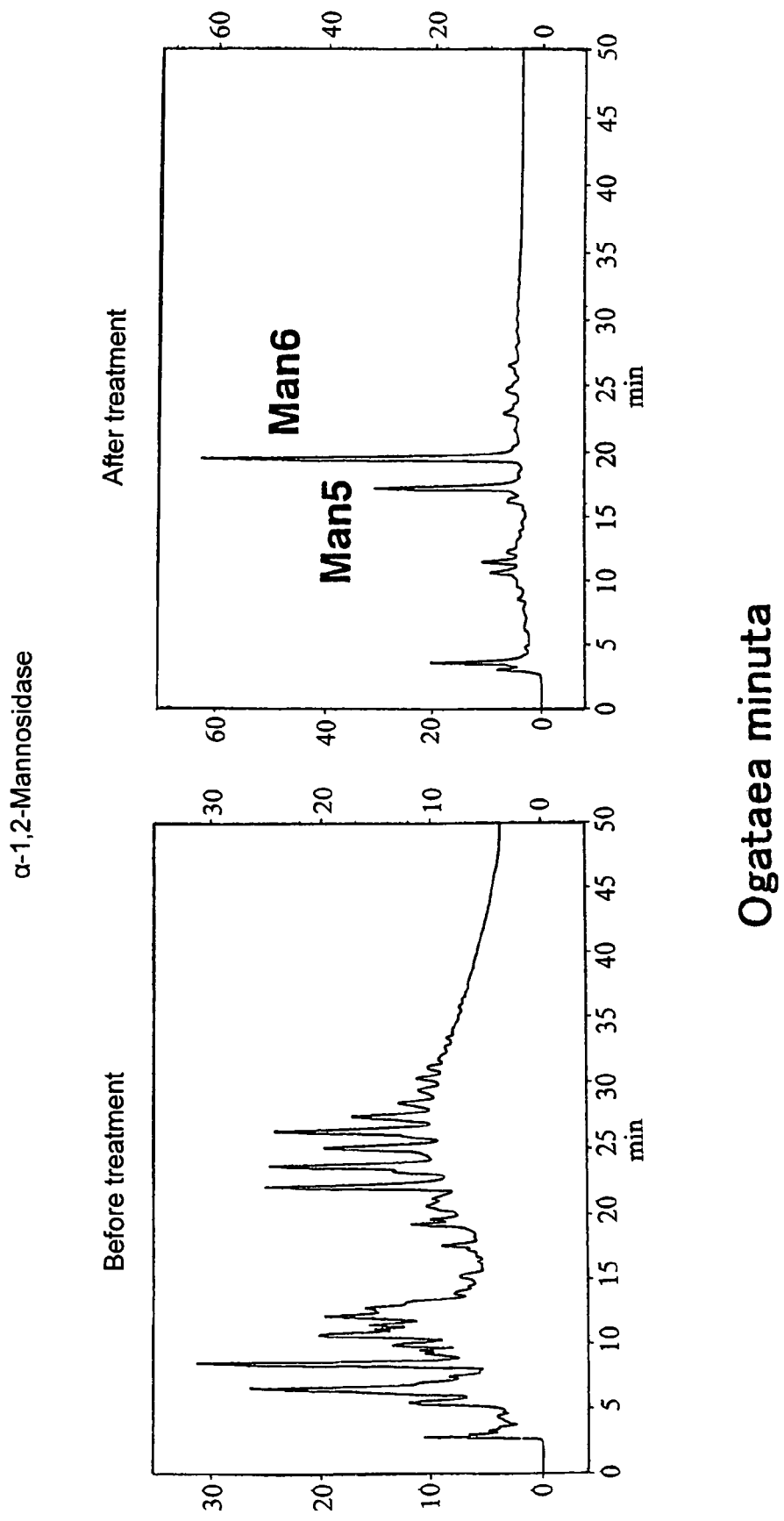
FIG. 4 shows the HPLC (amide column) analysis of digests which were obtained by digesting sugar chains prepared from mannoproteins of cell walls of various yeasts by *Aspergillus saitoi* α-1,2-mannosidase (product of Seikagaku Corporation).
Figure 4:
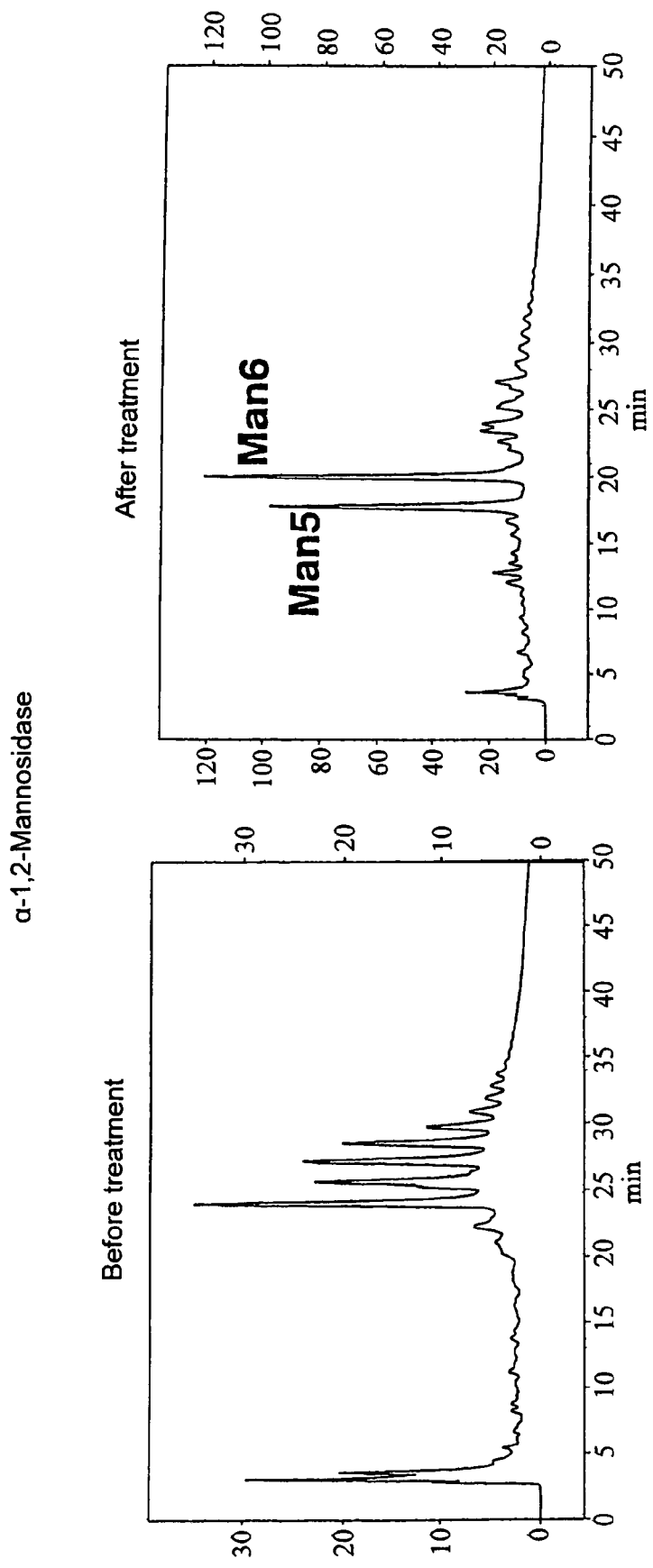
Figure 4:
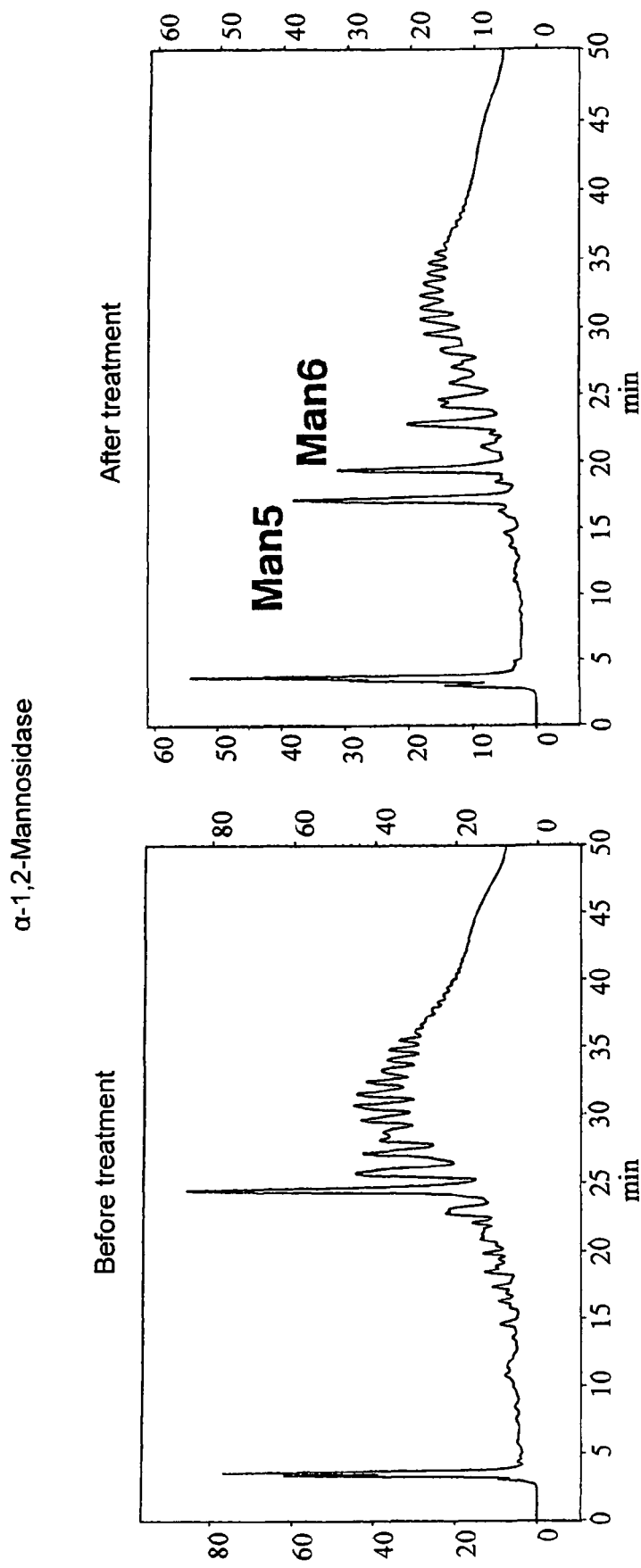
Figure 4:
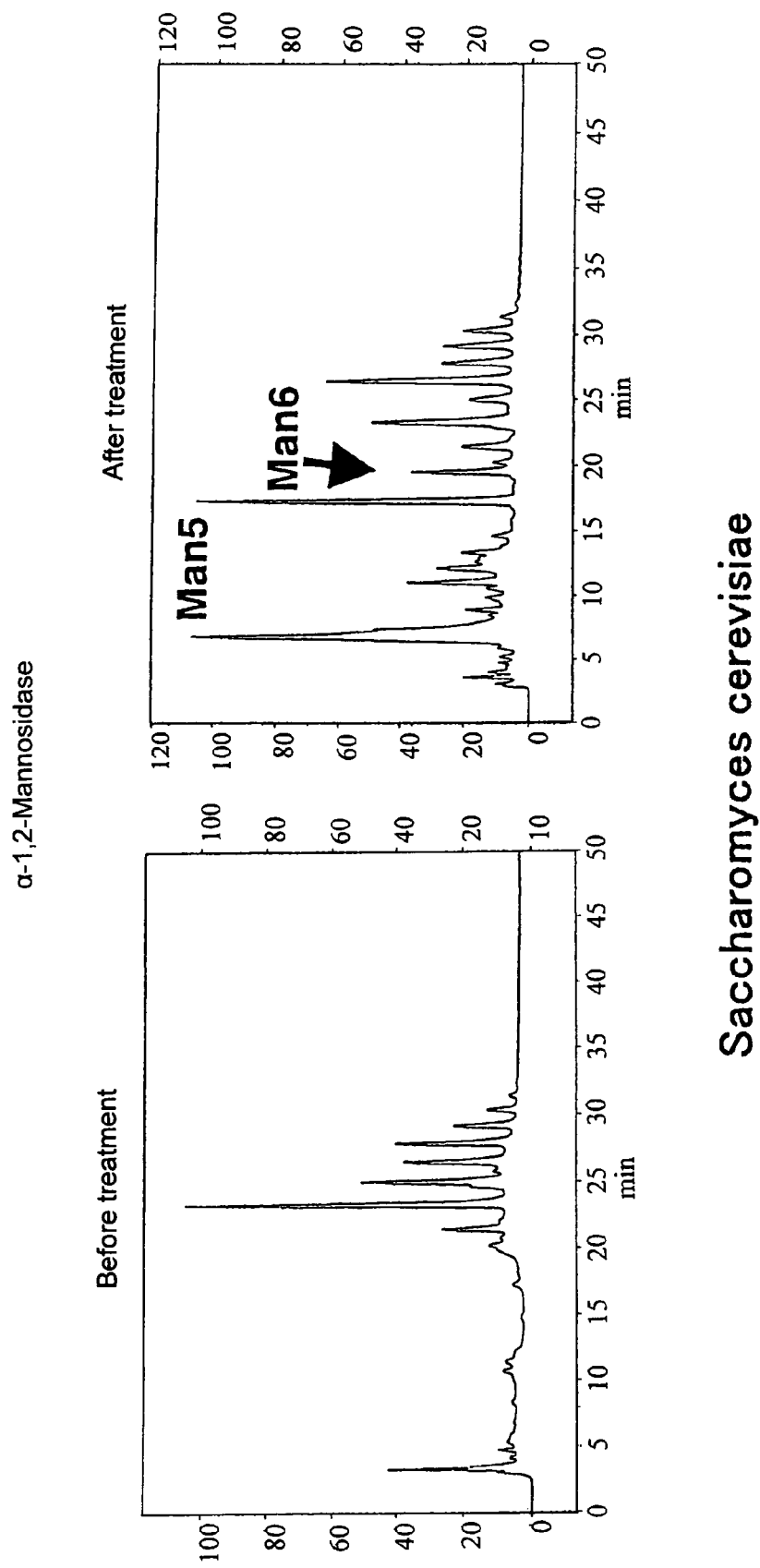

Column: TSK-Gel Amido-80 (4.6×250 mm, TOSOH CORPORATION, Japan)
Column temperature: 40° C.
Flow rate: 1 ml
Elution conditions: A: 200 mM triethylamine acetate pH 7.0+65% acetonitrile
B: 200 mM triethylamine acetate pH 7.0+30% acetonitrile
Linear gradient of 0 minute A=100% and 50 minutes A=0%
Excitation wavelength: 320 nm
Fluorescence wavelength: 400 nm The results are shown in FIG. 4. The results revealed that N-linked sugar chains derived from *Ogataea minuta* and *Candida Succiphila* were degraded to small molecules of Man5 or Man6 by α-1,2-mannosidase treatment, and thus suggested that sugar chain mutants (Man5 producing strains) corresponding to och1, mnn1 and mnn4 in *Saccharomyces cerevisiae* could be prepared by inactivation of OCH1 gene and expression of α-1,2-mannosidase. On the other hand, for *Candida boidinii*, sugar chains remained undegraded at a considerably high rate. This is possibly due to the linkage of a unit other than α-1,2-mannosidic linkage at the terminus of the sugar chains. Similarly, for *Saccharomyces cerevisiae* as the control, there existed sugar chains undegraded, because possible addition of α-1,3-mannose resulting from the action of MNN1 gene.

Example 2

**Cloning of glyceraldehyde-3-phosphate Dehydrogenase (GAP) Gene of *Ogataea minuta***

The GAP gene was obtained from *Ogataea minuta* IFO 10746 and its nucleotide sequence was determined.

(2-1) Preparation of Probe

Oligonucleotides comprising nucleotide sequences corresponding to the following amino acid sequences conserved in glyceraldehyde-3-phosphate dehydrogenases from *Saccharomyces cerevisiae* (GenBank accession number; P00359) and from *Pichia pastoris* (GenBank accession number; Q92263):

AYMFKYDSTHG;           (SEQ ID NO: 1)
and

DGPSHKDWRGG            (SEQ ID NO: 2)

were synthesized as follows.

(SEQ ID NO: 3)
PGP5;     5'-GCNTAYATGTTYAARTAYGAYWSNACNCAYGG-3'

(SEQ ID NO: 4)
PGP3;     5'-CCNCCNCKCCARTCYTTRTGNSWNGGNCCRTC-3'

The primer PGP5 has a sequence complementary to the nucleotide sequence corresponding to the amino acid sequence AYMFKYDSTHG, and the primer PGP3 has a sequence complementary to the nucleotide sequence corresponding to the amino acid sequence DGPSHKDWRGG.

Chromosomal DNA was prepared from the cells of *Ogataea minuta* IFO 10746, which were cultured until stationary phase in YPD medium (comprising 1% yeast extract, 2% peptone, 2% glucose, pH 6.0), by means of potassium acetate method (Methods in yeast genetics (1986), Cold Spring Harbor Laboratory, Cols Spring Harbor, N.Y.).

PCR by Ex Taq polymerase (TAKARA SHUZO CO., LTD., Japan) ((94° C. for 30 seconds, 50° C. for 1 minute and 72° C. for 45 seconds)×25 cycles) was carried out using the obtained chromosomal DNA of *Ogataea minuta* IFO 10746, as a template, and primers PGP5, PGP3. An amplified DNA fragment of approximately 0.5 kb was recovered and cloned using TOPO TA Cloning Kit (Invitrogen). Plasmid DNA was isolated from the obtained clones and sequenced using Big-Dye Terminator Cycle Sequencing FS Ready Reaction Kit (Applied Biosystems). For a DNA insert of the plasmid, a clone was selected, which had a nucleotide sequence encoding an amino acid sequence having a high homology with the amino acid sequences for GAP genes from *Saccharomyces cerevisiae* and *Pichia pastoris*. The 0.5-kb DNA insert was recovered after EcoRI digestion of the plasmid and agarose gel electrophoresis.

(2-2) Construction of Library and Screening

The chromosomal DNA of Ogataea minuta IFO 10746 was cleaved with different restriction enzymes and subjected to 0.8% agarose gel electrophoresis. The separated DNA was transferred to Hybond N+ nylon membrane (Amersham). The DNA fragment obtained in Example (2-1) was radiolabeled using Megaprimar DNA Labeling System (Amersham) and subjected to Southern analysis. The hybridization was carried out by conventional procedure (Molecular cloning 2$^{nd}$ edn., ed. Sambrook, J., et al., Cold Spring Harbor Laboratory U.S.A., 1989). The results suggested that there existed a GAP gene in the HindIII-EcoRV fragment of approximately 6 kb. Then, to clone the DNA fragment, a library was constructed. The chromosomal DNA of *Ogataea minuta* was cleaved with HindIII and EcoRV and subsequently electrophoresed on agarose gel, and the approximately 6-kb DNA fragment was recovered from the gel. The recovered DNA fragment was ligated with HindIII- and HincII-cleaved pUC 118 and then transformed into *Escherichia coli* DH5 α strain by the Hanahan method (Gene, 10, 63 (1980)) to obtain a library.

Approximately 4,000 clones were screened by colony hybridization using the above described DNA fragment as a probe. A clone bearing plasmid pOMGP1 was selected from the 11 positive clones obtained.

(2-3) Sequencing of Nucleotide Sequence

The nucleotide sequence of the HindIII-BamHI region of the plasmid pOMGP1 (FIG. 5) was determined by deletion mutant and primer walking method using Double-Stranded Nested Deletion Kit (Pharmacia). The nucleotide sequence represented by SEQ ID NO:5 was determined by aligning the obtained nucleotide sequences.

In the nucleotide sequence of SEQ ID NO:5 there existed an open reading frame of 1,011 bp, starting at position 1,492 and ends at position 2,502. The homology studies between the amino acid sequence (SEQ ID NO:6) deduced from the open reading frame and the glyceraldehyde-3-phosphate dehydrogenase from *Saccharomyces cerevisiae* or *Pichia pastoris* showed that 77% or 81% of amino acids were respectively identical between them.

Example 3

Construction of Expression Cassette Using GAP Gene Promoter and Terminator

Figure 5:
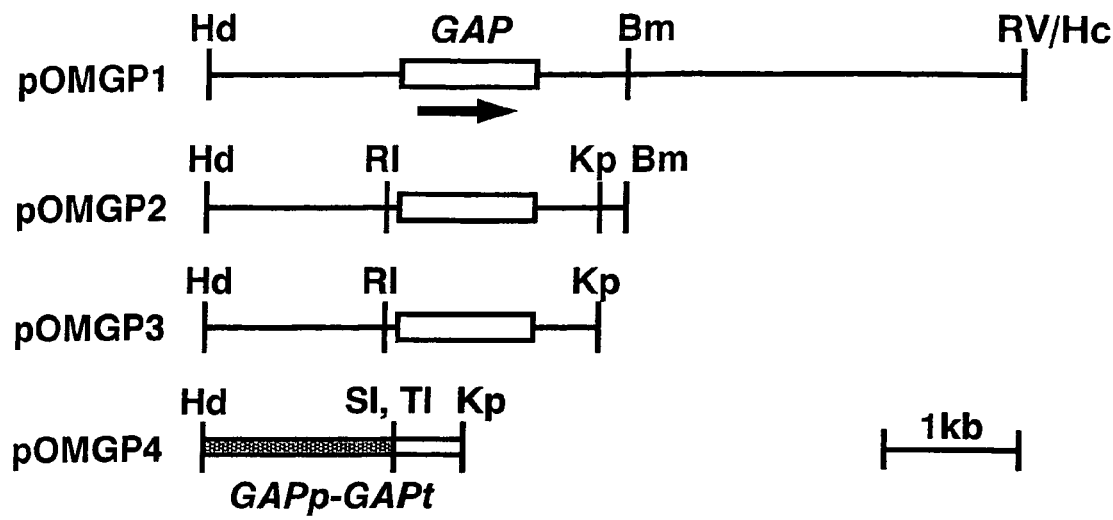
FIG. 5 shows the restriction maps of plasmids pOMGP1, pOMGP2, pOMGP3 and pOMGP4.

An expression cassette for transferring foreign genes was constructed between the GAP gene promoter (SEQ ID NO:7) and terminator (SEQ ID NO: 8) of *Ogataea minuta*. A 3.2-kb HindIII-BamHI fragment was isolated from pOMGP1 described in Example 2-2 and inserted into the HindIII-BamHI of pBluscript II SK–. The obtained plasmid was named pOMGP2 (FIG. 5). A 3-kb HindIII-KpnI fragment was isolated from the pOMGP2 and the EcoRI site was inserted into the HindIII-KpnI of blunt-ended pUC19. The resultant plasmid was named pOMGP3 (FIG. 5). To transfer SalI and EcoT22I sites between the GAP gene promoter and terminator, the primers:

5'-GTTTGAATTCACTCAATTAACATACACAAATACAATACAAAGTCGACAAAAA      (SEQ ID NO: 9)
ATGCATGTGGATAGATGACCAATGGCCTCTTTAAGTAAACATTTCGTTTTGAATAT
ATTTC-3',
and

5'-TTTTTACTAGTACGGTACCGCTCGAATCGACACAGGAG-3'                (SEQ ID NO: 10)

were synthesized. These primers were used to carry out PCR using the pOMGP2 as a template ((94° C. for 30 seconds, 55° C. for 1 minute and 72° C. for 45 seconds)×20 cycles)). An amplified DNA fragment of approximately 0.6 kb was recovered and cloned using TOPO TA Cloning Kit. An inserted DNA fragment of 0.6 kb was isolated as an EcoRI-KpnI fragment and inserted into the EcoRI-KpnI of the pOMGP3. The obtained plasmid was named pOMGP4 (FIG. 5). The pOMGP4 comprises an expression cassette controlled by GAP gene promoter and terminator, which cassette allows foreign genes to transfer into SalI-EcoT22I.

Example 4

Construction of G418 Resistant Gene Expression Cassette

To perform the transformation comprising selection of an antibiotic G418 resistant gene, a plasmid was constructed which comprised an expression cassette of a G418 resistant gene (aminoglycoside phosphotransferase gene). A 1.1-kb G418 resistant gene isolated, as a XhoI-PstI fragment, from plasmid pUC4K (Amersham Pharmacia) was inserted into the SalI-EcoT22I of the pOMGP4 constructed in Example 3. The resultant plasmid was named pOMKmR1.

Example 5

Cloning of orotidin-5'-phosphate Decarboxylase (URA3) Gene of *Ogataea minuta*

The URA3 gene was obtained from *Ogataea minuta* IFO 10746, and its nucleotide sequence was determined.

(5-1) Preparation of Probe

Oligonucleotides having the nucleotide sequences corresponding to the amino acid sequences conserved in orotidin-5'-phosphate decarboxylases from *Saccharomyces cerevisiae* (GenBank accession number; K02207) and *Pichia pastoris* (GenBank accession number; AF321098):

```
      GPYICLVKTHID;        (SEQ ID NO: 11)
      and

GRGLFGKGRDP          (SEQ ID NO: 12)
``` were synthesized as follows.

```
                                           (SEQ ID NO: 13)
PUR5;   5'-GGNCCNTAYATHTGYYTNGTNAARACNCAYATHGA-3'

(SEQ ID NO: 14)
PUR3;   5'-GGRTCNCKNCCYTTNCCRAANARNCCNCKNCC-3'
```

The primer PUR5 has a sequence complementary to the nucleotide sequence corresponding to the amino acid sequence GPYICLVKTHID, and the primer PUR3 has a sequence complementary to the nucleotide sequence corresponding to the amino acid sequence GRGLFGKGRDP.

PCR by primers PUR5 and PUR3 was performed using the chromosomal DNA of *Ogataea minuta* IFO 10746 as a template ((94° C. for 30 seconds, 50° C. for 1 minute and 72° C. for 30 seconds)×25 cycles). The amplified DNA fragment of approximately 0.6 kb was recovered and cloned using TOPO TA Cloning Kit. Plasmid DNA was isolated from the obtained clone and sequenced. For a DNA insert of the plasmid, a clone was selected which had a nucleotide sequence encoding an amino acid sequence highly homologous to the amino acid sequences of orotidin-5'-phosphate decarboxylases from *Saccharomyces cerevisiae* and *Pichia pastoris*. The 0.6-kb DNA insert was recovered after EcoRI cleavage of the plasmid and agarose gel electrophoresis.

(5-2) Preparation of Library and Screening

The chromosomal DNA of *Ogataea minuta* IFO 10746 was cleaved with different restriction enzymes, and subjected to Southern analysis using the DNA fragment obtained in (5-1) as a probe by the method described in Example (2-2). The results suggested that there was present URA3 gene in the HindIII fragment of approximately 4.5 kb. Then, to clone the DNA fragment, a library was constructed. The chromosomal DNA of *Ogataea minuta* was cleaved with HindIII and electrophoresed on agarose gel, and then the approximately 4.5-kb DNA fragment was recovered from the gel. The resultant DNA fragment was ligated with HindIII-cleaved pUC18 and then transformed into *Escherichia coli* DH5 α strain to obtain a library.

Approximately 6,000 clones were screened by colony hybridization using the above described DNA fragment as a probe. A clone bearing plasmid pOMUR1 was selected from the 3 positive clones obtained.

(5-3) Sequencing of Nucleotide Sequence

The nucleotide sequence of the NotI-HindIII region of the plasmid pOMUR1 (FIG. 6) was determined by deletion mutant and primer walking method to obtain a nucleotide sequence represented by SEQ ID NO:15.

In the nucleotide sequence of SEQ ID NO:15, there existed an open reading frame of 798 bp, starting at position 1,732 and ends at position 2,529. The homology studies between the amino acid sequence (SEQ ID NO:16) deduced from the open reading frame and the orotidin-5'-phosphate decarboxylase from *Saccharomyces cerevisiae* or *Pichia pastoris* showed that 82% or 75% of amino acids were respectively identical between them.

Example 6

Preparation of *Ogataea minuta* URA 3 Knockout Mutant

An *Ogataea minuta* URA3 knockout mutant was prepared by the "pop-in, pop-out" method (Rothstein R., Methods Enzymol., 194 (1991)).

(6-1) Preparation of UR43 Gene Disruption Vector

A 3-kb NotI-KpnI fragment was isolated from the plasmid pOMUR1 (FIG. 6) described in Example (5-2) and inserted into the NotI-KpnI of pBluescript II SK–. After cleaving the plasmid with NotI and StyI, plasmid pOMUM1 (FIG. 6) was obtained by blunt-end treatment and self-ligation. Primers 5'-ATGGAGAAAAAAACTAGTGGATATACCACC-3' (SEQ ID NO:17) and 5'-CTGAGACGAAAAAGATATCT-CAATAAACCC-3' (SEQ ID NO:18) were used to carry out PCR using plasmid pHSG398 (TAKARA SHUZO CO., LTD., Japan) as a template ((94° C. for 30 seconds, 55° C. for 1 minute and 72° C. for 45 seconds)×20 cycles)) to amplify part of chloramphenicol resistant gene. The 0.4-kb amplified DNA fragment was cleaved with SpeI and EcoRV and inserted into the SpeI-RcoRV of the pOMUM1. The obtained plasmid was named pOMUM2.

Figure 6:
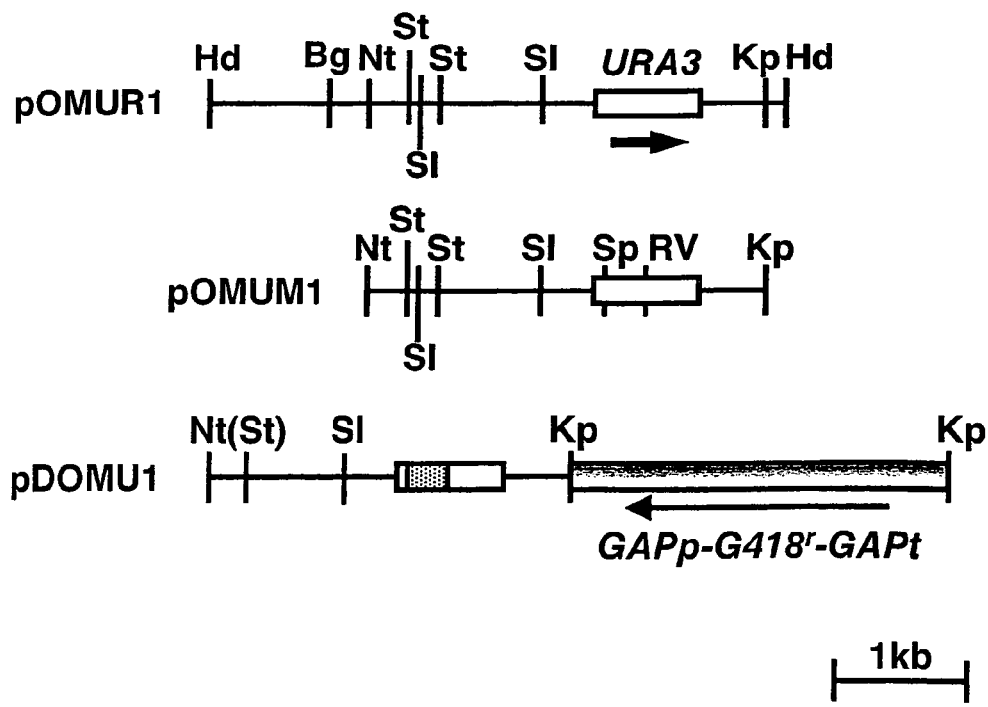
FIG. 6 shows the restriction maps of plasmids pOMUR1, pOMUM1 and pDOMU1.

The plasmid pOMKmR1, which contained the G418 resistant gene expression cassette controlled by the GAP gene promoter and terminator as prepared in Example 4, was cleaved with HindIII, blunt-ended, and ligated with a KpnI linker. The G418 resistant gene expression cassette was isolated as a 3-kb KpnI fragment from the plasmid and transferred at KpnI of the pOMUM2. The obtained plasmid was named pDOMU1 (FIG. 6).

(6-2) Transformation

The pDOMU1 constructed in Example (6-1) was cleaved with SalI and transformed into *Ogataea minuta* IFO 10746 by the electric pulse method. The transformants were precultured in YPD medium at 30° C. overnight, inoculated into 100 ml of YPD medium, and cultured at 30° C. for 8-16 hours until logarithmic growth phase ($OD_{600}$=about 1.5). The cells were harvested by centrifugation at 1400×g for 5 minutes, washed once with 100 ml of sterilized ice-cooled water, then once with 40 ml of sterilized ice-cooled water. Then the cells were suspended in 20 ml of LC buffer (100 mM LiCl, 50 mM potassium phosphate buffer, pH 7.5) and shaken at 30° C. for 45 minutes, and then 0.5 ml of 1 M DTT was added to the suspension and shaken for another 15 minutes. After washed with 80 ml of ice-cooled STM buffer (270 mM sucrose, 10 mM Tris-HCl buffer, pH 7.5, 1 mM $MgCl_2$), the cells were suspended in 320 μl of STM buffer. The transformation by the electric pulse method was performed with Gene Pulser (BIO-RAD). After mixing 50 μl of the cell suspension and 5 μl of DNA sample, the mixture was put into a 0.2 cm disposable cuvette, and an electric pulse was applied to the mixture under appropriate conditions (voltage: 1.0 to 1.5 kv, resistance: 200-800 Ω). After application of the pulse, 1 ml of ice-cooled YDP medium containing 1 M sorbitol was added and subjected to shaking culture at 30° C. for 4-6 hours. After the culture, the cell liquid was applied on a YPD selection medium containing 400-1000 μg/ml G418, and the plate was incubated at 30° C. to obtain transformant colonies.

Figure 7:
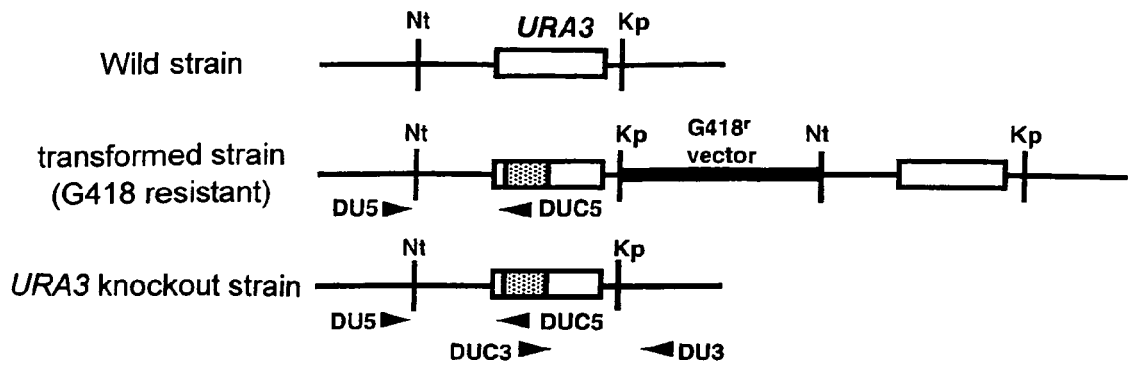
FIG. 7 shows the structures of the URA3 loci of a wild strain of *Ogataea minuta*, a strain transformed with plasmid pDOMU1 and a URA3 gene knockout mutant, along with positions of PCR primers.

To confirm that the URA3 gene was disrupted, the following primers were synthesized (see FIG. 7 with regard to the position of each primer).

```
DU5;
5'-AGGAAGAAGAGGAGGAAGAGGAAGAAAC-3'  (SEQ ID NO: 19)

DUC5;
5'-CGATGCCATTGGGATATATCAACGGTGG-3'  (SEQ ID NO: 20)

DU3;
5'-CCGTGTTTGAGTTTGTGAAAAACCAGGGC-   (SEQ ID NO: 21)
3'

DUC3;
5'-TGTGGCGTGTTACGGTGAAAACCTGGCC-3'  (SEQ ID NO: 22)
```

PCR by primers DU5 and DUC5 was performed using the chromosomal DNA isolated from the transformant as a template ((94° C. for 30 seconds, 60° C. for 1 minute and 72° C. for 1 minute)×25 cycles). As shown in FIG. 7, a 1.1-kb amplified DNA fragment was detected from the strain whose URA3 locus had the plasmid integrated there into. After culturing the selected strain in the YPD medium until stationary phase, a strain resistant to 5-fluoroorotic acid (5-FOA) was obtained in accordance with the method described in a manual for experimental procedures (Methods Enzymol., 154, 164 (1987)). PCR by primers DU5 and DU3 ((94° C. for 30 seconds, 60° C. for 1 minute and 72° C. for 3 minutes)×25 cycles), PCR by primers DU5 and DUC5 ((94° C. for 30 seconds, 60° C. for 1 minute and 72° C. for 1 minute)×25 cycles), and PCR by primers DU3 and DUC3 ((94° C. for 30 seconds, 60° C. for 1 minute and 72° C. for 1 minute)×25 cycles), were performed using the chromosomal DNA isolated from the 5-FOA resistant strain as a template. As shown in FIG. 7, in the strain in which G418 resistant gene was deleted and the ORF of URA3 gene was replaced with the chloramphenicol resistant gene region, a 2.6-kb amplified DNA fragment was detected by PCR using DU5 and DU3, a 1.1-kb amplified DNA fragment by PCR using DU5 and DUC5, and a 1.0-kb amplified DNA fragment by PCR using DU3 and DUC3, respectively. The yeast was named *Ogataea minuta* strain TK1-3 (ura3A).

Example 7

Cloning of ADEI (phosphoribosyl-amino-imidazole succinocarboxamide synthase) Gene from *Ogataea minuta*

The ADE1 gene was obtained from *Ogataea minuta* IFO 10746 and its nucleotide sequence was determined.

(7-1) Preparation of Probe

Oligonucleotides having nucleotide sequences corresponding to the amino acid sequences conserved in the ADE1 gene products from *Saccharomyces cerevisiae* (GenBank accession number; M61209) and *Candida maltosa* (GenBank accession number; M58322):

```
      FVATDRISAYDVIM;       (SEQ ID NO: 23)
      and

QDSYDKQFLRDWLT        (SEQ ID NO: 24)
``` were synthesized as follows.

```
                                    (SEQ ID NO: 25)
PAD5; 5'-
      TTYGTNGCNACNGAYMGNATHWSNGCNTAYGAYGTNATHATG-
      3'

(SEQ ID NO: 26)
PAD3; 5'-
      GTNARCCARTCNCKNARRAAYTGYTTRTCRTANSWRTCYTG-
      3'
```

The primer PAD5 has a sequence complementary to the nucleotide sequence corresponding to the amino acid sequence FVATDRISAYDVIM, and the primer PAD3 has a sequence complementary to the nucleotide sequence corresponding to the amino acid sequence QDSYDKQFLRDWLT.

PCR by primers PAD5 and PAD3 was performed using the chromosomal DNA of *Ogataea minuta* IFO 10746 as a template ((94° C. for 30 seconds, 50° C. for 1 minute and 72° C. for 1 minute)×25 cycles). The amplified DNA fragment of approximately 0.7 kb was recovered and cloned using TOPO TA Cloning Kit. Plasmid DNA was isolated from the obtained clone and sequenced. For a DNA insert of the plasmid, a clone was selected which had a nucleotide sequence encoding an amino acid sequence highly homologous to the amino acid sequences of the ADE1 genes from *Saccharomyces cerevisiae* and *Candida maltosa*.

The 0.7-kb DNA insert was recovered after EcoRI cleavage of the plasmid and agarose gel electrophoresis.

(7-2) Preparation of Library and Screening

The chromosomal DNA of *Ogataea minuta* IFO 10746 was cleaved with different restriction enzymes, and subjected to Southern analysis using the DNA fragment obtained in (7-1) as a probe by the method described in Example (2-2). The results suggested that there existed ADE1 gene in the approximately 5 kb HindIII-BamHI fragment. Then, to clone the DNA fragment, a library was prepared. The chromosomal DNA of *Ogataea minuta* was cleaved with HindIII and BamHI and electrophoresed on agarose gel, and then the approximately 5-kb DNA fragment was recovered from the gel. The DNA fragment was ligated with HindIII- and BamHI-cleaved pBluescript II SK– and then transformed into *Escherichia coli* strain DH5 α to prepare a library.

Approximately 6,000 clones were screened by colony hybridization using the above described DNA fragment as a probe. A clone bearing plasmid pOMAD1 was selected from the 9 positive clones obtained.

(7-3) Sequencing of Nucleotide Sequence

The nucleotide sequence of the EcoRV-SmaI region of the plasmid pOMAD1 (FIG. 8) was determined by deletion mutant and primer walking method to obtain a nucleotide sequence represented by SEQ ID NO:27.

In the nucleotide sequence of SEQ ID NO:27, there existed an open reading frame of 912 bp, starting at position 939 and ends at position 1,850. The homology studies between the amino acid sequence (SEQ ID NO:28) deduced from the open reading frame and the ADE1 gene product from *Saccharomyces cerevisiae* or *Pichia pastoris* showed that 69% or 74% of amino acids were respectively identical between them.

Example 8

Preparation of *Ogataea minuta* ADE1 Knockout Mutant

The ADE1 gene was disrupted by transformation using the URA43 gene of *Ogataea minuta* as a marker.

(8-1) Preparation of ADE1 Disruption Vector

Figure 8:
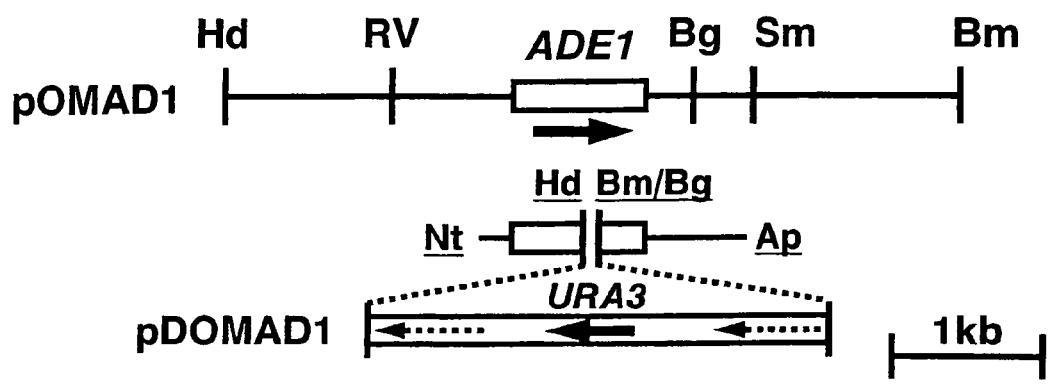
FIG. 8 shows the restriction maps of plasmids pOMAD1 and pDOMAD1. The restriction enzyme sites added artificially are underlined.

As shown in FIG. 8, plasmid pDOMAD1 was prepared by replacing approximately 70-bp region of the ADE1 structural gene by the URA3 gene. To obtain a uracil auxotrophic mutant again from ADE1 gene knockout mutants, the URA3 gene having repetitive structures before and after the structural gene was used as a marker. PCR by the primers:

5'-CCCCGAGCTCAAAAAAAAGGTACCAATTTCAGCTCCGACGCCGGAGCCCACT  (SEQ ID No. 29)
ACGCCTAC-3';
and 5'-GGGAAGCTTCCCCAGTTGTACACCAATCTTGTCGACAG-3'  (SEQ ID No. 30)

was performed using, as a template, the plasmid pOMUR1 having the URA3 gene region as described in Example 5 ((94° C. for 30 seconds, 50° C. for 1 minute and 72° C. for 45 seconds)×20 cycles) to amplify the upstream region of the URA3 structural gene. The amplified DNA fragment of approximately 0.8 kb was recovered, cleaved with SacI and HindIII, and inserted into the SacI-HindIII of the pUC18.

Figure 9:
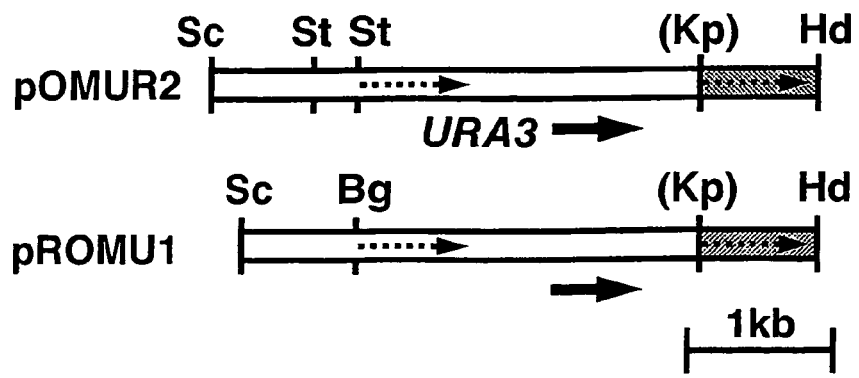
FIG. 9 shows the restriction maps of plasmids pOMUR2 and pROMU1.

The 3.3-kb SacI-KpnI fragment isolated from the pOMUR1 was inserted into the SacI-KpnI of the obtained plasmid. The resultant plasmid was cleaved with KpnI, blunt-ended, and self-ligated. The obtained plasmid was named pOMUR2 (FIG. 9). The pOMUR2 was cleaved with StyI, blunt-ended, and ligated with a BglII linker. The obtained plasmid was named pROMU1. In the 3.3-kb DNA fragment obtained by cleaving the pROMU1 with BglII and HindIII, there existed approximately 0.8-kb repetitive sequences before and after the URA3 structural gene (FIG. 9).

PCR by the primers:

Dad1-5:  5'-AAAAAGCGGCCGCTCCCGGTGTCCCGCAGAAATCTTTATGCGTAGTCTT  (SEQ ID NO: 31)
         G-3';
and Dad1-3:  5'-CCCCCGGATCCTTTTTTTTAAGCTTGTTGTACTCCTTCCATGCACTTCCGG  (SEQ ID NO: 32)
         TGATG-3'

((94° C. for 30 seconds, 50° C. for 1 minute and 72° C. for 1 minute)×20 cycles), and PCR by the primers:

Dad2-5:  (SEQ ID NO: 33)
5'-
TTTTCACCCCGTCAAGGATCCCTGAACAAGGCGAACACGACGAAAACA
TTTCCCCCGAG-3';
and Dad2-3:  (SEQ ID NO: 34)
5'-
TTTTTGGGCCCACCTGGGTGAAGATTTGCCAGATCAAGTTCTCC-3'

((94° C. for 30 seconds, 50° C. for 1 minute and 72° C. for 1 minute)×20 cycles) were performed using, as a template, the plasmid pOMAD1 having the ADE1 gene region as described in Example 7. The amplified DNA fragments of approximately 0.7 kb and 1 kb were recovered and cleaved with NotII and BamHI and with BamHI and ApaI, respectively. Both of the NotI-BamHI and BamHII-ApaI DNA fragments obtained were inserted into the NotI-ApaI of the pBluescript II SK–. The 3.3-kb BglII-HindIII fragment isolated from the pROMU1 was inserted into the BamHI-HindIII of the obtained plasmid. The resultant plasmid was named pDOMAD1 (FIG. 8).

(8-2) Transformation

The pDOMAD1 obtained in Example (8-1) was cleaved with ApaI and NotI and transformed into Ogataea minuta strain TK1-3 (ura3Δ) obtained in Example (6-2) by the electric pulse method. Strains exhibiting ade1 trait produce a red pigment, which is an intermediate metabolite in the adenine biosynthesis, and their colonies are dyed red. Thus, strains whose colonies were dyed red compared with the transformants were selected. To confirm that the ADE1 genes of these strains were disrupted, the following primers were synthesized (see FIG. 10 with regard to the position of each primer).

DA5;
5'-                                                 (SEQ ID NO: 35)
GATGCTTGCGCCTTCAACCACATACTCCTC-3'

DA3;
5'-                                                 (SEQ ID NO: 36)
AAAAGTTCTTGCACAGCCTCAATATTGACC-3'

DOU5;
5'-                                                 (SEQ ID NO: 37)
ATCGATTTCGAGTGTTTGTCCAGGTCCGGG-3'

Figure 10:
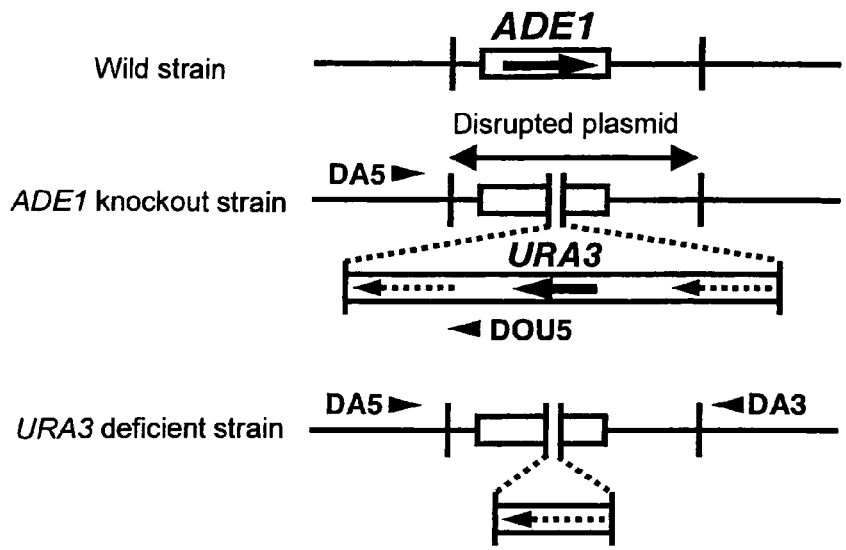
FIG. 10 shows the structures of the ADE1 loci of a wild strain of *Ogataea minuta*, an ADE1 gene knockout mutant disrupted by plasmid pDOMAD1, and a URA3 gene deficient mutant, along with positions of PCR primers.

PCR by primers DA5 and DOU5 was performed using the chromosomal DNA isolated from the transformant as a template ((94° C. for 30 seconds, 60° C. for 1 minute and 72° C. for 2 minutes)×25 cycles). As shown in FIG. 10, a 1.6-kb amplified DNA fragment was detected from the strain whose ADE1 locus had the plasmid integrated thereinto. After culturing the selected strain in the YPD medium until stationary phase, a strain resistant to 5-fluoroorotic acid (5-FOA) was obtained. PCR by primers DA5 and DA3 was performed using the chromosomal DNA isolated from the 5-FOA resistant strain as a template ((94° C. for 30 seconds, 60° C. for 1 minute and 72° C. for 3 minutes)×25 cycles). As shown in FIG. 10, in the strain in which URA3 gene was deleted, a 2.9-kb amplified DNA fragment was detected. The ura3Δ ade1Δ strain was named Ogataea minuta strain TK4-1.

Example 9

Cloning of OCH1 Gene from Ogataea minuta

The OCH1 gene was obtained from Ogataea minuta IFO 10746 and its nucleotide sequence was determined.

(9-1) Preparation of Probe

Oligonucleotides having nucleotide sequences corresponding to the amino acid sequences conserved in OCH1 gene products from Saccharomyces cerevisiae (GenBank accession number; P31755) and Pichia pastoris (Japanese Patent Publication (Kokai) No. 9-3097A):

PQH(R)I(V)WQTWKV;  (SEQ ID NO: 38)
and

-continued

WYARRIQFCQW (SEQ ID NO: 39)

were synthesized as follows.

POH5;
5'-CCNCARCRYRTHTGGCARACNTGGAARGT-3' (SEQ ID NO: 40)

POH3;
5'-CCAYTGRCARAAYTGDATNCKNCKNGCRTACCA-3' (SEQ ID NO: 41)

The primer POH5 has a sequence complementary to the nucleotide sequence corresponding to the amino acid sequence PQH(R)I(V)WQTWKV, and the primer POH3 has a sequence complementary to the nucleotide sequence corresponding to the amino acid sequence WYARRIQFCQW.

PCR by primers POH5 and POH3 was performed using the chromosomal DNA of *Ogataea minuta* IFO 10746 as a template ((94° C. for 30 seconds, 50° C. for 1 minute and 72° C. for 30 seconds)×25 cycles). The amplified DNA fragment of approximately 0.4 kb was recovered and cloned using TOPO TA Cloning Kit. Plasmid DNA was isolated from the obtained clone and sequenced. For a DNA insert of the plasmid, a clone was selected which had a nucleotide sequence encoding an amino acid sequence highly homologous to the amino acid sequences of OCH1 gene products from *Saccharomyces cerevisiae* and *Pichia pastoris*. The 0.4-kb DNA insert was recovered after EcoRI cleavage of the plasmid and agarose gel electrophoresis.

(9-2) Preparation of Library and Screening

The chromosomal DNA of *Ogataea minuta* IFO 10746 was cleaved with different restriction enzymes, and subjected to Southern analysis using the DNA fragment obtained in Example (9-1) as a probe by the method described in Example (2-2). The results suggested that there existed OCH1 gene in the XbaI fragment of approximately 5 kb. Then, to clone the DNA fragment, a library was prepared. The chromosomal DNA of *Ogataea minuta* was cleaved with XbaI and subjected to agarose gel electrophoresis, and then the approximately 5-kb DNA fragment was recovered from the gel. The recovered DNA fragment was ligated with XbaI-cleaved pBluescript II SK– and then transformed into *Escherichia coli* DH5 α strains to prepare a library.

Approximately 6,000 clones were screened by colony hybridization using the above described DNA fragment as a probe. A clone bearing plasmid pOMOC1 was selected from the 4 positive clones obtained.

(9-3) Sequencing of Nucleotide Sequence

The nucleotide sequence of the BglII-SpeI region of the plasmid pOMOC1 (FIG. 11) was determined by deletion mutant and primer walking method to obtain a nucleotide sequence represented by SEQ ID NO:42.

In the nucleotide sequence of SEQ ID NO:42 there existed an open reading frame consisting of 1,305 bp, starting at position 508 and ends at position 1,812. The homology studies between the amino acid sequence (SEQ ID NO:43) deduced from the open reading frame and the mannosyltransferase OCH1 gene product from *Saccharomyces cerevisiae* or *Pichia pastoris* showed that 42% or 29% of amino acids were respectively identical between them. It remains unknown whether or not the *Pichia pastoris*-derived OCH1 gene disclosed in Japanese Patent Publication (Kokai) No. 9-3097A substantially encodes the OCH1 (α-1,6 mannosyltransferase), or whether or not the same *Pichia pastoris*-derived OCH1 gene has the functions of the OCH1 gene of *Ogataea minuta* described in this Example and Examples 10 and 11. The reasons are that the homology to the *Pichia pastoris*-derived OCH1 was 29% in amino acid, and that it has not been studied whether the *Pichia pastoris*-derived OCH1 has the activity of the *Saccharomyces cerevisiae*-derived OCH1 (α-1,6 mannosyltransferase).

Example 10

Preparation of *Ogataea minuta*-derived OCH1 Knockout Mutant

The OCH1 gene was disrupted by transformation using the URA3 gene of *Ogataea minuta* as a marker.

(10-1) Preparation of OCH1 Gene Disruption Vector

Figure 11:
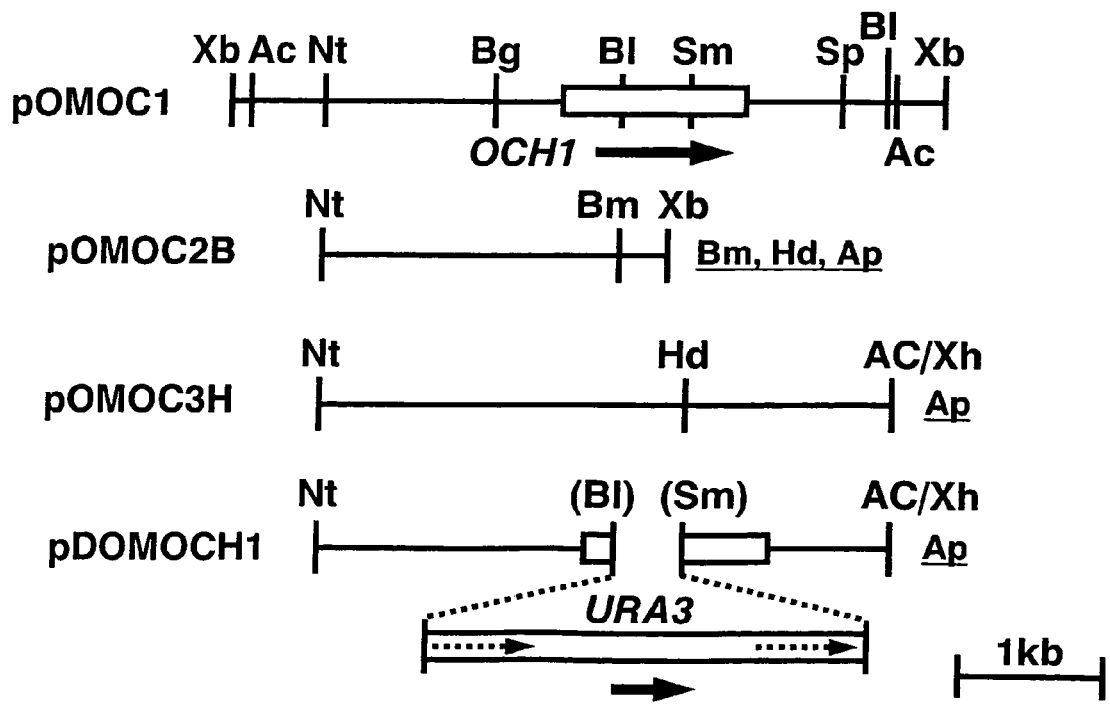
FIG. 11 shows the restriction maps of plasmids pOMOC1, pOMOC2B, pOMOC3H and pDOMOCH1. The restriction enzyme sites of the vector are underlined.

Plasmid pDOMOCH1 was prepared by replacing approximately 0.5-kb BalI-SmaI region of the OCH1 gene by the URA3 gene (FIG. 11). To obtain a uracil auxotrophic mutant again from OCH1 knockout mutant, the URA3 gene having repetitive structures before and after the structural gene, as described in Example (8-1), was used as a marker.

The 4.4-kb NotI-XbaI fragment was isolated from the pOMOC1 and inserted into the NotI-XbaI of pBluescript II SK–. The obtained plasmid was named pOMOC2. The pOMOC2 was cleaved with AccI and XhoI, blunt-ended, and self-ligated. The obtained plasmid was named pOMOC3. The pOMOC2 was cleaved with BalI, and ligated with a BamHI linker. The obtained plasmid was named pOMOC2B (FIG. 11). The pOMOC3 was cleaved with SmaI, and ligated with a HindIII linker. The obtained plasmid was named pOMOC3H (FIG. 11). The 3.3-kb BglII-HindIII fragment isolated from the pROMU1 described in Example (8-1) was inserted into the BamHI-HindIII of the pOMOC2B. The 1.5-kb HindIII-ApaI fragment isolated from the pOMOC3H was inserted into the HindIII-ApaI of the obtained plasmid. The resultant plasmid was named pDOMOCH1.

(10-2) Transformation

The pDOMOCH1 obtained in Example (10-1) was cleaved with ApaI and NotI, and transformed into *Ogataea minuta* TK1-3 strain (ura3Δ), which was obtained in Example (6-2), and into *Ogataea minuta* TK4-1 strain (ura3Δ Ade11Δ), which was obtained in Example (8-2), by electric pulse method. The transformation was performed in accordance with the method described in Example (6-2).

Figure 12:
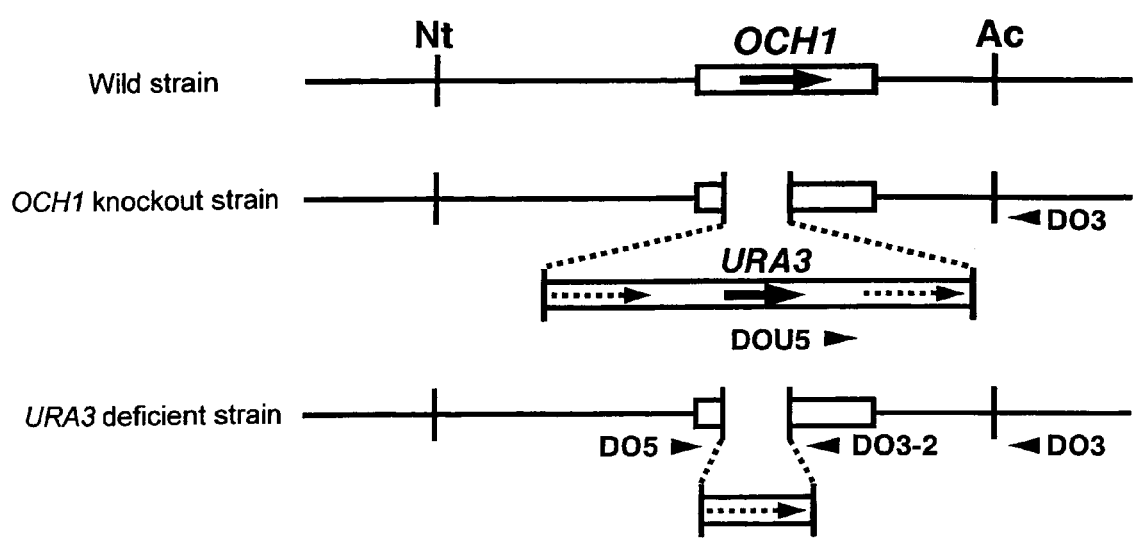
FIG. 12 shows the structures of the OCH1 gene loci of a wild strain of *Ogataea minuta*, an OCH1 gene knockout mutant disrupted by the plasmid pDOMOCH1, and a URA3 gene deficient mutant, along with positions of PCR primers.

To confirm that the OCH1 genes of these strains were disrupted, the following primers were synthesized (see FIG. 12 with regard to the position of each primer).

DO3;
5'-CCATTGTCAGCTCCAATTCTTTGATAAACG-3' (SEQ ID NO: 44)

DOU5;
5'-ATCGATTTCGAGTGTTTGTCCAGGTCCGGG-3' (SEQ ID NO: 37)

DO5;
5'-ACACTTCCGTAAGTTCCAAGAGACATGGCC-3' (SEQ ID NO: 45)

DO3-2;
5'-TCACCACGTTATTGAGATAATCAAACAGGG-3' (SEQ ID NO: 46)

PCR by primers DO5 and DOU5 was performed using the chromosomal DNA isolated from the transformant as a template ((94° C. for 30 seconds, 60° C. for 1 minute and 72° C. for 3 minutes)×25 cycles). As shown in FIG. 12, a 2.4-kb amplified DNA fragment was detected in the strain whose OCH1 locus had the plasmid integrated thereinto. After culturing the selected strain in the YPD medium until stationary phase, a strain resistant to 5-fluoroorotic acid (5-FOA) was obtained. PCR by primers DO3 and DO5 ((94° C. for 30 seconds, 60° C. for 1 minute and 72° C. for 3 minutes)×25 cycles) and PCR by primers DO5 and DOC3-2 ((94° C. for 30 seconds, 60° C. for 1 minute and 72° C. for 1 minute)×25 cycles) were performed using the chromosomal DNA isolated from the 5-FOA resistant strain as a template. As shown in FIG. 12, in the strain in which URA3 gene was deleted, a 2.4-kb amplified DNA fragment was detected by the PCR using primers DO3 and DO5 and a 0.9 kb amplified DNA fragment by the PCR using primers DO5 and DOC3-2. The och1Δ ura3Δ strain obtained was named *Ogataea minuta* TK3-A strain, and the och1Δ ura3Δ ade1Δ strain was named *Ogataea minuta* TK5-3 strain.

Example 11

Isolation of Cell Surface Mannan Protein from *Ogataea minuta* OCH1 Knockout Mutant and Structure Analysis of Sugar Chain Contained Therein Structure analysis of sugar chains of cell surface mannan proteins was performed for *Ogataea minuta* OCH1 knockout mutant strain TK3-A and its parent strain TK1-3. The preparation of PA-oligosaccharides was performed by the method described in Example 1.

The prepared sugar chains were cleaved with *Aspergillus saitoi* α-1,2-mannosidase (SEIKAGAKU CORPORATION, Japan). Analysis was performed by HPLC. HPLC on amide column enables PA-oligosaccharides to be separated depending on the chain length. HPLC using a reverse-phase column enables PA-oligosaccharides to be separated depending on the hydropholicity, thereby to identify sugar chain structures. The HPLC conditions were as follows.
1) Size Analysis by Amide Column
  Column: TSK-Gel Amido-80 (4.6×250 mm, TOSOH CORPORATION, Japan)
  Column temperature: 40° C.
  Flow rate: 1 ml
  Elution conditions: A: 200 mM triethylamine acetate pH 7.0+65% acetonitrile
  B: 200 mM triethylamine acetate pH 7.0+30% acetonitrile
  Linear gradient of 0 minute A=100% and 50 minutes A=0%
2) Structure Analysis by Reverse Phase Column
  Column: TSK-Gel ODS80TM (4.6×250 mm, TOSOH CORPORATION, Japan)
  Column temperature: 50° C.
  Flow rate: 1.2 ml
  Elution conditions: 100 mM ammonium acetate containing 0.15% n-butanol pH 6.0

Figure 13:
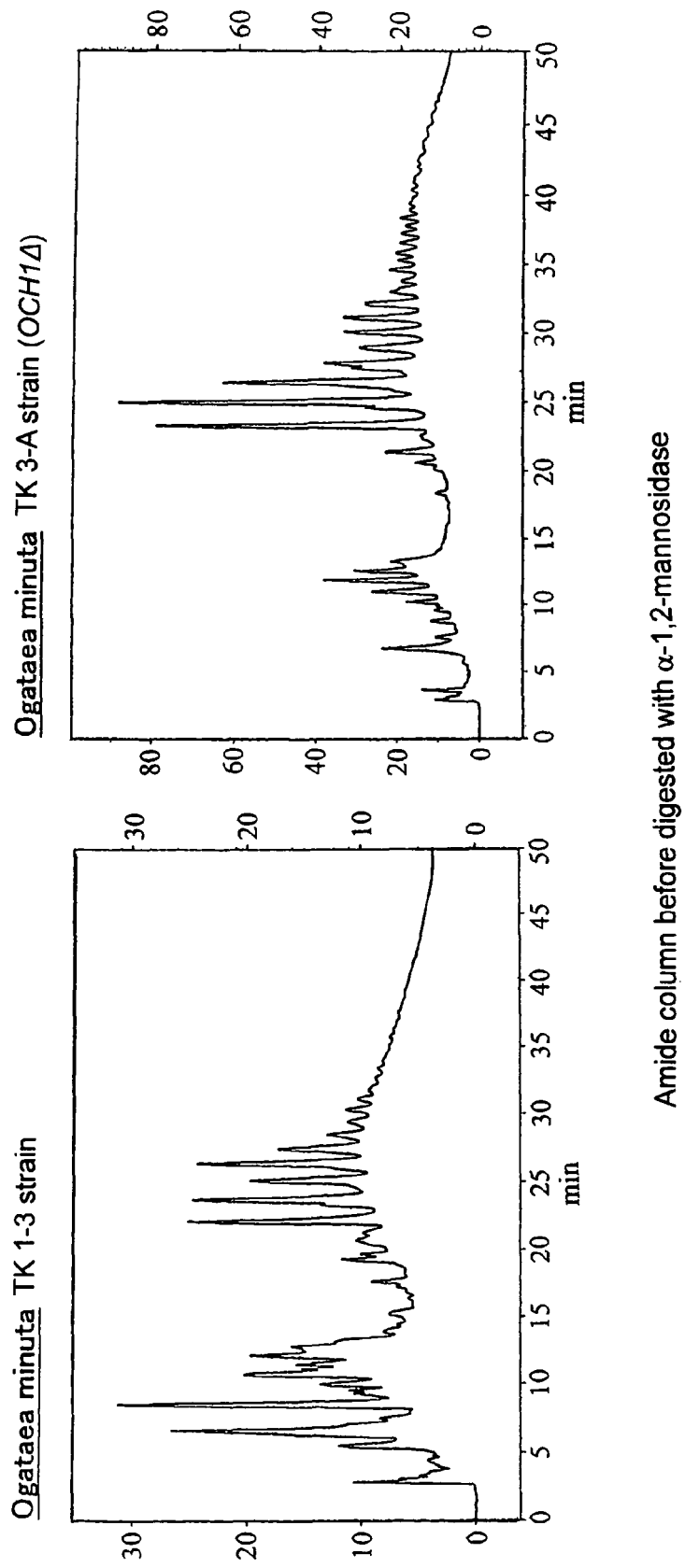
FIG. 13 shows the structure analysis by an amide and reverse phase columns for sugar chains of the mannan glycoproteins of *Ogataea minuta* strain TK3-A which is an OCH1 gene knockout mutant and of its parent strain *Ogataea minuta* strain TK1-3.
Figure 13:
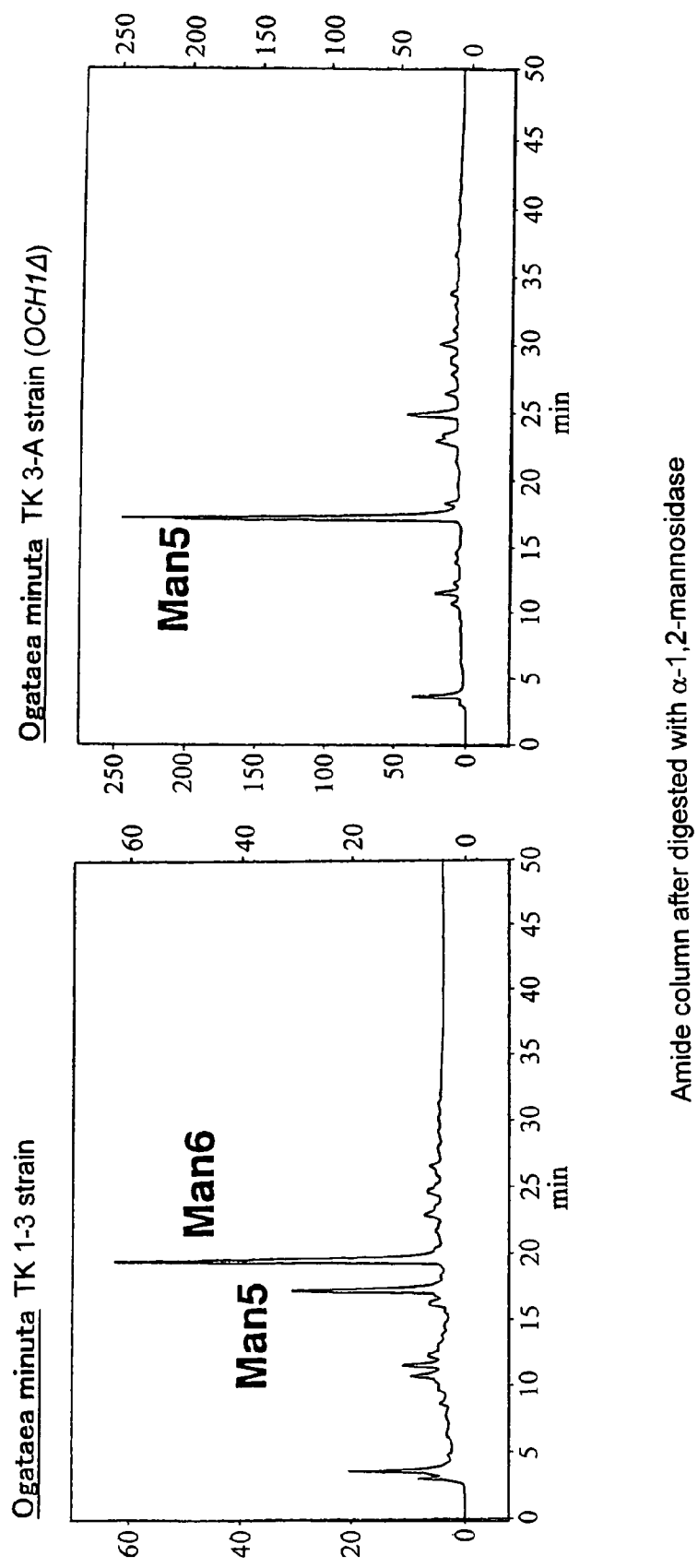
Figure 13:
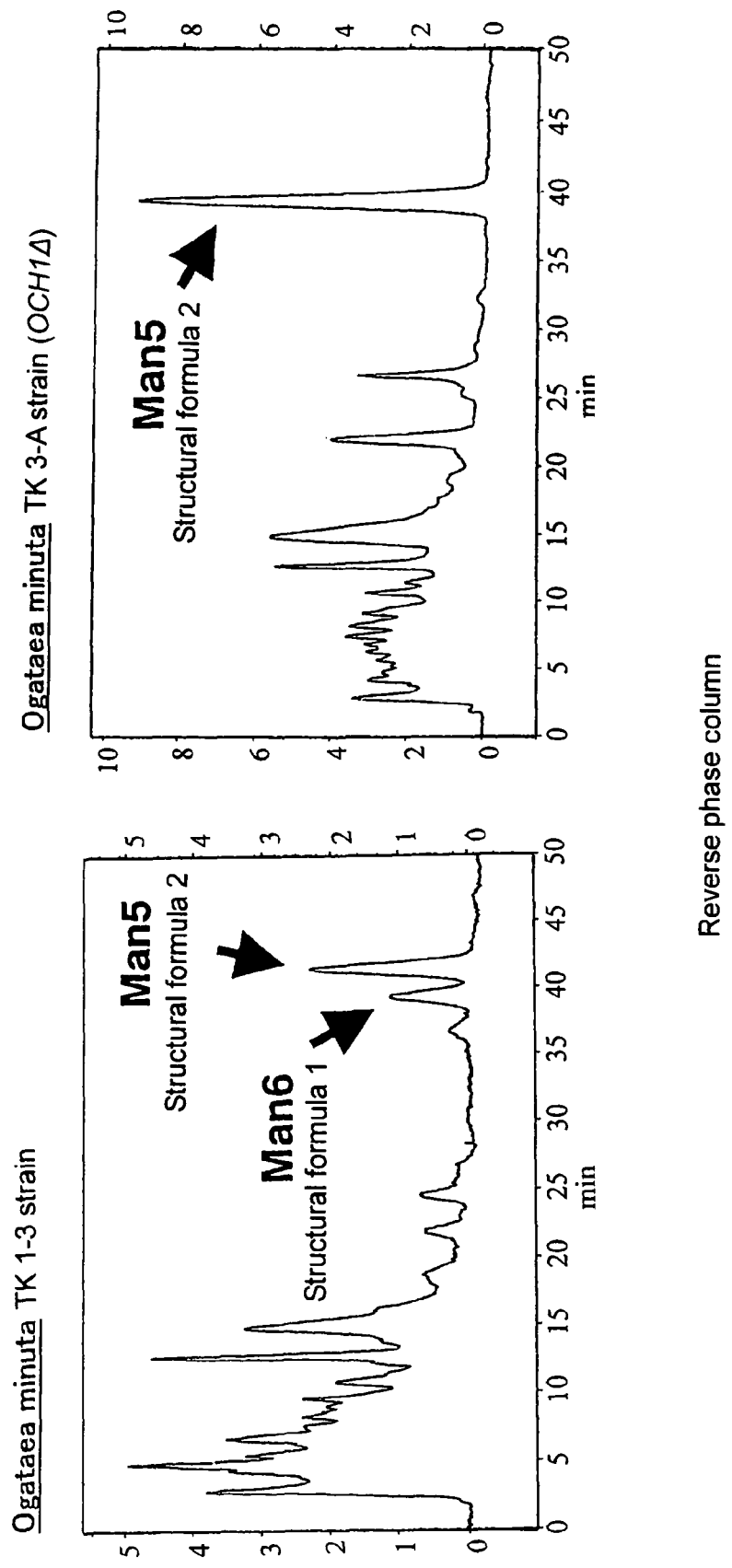

The results are shown in FIG. 13. From the size analysis using an amide column, it was confirmed that the TK1-3 strain as a parent strain produced both Man5 and Man6 as shown in FIG. 13, whereas the TK3-A strain, i.e., a ΔOCH1 strain, mainly produced Man5. Further, from the structure analysis using a reverse phase column and the comparison with commercially available standard sugar chains (TAKARA SHUZO CO., LTD., Japan), it was found that Man6 of the TK1-3 strain was a sugar chain having the structural formula 1 below, Man5 of the TK1-3 strain a sugar chain having the structural formula 2 below, and Man5 of the TK3-A strain a sugar chain having the structural formula 2 below.

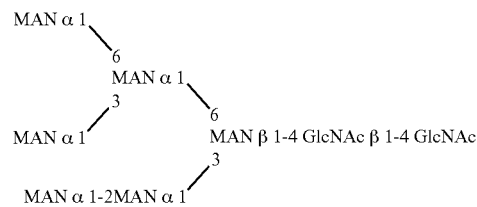

Structural Formula 1

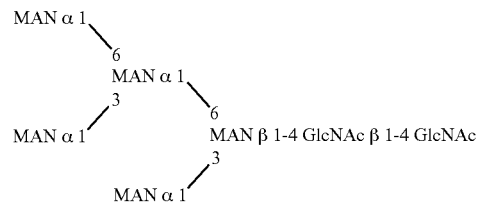

Structural Formula 2

From the above results, it was confirmed that the obtained gene was substantially *Ogataea minuta* OCH1 gene and that it was possible to prepare sugar chain mutants corresponding to the och1, mnn1 and mnn4 strains in *Saccharomyces cerevisiae* in which α-1,2-mannosidase gene was expressed.

Example 12

Cloning of Proteinase A (PEP4) Gene of *Ogataea minuta*

The PEP4 gene was obtained from *Ogataea minuta* IFO 10746 and its nucleotide sequence was determined.
(12-1) Preparation of Probe Oligonucleotides having nucleotide sequences corresponding to the following amino acid sequences conserved in PEP4 gene from *Saccharomyces cerevisiae* (GenBank accession number; M13358) and *Pichia angusta* (GenBank accession number; U67173):

```
TNYLNAQY;        (SEQ ID NO: 47)
and

KAYWEVKF         (SEQ ID NO: 48)
``` were synthesized as follows.

```
PPA5;   5'-                        (SEQ ID NO: 49)
        ACNAAYTAYYTNAAYGCNCARTA-3'

PPA3;   5'-                        (SEQ ID NO: 50)
        AAYTTNACYTCCCARTANGCYTT-3'
```

The primer PPA5 has a sequence complementary to the nucleotide sequence corresponding to the amino acid sequence TNYLNAQY, and the primer PPA3 has a sequence complementary to the nucleotide sequence corresponding to the amino acid sequence KAYWEVKF.

PCR by primers PPA5 and PPA3 was performed using the chromosomal DNA of *Ogataea minuta* IFO 10746 as a template ((94° C. for 30 seconds, 55° C for 1 minute and 72° C. for 1 minute)×25 cycles). The amplified DNA fragment of approximately 0.6 kb was recovered and cloned using TOPO TA Cloning Kit. Plasmid DNA was isolated from the obtained clone and sequenced. For a DNA insert of the plasmid, a clone was selected which had a nucleotide sequence encoding an amino acid sequence highly homologous to the amino acid sequences for PEP4 genes from *Saccharomyces cerevisiae* and *Pichia angusta*. The 0.6-kb DNA insert was recovered after EcoRI cleavage of the plasmid and agarose gel electrophoresis.

(12-2) Preparation of Library and Screening

The chromosomal DNA of *Ogataea minuta* IFO 10746 was cleaved with different restriction enzymes, and subjected to Southern analysis using the DNA fragment obtained in Example (12-1) as a probe by the method described in Example (6-2). The results suggested that there existed PEP4 gene in the approximately 6 kb BamHI fragment. Then, to clone the DNA fragment, a library was prepared. The chromosomal DNA of *Ogataea minuta* was cleaved with BamHI and subjected to agarose gel electrophoresis, and then the approximately 6-kb DNA fragment was recovered from the gel. The recovered DNA fragment was ligated with BamHI-cleaved pUC18 and then transformed into *Escherichia coli* strain DH5 α to prepare a library.

About 5,000 clones were screened by colony hybridization using the above described DNA fragment as a probe. A clone bearing plasmid pOMPA1 was selected from the 8 positive clones obtained.

(12-3) Sequencing of Nucleotide Sequence

The nucleotide sequence of the NdeI-XbaI region of the plasmid pOMPA1 (FIG. 14) was determined by deletion mutant and primer walking method to obtain a nucleotide sequence represented by SEQ ID NO:51.

In the nucleotide sequence represented by SEQ ID NO:51, there existed an open reading frame of 1,233 bp, starting at position 477 and ends at position 1,709. The homology studies between the amino acid sequence (SEQ ID NO:52) deduced from the open reading frame and the PEP4 from *Saccharomyces cerevisiae* or *Pichia angusta* showed that 67% or 78% of amino acids were respectively identical between them.

Example 13

Preparation of *Ogataea minuta* PEP4 Knockout Mutant

The PEP4 gene was disrupted by transformation using the URA3 gene of *Ogataea minuta* as a marker.

(13-1) Preparation of PEP4 Disruption Vector

Figure 14:
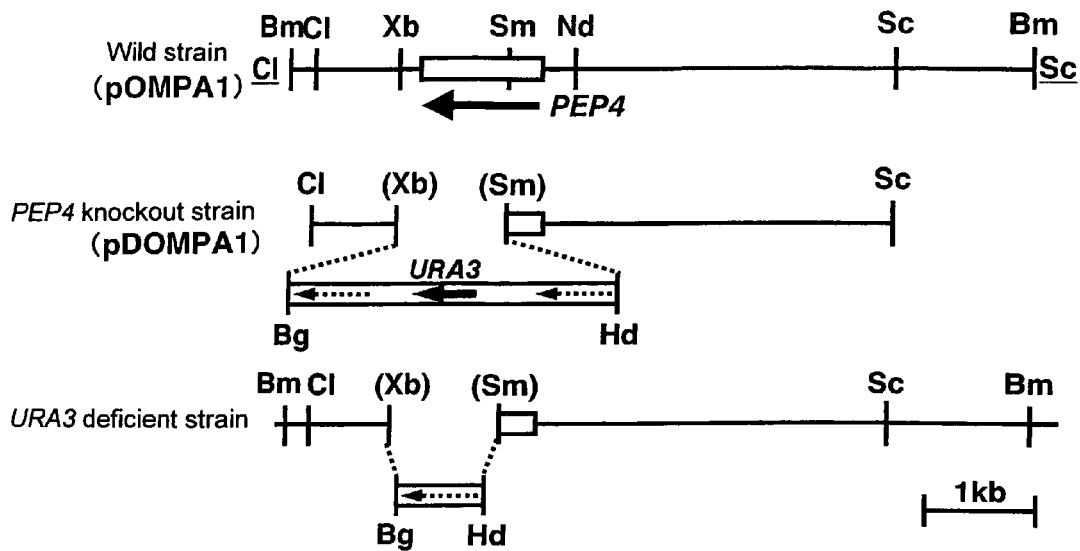
FIG. 14 shows the restriction maps of plasmids pOMPA1 and pDOMPA1, and the structures of the PEP4 loci of a wild strain of *Ogataea minuta*, a PEP4 gene knockout mutant disrupted by plasmid pDOMPA1, and a URA3 gene deficient mutant. The restriction enzyme sites of the vector origin are underlined.

As shown in FIG. 14, plasmid pDOMPA1 was prepared by replacing the approximately 1.1-kb SmaI-XbaI region of the PEP4 structural gene by the URA3 gene. To obtain a uracil auxotrophic mutant again from PEP4 knockout mutants, the URA3 gene having repetitive structures before and after the structural gene was used as a marker. Plasmid was prepared by SacI cleavage, self-ligation, ClaI cleavage, and self-ligation of the plasmid pOMPA1 carrying the PEP4 gene region, as described in Example (12-2).

The obtained plasmid was cleaved with SmaI, ligated with a HindIII linker, cleaved with XbaI, blunt0ended, and ligated with a BglII linker.

The 3.3-kb BglII-HindIII fragment isolated from the pROMMI described in Example (8-1) was inserted into the BglII-HindIII of the obtained plasmid. The resultant plasmid was named pDOMPA1 (FIG. 14).

(13-2) Transformation

The pDOMPA1 obtained in Example (13-1) was cleaved at SacI-ClaI, and then transformed into the *Ogataea minuta* TK3-A strain (och1Δ ura3Δ) and the *Ogataea minuta* TK5-3 strain (och1Δ ura3Δ ade1Δ) obtained in Example (10-2), by means of the electric pulse method.

The PEP4 knockout mutants were screened by subjecting the chromosomal DNAs of the obtained transformants to Southern analysis. Specifically, when cleaving the chromosomal DNAs of the host strain and the transformants with BamHI and subjecting the cleaved chromosomal DNAs to Southern analysis using the 4.8-kb SacI-ClaI fragment isolated from the pDOMPA1 (FIG. 14) as a probe, a band was detected at 6 kb in the host strain, while a band was detected at 9 kb in the knockout mutants. After culturing the knockout mutants in the YPD medium until stationary phase, a strain resistant to 5-fluoroorotic acid (5-FOA) was obtained. The chromosomal DNA of the 5-FOA resistant strain was cleaved with BamHI and again subjected to Southern analysis using the 4.8-kb SacI-ClaI fragment isolated from the pDOMPA1 (FIG. 14) as a probe, and a strain was selected from which the UR43 gene was deleted and in which a band was detected at 5.5 kb. The och1Δ pep4Δ ura3Δ strain obtained was named *Ogataea minuta* TK6 strain, and the och1Δ pep4Δ ura3Δ ade1Δ strain was named *Ogataea minuta* TK7 strain.

Example 14

Cloning of PRB1 Gene of *Ogataea minuta*

The PRB1 gene was obtained from *Ogataea minuta* IFO 10746 and its nucleotide sequence was determined.

(14-1) Preparation of Probe

Oligonucleotides having nucleotide sequences corresponding to the following amino acid sequences conserved in PRB1 from *Saccharomyces cerevisiae* (GenBank accession number; M18097) and *Kluyveromyces lactis* (GenBank accession number; A75534) and their homologues:

```
DG(L)NGHGTHCAG              (SEQ ID NO: 53)

GTSMAS (T) PHV (I) A (V) G   (SEQ ID NO: 54)
``` were synthesized as follows.

```
PPB5;
5'-                         (SEQ ID NO: 55)
GAYBKNAAYGGNCAYGGNACNCAYTGYKCNGG-
3'

PPB3;
5'-                         (SEQ ID NO: 56)
CCNRCNAYRTGNGGNWSNGCCATNWSNGTNCC-
3'
```

The primer PPB5 has a sequence complementary to the nucleotide sequence corresponding to the amino acid sequence DG(L)NGHGTHCAG, and the primer PPB3 has a sequence complementary to the nucleotide sequence corresponding to the amino acid sequence GTSMAS(T)PHV(I)A (V)G.

PCR by primers PPB5 and PPB3 was performed using the chromosomal DNA of *Ogataea minuta* IFO 10746 as a template ((94° C. for 30 seconds, 50° C. for 1 minute and 72° C. for 1 minute)×25 cycles). The amplified DNA fragment of approximately 0.5 kb was recovered and cloned using TOPO TA Cloning Kit. Plasmid DNA was isolated from the obtained clone and sequenced. For a DNA insert of the plasmid, a clone was selected which had a nucleotide sequence encoding an amino acid sequence highly homologous to the amino acid sequences for PRB1 genes from *Pichia pastoris* and *Kluyveromyces lactis*. The 0.5-kb DNA insert was recovered after EcoRI cleavage of the plasmid and agarose gel electrophoresis.

(14-2) Preparation of Library and Screening

The chromosomal DNA of *Ogataea minuta* IFO 10746 was cleaved with different restriction enzymes, and subjected to Southern analysis using the DNA fragment obtained in Example (14-1) as a probe by the method described in Example (2-2). The results suggested that there existed PRB1 gene in the BamHI fragment of approximately 5 kb. Then, to clone the DNA fragment, a library was prepared. The chromosomal DNA of *Ogataea minuta* was cleaved with BamHI and electrophoresed on agarose gel, and then the approximately 5-kb DNA fragment was recovered from the gel. The DNA fragment was ligated with BamHI-cleaved and BAP-treated pUC18 and then transformed into *Escherichia coli* strain DH5 α to prepare a library.

About 6,000 clones were screened by colony hybridization using the above described DNA fragment as a probe. A clone bearing plasmid pOMPB 1 was selected from the 2 positive clones obtained.

(14-3) Sequencing of Nucleotide Sequence

The nucleotide sequence of the BamHI-HindIII region of the plasmid pOMPB1 (FIG. 15) was determined by deletion mutant and primer walking method to obtain a nucleotide sequence represented by SEQ ID NO:57.

In the nucleotide sequence of SEQ ID NO:57, there existed an open reading frame of 1,620 bp, starting at position 394 and ends at position 2,013. The homology studies between the amino acid sequence (SEQ ID NO:) deduced from the open reading frame and the PRB1 gene product from *Pichia pastoris* or *Kluyveromyces lactis* showed that 47% or 55% of amino acids were respectively identical between them.

Example 15

Preparation of *Ogataea minuta* PRB1 Knockout Mutant

The PRB1 gene was disrupted by transformation using the URA3 gene of *Ogataea minuta* as a marker.

(15-1) Preparation of PRB1 Gene Disruption Vector

Figure 15:
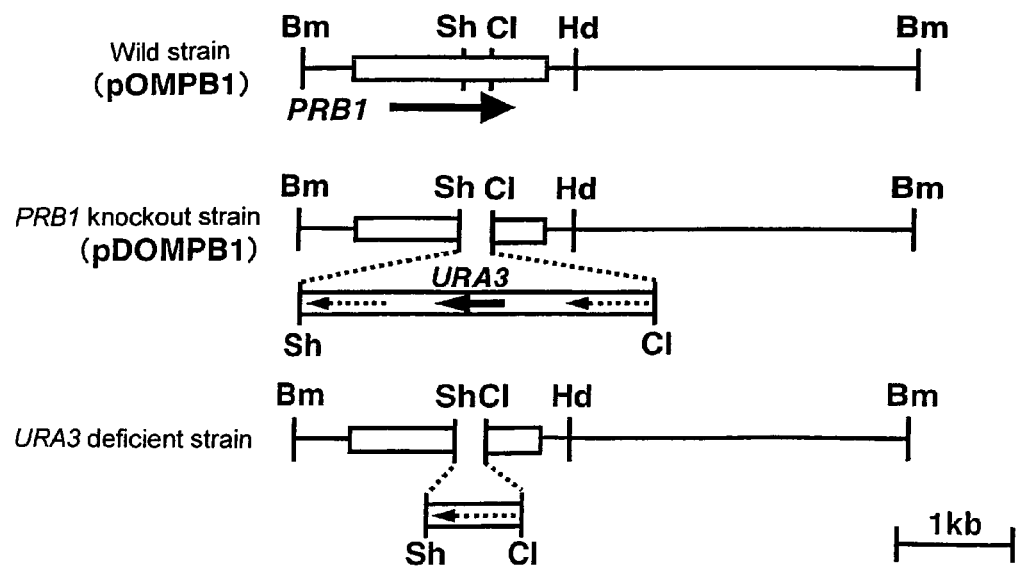
FIG. 15 shows the restriction maps of plasmids pOMPB1 and pDOMPB1, and the structures of the PRB1 loci of a wild strain of *Ogataea minuta*, a PRB1 gene knockout mutant disrupted by plasmid pDOMPB1, and a URA3 gene deficient mutant.

As shown in FIG. 15, plasmid pDOMPB1 was prepared by replacing the approximately 0.2-kb ClaI-SphI region of the PRB1 structural gene by the URA3 gene. To obtain a uracil auxotrophic mutant again from PRB1 knockout mutants, the URA3 gene having repetitive structures before and after the structural gene was used as a marker. The BamHI fragment was isolated from the plasmid pOMPB1 having the PRB1 gene region as described in Example (14-2) and inserted into pTV19ΔSph (i.e., pTV19 which was cleaved with SphI, blunt-ended and self-ligated, and from which SphI site was deleted), which had been cleaved with BamHI and treated with BAP.

The 3.3-kb ClaI-SphI fragments isolated from the plasmid, as described in Example (8-1), which were obtained by changing the BglII site of the pROMU1 to a ClaI site and changing the HindIII site of the pROMU1 to a SphI site, respectively, by linker ligation method, were inserted into the ClaI-SphI of the obtained plasmid. The resultant plasmid was named pDOMPB1 (FIG. 15).

(15-2) Transformation

The pDOMPB1 obtained in Example (15-1) was cleaved with BamHI and transformed into the *Ogataea minuta* TK6 strain (och1Δ pep4Δ ura3Δ) and the *Ogataea minuta* TK7 strain (och1Δ pep4Δ ura3Δ ade1Δ) obtained in Example (13-2) by electric pulse method.

The PRB1 knockout mutants were screened by subjecting the chromosomal DNAs of the obtained transformants to Southern analysis. Specifically, when cleaving the chromosomal DNAs of the host strain and the transformants with BamHI and subjecting the cleaved chromosomal DNAs to Southern analysis using the 5-kb BamHI fragment isolated from the pDOMPB1 (FIG. 15) as a probe, 5 kb band was detected in the host strain, while 8.5 kb band was detected in the knockout mutants. After culturing the knockout mutants in the YPD medium until stationary phase, a strain resistant to 5-fluoroorotic acid (5-FOA) was obtained. The chromosomal DNA of the 5-FOA resistant strain was cleaved with BamHI and again subjected to Southern analysis using the 5-kb BamHI fragment isolated from the pDOMPB1 (FIG. 15) as a probe, and a strain was selected from which the URA3 gene was deleted and for which 5 kb band was detected. The och1Δ pep4Δ prb1Δ ura3Δ strain obtained was named *Ogataea minuta* TK8 strain, and the och1Δ pep4Δ prb1Δ ura3Δ ade1Δ strain was named *Ogataea minuta* TK9 strain.

Example 16

Cloning of KTR1 Gene of *Ogataea minuta*

The KTR1 gene was obtained from *Ogataea minuta* IFO 10746 and its nucleotide sequence was determined.

(16-1) Preparation of Probe

The amino acid sequences conserved in the KTR gene family from *Saccharomyces cerevisiae* (Biochim. Biophys, Acta, (1999) Vol. 1426, p326) was extracted:

```
H(N)YDWV(T)FLND;        (SEQ ID NO: 59)
and

YNLCHFWSNFEI,           (SEQ ID NO: 60)
``` and oligonucleotides having nucleotide sequences corresponding the above amino acid sequences were synthesized as follows.

```
                                    (SEQ ID NO: 61)
PKR5;   5'-MAYTAYGAYTGGRYNTTYYTNAAYGA-3'

(SEQ ID NO: 62)
PKR3;   5'-ATYTCRAARTTNSWCCARAARTGRCANARRTTRTA-3'
```

The primer PKR5 has a sequence complementary to the nucleotide sequences corresponding to the amino acid sequence H(N)YDWV(T)FLND, and the primer PKR3 has a sequence complementary to the nucleotide sequences corresponding to the amino acid sequence YNLCHFWSNFEI.

PCR by primers PKR5 and PKR3 was performed using the chromosomal DNA of *Ogataea minuta* IFO 10746 as a template ((94° C. for 30 seconds, 50° C. for 1 minute and 72° C. for 1 minute)×25 cycles). The amplified DNA fragment of approximately 0.6 kb was recovered and cloned using TOPO TA Cloning Kit. Plasmid DNA was isolated from the obtained clone and sequenced. From the nucleotide sequence analysis for 60 clones, it was confirmed that total 4 types of gene fragments existed, all of which had a high homology with the amino acid sequences of the KTR1 gene family from *Saccharomyces cerevisiae*. One clone was selected from the 60 clones and the 0.6-kb DNA insert was recovered after EcoRI cleavage of the plasmid and separation by agarose gel electrophoresis.

(16-2) Preparation of Library and Screening

The chromosomal DNA of *Ogataea minuta* IFO 10746 was cleaved with different restriction enzymes and subjected to Southern analysis using the DNA fragment obtained in Example (12-1) as a probe by the method described in Example (2-2). The results suggested that there existed the KTR1 gene in the SacI fragment of approximately 2 kb. Then, to clone the DNA fragment, a library was prepared. The chromosomal DNA of *Ogataea minuta* was cleaved with SacI and subjected to agarose gel electrophoresis, and then the approximately 2-kb DNA fragment was recovered from the gel. The DNA fragment was ligated with SacI-cleaved and BAP-treated pUC18 and then transformed into *Escherichia coli* strain DH5 α to prepare a library.

About 4,000 clones were screened by colony hybridization using the above described DNA fragment as a probe. A clone bearing plasmid pOMKR1 was selected from the 2 positive clones obtained.

(16-3) Sequencing of Nucleotide Sequence

The nucleotide sequence of the SacI insert in the plasmid pOMKR1 (FIG. 16) was determined by deletion mutant and primer walking method to obtain a nucleotide sequence represented by SEQ ID NO:63.

In the nucleotide sequence of SEQ ID NO:63, there existed an open reading frame of 1,212 bp, starting at position 124 and ends at position 1,335. The homology studies between the amino acid sequence (SEQ ID NO:64) deduced from the open reading frame and the KTR1 or KRE2 gene product, as KTR family, from *Saccharomyces cerevisiae*, showed that 53% or 49% of amino acids were respectively identical between them Example 17

Preparation of *Ogataea minuta* KTR1 Knockout Mutant

The KTR1 gene was disrupted by transformation using the URA3 gene of *Ogataea minuta* as a marker.

(17-1) Preparation of KTR1 Gene Disruption Vector

Figure 16:
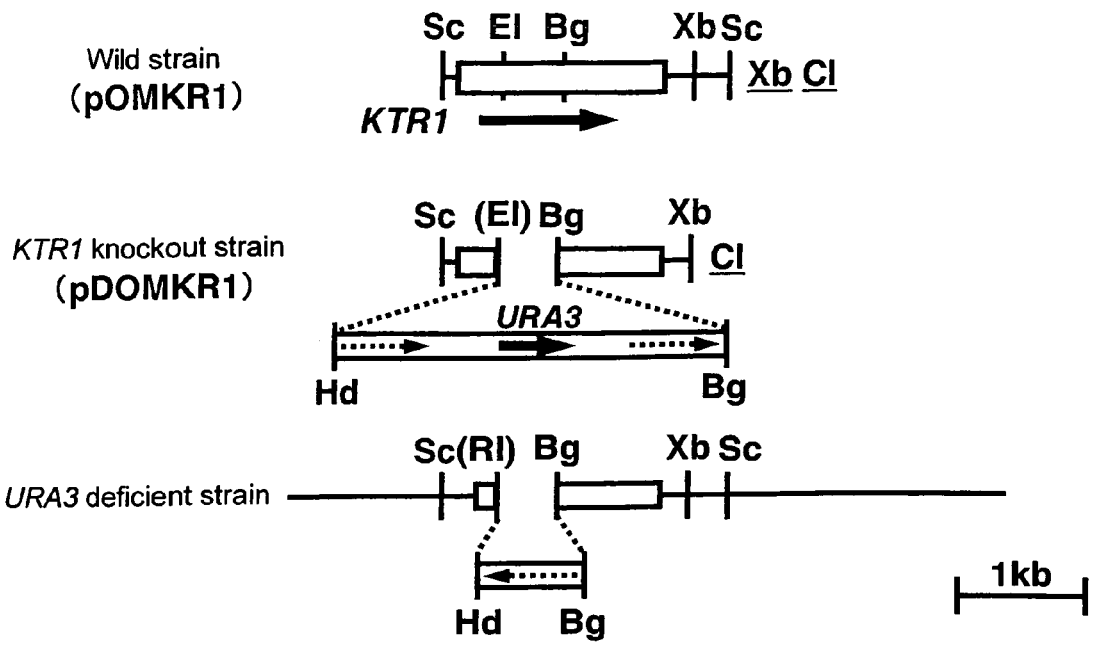
FIG. 16 the restriction maps of plasmids pOMKR1 and pDOMKR1, and the structures of the KTR1 loci of a wild strain of *Ogataea minuta*, a KTR1 gene knockout mutant disrupted by plasmid pDOMKR1, and a URA3 gene deficient mutant. The restriction enzyme sites of the vector are underlined.

As shown in FIG. 16, plasmid pDOMKR1 was prepared by replacing the 0.3-kb EcoRI-BglII region of the KTR1 structural gene by the URA3 gene. To obtain a uracil auxotrophic mutant again from KTR1 knockout mutants, the URA3 gene having repetitive structures before and after the structural gene was used as a marker. The plasmid pOMKR1 carrying the KTR1 gene region as described in Example (16-2) was cleaved at HindIII-XbaI, blunt-ended, and ligated. The obtained plasmid was cleaved with EcoRI and ligated with a HindIII linker.

The 3.3-kb BglII-HindIII fragment isolated from the pROMU1 as described in Example (8-1) was inserted into the BglII-HindIII of the obtained plasmid. The resultant plasmid was named pDOMKR1 (FIG. 16).

(17-2) Transformation

The pDOMKR1 obtained in Example (17-1) was cleaved at SacI-ClaI and transformed into the *Ogataea minuta* TK8 strain (och1Δ pep4Δ prb1Δ ura3Δ) and the *Ogataea minuta* TK9 strain (och1Δ pep4Δ prb1Δ ura3Δ ade1Δ) obtained in Example (15-2), by electric pulse method.

The KTR1 knockout mutants were screened by subjecting the chromosomal DNAs of the obtained transformants to Southern analysis. Specifically, the chromosomal DNAs of the host strain and the transformants were cleaved with SacI and subjected to Southern analysis using the 2-kb SacI fragment isolated from the pDOMKR1 (FIG. 16) as a probe. As a result, 2 kb band was detected in the host strain, while 5 kb band was detected in the knockout mutants. After culturing the knockout mutants in the YPD medium until stationary phase, a strain resistant to 5-fluoroorotic acid (5-FOA) was obtained. The chromosomal DNA of the 5-FOA resistant strain was cleaved with SacI and again subjected to Southern analysis using the 2-kb SacI fragment isolated from the pDOMKR1 (FIG. 16) as a probe, and a strain was selected from which the URA3 gene was deleted and for which 5 kb band was detected. The och1Δ ktr1Δ pep4Δ prb1Δ ura3Δ strain obtained was named *Ogataea minuta* TK10 strain, and the och1Δ ktr1Δ pep4Δ prb1Δ ura3Δ ade1Δ strain was named *Ogataea minuta* TK11 strain.

The sensitivity of *Ogataea minuta* TK10 and *Ogataea minuta* TK11 strains to hygromycin B was examined. *Ogataea minuta* IFO 10746, a wild strain, yielded colonies on a plate containing 50 µg/ml hygromycin B, but neither *Ogataea minuta* TK10 nor *Ogataea minuta* TK11 strain yielded a colony even on a plate containing 5 µg/ml hygromycin B. It is known that sugar chain mutants of *Saccharomyces cerevisiae* have higher sensitivity to a drug like hygromycin B than the wild strain of the same. Thus, it was presumed that these *Ogataea minuta* ktr1Δ strains had short sugar chains.

Further, in the *Ogataea minuta* ktr1Δ strains, the precipitation of cells was markedly increased just like the *Saccharomyces cerevisiae* och1Δ strain. This may show that the sugar chains of these *Ogataea minuta* ktr1Δ strains were short.

Example 18

Cloning of MNN9 Gene of *Ogataea minuta*

The MNN9 gene was obtained from *Ogataea minuta* IFO 10746 and its nucleotide sequence was determined.

(18-1) Preparation of Probe

Oligonucleotides having nucleotide sequences corresponding to the following amino acid sequences conserved in MNN9 from *Saccharomyces cerevisiae* (GenBank accession number; L23752) and *Candida albicans* (GenBank accession number; U63642):

```
TSWVLWLDAD;      (SEQ ID NO: 65)
and

ETEGFAKMAK       (SEQ ID NO: 66)
``` were synthesized as follows.

```
PMN5;
5'-                                   (SEQ ID NO: 67)
ACNWSNTGGGTNYTNTGGYTNGAYGCNGA-3'

PMN3;
5'-                                   (SEQ ID NO: 68)
TTNGCCATYTTNGCRAANCCYTCNGTYTC-3'
```

The primer PMN5 has a sequence complementary to the nucleotide sequence corresponding to the amino acid sequence TSWVLWLDAD, and the primer PMN3 has a sequence complementary to the nucleotide sequence corresponding to the amino acid sequence ETEGFAKMAK.

PCR by primers PMN5 and PMN3 was performed using the chromosomal DNA of *Ogataea minuta* IFO 10746 as a template ((94° C. for 30 seconds, 50° C. for 1 minute and 72° C. for 1 minute)×25 cycles). The amplified DNA fragment of approximately 0.4 kb was recovered and cloned using TOPO TA Cloning Kit. Plasmid DNA was isolated from the obtained clone and sequenced. For a DNA insert of the plasmid, a clone was selected which had a nucleotide sequence encoding an amino acid sequence highly homologous to the amino acid sequences for MNN9 genes from *Saccharomyces cerevisiae* and *Candida albicans*. The 0.4-kb DNA insert was recovered after EcoRI cleavage of the plasmid and agarose gel electrophoresis.

(18-2) Preparation of Library and Screening

The chromosomal DNA of *Ogataea minuta* IFO 10746 was cleaved with different restriction enzymes, and subjected to Southern analysis using the DNA fragment obtained in Example (18-1) as a probe by the method described in Example (2-2). The results suggested that there existed the MNN9 gene in the BamHI fragment of approximately 8 kb. Then, to clone the DNA fragment, a library was prepared. The chromosomal DNA of *Ogataea minuta* was cleaved with BamHI and subjected to agarose gel electrophoresis, and then the approximately 8-kb DNA fragment was recovered from the gel. The DNA fragment was ligated with BamHI-cleaved pUC 118 and then transformed into *Escherichia coli* strain DH5 α to prepare a library.

About 6,000 clones were screened by colony hybridization using the above described DNA fragment as a probe. A clone bearing plasmid pOMMN9 was selected from the 2 positive clones obtained.

(18-3) Sequencing of Nucleotide Sequence

The nucleotide sequence of the ApaI-BglII region of the plasmid pOMMN9 (FIG. 17) was determined by deletion mutant and primer walking method to obtain a nucleotide sequence represented by SEQ ID NO:69.

In the nucleotide sequence of SEQ ID NO:69, there existed an open reading frame of 1,104 bp, starting at position 931 and ends at position 2,034. The homology studies between the amino acid sequence (SEQ ID NO:70) deduced from the open reading frame and the MNN9 gene product from *Saccharomyces cerevisiae* or *Candida albicans* showed that 59% or 62% of amino acids were respectively identical between them.

Example 19

Preparation of *Ogataea minuta* MNN9 Knockout Mutant

The MNN9 gene was disrupted by transformation using the URA3 gene of *Ogataea minuta* as a marker.

(19-1) Preparation of MNN9 Disruption Vector

Figure 17:
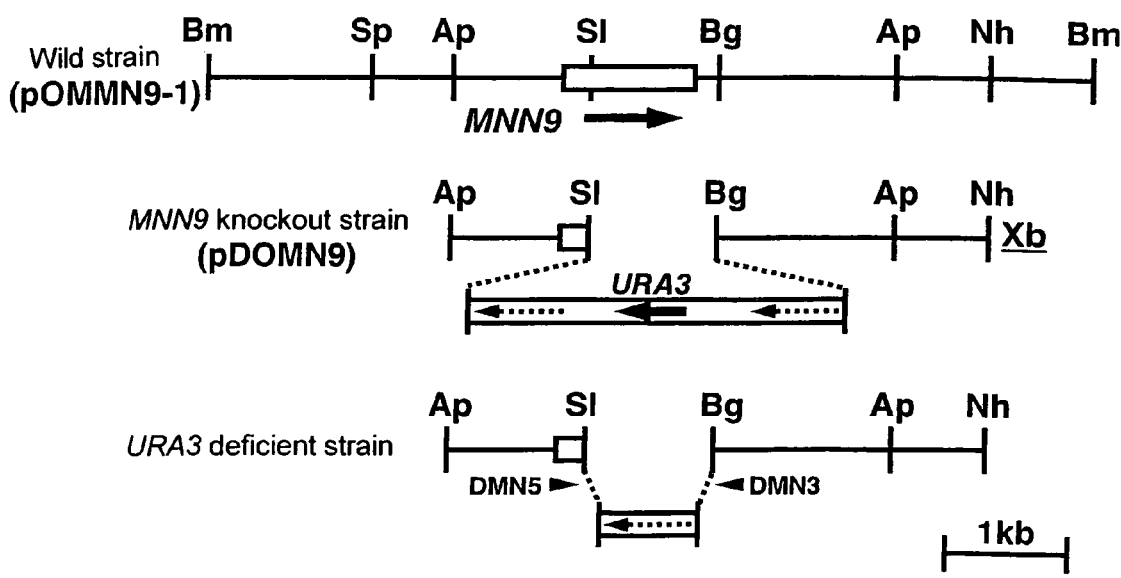
FIG. 17 shows the restriction maps of plasmids pOMMN9-1 and pDOMN9, and the structures of the MNN9 loci of a wild strain of *Ogataea minuta*, an MNN9 gene knockout mutant disrupted by the plasmid pDOMN9 and a URA3 gene deficient mutant, along with positions of PCR primers.

As shown in FIG. 17, plasmid pDOMN9 was prepared by replacing the approximately 1-kb SaI-BglII region of the MNN9 structural gene by the URA3 gene. To obtain a uracil auxotrophic mutant again from MNN9 knockout mutants, the URA3 gene having repetitive structures before and after the structural gene was used as a marker. The 1.2-kb ApaI-SalI fragment isolated from the plasmid pOMMN9-1 having the MNN9 gene region described in Example 18 was inserted into the ApaI-SalI of the pBluescript II SK–. The 2.2-kb NheI-BglII fragments isolated from the plasmid pOMMN9-1 and the 3.3 kb BglII-HindIII fragment isolated from the pROMU1 described in Example (8-1) were inserted into the XbaI-HindIII of the obtained plasmid. The resultant plasmid was named pDOMN9 (FIG. 17).

(19-2) Transformation

The pDOMN9 obtained in Example (19-1) was cleaved with ApaI and transformed into the *Ogataea minuta* TK8 strain (och1Δ pep4Δ prb1Δ ura3Δ), the *Ogataea minuta* TK9 strain (och1Δ pep4Δ prb1Δ ura3Δ ade1Δ) obtained in Example (15-2) and the *Ogataea minuta* TK10 strain (och1Δ ktr1Δ pep4Δ prb1Δ ura3Δ), the *Ogataea minuta* TK11 strain (och1Δ ktr1Δ pep4Δ prb1Δ ura3Δ ade1Δ) obtained in Example (17-2), by electric pulse method.

The MNN9 knockout mutants were screened by subjecting the chromosomal DNAs of the obtained transformants to Southern analysis. Specifically, the chromosomal DNAs of the host strain and the transformants were cleaved with ApaI and BglII and subjected to Southern analysis using the 1.2-kb ApaI-SalI fragment isolated from the pOMMN9-1 (FIG. 17) as a probe. As a result, a band was detected at 2.2 kb in the host strain, while a band at 5.5 kb in the knockout mutants. After culturing the knockout mutants on the YPD medium until stationary phase, a strain resistant to 5-fluoroorotic acid (5-FOA) was obtained. PCR by primers DMN5; 5'-AGAT-GAGGTGATTCCACGTAATTTGCCAGC-3' (SEQ ID NO:71) and DMN3; 5'-TTTTGATTGTCATCTATTTCG-CACACCCTG-3' (SEQ ID NO:72) was performed using the chromosomal DNA of the 5-FOA resistant strain as a template ((94° C. for 30 seconds, 60° C. for 1 minute and 72° C. for 1 minute)×25 cycles). As a result, a 1 kb amplified DNA fragment was detected in the strain from which the URA3 gene was deleted. The och1Δ mnn9Δ pep4Δ prb1Δ ura3Δ strain obtained was named *Ogataea minuta* TK12 strain, the och1Δ mnn9Δ pep4Δ prb1Δ ura3Δ ade1Δ strain *Ogataea minuta* TK13 strain, the och1Δ ktr1Δ mnn9Δ pep4Δ prb1Δ ura3Δ strain was named *Ogataea minuta* TK14 strain, and the och1Δ ktr1Δ mnn9Δ pep4Δ prb1Δ ura3Δ ade1Δ strain was named *Ogataea minuta* TK15 strain.

The sensitivity of the *Ogataea minuta* TK14 and *Ogataea minuta* TK15 strains to hygromycin B was examined. *Ogataea minuta* IFO 10746, a wild strain, yielded colonies on a plate containing 50 μg/ml hygromycin B as described in Example (17-2), but neither *Ogataea minuta* TK12 nor *Ogataea minuta* TK13 strain yielded a colony even on a plate containing 20 μg/ml hygromycin B. Thus, it was presumed that these *Ogataea minuta* mnn9Δ strains had short sugar chains.

Example 20

Cloning of Alcohol Oxidase (AOX1) Gene of *Ogataea minuta*

The AOX1 gene was obtained from *Ogataea minuta* IFO 10746 and its nucleotide sequence was determined.

(20-1) Preparation of Probe

Oligonucleotides having nucleotide sequences corresponding to the following amino acid sequences conserved in alcohol oxidase from *Pichia pastoris* (GenBank accession number; U96967, U96968) and *Candida boidinii* (GenBank accession number; Q00922):

```
GGGSSINFMMYT;      (SEQ ID NO: 73)
and

DMWPMVWAYK        (SEQ ID NO: 74)
``` were synthesized as follows.

```
                             (SEQ ID NO: 75)
PAX5;   5'-GGNGGNGGNWSNWSNATHAAYTTYATGATGTAYAC-3'

(SEQ ID NO: 76)
PAX3;   5'-TTRTANGCCCANACCATNGGCCACATRTC-3'
```

The primer PAX5 has a sequence complementary to the nucleotide sequence corresponding to the amino acid sequence GGGSSINFMMYT, and the primer PAX3 has a sequence complementary to the nucleotide sequence corresponding to the amino acid sequence DMWPMVWAYK.

PCR by primers PAX5 and PAX3 was performed using the chromosomal DNA of *Ogataea minuta* IFO 10746 as a template ((94° C. for 30 seconds, 50° C. for 1 minute and 72° C. for 1 minute)×25 cycles). The amplified DNA fragment of approximately 1.1 kb was recovered and cloned using TOPO TA Cloning Kit. Plasmid DNA was isolated from the obtained clone and sequenced. For a DNA insert of the plasmid, a clone was selected which had a nucleotide sequence encoding an amino acid sequence highly homologous to the amino acid sequences for alcohol oxidase genes from *Pichia pastoris* and *Candida boidinii*. The 1.1-kb DNA insert was recovered after EcoRI cleavage of the plasmid and agarose gel electrophoresis.

(20-2) Preparation of Library and Screening

The chromosomal DNA of *Ogataea minuta* IFO 10746 was cleaved with different restriction enzymes, and subjected to Southern analysis using the DNA fragment obtained in Example (20-1) as a probe by the method described in Example (2-2). The results suggested that there existed AOX1 gene in the HindIII fragment of approximately 8 kb. Then, to clone the DNA fragment, a library was prepared. The chromosomal DNA of *Ogataea minuta* was cleaved with HindIII and subjected to agarose gel electrophoresis, and then the approximately 6-kb DNA fragment was recovered from the gel. The DNA fragment was ligated with HindIII-cleaved pUC 118 and then transformed into *Escherichia coli* strain DH5 α to prepare a library.

About 6,000 clones were screened by colony hybridization using the above described DNA fragment as a probe. A clone bearing plasmid pOMAX1 was selected from the 6 positive clones obtained.

(20-3) Sequencing of Nucleotide Sequence

The nucleotide sequence of the HindIII-SmaI region of the plasmid pOMAX1 (FIG. 18) was determined by deletion mutant and primer walking method to obtain a nucleotide sequence represented by SEQ ID NO:77.

In the nucleotide sequence of SEQ ID NO:77 there existed an open reading frame of 1,992 bp, starting at position 2,349 and ends at position 4,340. The homology studies between the amino acid sequence (SEQ ID NO:78) deduced from the open reading frame and the alcohol oxidase from Pichia pastoris or Candida boidinii showed that 72% or 74% of amino acids were respectively identical between them.

Example 21

Construction of Heterologous Gene Expression Plasmid Using AOX1 Gene Promoter and Terminator (21-1) Construction of Expression Cassette Using AOX1 Gene Promoter and Terminator An expression cassette was constructed for transferring foreign genes between the *Ogataea minuta* AOX1 gene promoter (SEQ ID NO:79) and terminator (SEQ ID NO:80). To transfer XbaI, SmaI and BamHI sites between the AOX1 gene promoter and terminator, the following primers were synthesized:

```
                                         (SEQ ID NO: 81)
OAP5;
5'-CTGCAGCCCCTTCTGTTTTTCTTTTGACGG-3'

(SEQ ID NO: 82)
OAP3;
5'-
CCCCCGGATCCAGGAACCCGGGAACAGAATCTAGATTTTTTCGTAAGT
CGTAAGTCGTAACAGAACACAAGAGTCTTTGAACAAGTTGAG-3'

(SEQ ID NO: 83)
OAT5;
5'-
CCCCCCCGGATCCGAGACGGTGCCCGACTCTTGTTCAATTCTTTTGG-3'

(SEQ ID NO: 84)
OAT3;
5'-CCCATAATGGTACCGTTAGTGGTACGGGCAGTC-3'
```

Figure 18A:
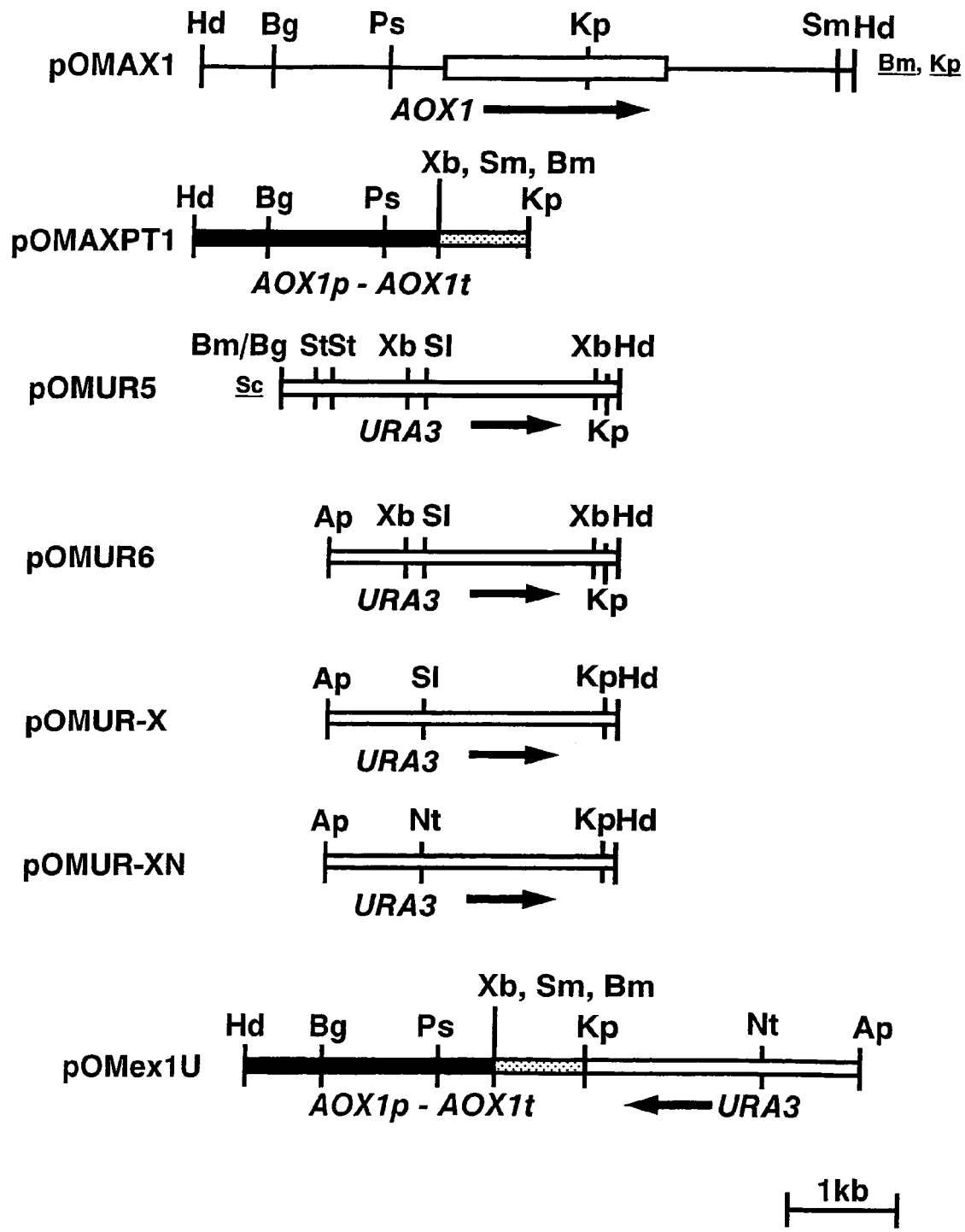
FIGS. 18A and 18B show the restriction maps of plasmids pOMAX1, pOMAXPT1, pOMUR5, pOMUR6, pOMUR-X, pOMUR-XN, pOMex1U, pOMex2U, pOMex3G, pOMex4A, pOMex5H, pOMexGP1U and pOMexGP4A. The restriction enzyme sites of the vector are underlined.
Figure 18B:
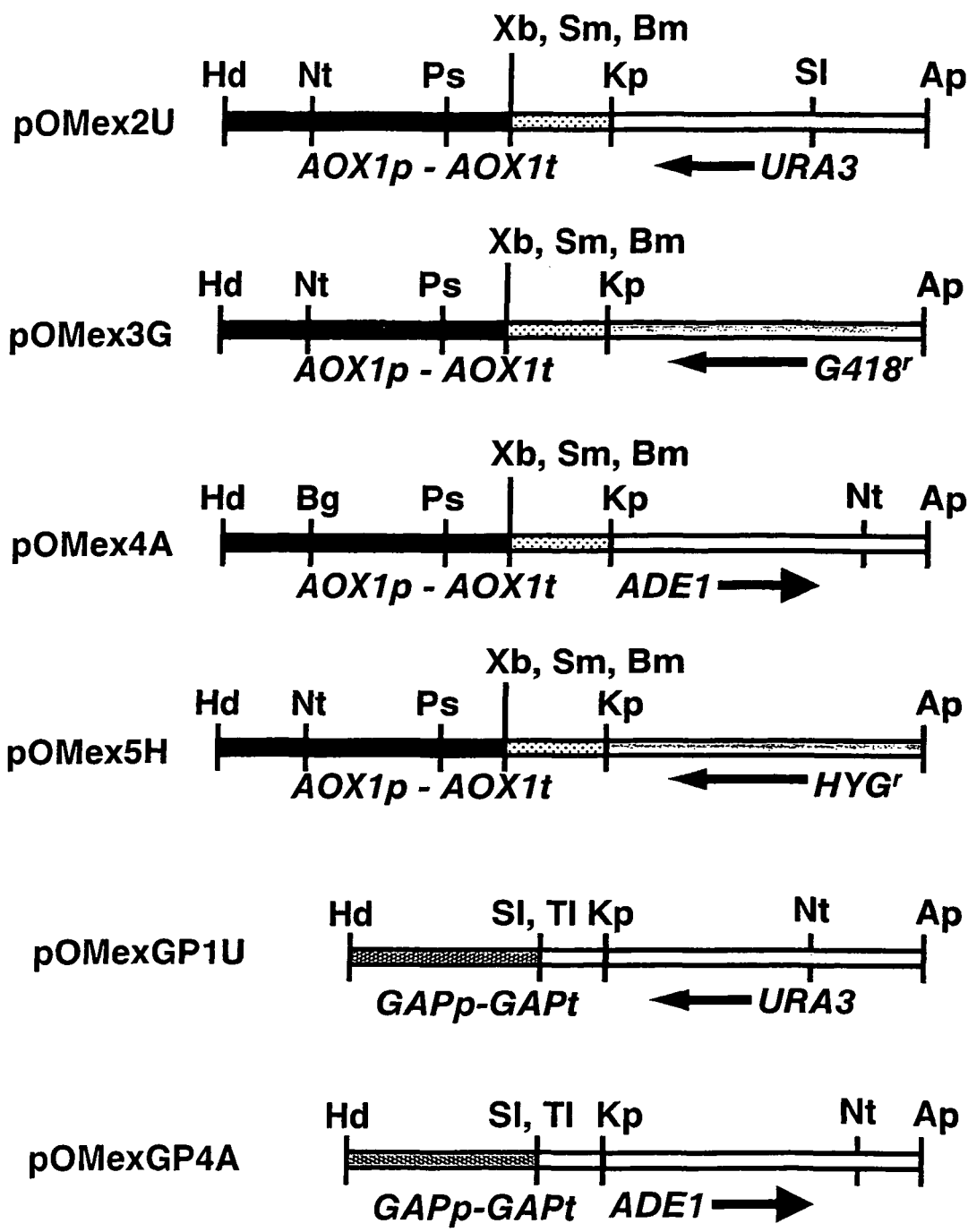

PCR by primers OAP5 and OAP3 ((94° C. for 30 seconds, 55° C. for 1 minute and 72° C. for 1 minute)×20 cycles), and PCR by primers OAT5 and OAT3 ((94° C. for 30 seconds, 55° C. for 1 minute and 72° C. for 1 minute)×20 cycles) were performed using the pOMAX1 shown in FIG. 18 as a template. The amplified DNA fragments of 0.5 kb and 0.8 kb were recovered and cloned using TOPO TA Cloning Kit. The nucleotide sequences of DNA inserts were determined, and then clones having correct nucleotide sequences were selected. The DNA inserts of 0.5 kb and 0.8 kb were isolated as PstI-BamHII fragment and BamHI-KpnI fragment, respectively. The above described 0.5-kb PstI-BamHII fragment was inserted into the PstI-BamHII of the pOMAX1. Then, the 0.8-kb BamHI-KpnI fragment was inserted into the BamHI-KpnI of the obtained plasmid. The resultant plasmid was named pOMAXPT1 (FIG. 18).

The pOMAXPT1 had an expression cassette controlled by the AOX1 promoter and terminator that allowed foreign genes to be transferred at the XbaI, SmaI and BamHI sites.

(21-2) Construction of Heterologous Gene Expression Plasmid Using AOX1 Gene Promoter and Terminator and Using URA3 Gene as a Selectable Marker The 3.1-kb BglIH-HindIII fragment containing the *Ogataea minuta* URA3 gene and isolated from the pOMUR1 described in Example (5-2) was inserted into the BamHI-HindIII of pUC19. The obtained plasmid was named pOMUR5 (FIG. 18). The pOMUR5 was cleaved with StyI and SacI and blunt-ended, and ApaI linkers were then inserted thereinto. The obtained plasmid was named pOMUR6. The pOMUR6 was cleaved with XbaI and blunt-ended, and ligated. The obtained plasmid was named pOMUR-X. The pOMUR-X was cleaved with SalI and blunt-ended, and a NotI linker was inserted thereinto.

The resultant plasmid was named pOMUR-XN. The 3.1-kb HindIII-KpnI fragment containing the expression cassette controlled by the *Ogataea minuta* AOX1 promoter and terminator which was isolated from the pOMAXPT1 as described in Example (21-1), was inserted into the HindIII-KpnI of the pOMUR-XN. The obtained plasmid was named pOMex1U (FIG. 18).

The pOMex1U was cleaved with BglII and blunt-ended, and a NotI linker was inserted thereinto. The obtained plasmid was named pOMex1U-NO (FIG. 18). The 3.1-kb HindIII-KpnI fragment containing the expression controlled by the *Ogataea minuta* AOX1 gene promoter and terminator which was isolated from the pOMex1U-NO, was inserted into the HindIII-KpnI of the pOMUR-X. The resultant plasmid was named pOMex2U (FIG. 18).

(21-3) Construction of Heterologous Gene Expression Plasmid Using AOX1 Gene Promoter and Terminator and Using G418 Resistant Gene as a Selectable Marker The pOMKmR1, which comprised the G418 resistant gene expression cassette controlled by the GAP gene promoter and terminator described in Example 4, was cleaved with PstI and blunt-ended, and an ApaI linker was inserted thereinto. The G418 resistant gene expression cassette was isolated, as a 2.3-kb ApaI-KpnI fragment, from the obtained plasmid and inserted into the ApaI-KpnI of the POMex1U-NO described in Example (21-2). The resultant plasmid was named pOMex3G (FIG. 18).

(21-4) Construction of Heterologous Gene Expression Plasmid Using AOX1 Gene Promoter and Terminator, and Using ADE1 Gene as a Selectable Marker A plasmid was prepared by cleaving with SmaI the pOMAD1, which contained the ADE1 gene described in Example 7, transferring an ApaI linker, cleaving with EcoRV, transferring a KpnI linker, cleaving with BglII, blunt-ending, and transferring a NotI linker. The ADE1 gene expression cassette was isolated, as a 3.1-kb ApaI-KpnI fragment, from the obtained plasmid, and inserted into the ApaI-KpnI containing the expression cassette controlled by the *Ogataea minuta* AOX1 gene promoter and terminator which was obtained by ApaI-KpnI from the pOMex1U. The resultant plasmid was named pOMex4A (FIG. 18).

(21-5) Construction of Heterologous Gene Expression Plasmid Using AOX1 Gene Promoter and Terminator and Using Hygromycin B Resistant Gene as a Selectable Marker To perform transformation by the selection of antibiotic hygromycin B resistance, a plasmid containing the hygromycin B resistant gene (hygromycin B phosphotransferase gene) expression cassette was constructed.

To isolate the hygromycin B resistant gene, the following primers were synthesized:

HGP5;
5'-GTCGACATGAAAAAGCCTGAACTCACCGC-3'; (SEQ ID NO: 85)
and

HGP3;
5'-ACTAGTCTATTCCTTTGCCCTCGGACG-3'. (SEQ ID NO: 86)

PCR by primers HGP5 and HGP3 was performed using the plasmid pGARH containing the hygromycin B resistant gene (Applied Environ. Microbiol., Vol. 64 (1998) p2676) as a template ((94° C. for 30 seconds, 50° C. for 1 minute and 72° C. for 1 minute)×20 cycles). The 1.0 kb amplified DNA fragment was recovered and cloned using TOPO TA Cloning Kit.

The nucleotide sequence of the DNA insert was determined, and a clone having the correct nucleotide sequence was selected. The 1.0 kb DNA insert was isolated as a SalII-EcOT22II fragment and inserted into the SalI-EcoT22I of the pOMGP4 constructed in Example 3. The obtained plasmid was named pOMHGR1. The obtained plasmid was cleaved with HindIII and blunt-ended, and an ApaI linker was inserted thereinto. The hygromycin B resistant gene expression cassette was isolated, as a 3.0-kb ApaI-KpnI fragment, from the obtained plasmid, and then inserted into the ApaI-KpnI of the pOMex1U-NO described in Example 21-2. The resultant plasmid was named pOMex5H (FIG. 18).

Example 22

Construction of Heterologous Gene Expression Plasmid Using GAP Gene Promoter and Terminator, and Using URA3 Gene as a Selectable Maker The gene expression cassette using the GAP gene promoter and terminator, as described in Example 3, was isolated as a 2.0-kb HindIII-KpnI, and then inserted into the HindIII-KpnI of each of the pOMUR-XN described in Example (21-2) and the pOMex4A described in Example (21-4) (where pOMex4A was a fragment comprising pUC19-ADE1). The obtained plasmids were named pOMexGP1U and pOMexGP4A, respectively (FIG. 18).

Example 23

Construction of *Aspergillus saitoi*-Derived α-1,2-Mannosidase Expression Plasmid Ysing AOX1 Gene Promoter and Terminator Example 11 suggested that expression of α-1,2-mannosidase in the *Ogataea minuta* Δoch1 strain enabled the preparation of a Man5 producing yeast. So, *Ogataea minuta* Δoch1 strain in which α-1,2-mannosidase was expressed was prepared. The *Aspergillus saitoi*-derived α-1,2-mannosidase gene, which comprised a signal sequence of asperginopepsin I (apnS) at the amino terminus and a yeast endoplasmic reticulum (ER) retention signal (HDEL) (SEQ ID NO: 121) at the carboxyl terminus (J. Biol. Chem., 273 (1998) 26298), was used for expression. PCR by the primers:

(SEQ ID NO: 87)
5'-GGGGGGTCGACATGGTGGTCTTCAGCAAAACCGCTGCCC-3';
and (SEQ ID NO: 88)
5'-GGGGGGCGGCCGCGTGATGTTGAGGTTGTTGTACGGAACCCCC-3' was performed using the plasmid pGAMH1 comprising the above described gene as a template ((94° C. for 30 seconds, 50° C. for 1 minute and 72° C. for 30 seconds) ×20 cycles). The approximately 0.5-kb DNA fragment 5'-upstream of the amplified α-1,2-mannosidase gene was recovered, cleaved with SalI and NotI, and inserted into the SalI-NotI of the pBluescript II SK-. The nucleotide sequence of the DNA insert was determined and a clone comprising the correct nucleotide sequence was selected. The 1.2-kb BglII-NotI fragment downstream of the BglII site in the α-1,2-mannosidase gene isolated from the pGAMH1 was inserted into the BglII-NotI of the obtained plasmid. This plasmid was named paMSN. The paMSN was cleaved with SalI and blunt-ended, and an XbaI linker was inserted thereinto. This plasmid was named paMXN. Separately, the paMSN was cleaved with NotI and blunt-ended, and a BamHI linker was inserted thereinto. The resultant plasmid was named paMSB. The 0.4-kb XbaI-BglII fragment upstream of the α-1,2-mannosidase gene isolated after cleaving the paMXN with XbaI-ApaI, and the 1.1-kb ApaI-BamHI fragment downstream of the α-1,2-mannosidase gene isolated after cleaving the paMSB with ApaI-BamHI, were inserted into the XbaI-BamHII of the pOMex1U described in Example (21-2) and of the pOMex3G described in Example (21-3), respectively, by three points ligation. The obtained plasmids were named pOMaM1U and pOMaM3G, respectively.

Example 24

Preparation of *Aspergillus saitoi*-derived α-1,2-mannosidase Gene Expressing *Ogataea minuta* Δoch1 Strain and Sugar Chain Analysis of Same The pOMaM1U obtained in Example 23 was cleaved with NotI, and the *Ogataea minuta* TK3-A strain (och1Δ ura3Δ) obtained in Example (10-2) was transformed with it. The intracellular α-1,2-mannosidase activity of the obtained transformant was measured. The transformants cultured in the BYPM medium (0.67% yeast nitrogen base, 1% yeast extract, 2% polypeptone, 100 mM potassium phosphate buffer pH 6.0, 0.5% methanol) were harvested and suspended in 0.1 M sodium acetate buffer pH 5.0 containing 1% Triton X100 and 1 mM PMSF, then the cells were disrupted with glass beads to obtain a cell extract. The extract was appropriately diluted, 20 pmol of Man6b sugar chain (TAKARA SHUZO CO., LTD., Japan) was added, and the mixture was incubated for reaction at 37° C. for 10-60 minutes. After the incubation, the mixture was boiled to inactivate the enzyme and subjected to HPLC to analyze the produced Man5 sugar chain. The HPLC conditions were as follows.

Column: TSK-Gel ODS 80TM (6×150 mm, TOSOH CORPORATION, Japan)
Column temperature: 50° C.
Flow rate: 1.2 ml
Elution conditions: A: 100 mM ammonium acetate pH 6.0
B: 100 mM ammonium acetate pH 6.0+0.15% butanol
Linear gradient of 0 minute A=70% and 12 minutes A=0%

A yeast strain having the highest α-1,2-mannosidase activity was selected and named *Ogataea minuta* TK3-A-MU1 strain. The yeast strain was cultured again in the BYPM medium, and the structure of the sugar chain of cell surface mannan proteins was analyzed. The preparation of PA-oligosaccharides was carried out in accordance with the method described in Example 1. And HPLC analysis was performed by the method described in Example 11.

Figure 19:
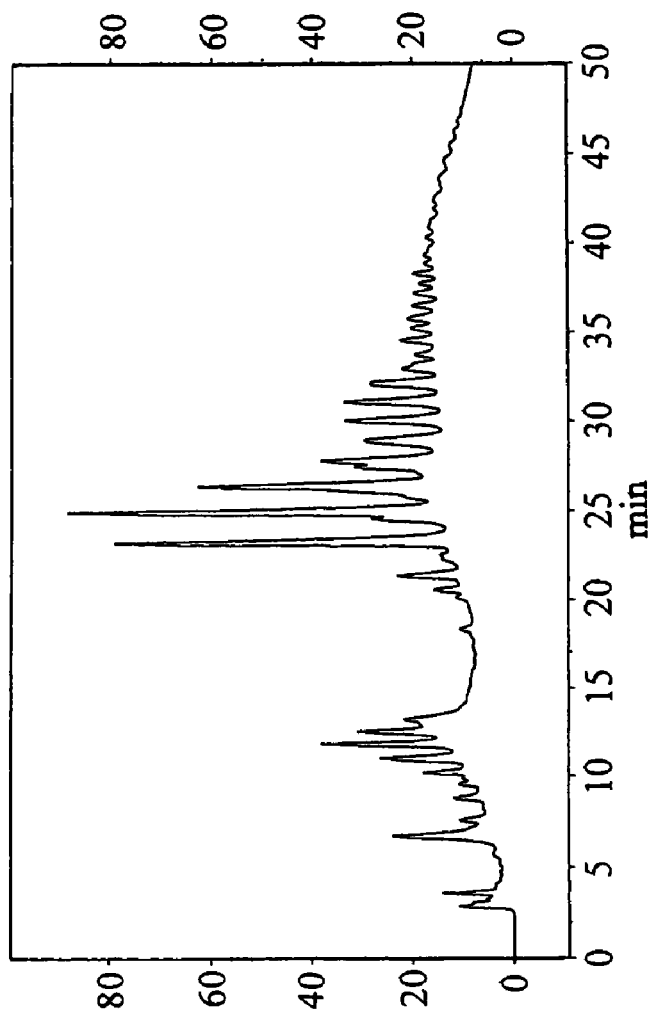
FIG. 19 shows the structure analysis by amide and reverse phase columns for sugar chains of the mannan glycoprotein of *Ogataea minuta* strain TK3-A-MU1, which is an och1Δ strain expressing an *Aspergillus saitoi*-derived α-1,2-mannosidase gene.
Figure 19:
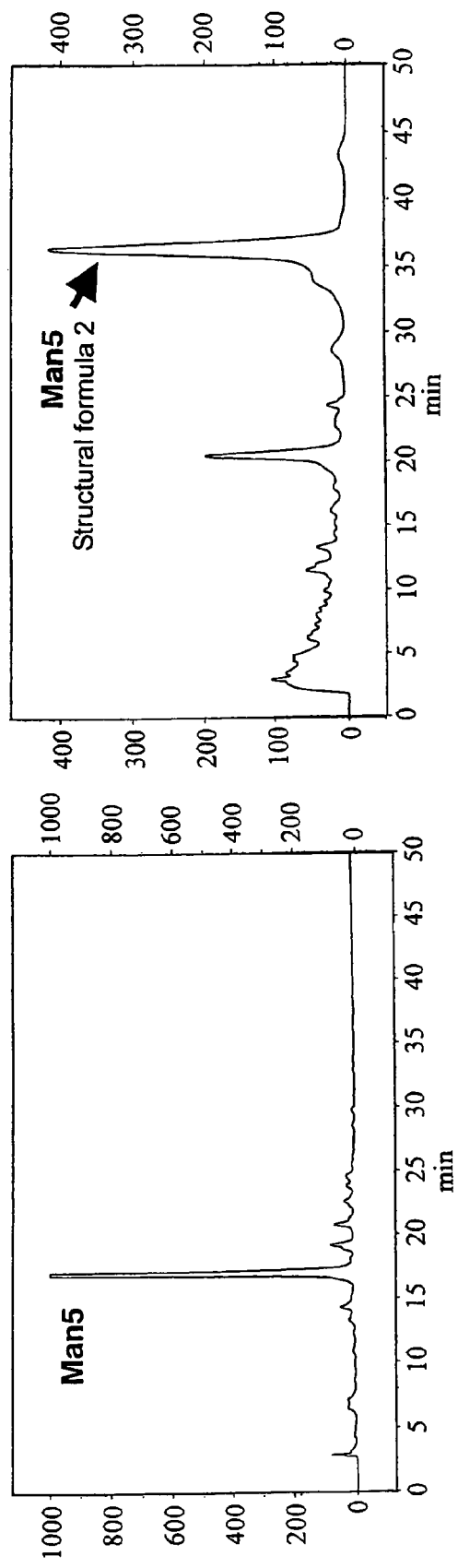

The results are shown in FIG. 19. The size analysis by normal phase column revealed that the *Ogataea minuta* TK3-A-MU1 strain mainly produced Man5GlcNAc2. The structure analysis by reverse phase column revealed that the Man5GlcNAc2 was the sugar chain of the following structural formula 2:

Structural Formula 2

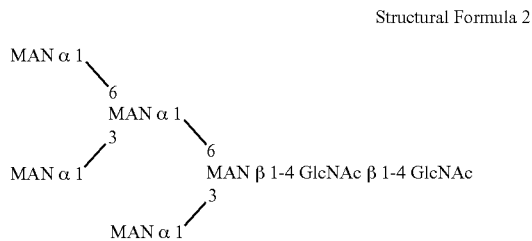

which sugar chain was consistent with the human-type, high mannose-type sugar chain, and precursor of hybrid type or complex type sugar chains.

Example 25

Construction of *Saccharomyces cerevisiae*-derived Invertase Expression Plasmid Using AOX1 Gene Promoter and Terminator Invertase (SUC2) gene of *Saccharomyces cerevisiae* (GenBank accession number; V01311) was obtained by PCR. PCR by the primers:

```
                                          (SE ID NO: 89)
5'-GGGGACTAGTATGCTTTTGCAAGCTTTCCTTTTCCTTTTG-3';
and
                                          (SEQ ID NO: 90)
5'-CCCCAGATCTTATTTTACTTCCCTTACTTGGAACTTGTC-3'
``` was performed using the chromosomal DNA of *Saccharomyces cerevisiae* S288C strain as a template ((94° C. for 30 seconds, 50° C. for 1 minute and 72° C. for 1.5 minute)×20 cycles). The amplified DNA fragment of approximately 1.4 kb was recovered, cleaved with SpeI and BglII, and inserted into the XbaI-BamHI of the pOMex1U described in Example (21-2) and of the pOMex3G described in Example (21-3). The obtained plasmids were named pOMIV1U and pOMIV3G, respectively.

Example 26

Transferring of *Saccharomyces cerevisiae*-derived Invertase Gene Into *Aspergillus saitoi*-derived α-1,2-mannosidase Gene Expressing *Ogataea minuta* OCH1 Knockout Mutant and Expression of Same The pOMIV3G obtained in Example 25 was cleaved with NotI and transferred into the *Ogataea minuta* TK3-A-MU1 strain described in Example 24. The transformant was cultured in the BYPM medium (0.67% yeast nitrogen base, 1% yeast extract, 2% polypeptone, 100 mM potassium phosphate buffer pH 6.0, 0.5% methanol). The culture was centrifuged and the resultant supernatant was assayed for invertase activity by the following procedures. Specifically, 2 µl of appropriately diluted culture supernatant and 200 µl of 100 mM sodium acetate buffer (pH 5.0) containing 2% sucrose were mixed together and incubated at 37° C. for 10-30 minutes, and 500 µl of Glucose-Test Wako (Wako Pure Chemical Industries, Ltd., Japan) was added to 2 µl of the reaction mixture to develop color. An absorbance based on free glucose generated by invertase was measured at 505 nm. The most productive yeast strain *Ogataea minuta* TK3-A-MU-IVG1 strain produced about 600 mg invertase/l medium, and the invertase was most part of proteins in the culture supernatant.

Example 27

Structure Analysis of Sugar Chain of *Saccharomyces cerevisiae*-derived Invertase Secreted by the Strain Prepared in Example 26

Figure 20:
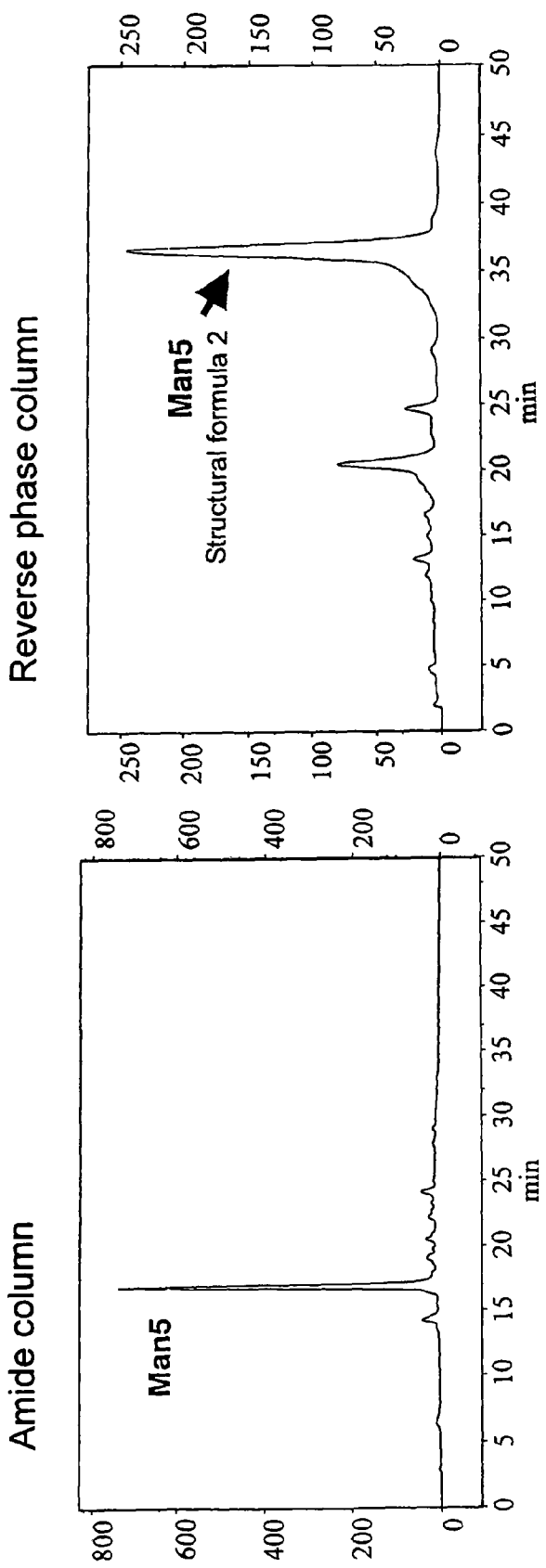
FIG. 20 shows the structure analysis by amide and reverse phase columns of the *Saccharomyces cerevisiae*-derived invertase produced by *Ogataea minuta* strain TK3-A-MU-IVG1, which is an *Ogataea minuta* OCH1 gene knockout mutant expressing *Aspergillus saitoi*-derived α-1,2-mannosidase gene.

The culture supernatant of the *Ogataea minuta* TK3-A-MU-IVG1 strain obtained in Example 26 was concentrated by ultrafiltration using Amicon YM76 membrane (Amicon), desalted, and subjected to an anion exchange column chromatography (Q-Sepharose FF, Amersham Pharmacia Biotech) to purify invertase fractions. The fractions were freeze-dried and PA-N-linked sugar chain was prepared by the method described in Example 1. The analysis by HPLC was performed by the method described in Example 11. The results are shown in FIG. 20. The results of the size analysis by amide column revealed that 90% or more sugar chains of the invertase was composed of Man5GlcNAc2. The structure analysis by reverse phase column showed that the Man5GlcNAc2 was the sugar chain represented by the structural formula 2 described in Example 24:

Structural Formula 2

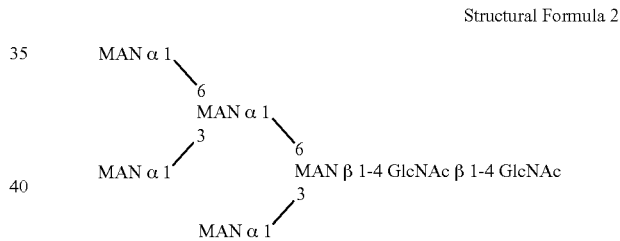

This sugar chain was consistent with the Man5 type, high mannose type sugar chain, which is a precursor of hybrid type or complex type sugar chain.

Example 28

Preparation of Human Antibody Gene-transferred *Ogataea minuta* OCH1 Knockout Mutant, Transfer and Expression of *Aspergillus saitoi*-derived α-1,2-mannosidase Gene in the Mutant, and Production of Human Antibody Using Same Anti-human G-CSF antibody gene was transferred into the *Ogataea minuta* TK9 strain (och1Δ pep4Δ prb1Δ ura3Δ ade1Δ) obtained in Example (15-2).

Anti-human G-CSF antibody producing hybridoma was obtained by producing a mouse producing anti-human G-CSF antibodies using human G-CSF as an antigen in accordance with the method by Tomiduka et al. (Proc. Natl. Acad. Sci. U.S.A. 97(2), 722-7 (2000)), removing the spleen from the mouse by conventional procedure (Muramatsu et al., Jikken Seibutsugaku Koza, Vol. 14, pp. 348-364 ), and fusing the B cells with a mouse myeloma. The antibody gene was obtained from the hybridoma by the method described by Welschof, M et al. (J. Immunol. Methods. 179 (2), 203 -14 (1995)).

XbaI linker and BamHI linker were added at the N-terminus and the C-terminus, respectively, of each of the anti-G-CSF light chain gene (SEQ ID NO:91; the coded amino acid sequence, SEQ ID NO:92) and anti-G-CSF heavy chain gene (SEQ ID NO:93, the coded amino acid sequence, SEQ ID NO:94). Subsequently, the light chain gene was transferred at the XbaI-BamHI site of the pOMex4A described in Example (21-4) while the heavy chain gene at the XbaI-BamHI site of the pOMex3G described in Example (21-3), respectively. Each of the constructed expression vectors was cleaved with NotI, and the *Ogataea minuta* TK9 strain was in turn transformed. The obtained transformants were cultured in the BYPMG medium (0.67% yeast nitrogen base, 1% yeast extract, 2% polypeptone, 100 mM potassium phosphate buffer pH 6.0, 0.1% methanol, 0.2% glycerol) at 20° C. for 72 hours, and then centrifuged. The culture supernatant was subjected to Western analysis using a horseradish peroxidase labeled anti-human IgG sheep antibody (Amersham Pharmacia Biotech). First, 100 μl of the culture supernatant was concentrated through Microcon YM30 membrane and subjected to SDS-PAGE. Then, the electrophoresed proteins were blotted on PVDF membrane (Immobilon, Millipore), which membrane was then blocked over 1 hour using Block Ace (Dainippon Pharmaceutical Co., Ltd., Japan). Proteins on the membrane were incubated for 1 hour in TBS solution (Tris buffer containing 0.15 M NaCl) containing the horseradish peroxidase labeled anti-human IgG sheep antibody (1000:1 dilution), and unbound antibodies were washed out with TBS containing 0.04% Tween 20. The detection of signal was carried out using Super Signal WestDura (Pierce). Thus, the transformant producing the antibody in the culture supernatant was selected. The *Ogataea minuta* TK9-derived antibody producing strain was named *Ogataea minuta* TK9-IgB1.

Then, the *Aspergillus saitoi*-derived α-1,2-mannosidase gene was transferred into the Ogataea minuta TK9-IgB1 strain. After transformation, α-1,2-mannosidase expressing strain was selected from the obtained transformants by the method described in Example 24 using the plasmid pOMaM1U prepared in Example 23. The resultant strain was named Ogataea minuta TK9-IgB-aM. This strain was cultured in the BYPMG medium at 20° C. for 72 hours and centrifuged. The culture supernatant obtained by the centrifugation was subjected to Western analysis.

Figure 21:
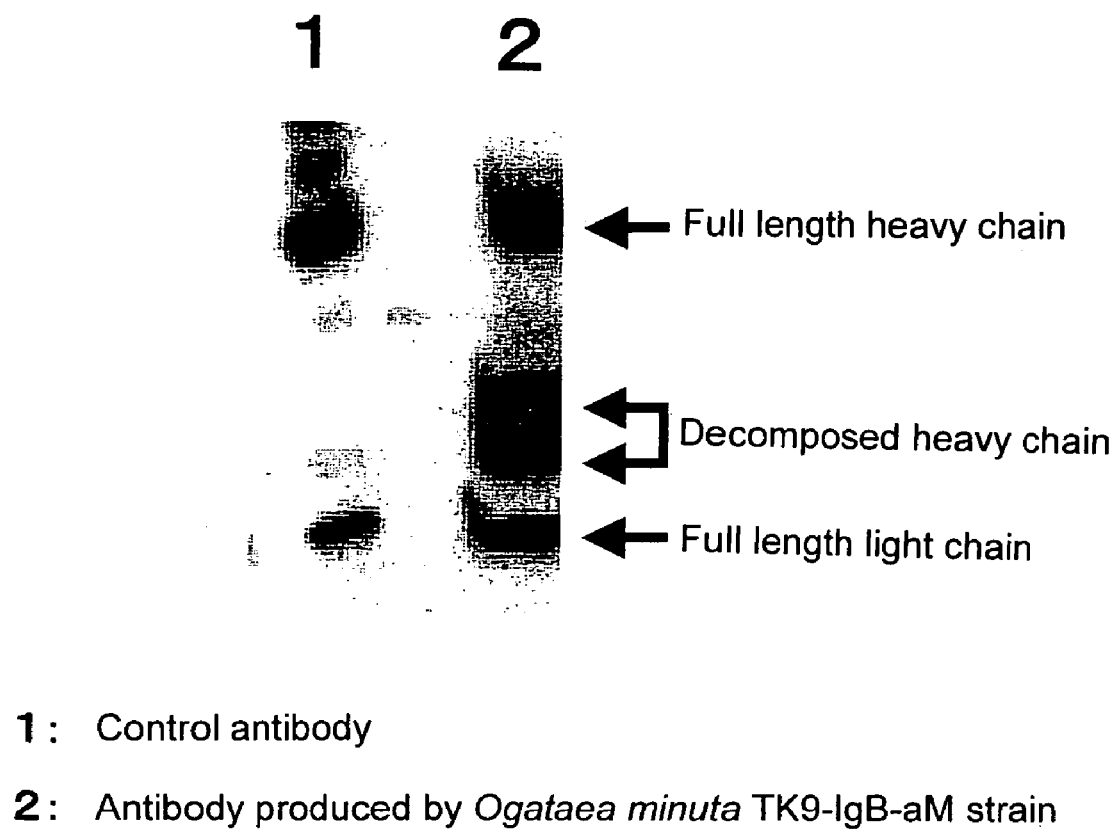
FIG. 21 shows the Western analysis of the antibody produced by using *Ogataea minuta* strain TK9-IgB-aM.

The results are shown in FIG. 21. The results revealed that the *Ogataea minuta* TK9-IgB-aM strain produced both antibody heavy chains and light chains, although part of the antibody heavy chains was degraded.

Figure 22:
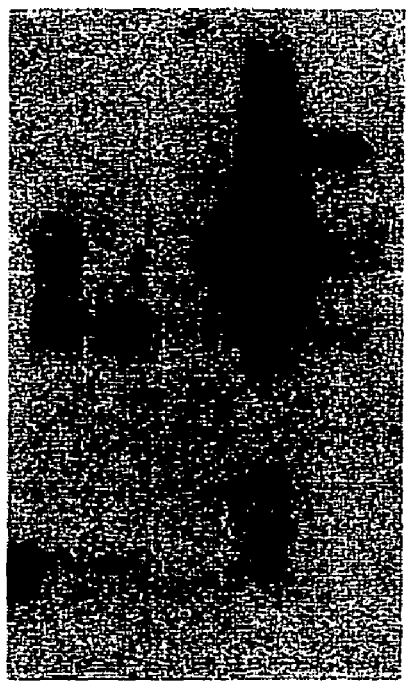
FIG. 22 shows the purification of the antibody produced by using *Ogataea minuta* strain TK9-IgB-aM.
Figure 23:
FIG. 23 shows the binding activity to G-CSF of the antibody produced by using *Ogataea minuta* strain TK9-IgB-aM.

Further, the culture supernatant of the *Ogataea minuta* TK9-IgB-aM strain was concentrated by ultrafiltration using Amicon YM76 membrane (Amicon), desalted, and subjected to Protein A column chromatography (Hi-Trap ProteinA HP, Amersham Pharmacia Biotech) to purify the antibody fractions through the elution with glycine-HCl, pH 3.0 (FIG. 22). To detect the binding of the antibody to G-CSF as the antigen, Western analysis was performed. The analysis was done in accordance with the above described procedures using the purified antibody as a primary antibody and the horseradish peroxidase labeled anti-human IgG sheep antibody as a secondary antibody. The results are shown in FIG. 23. The results revealed that the antibody produced by the *Ogataea minuta* TK9-IgB1 strain bound to G-CSF as the antigen.

Example 29

Structure Analysis of Sugar Chains of Human Antibody Produced by the Strains Prepared in Example 28

Figure 24:
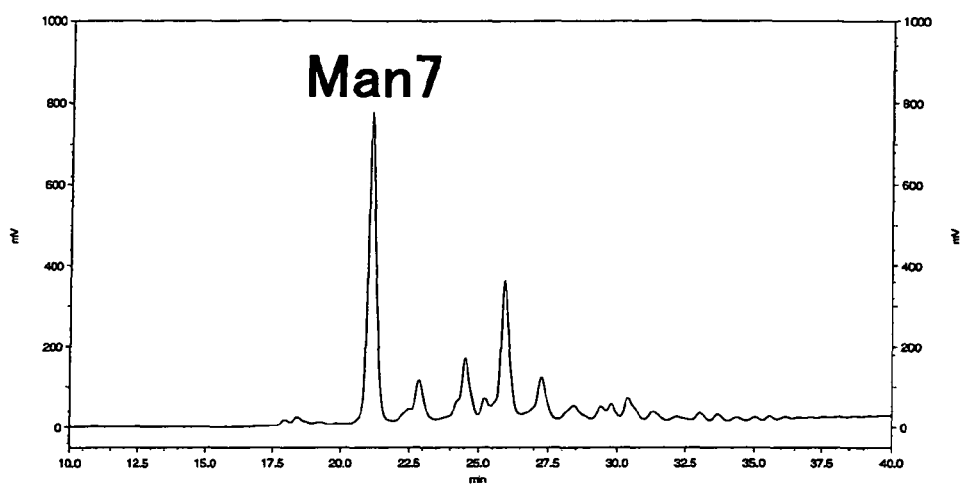
FIG. 24 shows the analysis of the sugar chains of antibodies produced by using *Ogataea minuta* strain TK9-IgB and *Ogataea minuta* strain TK9-IgB-aM.
Figure 24:
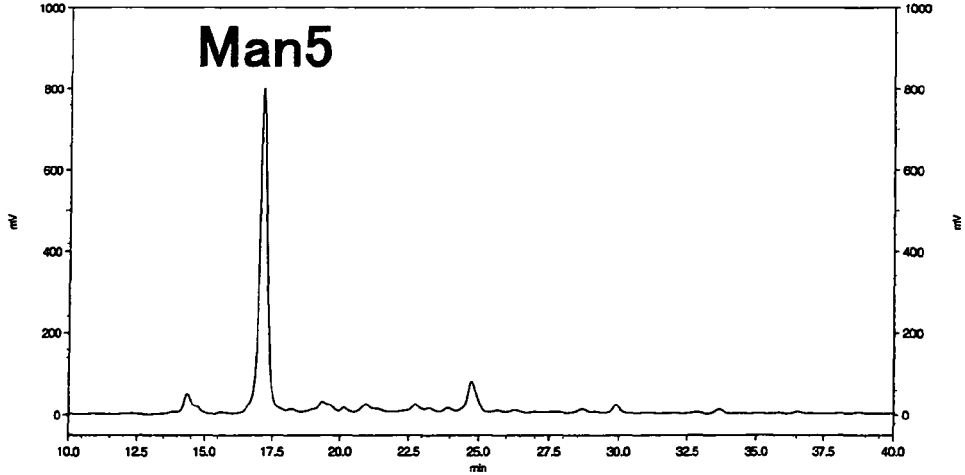

The purified antibodies produced using the *Ogataea minuta* TK9-IgB-aM strain and the *Ogataea minuta* TK9-IgB strain as shown in Example 28 were dialyzed and freeze-dried. PA-N-linked sugar chains were prepared by the method described in Example 11 and subjected to size analysis by normal phase column. The results are shown in FIG. 24. The results revealed that the sugar chain of the antibody produced by the Ogataea minuta TK9-IgB strain was composed mainly of $Man_7GlcNAc_2$, while the sugar chain of the antibody produced by the *Ogataea minuta* TK9-IgB-aM strain was composed mainly of $Man_5GlcNAc_2$, which was a mammalian type, high mannose type sugar chain. The results indicated that 80% or more sugar chains were composed of $Man_5GlcNAc_2$.

Example 30

Cloning of HIS3 (Imidazoleglycerol Phosphate Dehydratase) Gene from *Ogataea minuta*

The HIS3 gene was obtained from *Ogataea minuta* IFO 10746 strain, and its nucleotide sequence was determined.

(30-1) Preparation of Probe

Oligonucleotides having nucleotide sequences corresponding to the amino acid sequences conserved in HIS3 gene products from *Saccharomyces cerevisiae* (Accession number; CAA27003) and *Pichia pastoris* (Accession number; Q92447):

```
VGFLDHM;      (SEQ ID NO: 95)
and

PSTKGVL       (SEQ ID NO: 96)
``` were synthesized as follows.

```
PHI5;    5'-TNGGNTTYYTNGAYCAYATG-3'  (SEQ ID NO: 97)

PHI3;    5'-ARNACNCCYTTNGTNSWNGG-3'  (SEQ ID NO: 98)
```

The primer PHI5 has a sequence complementary to the nucleotide sequence corresponding to the amino acid sequence VGFLDHM, and the primer PHI3 has a sequence complementary to the nucleotide sequence corresponding to the amino acid sequence PSTKGVL.

PCR by primers PHI5 and PHI3 was performed using the chromosomal DNA of *Ogataea minuta* IFO 10746 strain as a template ((94° C. for 30 seconds, 50° C. for 30 seconds and 72° C. for 1 minute)×25 cycles). The amplified DNA fragment of approximately 0.5 kb was recovered and cloned using TOPO TA Cloning Kit. Plasmid DNA was isolated from the obtained clone and sequenced. For a DNA insert of the plasmid, a clone was selected which had a nucleotide sequence encoding an amino acid sequence highly homologous to the amino acid sequences of HIS3 gene products from *Saccharomyces cerevisiae* and *Pichia pastoris*. The 0.5-kb DNA insert was recovered after EcoRI digestion of the plasmid and agarose gel electrophoresis.

(30-2) Preparation of Library and Screening

The chromosomal DNA of *Ogataea minuta* IFO 10746 was cleaved with different restriction enzymes, and subjected to Southern analysis using the DNA fragment obtained in Example (30-1) as a probe by the method described in Example (2-2). The results indicated that there existed the HIS3 gene in the PstI fragment of approximately 4 kb. Then, to clone the DNA fragment, a library was constructed. The chromosomal DNA of *Ogataea minuta* was cleaved with PstI and subjected to agarose gel electrophoresis, and then the approximately 4-kb DNA fragment was recovered from the gel. The recovered DNA fragment was ligated with PstI-cleaved and BAP-treated pUC 118 and then transformed into *Escherichia coli* DH5 α strains to prepare a library.

About 2,000 clones were screened by colony hybridization using the above described DNA fragment as a probe. A clone bearing plasmid pOMHI1 was selected from the 4 positive clones obtained.

(30-3) Sequencing of Nucleotide Sequence

The nucleotide sequence of the PstI-PstI region of the plasmid pOMHI1 (FIG. 25) was determined by primer walking method to obtain a nucleotide sequence represented by SEQ ID NO:99.

In the nucleotide sequence of SEQ ID O: 99, there existed an open reading frame of 714 bp, starting at position 1,839 and ends at position 2,552. The homology studies between the amino acid sequence (SEQ ID NO: 100) deduced from the open reading frame and the HIS3 gene product from *Saccharomyces cerevisiae* or *Pichia pastoris* showed that 73% or 71% of amino acids were respectively identical between them.

Example 31

Preparation of *Ogataea minuta* HIS3 Knockout Mutant

The HIS3 gene was disrupted by transformation using the *Ogataea minuta* URA3 gene as a marker.

(31-1) Preparation of HIS3 Gene Disruption Vector

Figure 25:
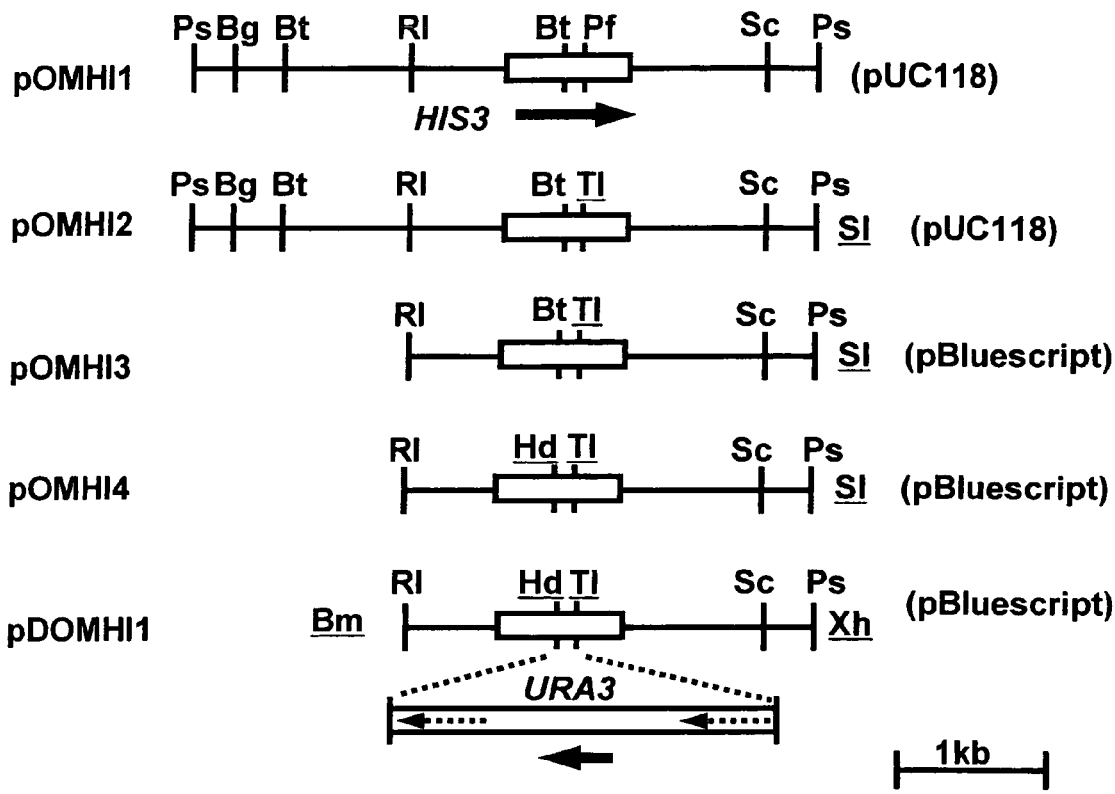
FIG. 25 shows the restriction maps of plasmids pOMHI1, pOMHI2, pOMHI3, pOMHI4 and pDOMHI1. The restriction enzyme sites of the vector and linker are underlined.

As shown in FIG. 25, plasmid pDOMH1 was prepared by replacing the approximately 70 bp region of the HIS3 structural gene by the URA3 gene.

The plasmid pROMU1 described in Example 8-1 was cleaved with BglII, blunt-ended, and ligated with an EcoT22I linker. The obtained plasmid was named pROMUHT.

The plasmid pOMHI1 containing the HIS3 gene region and described in Example (30-3) was cleaved with PflMI, blunt-ended, and ligated with an EcoT22I linker. The obtained plasmid was named pOMHI2. This plasmid was then cleaved with EcoRI and SalI and ligated with the EcoRI- and SalI-cleaved pBluescript II KS+. The obtained plasmid was named pOMHI3. The pOMHI3 was cleaved with BtgI, blunt-ended, and ligated with a HindIII linker. The obtained plasmid was named pOMHI4. The 3.3-kb EcoT22I-HindIII fragment isolated from the pROMUHT was inserted into the EcoT22I-HindIII of the obtained plasmid. The resultant plasmid was named pDOMHI1 (FIG. 25).

(31-2) Transformation

The pDOMHI1 obtained in Example (30-2) was cleaved with BamHI and XhoI and transformed into the *Ogataea minuta* TK11 strain (och1Δ ktr1Δ pep4Δ prb1Δ ura3Δ ade1Δ) obtained in Example (17-2) by electric pulse method. To confirm that the HIS3 gene was disrupted, the following primers were synthesized (see FIG. 26 with regard to the position of each primer):

```
DHI5;  5'-GGCCCAATAGTAGATATCCC-3'   (SEQ ID NO: 101)

DHI3;  5'-CACGGCCCGTGTAGCTCGTGG-3'  (SEQ ID NO: 102)
```

Figure 26:
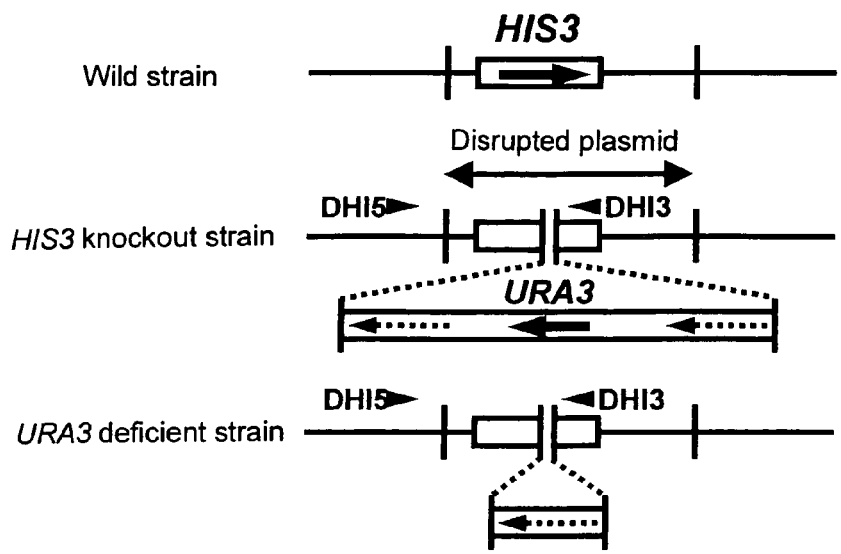
FIG. 26 shows the structures of the HIS3 loci of a wild strain of *Ogataea minuta*, an HIS3 gene knockout mutant disrupted by plasmid pDOMHI1, and a URA3 gene deficient mutant, along with positions of PCR primers.
Figure 27:
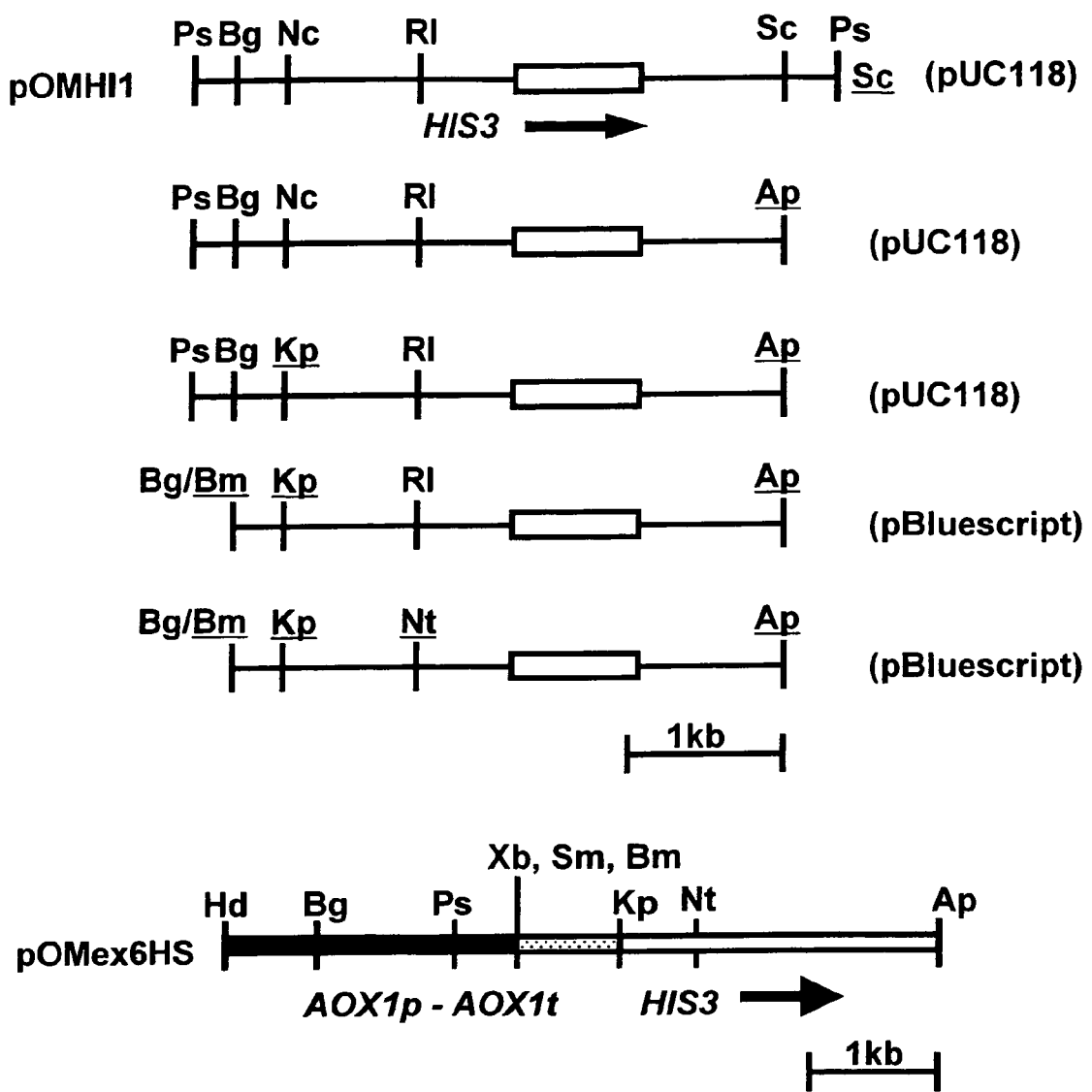
FIG. 27 shows the construction of plasmid pOMex6HS and its restriction map. The restriction enzyme sites of the vector and linker are underlined.

PCR by primers DHI5 and DHI3 was performed using the chromosomal DNA isolated from the transformant as a template ((94° C. for 30 seconds, 60° C. for 1 minute and 72° C. for 2 minutes)×25 cycles). As shown in FIG. 26, a 4.6 kb amplified DNA fragment was detected in the strain whose HIS3 locus had the plasmid integrated thereinto. The selected strain was cultured on the YPD medium until stationary phase and a strain resistant to 5-fluoroorotic acid (5-FOA) was obtained. PCR by primers DHI5 and DHI3 was performed using the chromosomal DNA of the 5-FOA resistant strain as a template ((94° C. for 30 seconds, 60° C. for 1 minute and 72° C. for 3 minutes)×25 cycles). As shown in FIG. 26, in the strain from which the URA3 gene was deleted, a 2 kb amplified DNA fragment was detected. This och1Δ ktr1Δ pep4Δ prb1Δ ura3Δ ade1Δ his3Δ strain was named *Ogataea minuta* YK1.

Example 32

Figure 32:
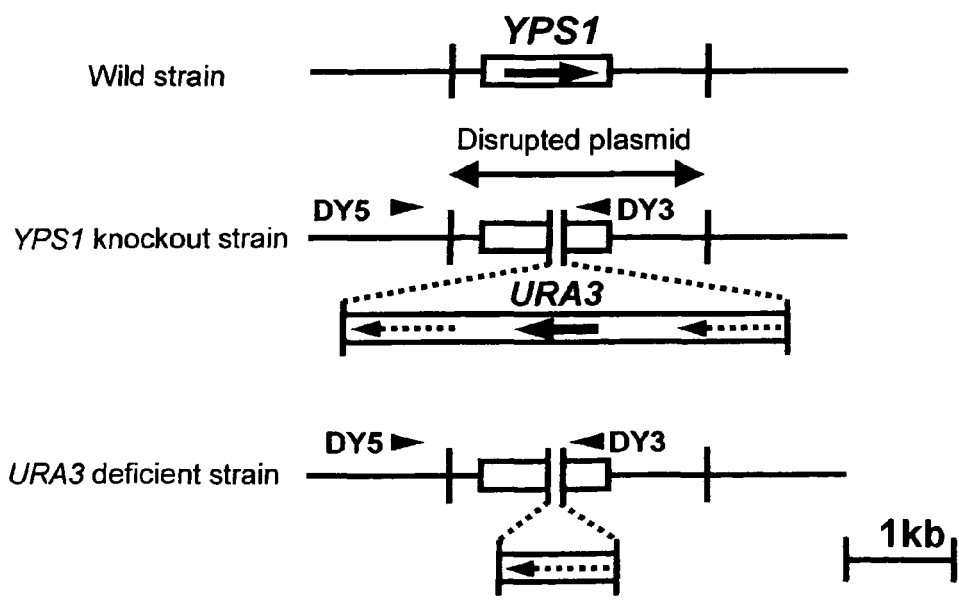
FIG. 32 shows the structures of the YPS1 loci of a wild strain of *Ogataea minuta*, a YPSI gene knockout mutant disrupted by plasmid pDOMLE1 and a URA3 gene deficient mutant, along with positions of PCR primers.

Construction of Heterologous Gene Expression Plasmid Using AOX1 Gene Promoter and Terminator and HIS3 Gene as a Selectable Marker A plasmid was prepared by the steps of cleaving with SacI the pOMHI1 containing the HIS3 gene as described in Example (30-3); blunt-ending; transferring an ApaI; cleaving with NcoI; blunt-ending; transferring a KpnI linker; cleaving with EcoRI; blunt-ending; and transferring a NotI linker. The HIS3 gene expression cassette was isolated, as a 2.6-kb ApaI-KpnI fragment, from the obtained plasmid, and inserted into the ApaI-KpnI of the POMex1U. The resultant plasmid was named pOMex6HS (FIG. 32).

The approximately 1.4-kb SpeI-BglII fragment comprising *Saccharomyces cerevisiae*-derived invertase gene, which was prepared in Example 25, was inserted into the XbaI-BamHI of the pOMex6HS to prepare pOMIV6HS. This plasmid was cleaved with NotI and transferred into the *Ogataea minuta* YK1 strain described in Example (31-2). The transformants were cultured in the BYPM medium (0.67% yeast nitrogen base, 1% yeast extract, 2% polypeptone, 100 mM potassium phosphate buffer pH 6.0, 0.5% methanol). The culture was centrifuged, and invertase activity was measured for the supernatant by the following procedures. Specifically, 2 μl of the culture supernatant appropriately diluted and 200 μl of 100 mM sodium acetate buffer (pH 5.0) containing 2% sucrose were mixed and incubated at 37° C. for 10-30 minutes, and then 500 μl of Glucose-Test Wako (Wako Pure Chemical Industries, Ltd., Japan) was added to the reaction mixture to develop color. An absorbance based on free glucose generated by invertase was measured at 505 nm. In the yeast strain *Ogataea minuta* YK1-WH1, a significant amount of invertase was produced in the medium.

Example 33

Cloning of LEU2 (3-isopropylmalate dehydrogenase) Gene from *Ogataea minuta*

The LEU2 gene was obtained from *Ogataea minuta* strain IFO 10746, and its nucleotide sequence was determined.

(33-1) Preparation of Probe

Oligonucleotides having nucleotide sequences corresponding to the amino acid sequences conserved in LEU2 gene products from *Saccharomyces cerevisiae* (Accession number; CAA27459) and *Pichia angusta* (P34733):

```
AVGGPKWG;    (SEQ ID NO: 103)
and

AAMMLKL      (SEQ ID NO: 104)
``` were synthesized as follows.

```
PLE5;  5'-                                    (SEQ ID NO: 105)
       GCNGTNGGNGGNCCNAARTGGGG-3'

PLE3;  5'-NARYTTNARCATCATNGCNGC-3'            (SEQ ID NO: 106)
```

The primer PLE5 has a sequence complementary to the nucleotide sequence corresponding to the amino acid sequence AVGGPKWG, and the primer PLE3 has a sequence complementary to the nucleotide sequence corresponding to the amino acid sequence AAMMLKL.

PCR by primers PLE5 and PLE3 was performed using the chromosomal DNA of *Ogataea minuta* IFO 10746 as a template ((94° C. for 30 seconds, 50° C. for 1 minute and 72° C. recovered and cloned using TOPO TA Cloning Kit. Plasmid DNA was isolated from the obtained clone and sequenced. For a DNA insert of the plasmid, a clone was selected which had a nucleotide sequence encoding an amino acid sequence highly homologous to the amino acid sequence of LEU2 gene products from *Saccharomyces cerevisiae* and *Pichia angusta*. The 0.7-kb DNA insert was recovered after EcoRI cleavage of the plasmid and agarose gel electrophoresis.

(33-2) Preparation of Library and Screening

The chromosomal DNA of *Ogataea minuta* IFO 10746 strain was cleaved with different restriction enzymes, and subjected to Southern analysis using the DNA fragment obtained in Example (33-1) as a probe by the method described in Example (2-2). The results suggested that there existed the LEU2 gene in the BamHI-ClaI fragment of approximately 6 kb. Then, to clone the DNA fragment, a library was prepared. The chromosomal DNA of *Ogataea minuta* was cleaved with BamHI and ClaI and subjected to agarose gel electrophoresis, and then the approximately 6-kb DNA fragment was recovered from the gel. The recovered DNA fragment was ligated with BamHI- and ClaI-cleaved pBluescript II KS+ and then transformed into *Escherichia coli* strain DH5 α to prepare a library.

About 3,000 clones were screened by colony hybridization using the above described DNA fragment as a probe. A clone bearing plasmid pOMYP1 was selected from the 7 positive clones obtained.

(33-3) Sequencing of Nucleotide Sequence

The nucleotide sequence of the BamHI-ClaI region of the plasmid pOMLE1 (FIG. 28) was determined by primer walking method to obtain the nucleotide sequence represented by SEQ ID NO:107.

In the nucleotide sequence of SEQ ID NO:107, there existed an open reading frame of 1,089 bp, starting at position 1,606 and ends at position 2,694. The homology studies between the amino acid sequence (SEQ ID NO:108) deduced from the open reading frame and the LEU2 gene product from *Saccharomyces cerevisiae* or *Pichia angusta* showed that 80% or 85% of amino acids were respectively identical between them.

Example 34

Preparation of *Ogataea minuta* LEU2 Knockout Mutant

The LEU2 gene was disrupted by transformation using the URA3 gene of *Ogataea minuta* as a marker.

(34-1) Preparation of LEU2 Gene Disruption Vector

Figure 28:
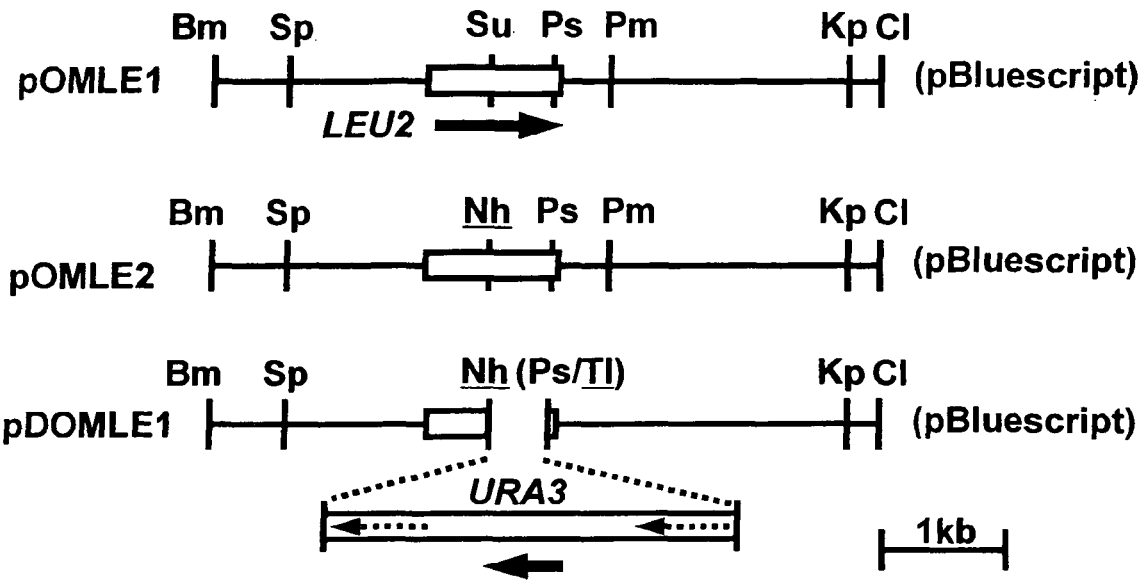
FIG. 28 shows the restriction maps of plasmids pOMLE1, pOMLE2 and pDOMLE1. The restriction enzyme sites of the vector and linker are underlined.

As shown in FIG. 28, plasmid pDOMLE1 was prepared by replacing the approximately 540-bp region of the LEU2 structural gene by the URA3 gene. To obtain a uracil auxotrophic mutant again from LEU2 gene knockout mutants, the URA3 gene having repetitive structures before and after the structural gene was used as a marker. The pROMUHT described in Example (31-1) was cleaved with HindIII, blunt-ended, and ligated with a NheI linker. The obtained plasmid was named pROMUNT.

The pOMLE1 was cleaved with StuI, blunt-ended, and ligated with a NheI linker. The obtained plasmid was named pOMLE2. The 3.3-kb Nhe-EcoT22I fragment isolated from the pOMURNT was inserted into the NheI-PstI of the pOMLE2. The obtained plasmid was named pDOMLE1.

(34-2) Transformation

The pDOMLE1 obtained in Example (34-1) was cleaved with BamHI and ClaI, and transformed into the *Ogataea minuta* TK11 strain (och1Δ ktr1Δ pep4Δ prb1Δ ura3Δ ade1Δ) obtained in Example (17-2) by electric pulse method. To confirm that the LEU2 gene of these strains was disrupted, the following primers were synthesized (see FIG. 29 with regard to the position of each primer):

```
DL5;   5'-CAGGAGCTACAGAGTCATCG-3'  (SEQ ID NO: 109)

DL3;   5'-ACGAGGGACAGGTTGCTCGC-3'  (SEQ ID NO: 110)
```

Figure 29:
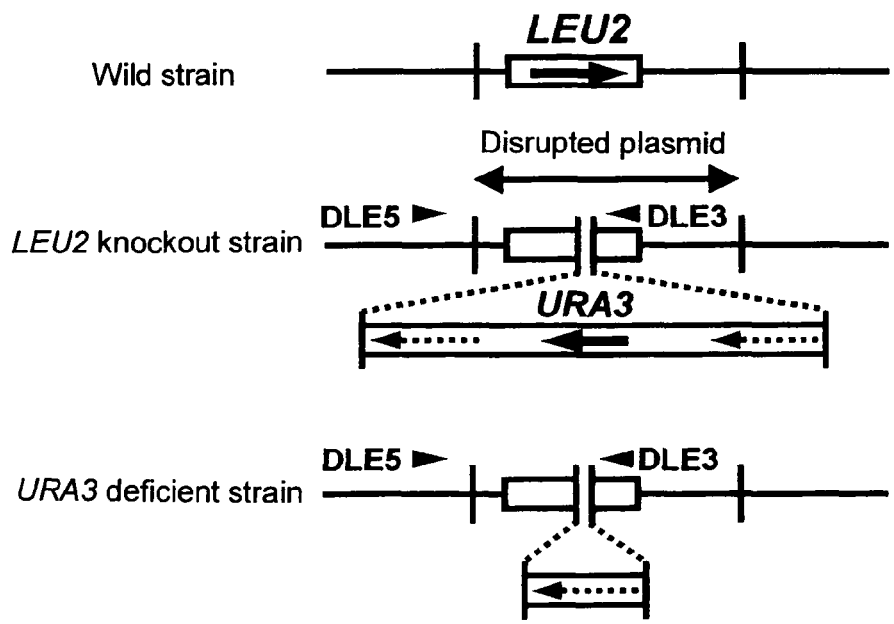
FIG. 29 shows the structures of the LEU2 loci of a wild strain of *Ogataea minuta*, a LEU2 gene knockout mutant disrupted by the plasmid pDOMLE1, and a URA3 gene deficient mutant, along with positions of PCR primers.

PCR by primers DL5 and DL3 was performed using the chromosomal DNA isolated from the transformant as a template ((94° C. for 30 seconds, 60° C. for 1 minute and 72° C. for 2 minutes)×25 cycles). As shown in FIG. 29, a 4 kb amplified fragment was detected in the strain whose LEU2 locus had the plasmid integrated thereinto. The selected strain was cultured on the YPD medium until stationary phase, and a strain resistant to 5-fluoroorotic acid (5-FOA) was obtained. PCR by primers DL5 and DL3 was performed using the chromosomal DNA of the 5-FOA resistant strain as a template ((94° C. for 30 seconds, 60° C. for 1 minute and 72° C. for 3 minutes)×25 cycles). As shown in FIG. 29, in the strain from which the URA3 gene was deleted, a 1.6 kb amplified DNA fragment was detected. This och1Δ ktr1Δ pep4Δ prb1Δ ura3Δ ade1Δ leu2Δ strain was named *Ogataea minuta* YK2.

Example 35

Figure 30:
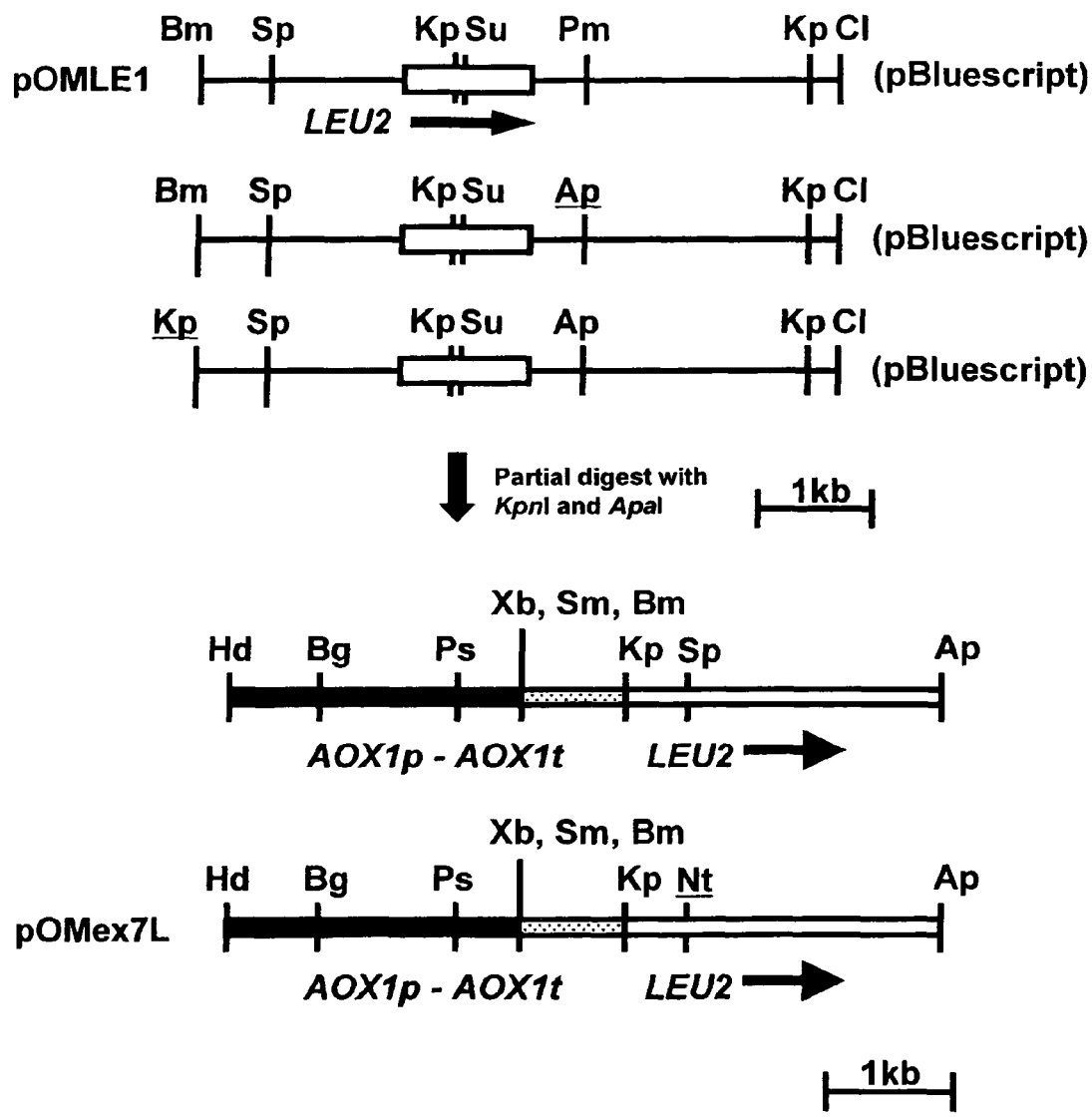
FIG. 30 shows the construction of plasmid pOMex7L and its restriction map. The restriction enzyme sites of the vector and linker are underlined.

Construction of Heterologous Gene Expression Plasmid Using AOX1 Gene Promoter and Terminator, and LEU2 Gene as a Selectable Marker The pOMLE1 comprising the LEU2 gene described in Example (33-2) was cleaved with PmaCI, ligated with an ApaI linker, cleaved with BamHI, blunt-ended, and ligated with a KpnI linker. The LEU2 gene expression cassette was isolated, as a 3.3-kb ApaI-KpnI fragment, from the obtained plasmid, and then inserted into the ApaI-KpnI of the POMex1U. The obtained plasmid was cleaved with SpeI, blunt-ended, and ligated with a NotI linker. The resultant plasmid was named pOMex7L (FIG. 30).

The approximately 1.4-kb SpeI-BglII fragment comprising the *Saccharomyces cerevisiae*-derived invertase gene, obtained in Example 25, was inserted into the XbaI-BamHI of the pOMex7L to prepare pOMIV7L. This plasmid was cleaved with NotI and transferred into the *Ogataea minuta* YK2 strain described in Example (34-2). The transformant was cultured in the BYPM medium (0.67% yeast nitrogen base, 1% yeast extract, 2% polypeptone, 100 mM potassium phosphate buffer pH 6.0, 0.5% methanol). The culture was centrifuged and the supernatant was measured for invertase activity by the following procedures. Specifically, 2 µl of the culture supernatant appropriately diluted and 200 µl of 100 mM sodium acetate buffer (pH 5.0) containing 2% sucrose were mixed together and incubated at 37° C. for 10-30 minutes, and 500 µl of Glucose-Test Wako (Wako Pure Chemical Industries, Inc., Japan) was added to the 2 µl of the reaction mixture to develop color. The absorbance based on free glucose generated by invertase was measured at 505 nm. In the most productive yeast strain *Ogataea minuta* YK2-IVL1, a significant amount of invertase was produced in the medium.

Example 36

Cloning of YPS1 Gene from *Ogataea minuta*

The YPS1 gene was obtained from *Ogataea minuta* IFO 10746, and its nucleotide sequence was determined.
(36-1) Preparation of Probe Oligonucleotides having nucleotide sequences corresponding to the following amino acid sequences conserved in YPS1 gene products from *Saccharomyces cerevisiae* (Accession number; NP_013221) and *Candida albicans* (Accession number; AAF66711):

```
    DTGSSDLW;            (SEQ ID NO: 111)
    and

FGAIDHAK             (SEQ ID NO: 112)
``` were synthesized as follows.

```
PLE5;
5'-GAYACNGGHTCNTCNGAYYTNTGG-3'    (SEQ ID NO: 113)

PLE3;
5'-TTYGGHGCNATYGAYCAYGCNAA-3'     (SEQ ID NO: 114)
```

The primer PYP5 has a sequence complementary to the nucleotide sequence corresponding to the amino acid sequence DTGSSDLW, and the primer PYP3 has a sequence complementary to the nucleotide sequence corresponding to the amino acid sequence FGAIDHAK.

PCR by primers PYP5 and PYP3 was performed using the chromosomal DNA of *Ogataea minuta* IFO 10746 as a template ((94° C. for 30 seconds, 50° C. for 1 minute and 72° C. for 1 minute)×25 cycles). Approximately 0.6 kb amplified DNA fragment was recovered and cloned using TOPO TA Cloning Kit. Plasmid DNA was isolated from the obtained clone and sequenced. For a DNA insert of the plasmid, a clone was selected which had a nucleotide sequence encoding an amino acid sequence highly homologous to the amino acid sequences of YPS1 gene products from *Saccharomyces cerevisiae* and *Candida albicans*. The 0.6-kb DNA insert was recovered after EcoRI digestion of the plasmid and agarose gel electrophoresis.
(36-2) Preparation of Library and Screening The chromosomal DNA of *Ogataea minuta* IFO 10746 was cleaved with different restriction enzymes, and subjected to Southern analysis using the DNA fragment obtained in Example (36-1) as a probe by the method described in Example (2-2). The results suggested that there existed YPS1 gene in the EcoRI fragment of approximately 4 kb. Then, to clone the DNA fragment, a library was constructed. The chromosomal DNA of the *Ogataea minuta* was cleaved with EcoRI and subjected to agarose gel electrophoresis, and then the approximately 6-kb DNA fragment was recovered from the gel. The recovered DNA fragment was ligated with EcoRI-cleaved and BAP-treated pUC118 and then transformed into *Escherichia coli* strain DH5 α to prepare a library.

About 2,000 clones were screened by colony hybridization using the above described DNA fragment as a probe. A clone bearing plasmid pOMYP1 was selected from the 4 positive clones obtained.

(36-3) Sequencing of Nucleotide Sequence

The nucleotide sequence of the EcoRI region of the plasmid pOMLE1 (FIG. 31) was determined by primer walking method to obtain a nucleotide sequence represented by SEQ ID NO:115.

In the nucleotide sequence of SEQ ID NO:115, there existed an open reading frame of 1,812 bp, starting at 1position 1,712 and ends at position 3,523. The homology studies between the amino acid sequence (SEQ ID NO:16) deduced from the open reading frame and the YPS1 gene product from *Saccharomyces cerevisiae* or *Candida albicans* showed that 40% or 27% of amino acids were respectively identical between them.

Example 37

Preparation of *Ogataea minuta* YPS1 Knockout Mutant

Figure 31:
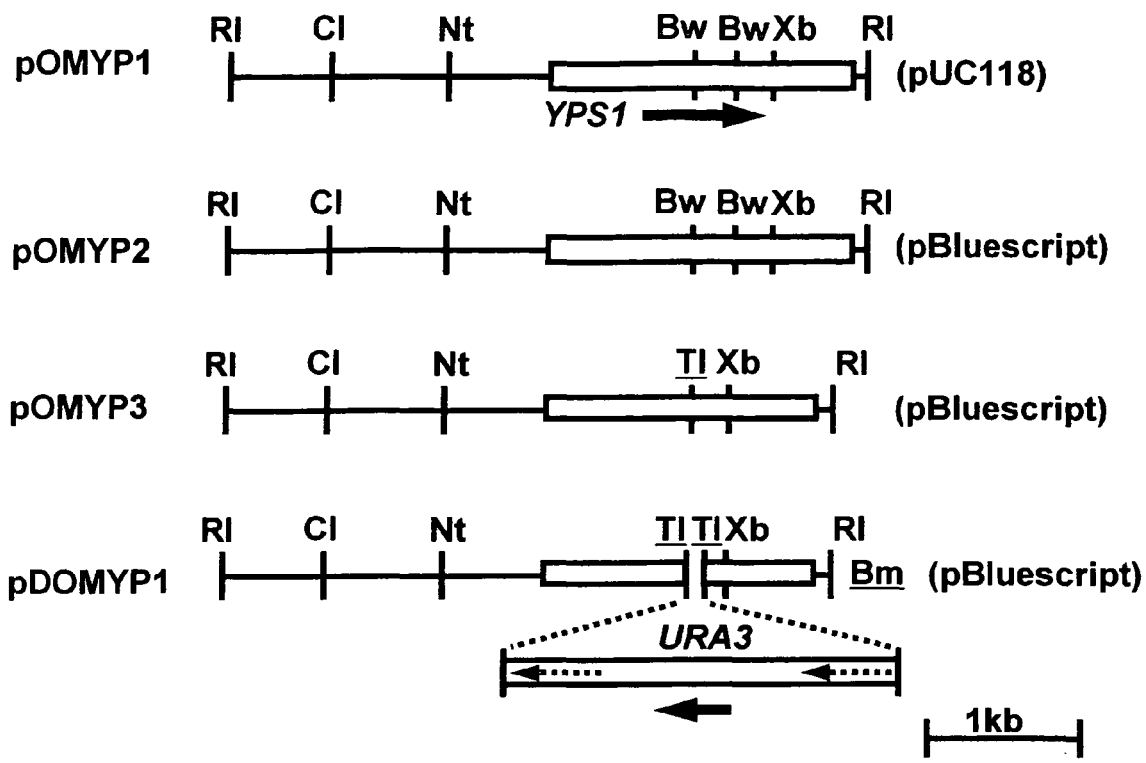
FIG. 31 shows the restriction maps of plasmids pOMYP1, pOMYP2, pOMYP3 and pDOMYP1. The restriction enzyme sites of the vector and linker are underlined.

The YPS1 gene was disrupted by transformation using the UR43 gene of *Ogataea minuta* as a marker.
(37-1) Preparation of YPS1 Gene Disruption Vector As shown in FIG. 31, plasmid pDOMYP1 was prepared by replacing the approximately 300-bp region of the YPS1 structural gene by the URA3 gene. To obtain a uracil auxotrophic mutant again from YPS1 knockout mutants, the URA3 gene having repetitive structures before and after the structural gene was used as a marker. The pROMUHT described in Example (31-1) was cleaved with HindIII, blunt-ended, and ligated with an EcoT22I linker. The obtained plasmid was named pROMUTT.

The pOMYP1 was cleaved with EcoRI, and the obtained fragment was ligated with EcoRI-cleaved and BAP-treated pBluescript II KS+. The obtained plasmid was named pOMYP2. This plasmid was cleaved with BsiWI and blunt-ended, and an EcoT22I linker was inserted thereinto. The obtained plasmid was named pOMYP3. The 3.3-kb EcoT22I fragment isolated from the pOMURTT was inserted at the EcoT22I of the pOMYP3. The obtained plasmid was named pDOMYP1.
(37-2) Transformation The pDOMYP1 obtained in Example (37-1) was cleaved with BamHI and ClaI, and transformed into the *Ogataea minuta* TK11 strain (och1Δ ktr1Δ pep4Δ prb1Δ ura3Δ ade1Δ) obtained in Example (17-2) by electric pulse method. To confirm that the YPS1 gene was disrupted, the following primers were synthesized (see FIG. 32 with regard to the position of each primer).

```
DY5; 5'-CTCAAGGGCCTGGAGACTACG-3'    (SEQ ID NO: 117)

DY3; 5'-CGGGATTCCCGAGTCGCTCACC-3'   (SEQ ID NO: 118)
```

PCR by primers DY5 and DY3 was performed using the chromosomal DNA isolated from the transformant as a template ((94° C. for 30 seconds, 60° C. for 1 minute and 72° C. for 2 minutes)×25 cycles). As shown in FIG. 8, a 3.7 kb amplified DNA fragment was detected in the strain whose YPS1 locus had the plasmid integrated thereinto. The selected strain was cultured on the YPD medium until stationary phase, and a strain resistant to 5-fluoroorotic acid (5-FOA) was obtained. PCR by primers DY5 and DY3 was performed using the chromosomal DNA of the 5-FOA resistant strain as a template ((94° C. for 30 seconds, 60° C. for 1 minute and 72° C. for 3 minutes)×25 cycles). As shown in FIG. 32, a 1.2 kb amplified DNA fragment was detected in the strain from which the URA3 gene was deleted. This och1Δ ktr1Δ pep4Δ prb1Δ ura3Δ ade1Δ yps1Δ strain was named *Ogataea minuta* YK3.

Example 38

Transferring of Human Antibody Gene into *Ogataea minuta* YPS1 Knockout Mutant and Expression of Same Human G-CSF light chain gene (SEQ ID NO:91) and heavy chain gene (SEQ ID NO:92) were transferred into the *Ogataea minuta* YK3 strain (och1Δ ktr1Δ pep4Δ prb1Δ ura3Δ ade1Δ yps1Δ) obtained in Example (37-2). The plasmid vector expressing anti-G-CSF light chain and heavy chain genes, described in Example 28, was cleaved with NotI, the *Ogataea minuta* YK3 strain was transformed in turn. In accordance with the method described in Example 28, a transformant that produced the antibodies in the culture supernatant was selected from the obtained transformants, and the *Ogataea minuta* YK3-derived antibody producing strain was named *Ogataea minuta* YK3-IgB1.

Figure 33:
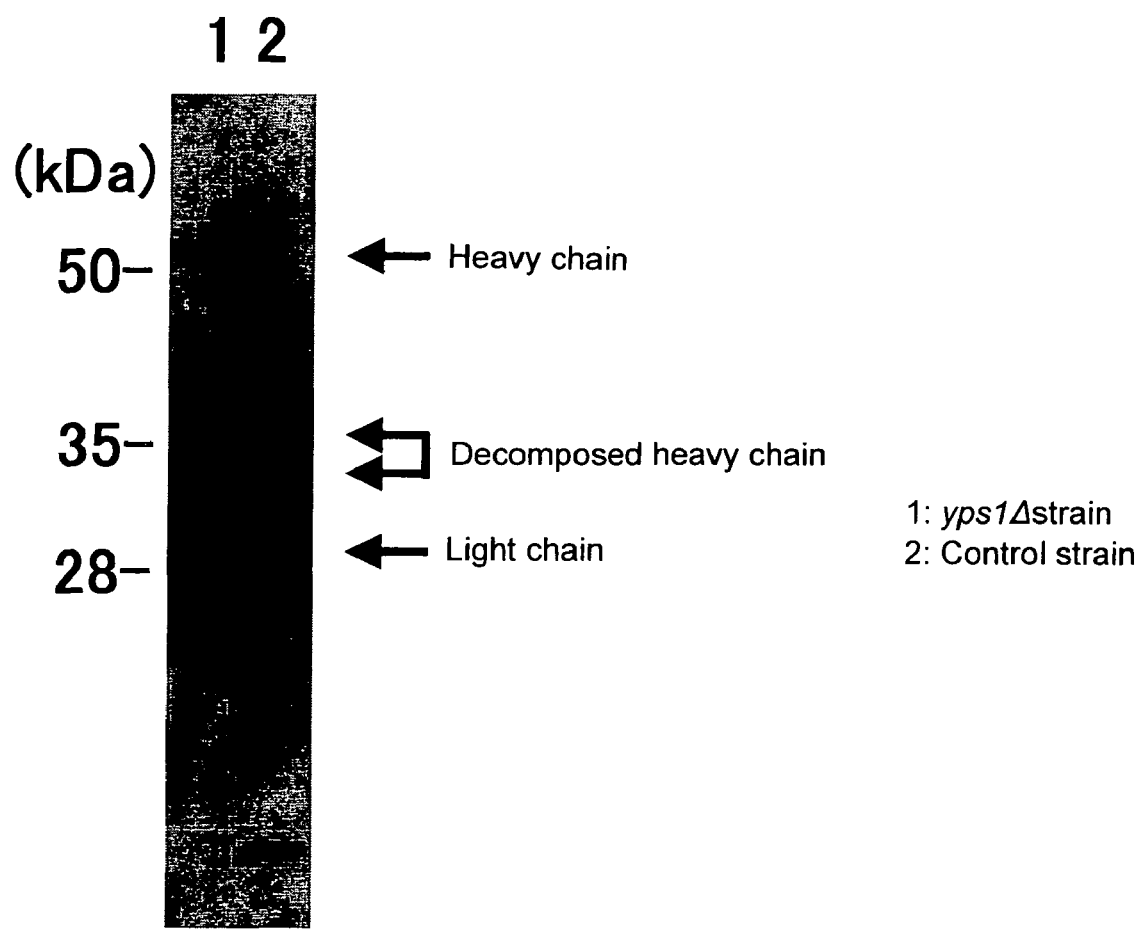
FIG. 33 shows the Western analysis of the antibody produced by using *Ogataea minuta* strain YK3-IgB-aM.

Then *Aspergillus saitoi*-derived α-1,2-mannosidase gene was transferred into the *Ogataea minuta* YK3-IgB1 strain. After transformation using the plasmid pOMaM1U prepared in Example 23 by the method described in Example 24, an α-1,2-mannosidase expressing strain was selected from the obtained transformants. The resultant strain was named *Ogataea minuta* YK3-IgB-aM. The *Ogataea minuta* YK3-IgB-aM strain and the *Ogataea minuta* TK9-IgB-aM strain prepared in Example 28 as a control were cultured in the BYPMG medium at 28° C. for 72 hours and centrifuged. The culture supernatant obtained by the centrifugation was subjected to Western analysis. The results are shown in FIG. 33. The results revealed that in antibody molecules produced by the *Ogataea minuta* TK9-IgB-aM strain, as a control, molecules with degraded heavy chains were detected, whereas in the antibody molecules produced by the *Ogataea minuta* YK3-IgB-aM strain, the degradation of the heavy chains was retarded.

Figure 34:
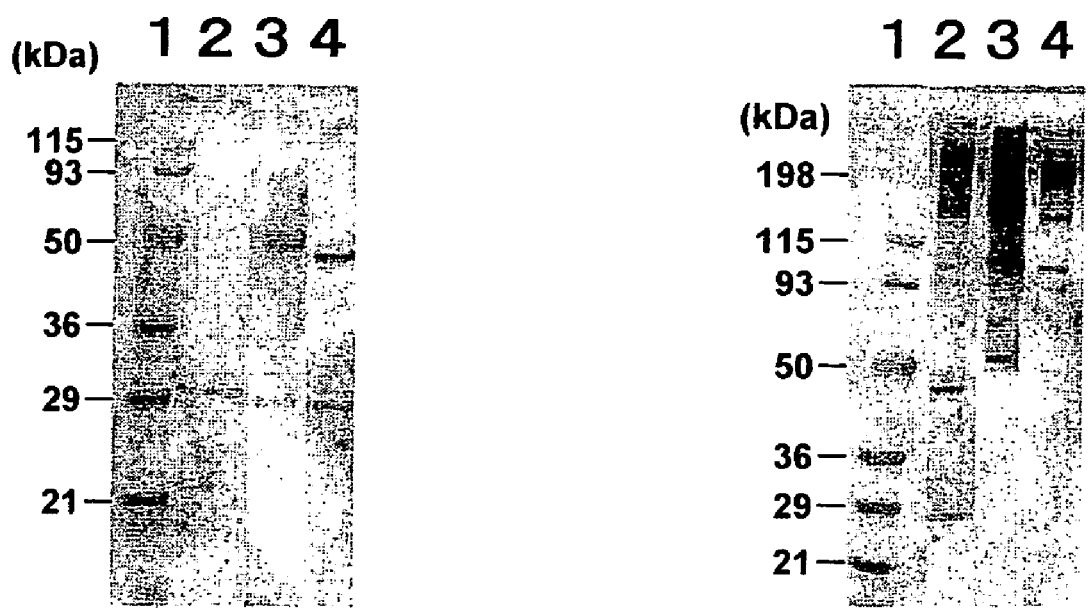
FIG. 34 shows the purification of the antibody produced by using *Ogataea minuta* strain YK3-IgB-aM (Western analysis, and reducing & non-reducing condition).

Further, the culture supernatant of the *Ogataea minuta* YK3-IgB-aM strain was concentrated by ultrafiltration using an Amicon YM76 membrane (Amicon), desalted, and subjected to Protein A column chromatography (Hi-Trap ProteinA HP, Amersham Pharmacia Biotech) to purify the antibody fractions through the elution with glycine—HCl, pH 3.0. Western analysis was performed for the purified antibody samples (FIG. 34). The results of SDS-PAGE under non-reducing conditions, it was found that a full-length antibody molecule, which was composed mainly of two light chain molecules and two heavy chain molecules, was produced. The binding of the purified antibody to G-CSF was confirmed by the method described in Example 28. The antibody was dialyzed and freeze-dried. PA-N-linked sugar chains were prepared by the method described in Example 11 and subjected to size analysis by normal phase column. From the results, it was confirmed that the sugar chain of the antibody contained $Man_5GlcNAc_2$, which was a mammalian and high mannose type sugar chain.

Example 39

Figure 35:
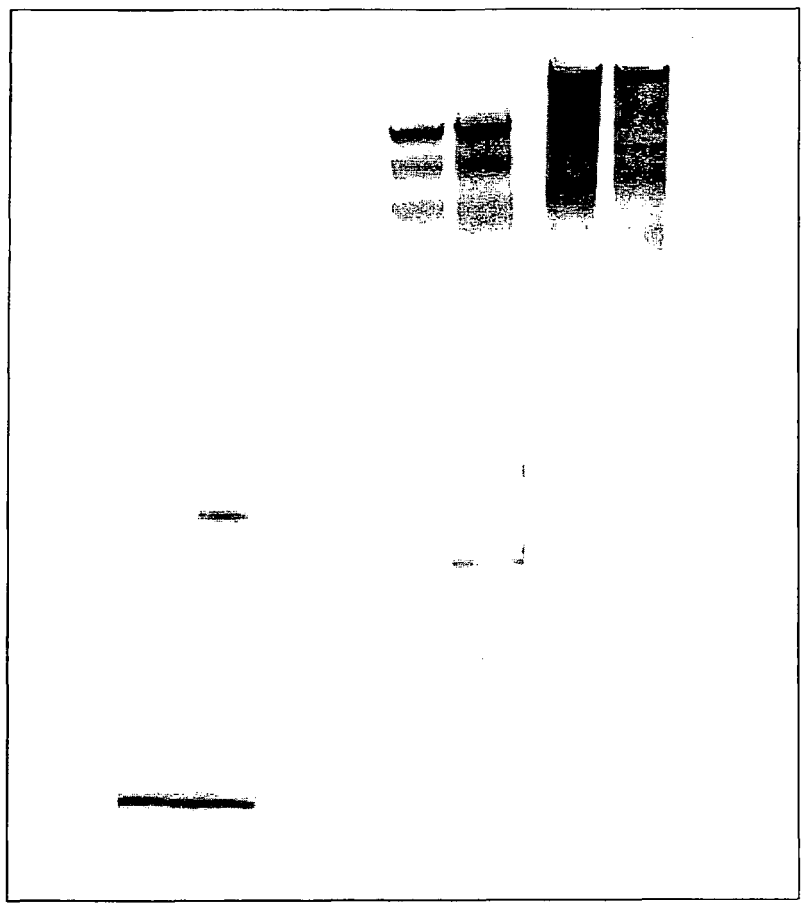
FIG. 35 shows the Western analysis of the antibody produced by using *Ogataea minuta* strain YK3-IgB-aM-PDI.

Transferring of a Molecular Chaperone Protein Disulfide Isomerase (PDD) Gene into Human Antibody Producing Strain Prepared in Example 38, and Expression of Same The results obtained above confirmed that the *Ogataea minuta* YK3-IgB1-aM strain produced only a trace amount of the antibody in the culture supernatant, while the results of the Western analysis revealed that a significant amount of the antibody was accumulated in the cells (FIG. 35, lanes 1, 5). As it was presumed that the antibody protein was not fully folded, we attempted to express Protein Disulfide Isomerase (PDI) gene, as a molecular chaperone. To express the PDI gene, we constructed a plasmid, which expressed PDI gene using AOX1 gene promoter and a hygromycin resistant gene as a selectable marker.

To obtain the PDI gene (M62815) from *Saccharomyces cerevisiae*, the following primers corresponding to the N-and C-termini of the PDI were synthesized.

```
PDI5;
5'-                                    (SEQ ID NO: 119)
TCTAGAATGAAGTTTTCTGCTGGTGCCGTCCTG-
3'

PDI3;
5'-                                    (SEQ ID NO: 120)
GGATCCTTACAATTCATCGTGAATGOCATCTTC-
3'
```

PCR by primers PDI5 and PDI3 was performed using the chromosomal DNA of *Saccharomyces cerevisiae* S288C as a template ((94° C. for 30 seconds, 55° C. for 1 minute and 72° C. for 1 minute)×20 cycles). 1.5 kb amplified DNA fragment was recovered and cloned using TOPO TA Cloning Kit. The nucleotide sequence of the DNA insert was determined and a clone having the correct nucleotide sequence was selected. The PDI gene of *Saccharomyces cerevisiae* can be isolated as a SpeI-BamHI fragment.

Then, the XbaI-BamHI fragment comprising the above-described PDI gene was inserted into the XbaI-BamHI of the expression cassette using the *Ogataea minuta* AOX1 gene promoter and terminator, as prepared in Example (21-5), and the expression plasmid pOMex5H comprising the hygromycin resistant gene as a selectable marker. The resultant plasmid was named pOMex5H-PDI.

The pOMex5H-PDI was cleaved with NotI, and the *Ogataea minuta* YK3-IgB1-aM strain was transformed therewith. The transformants were cultured in the BYPMG medium and centrifuged, the culture supernatant obtained by the centrifugation was subjected to Western analysis in the same manner as in Example 38, and a transformant that produced the antibody in the culture supernatant was selected. The *Ogataea minuta* YK3-IgB-aM-derived antibody producing strain was named *Ogataea minuta* YK3-IgB-aM-P. The *Ogataea minuta* YK3-IgB-aM-P strain produced a significant amount of the full-length antibody molecule as compared with the original strain *Ogataea minuta* YK3-IgB-aM into which no molecular chaperon was transferred (FIG. 35, lane 4), and in which the amount of antibody accumulated in the cells was decreased (FIG. 35, lane 6).

The antibody fractions were purified from the culture supernatant of the *Ogataea minuta* YK3-IgB-aM strain by the method described in Example 38. The antibody fractions were dialyzed and freeze-dried. PA-N-linked sugar chains were prepared by the method described in Example 11, and subjected to size analysis by normal phase column to confirm that the sugar chain of the antibody produced by the *Ogataea minuta* YK3-IgB-aM strain contained $Man_5GlcNAc_2$, which was a mammalian type, high mannose type sugar chain.

INDUSTRIAL APPLICABILITY

Using the methylotrophic yeast carrying a sugar chain mutation, which is newly prepared by genetic engineering techniques of the invention, a neutral sugar chain identical with a high mannose type sugar chain produced by mammalian cells such as human cells, or a glycoprotein having the same neutral sugar chain, can be produced in a large amount at a high purity. Further, by transferring a mammalian type sugar chain biosynthesis-associated gene(s) into the above described mutant strain, a hybrid type or complex type mammalian sugar chain or a protein comprising mammalian type sugar chain can be efficiently produced. The yeast strains and glycoproteins of the invention are applicable to medicaments, etc.

The disclosure of all the publications, patents and patent applications cited herein is incorporated herein by reference.

What is claimed is:

1. A process for producing a methylotrophic yeast that produces a mammalian type sugar chain, which comprises the steps of:
   1) disrupting an OCH1 gene which encodes α-1,6-mannosyl transferase and YPS1 gene which encodes Aspartic protease 3, in a methylotrophic yeast; and
   2) introducing an α-1,2-mannosidase gene into the yeast and expressing it therein,
wherein the methylotrophic yeast belongs to the genus *Pichia* or *Ogataea*.

2. A process according to claim 1, wherein the mammalian type sugar chain is represented by the following structural formula ($Man_5GlcNAc_2$):

Structural Formula 2

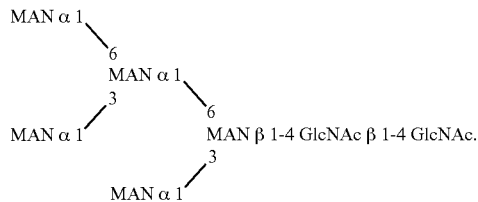

3. A process according to claim 1 or 2, wherein the methylotrophic yeast is *Ogataea minuta*.

4. A process according to claim 1, wherein the methylotrophic yeast is a strain from *Ogataea minuta* strain IFO 10746.

5. A process according to claim 1, wherein the α-1,2-mannosidase gene is expressed under the control of a methanol-inducible promoter.

6. A process according to claim 5, wherein the methanol-inducible promoter is a promoter of an alcohol oxidase (AOX) gene.

7. A process according to claim 6, wherein the alcohol oxidase (AOX) gene is from *Ogataea minuta*.

8. A process according to claim 1, characterized in that the α-1,2-mannosidase expressed from the α-1,2-mannosidase gene further comprises a yeast endoplasmic reticulum (ER) retention signal.

9. A process according to claim 1, wherein the α-1,2-mannosidase gene is from *Aspergillus saitoi*.

10. A process according to claim 1, which further comprises a step of transforming a heterologous gene into the yeast.

11. A process according to claim 10, wherein the heterologous gene is transferred using an expression vector and is expressed in the yeast.

12. A process according to claim 11, wherein the expression vector comprises a methanol-inducible promoter.

13. A process according to claim 12, wherein the methanol-inducible promoter is a promoter of an alcohol oxidase (AOX) gene.

14. A process according to claim 13, wherein the alcohol oxidase (AOX) gene is from *Ogataea minuta*.

15. A process according to claim 11, wherein the expression vector comprises a promoter of a glyceraldehyde-3-phosphate dehydrogenase (GAPDH) gene.

16. A process according to any one of claims 10 to 15, wherein 20% or more of N-linked sugar chains on the protein encoded by the heterologous gene is the mammalian type sugar chain represented by Structural Formula 2.

17. A process according to any one of claims 10 to 15, wherein 40% or more of N-linked sugar chains on the protein encoded by the heterologous gene is the mammalian type sugar chain represented by Structural Formula 2.

18. A process according to any one of claims 10 to 15, wherein 60% or more of N-linked sugar chains on the protein encoded by the heterologous gene is the mammalian type sugar chain represented by Structural Formula 2.

19. A process according to any one of claims 10 to 15, wherein 80% or more of N-linked sugar chains on the protein encoded by the heterologous gene is the mammalian type sugar chain represented by Structural Formula 2.

20. A process according to any one of claims 10 to 15, wherein the protein encoded by the heterologous gene is from humans.

21. A process according to any one of claims 10 to 15, wherein the protein encoded by the heterologous gene is an antibody or a fragment thereof.

22. A methylotrophic yeast produced by a process according to claim 1 or claim 10.

23. A process for producing a protein encoded by a heterologous gene, wherein the process comprises culturing the methylotrophic yeast produced by a process according to claim 10 in a medium to obtain the protein encoded by the heterologous gene comprising a mammalian type sugar chain from the culture.

24. A process for producing an *Ogataea minuta* strain, which produces a mammalian type sugar chain represented by the following structural formula ($Man_5GlcNAc_2$):

Structural Formula 2

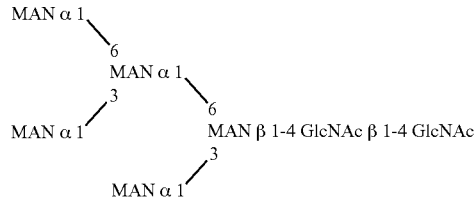

comprising a step of disrupting OCH1 gene in the *Ogataea minuta* strain; and a step of disrupting a YPS1 gene in the same strain.

25. A process of claim 24, wherein the *Ogataea minuta* strain is from the strain IFO 10746.

26. A process according to claim 24, which further comprises a step of disrupting at least one gene selected from the group consisting of a URA3 gene comprising the nucleotide sequence represented by SEQ ID NO:15, an ADE1 gene comprising the nucleotide sequence represented by SEQ ID NO:27, an HIS3 gene comprising the nucleotide sequence represented by SEQ ID NO:99, and a LEU2 gene comprising the nucleotide sequence represented by SEQ ID NO:107.

27. A process according to claim 24, which further comprises a step of disrupting at least one gene selected from the group consisting of a PEP4 gene comprising the nucleotide sequence represented by SEQ ID NO:51, a PRB1 gene comprising the nucleotide sequence represented by SEQ ID NO:57.

28. A process according to claim 27, which further comprises a step of disrupting a KTR1 gene comprising the nucleotide sequence represented by SEQ ID NO:63 and/or an MNN9 gene comprising the sequence represented by SEQ ID NO:69.

29. A process according to any one of claims 24 to 28, which further comprises a step of introducing and expressing an α-1,2-mannosidase gene from Aspergillus saitoi.

30. A process according to claim 29, wherein the α-1,2-mannosidase gene is expressed from a recombinant expression vector comprising a gene expression cassette comprising:
  (a) a DNA comprising a promoter of alcohol oxidase (AOX) gene which is substantially represented by SEQ ID NO:79;
  (b) the α-1,2-mannosidase gene; and
  (c) a terminator of alcohol oxidase (AOX) gene which is substantially represented by SEQ ID NO:80.

31. A process according to claim 24, which further comprises a step of introducing and expressing a PDI gene.

32. A process according to claim 31, wherein the PDI gene is a gene from Saccharomyces cerevisiae with the sequence found at GenBank Accession number M62815.

33. A process according to claim 32, wherein the PDI gene is expressed from a recombinant expression vector comprising a gene expression cassette comprising:
  (a) a DNA comprising a promoter of alcohol oxidase (AOX) gene which is substantially represented by SEQ ID NO:79;
  (b) the PDI gene; and
  (c) a terminator of alcohol oxidase (AOX) gene which is substantially represented by SEQ ID NO:80.

34. A process according claim 24, which further comprises a step of introducing and expressing a heterologous gene.

35. A process according to claim 34, wherein the heterologous gene is expressed from a recombinant expression vector comprising a gene expression cassette comprising:
  (a) a DNA comprising a promoter of alcohol oxidase (AOX) gene which is substantially represented by SEQ ID NO:79;
  (b) the heterologous gene; and
  (c) a terminator of alcohol oxidase (AOX) gene which is substantially represented by SEQ ID NO:80.

36. A process for producing a protein encoded by a heterologous gene, which comprises culturing Ogataea minuta produced by the process of claim 34 in a medium, to obtain the protein comprising a mammalian type sugar chain encoded by the heterologous gene from the culture.

37. A process for producing an Ogataea minuta strain, which produces a mammalian type sugar chain represented by the following structural formula ($Man_5GlcNAc_2$):

Structural Formula 2

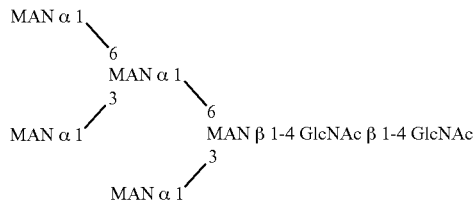

wherein the process comprises the steps of:
  disrupting an OCH1 gene comprising the nucleotide sequence represented by SEQ ID NO:42 in an Ogataea minuta strain; and
  disrupting a URA3 gene comprising the nucleotide sequence represented by SEQ ID NO:15 in the same strain; and
  disrupting a PEP4 gene comprising the nucleotide sequence represented by SEQ ID NO:51 in the same strain; and
  disrupting a PRB1 gene comprising the nucleotide sequence represented by SEQ ID NO:57 in the same strain; and
  disrupting a YPS1 gene comprising the nucleotide sequence represented by SEQ ID NO:115 in the same strain.

38. A process according to claim 37, wherein the Ogataea minuta strain is from the strain IFO 10746.

39. A process according to claim 37 or 38, which further comprises a step of disrupting an ADE1 gene comprising the nucleotide sequence represented by SEQ ID NO:27.

40. A process according to claim 39, which further comprises a step of disrupting a KTR1 gene comprising the nucleotide sequence represented by SEQ ID NO:63.

41. A process according to claim 40, which further comprises a step of disrupting an HIS3 gene comprising the nucleotide sequence represented by SEQ ID NO:99.

42. A process according to claim 40, which further comprises a step of disrupting a LEU2 gene comprising the nucleotide sequence represented by SEQ ID NO:107.

43. A process according claim 37, which further comprises a step of introducing and expressing an α-1,2-mannosidase gene.

44. A process according to claim 43, wherein the α-1,2-mannosidase gene is expressed from a recombinant expression vector comprising a gene expression cassette comprising:
  (a) a DNA comprising a promoter of alcohol oxidase (AOX) gene which is substantially represented by SEQ ID NO:79;
  (b) the α-1,2-mannosidase gene; and
  (c) a terminator of alcohol oxidase (AOX) gene which is substantially represented by SEQ ID NO:80.

45. A process according to claim 37, which further comprises a step of introducing and expressing a PDI gene from Saccharomyces cerevisiae with the sequence found at GenBank Accession number (M62815).

46. A process according to claim 45, wherein the PDI gene (M62815) is expressed from a recombinant expression vector comprising a gene expression cassette comprising:
  (a) a DNA comprising a promoter of alcohol oxidase (AOX) gene which is substantially represented by SEQ ID NO:79;
  (b) the PDI gene with the sequence found at GenBank Accession number M62815; and (c) a terminator of alcohol oxidase (AOX) gene which is substantially represented by SEQ ID NO:80.

47. A process according to claim 37, which further comprises a step of introducing and expressing a heterologous gene.

48. A process according to claim 47, wherein the heterologous gene is expressed from a recombinant expression vector comprising a gene expression cassette comprising:
(a) a DNA comprising a promoter of alcohol oxidase (AOX) gene which is substantially represented by SEQ ID NO:79;
(b) the heterologous gene; and
(c) a terminator of alcohol oxidase (AOX) gene which is substantially represented by SEQ ID NO:80.

49. A process for producing a protein encoded by a heterologous gene comprising a mammalian type sugar chain, wherein the process comprises culturing *Ogataea minuta* produced by the process of claim 47 in a medium to obtain the protein from the culture.

50. The process of claim 10, wherein the yeast endoplasmic reticulum (ER) retention signal has the sequence of SEQ ID NO: 121.

51. The process of claim 24, wherein the OCH1 gene has the sequence of SEQ ID NO: 42.

52. The process of claim 24, wherein the YPS1 gene has the sequence of SEQ ID NO: 115.

* * * * *

UNITED STATES PATENT AND TRADEMARK OFFICE
CERTIFICATE OF CORRECTION

PATENT NO. : 7,972,809 B2  
APPLICATION NO. : 10/511436  
DATED : July 5, 2011  
INVENTOR(S) : Kazuo Kobayashi et al.

Page 1 of 1

It is certified that error appears in the above-identified patent and that said Letters Patent is hereby corrected as shown below:

Title Page, Item (73) Assignee, should read as follows:

-- (73) Assignees: National Institute of Advanced Industrial Science & Technology, Tokyo (JP); Kirin Pharma Kabushiki Kaisha, Tokyo (JP) --.

Signed and Sealed this  
Twenty-fifth Day of October, 2011

David J. Kappos  
*Director of the United States Patent and Trademark Office*

UNITED STATES PATENT AND TRADEMARK OFFICE
CERTIFICATE OF CORRECTION

| | | |
|---|---|---|
| PATENT NO. | : 7,972,809 B2 | Page 1 of 1 |
| APPLICATION NO. | : 10/511436 | |
| DATED | : July 5, 2011 | |
| INVENTOR(S) | : Kazuo Kobayashi et al. | |

It is certified that error appears in the above-identified patent and that said Letters Patent is hereby corrected as shown below:

Claim 50, column 186, should read as follows:

50. The process of claim [10] 8, wherein the yeast endoplasmic reticulum (ER) retention signal has the sequence of SEQ ID NO: 121.

Signed and Sealed this
Third Day of January, 2012

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,972,809 B2 | Page 1 of 1 |
| APPLICATION NO. | : 10/511436 | |
| DATED | : July 5, 2011 | |
| INVENTOR(S) | : Kazuo Kobayashi et al. | |

It is certified that error appears in the above-identified patent and that said Letters Patent is hereby corrected as shown below:

Claim 50, column 186, lines 6-8, should read as follows:

50. The process of claim [10] 8, wherein the yeast endoplasmic reticulum (ER) retention signal has the sequence of SEQ ID NO: 121.

This certificate supersedes the Certificate of Correction issued January 3, 2012.

Signed and Sealed this
Thirty-first Day of January, 2012

David J. Kappos
*Director of the United States Patent and Trademark Office*

UNITED STATES PATENT AND TRADEMARK OFFICE
CERTIFICATE OF CORRECTION

PATENT NO. : 7,972,809 B2
APPLICATION NO. : 10/511436
DATED : July 5, 2011
INVENTOR(S) : Kazuo Kobayashi et al.

Page 1 of 1

It is certified that error appears in the above-identified patent and that said Letters Patent is hereby corrected as shown below:

Claim 50, column 186, lines 6-8, should read as follows:

50. The process of claim 8, wherein the yeast endoplasmic reticulum (ER) retention signal has the sequence of SEQ ID NO: 121.

This certificate supersedes the Certificates of Correction issued January 3, 2012 and January 31, 2012.

Signed and Sealed this
Nineteenth Day of March, 2013

Teresa Stanek Rea
*Acting Director of the United States Patent and Trademark Office*

UNITED STATES PATENT AND TRADEMARK OFFICE
CERTIFICATE OF CORRECTION

| | | |
|---|---|---|
| PATENT NO. | : 7,972,809 B2 | Page 1 of 1 |
| APPLICATION NO. | : 10/511436 | |
| DATED | : July 5, 2011 | |
| INVENTOR(S) | : Kazuo Kobayashi et al. | |

It is certified that error appears in the above-identified patent and that said Letters Patent is hereby corrected as shown below:

In the Claims

Claim 50, column 186, lines 6-8, should read as follows:

50. The process of claim 8, wherein the yeast endoplasmic reticulum (ER) retention signal has the sequence of SEQ ID NO: 121.

This certificate supersedes the Certificates of Correction issued January 3, 2012, January 31, 2012 and March 19, 2013.

Signed and Sealed this
Fourth Day of February, 2014

Michelle K. Lee
*Deputy Director of the United States Patent and Trademark Office*